(12) United States Patent
Marasco et al.

(10) Patent No.: US 11,104,722 B2
(45) Date of Patent: Aug. 31, 2021

(54) IMMUNOGENETIC RESTRICTION ON ELICITATION OF ANTIBODIES

(71) Applicant: Dana-Farber Cancer Institute, Inc., Boston, MA (US)

(72) Inventors: Wayne A. Marasco, Wellesley, MA (US); Yuval Avnir, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/259,209

(22) Filed: Jan. 28, 2019

(65) Prior Publication Data

US 2019/0276519 A1 Sep. 12, 2019

Related U.S. Application Data

(62) Division of application No. 15/127,404, filed as application No. PCT/US2015/021529 on Mar. 19, 2015, now abandoned.

(60) Provisional application No. 61/974,297, filed on Apr. 2, 2014, provisional application No. 61/955,678, filed on Mar. 19, 2014.

(51) Int. Cl.
| | |
|---|---|
| *A61K 47/68* | (2017.01) |
| *C12Q 1/68* | (2018.01) |
| *C07K 16/10* | (2006.01) |
| *C12Q 1/6876* | (2018.01) |
| *G01N 33/50* | (2006.01) |

(52) U.S. Cl.
CPC ...... *C07K 16/1018* (2013.01); *A61K 47/6841* (2017.08); *C12Q 1/6876* (2013.01); *G01N 33/5052* (2013.01); *C07K 2317/21* (2013.01); *C07K 2317/54* (2013.01); *C07K 2317/55* (2013.01); *C07K 2317/56* (2013.01); *C07K 2317/565* (2013.01); *C07K 2317/567* (2013.01); *C07K 2317/622* (2013.01); *C07K 2317/76* (2013.01); *C07K 2317/92* (2013.01); *C12Q 2600/106* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,485,045 A | 11/1984 | Regen | |
| 4,522,811 A | 6/1985 | Eppstein et al. | |
| 4,544,545 A | 10/1985 | Ryan et al. | |
| 4,676,980 A | 6/1987 | Segal et al. | |
| 4,816,567 A | 3/1989 | Cabilly et al. | |
| 4,946,778 A | 8/1990 | Ladner et al. | |
| 5,013,556 A | 5/1991 | Woodle et al. | |
| 5,030,719 A | 7/1991 | Umemoto et al. | |
| 5,091,513 A | 2/1992 | Huston et al. | |
| 5,132,405 A | 7/1992 | Huston et al. | |
| 5,223,409 A | 6/1993 | Ladner et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,916,771 A | 6/1999 | Nobuaki et al. | |
| 5,939,598 A | 8/1999 | Kucherlapati et al. | |
| 9,527,924 B2 | 12/2016 | Marasco et al. | |
| 9,951,122 B2 | 4/2018 | Marasco et al. | |
| 2012/0128684 A1* | 5/2012 | Marasco ............. | C07K 14/005 424/147.1 |

FOREIGN PATENT DOCUMENTS

| | | |
|---|---|---|
| WO | 1991/00360 | 1/1991 |
| WO | 1994/02602 | 2/1994 |
| WO | 1994/11026 | 5/1994 |
| WO | 1995/22618 | 8/1995 |
| WO | 1996/33735 | 10/1996 |
| WO | 1996/34096 | 10/1996 |
| WO | 1999/53049 | 10/1999 |
| WO | 2008/028946 | 3/2008 |
| WO | 2009/079259 | 6/2009 |
| WO | 2011/153380 | 12/2011 |
| WO | 2013/011347 | 1/2013 |
| WO | 2013/020074 | 2/2013 |
| WO | 2013/059524 | 4/2013 |

OTHER PUBLICATIONS

Yasuhara et al. (Nature Scientific Reports, 2017, p. 1-9).*
"Immunoassay", E. Diamandis and T. Christopoulus, Academic Press, Inc., San Diego, Calif., 1996.
"Conjugate Vaccines", Contributions to Microbiology and Immunology, J. M. Cruse and R. E. Lewis, Jr (eds), Carger Press, New York, (1989).
Antibodies: A Laboratory Manual, Harlow E, and Lane D, 1988, Cold Spring Harbor Laboratory Press, Cold Spring Harbor, N.Y.
Avnir et al., "Molecular Signatures of Hemagglutinin Stem-Directed Heterosubtypic Human Neutralizing Antibodies against Influenza A Viruses," PLOS Pathogens, vol. 10, No. 5, May 1, 2014, 13 pages.

(Continued)

*Primary Examiner* — Agnieszka Boesen
(74) *Attorney, Agent, or Firm* — Baker Donelson

(57) ABSTRACT

The present invention provides structural determinants important for binding to the stem domain of the HA protein of influenza virus, and methods of use thereof for production of high affinity neutralizing influenza virus antibodies based upon these determinants. The present invention further provides tools for determining the efficacy of an influenza virus vaccine. The present invention further provides a molecular signature useful for determining the efficacy of an influenza virus vaccine in a subject, or for predicting prior immunologic exposure or antigen responsiveness to vaccine or influenza virus infection.

1 Claim, 16 Drawing Sheets
Specification includes a Sequence Listing.

(56) References Cited

OTHER PUBLICATIONS

Barbas, Carlos F., et al. "Recombinant human Fab fragments neutralize human type 1 immunodeficiency virus in vitro." Proceedings of the National Academy of Sciences 89.19 (1992): 9339-9343.
Bobo, R. Hunt, et al. "Convection-enhanced delivery of macromolecules in the brain." Proceedings of the National Academy of Sciences 91.6 (1994): 2076-2080.
Bona, Constantin A., Sofia Casares, and Teodor-D Brumeanu. "Towards development of T-cell vaccines" Immunology today 19.3 (1998): 126-133.
Boyd, Scott D., et al. "Individual variation in the germline Ig gene repertoire inferred from variable region gene rearrangements." The Journal of Immunology 184.12 (2010): 6986-6992.
Brodeur et al., Monoclonal Antibody Production Techniques and Applications, Marcel Dekker, Inc, New York, (1987) pp. 51-63.
Burton, Dennis R. "Antibodies, viruses and vaccines." Nature Reviews Immunology 2.9 (2002): 706.
Carell, Thomas, et al. "A novel procedure for the synthesis of libraries containing small organic molecules." Angewandte Chemie International Edition in English 33.20 (1994): 2059-2061.
Carell, Thomas, et al. "A solution-phase screening procedure for the isolation of active compounds from a library of molecules." Angewandte Chemie International Edition in English 33.20 (1994): 2061-2064.
Caron, Philip C., et al. "Engineered humanized dimeric forms of IgG are more effective antibodies." Journal of Experimental Medicine 176.4(1992): 1191-1195.
Casadevall, Arturo. "Antibodies for defense against biological attack." Nature biotechnology 20.2 (2002): 114.
Casares, Sofia, et al. "Protective immunity elicited by vaccination with DNA encoding for a B cell and a T cell epitope of the A/PR/8/34 influenza virus." Viral immunology10.3 (1997): 129-136.
Cole, et al., 1985 In: Monoclonal Antibodies and Cancer Therapy, Alan R. Liss, Inc., pp. 77-96.
Corti, Davide, et al. "Heterosubtypic neutralizing antibodies are produced by individuals immunized with a seasonal nfluenza vaccine." The Journal of clinical investigation 120.5 (2010): 1663-1673.
Cote, Richard J., et al. "Generation of human monoclonal antibodies reactive with cellular antigens." Proceedings of the National Academy of Sciences 80.7 (1983): 2026-2030.
Cull, Millard G., Jeff F. Miller, and Peter J. Schatz. "Screening for receptor ligands using large libraries of peptides linked to the C terminus of the lac repressor." Proceedings of the National Academy of Sciences 89.5 (1992) 1865-1869.
Cwirla, Steven E., et al. "Peptides on phage: a vast library of peptides for identifying ligands." Proceedings of the National Academy of Sciences 87.16 (1990): 6378-6382.
Davidson, Beverly L., et al. "A model system for in vivo gene transfer into the central nervous system using an adenoviral vector." Nature genetics 3.3 (1993): 219.
Davies, David R., Eduardo A. Padlan, and Steven Sheriff. "Antibody-antigen complexes." Annual review of biochemistry 59.1 (1990): 439-473.
Devlin, James J., Lucy C. Panganiban, and Patricia E. Devlin. "Random peptide libraries: a source of specific protein binding molecules." Science 249 4967 (1990): 404-406.
DeWitt, S. Hobbs, et al. ""Diversomers": An approach to nonpeptide, nonoligomeric chemical diversity." Proceedings of the National Academy of Sciences 90.15 (1993): 6909-6913.
Dreyfus, Cyrille, et al. "Highly conserved protective epitopes on influenza B viruses." Science (2012): 1222908.
Ekiert, Damian C., et al. "Antibody recognition of a highly conserved influenza virus epitope." Science 324.5924 (2009) 246-251.
Eppstein, Deborah A., et al. "Biological activity of liposome-encapsulated murine interferon gamma is mediated by a cell membrane receptor." Proceedings of the National Academy of Sciences 82.11 (1985): 3688-3692.
Erb, Eric, Kim D. Janda, and Sydney Brenner. "Recursive deconvolution of combinatorial chemical libraries." Proceedings of the National Academy of Sciences 91.24 (1994): 11422-11426.
Felici, Franco, et al. "Selection of antibody ligands from a large library of oligopeptides expressed on a multivalent exposition vector." Journal of molecular biology 222.2 (1991): 301-310.
Fishwild, Dianne M., et al. "High-avidity human IgG? monoclonal antibodies from a novel strain of minilocus transgenic mice." Nature biotechnology 14.7 (1996): 845.
Gallop, Mark A., et al. "Applications of combinatorial technologies to drug discovery. 1. Background and peptide combinatorial libraries." Journal of medicinal chemistry 37.9 (1994): 1233-1251.
Garrity, Robert R., et al. "Refocusing neutralizing antibody response by targeted dampening of an immunodominant epitope." The journal of immunology 159.1 (1997): 279-289.
Geller, Alfred I., and Andrew Freese. "Infection of cultured central nervous system neurons with a defective herpes simplex virus 1 vector results in stable expression of *Escherichia coli* beta-galactosidase." Proceedings of the National Academy of Sciences 87.3 (1990): 1149-1153.
Geller, Alfred I., et al. "An HSV-1 Vector Expressing Tyrosine Hydroxylase Causes Production and Release of l-DOPA from Cultured Rat Striatal Cells." Journal of neurochemistry 64.2 (1995): 487-496.
Geller, Alfred I., et al. "Long-term increases in neurotransmitter release from neuronal cells expressing a constitutively active adenylate cyclase from a herpes simplex virus type 1 vector." Proceedings of the National Academy of Sciences 90.16 (1993): 7603-7607.
Gerioni, Mara, et al. "Immunity to Plasmodium falciparum malaria sporozoites by somatic transgene immunization." Nature biotechnology 15.9 (1997): 876.
Gerloni, Mara, et al. "Somatic transgene immunization with DNA encoding an immunoglobulin heavy chain." DNA and cell biology 16.5 (1997): 611-625.
Goding, James W. Monoclonal antibodies: principles and practice. Elsevier, 1996.
Hoogenboom, Hennie R., and Greg Winter. "By-passing immunisation: human antibodies from synthetic repertoires of germline VH gene segments rearranged in vitro" Journal of molecular biology 227.2 (1992): 381-388.
Houghten, Richard A., et al. "The use of synthetic peptide combinatorial libraries for the identification of bioactive peptides" Biotechniques 13.3 (1992): 412-421.
Hu et al., "Fully human broadly neutralizing monoclonal antibodies against influenza A viruses generated from the memory B cells of a 2009 pandemic H1 N1 influenza vaccine recipient," Virology, vol. 435, No. 2, Jan. 1, 2013 oas. 320-328.
Huse, William D., et al. "Generation of a large combinatorial library of the immunoglobulin repertoire in phage lambda." Science 246. 4935 (1989): 1275-1281.
Huston, James S., et al. "Protein engineering of antibody binding sites: recovery of specific activity in an anti-digoxin single-chain Fv analogue produced in *Escherichia coli*." Proceedings of the National Academy of Sciences 85.16 (1988): 5879-5883.
Hwang, Karl J., K. F. Luk, and Paul L. Beaumier. "Hepatic uptake and degradation of unilamellar sphingomyelin/cholesterol liposomes: a kinetic study." Proceedings of the National Academy of Sciences 77.7 (1980): 4030-4034.
Igarashi, Tatsuhiko, et al. "Human immunodeficiency virus type 1 neutralizing antibodies accelerate clearance of cell-free virions from blood plasma." Nature medicine 5.2 (1999): 211.
Ippolito, Gregory C., et al. "Antibody repertoires in humanized NOD-scid-IL2R?null mice and human B cells reveals human-like diversification and tolerance checkpoints in the mouse" PloS one 7.4 (2012): e35497.
Ivanov, Ivaylo I., et al. "Development of the expressed Ig CDR-H3 repertoire is marked by focusing of constraints in length, amino acid use, and charge that are first established in early B cell progenitors." The Journal of Immunology 174.12 (2005): 7773-7780.
Jansen, Franz K., et al. "Immunotoxins: hybrid molecules combining high specificity and potent cytotoxicity." Immunological reviews 62.1 (1982): 185-216.

(56) References Cited

OTHER PUBLICATIONS

Kaplitt, Michael G., et al. "Long-term gene expression and phenotypic correction using adeno-associated virus vectors in the mammalian brain." Nature genetics 8.2 (1994): 148.
Kashyap et al., "Combinatorial antibody libraries from survivors of the Turkish H5N1 avian influenza outbreak reveal virus neutralization strategies," PNAS, vol. 105, No. 16, Apr. 22, 2008, pp. 5986-5991.
You, Zhaoyang, et al. "Targeting dendritic cells to enhance DNA vaccine potency." Cancer research 61.9 (2001): 3704-3711.
Zaghouani, Habib, et al. "Induction of antibodies to the human immunodeficiency virus type 1 by immunization of baboons with immunoglobulin molecules carrying the principal neutralizing determinant of the envelope protein." Proceedings of the National Academy of Sciences 92.2 (1995): 631-635.
Zanetti, Maurizio. "Antigenized antibodies." Nature 355.6359 (1992): 476-477.
Zebedee, Suzanne L., et al. "Human combinatorial antibody libraries to hepatitis B surface antigen." Proceedings of the National Academy of Sciences 89.8 (1992): 3175-3179.
Zuckermann, Ronald N., et al. "Discovery of nanomolar ligands for 7-transmembrane G-protein-coupled receptors from a diverse N-(substituted) glycine peptoid library." Journal of medicinal chemistry 37.17 (1994): 2678-2685.
Keller, Margaret A., and E. Richard Stiehm. "Passive immunity in prevention and treatment of infectious diseases." Clinical microbiology reviews 13.4 (2000): 602-614.
Killen, J. A., and J. M. Lindstrom. "Specific killing of lymphocytes that cause experimental autoimmune myasthenia gravis by ricin toxin-acetylcholine receptor conjugates" The Journal of Immunology 133.5 (1984): 2549-2553.
Köhler, Georges, and Cesar Milstein. "Continuous cultures of fused cells secreting antibody of predefined specificity." Nature 256.5517 (1975): 495.
Kozbor, Danuta, and John C. Roder. "The production of monoclonal antibodies from human lymphocytes." Immunology Today 4.3 (1983): 72-79.
Kozbor, Danuta, et al. "A human hybrid myeloma for production of human monoclonal antibodies." The Journal of Immunology 133.6 (1984): 3001-3005.
Kwong, Peter D., and Ian A. Wilson. "HIV-1 and influenza antibodies: seeing antigens in new ways." Nature Immunology 10.6 (2009): 573.
La Salle, G. Le Gal, et al. "An adenovirus vector for gene transfer into neurons and glia in the brain." Science 259.5097 (1993): 988-990.
Lam, Kit S. "Mini-review. Application of combinatorial library methods in cancer research and drug discovery." Anti-cancer drug design 12.3 (1997): 145-167.
Lam, Kit S., et al. "A new type of synthetic peptide library for identifying ligand-binding activity." Nature 354.6348 (1991): 82.
Lanza, Paola, et al. "Active immunity against the CD4 receptor by using an antibody antigenized with residues 41-55 of the first extracellular domain." Proceedings of the National Academy of Sciences 90.24 (1993): 11683-11687.
Laursen et al., "Broadly neutralizing antibodies against influenza viruses," Antiviral Research, vol. 98, No. 3, Apr. 9, 2013, pp. 476-483.
Li, Gui-Mei, et al. "Pandemic H1N1 influenza vaccine induces a recall response in humans that favors broadly cross-reactive memory B cells." Proceedings of the National Academy of Sciences 109.23 (2012): 9047-9052.
Lim, F., et al., in DNA Cloning: Mammalian Systems, D. Glover, Ed. (Oxford Univ. Press, Oxford England) (1995).
Lonberg, Nils, and Dennis Huszar. "Human antibodies from transgenic mice." International reviews of immunology 13.1 (1995): 65-93.
Lonberg, Nils, et al. "Antigen-specific human antibodies from mice comprising four distinct genetic modifications." Nature 368.6474 (1994): 856.

Lunde, E., et al. "Troybodies and pepbodies." (2002): 500-506.
Malmqvist, Magnus. "Biospecific interaction analysis using biosensor technology." Nature 361.6408 (1993): 186-187.
Marasco, Wayne A., William A. Haseltine, and SiYi Chen. "Design, intracellular expression, and activity of a human anti-human immunodeficiency virus type 1 gp120 single-chain antibody." Proceedings of the National Academy of Sciences 90.16 (1993): 7889-7893.
Marks et al., Bio/Technology 10, 779-783 (1992).
Marks, James D., et al. "By-passing immunization: human antibodies from V-gene libraries displayed on phage." Journal of molecular biology 222.3 (1991): 581-597.
Martin, Francis J., and Demetrios Papahadjopoulos. "Irreversible coupling of immunoglobulin fragments to preformed vesicles. An improved method for liposome targeting " Journal of Biological Chemistry 257.1 (1982): 286-288.
Matthews, Leslie J., Robert Davis, and George P. Smith. "Immunogenically fit subunit vaccine components via epitope discovery from natural peptide libraries." The Journal of Immunology 169.2 (2002): 837-846.
Meireles, Lidio MC, Alexander S. Die, %mling, and Cados J. Camacho. "ANCHOR: a web serverand database for analysis of protein-protein interaction binding pockets for drug discovery." Nucleic acids research 38.suppl 2 (2010) W407-W411.
Miller, Matthew S., et al. "1976 and 2009 H1N1 influenza virus vaccines boost anti-hemagglutinin stalk antibodies in humans." The Journal of infectious diseases 207.1 (2012): 98-105.
Morrison, Paul F., et al. "High-flow microinfusion: tissue penetration and pharmacodynamics." American Journal of Physiology-Regulatory, Integrative and Comparative Physiology 266.1 (1994): R292-R305.
Morrison, Sherie L. "Immunology-Success in Specification." Nature 368.6474 (1994): 812-813.
Munson, Peter J., and David Rodbard. "Ligand: a versatile computerized approach for characterization of ligand-binding systems." Analytical biochemistry 107.1 (1980): 220-239.
Nakaya et al., "Systems biology of vaccination for seasonal influenza in humans," Nature Immunol. vol. 12, No. 8, Jul. 10, 2011, pp. 786-795.
Neuberger, Michael. "Generating high-avidity human Mabs in mice." Nature biotechnology 14.7 (1996): 826.
Parren, Paul WHI, and Dennis R. Burton. "The antiviral activity of antibodies in vitro and in vivo." (2001): 195-262.
Pica, Natalie, et al. "Hemagglutinin stalk antibodies elicited by the 2009 pandemic influenza virus as a mechanism for the extinction of seasonal H1N1 viruses." Proceedings of the National Academy of Sciences 109.7 (2012): 2573-2578.
Potter, K. N., et al. "Molecular characterization of the VH1-specific variable region determinants recognized by anti-idiotypic monoclonal antibodies G6 and G8." Scandinavian journal of immunology 50 (1999): 14-20.
Ramakrishnan, S., and L. L. Houston. "Comparison of the selective cytotoxic effects of immunotoxins containing ricin A chain or pokeweed antiviral protein and anti-Thy 1.1 monoclonal antibodies." Cancer research 44.1 (1984): 201-208.
Remington: The Science And Practice Of Pharmacy 19th ed. (Alfonso R. Gennaro, et al., editors) Mack Pub. Co., Easton, Pa., 1995.
Sasso, Eric H., Todd Johnson, and Thomas J. Kipps. "Expression of the immunoglobulin VH gene 51 p1 is proportional to its germline gene copy number." The Journal of clinical investigation 97.9 (1996): 2074-2080.
Scott, Jamie K., and George P. Smith. "Searching for peptide ligands with an epitope library." Science 249.4967 (1990): 386-390.
Shibata, Riri, et al. "Neutralizing antibody directed against the HIV-1 envelope glycoprotein can completely block HIV-1/SIV chimeric virus infections of macaque monkeys." Nature medicine 5.2 (1999): 204.
Shopes, Bob. "A genetically engineered human IgG mutant with enhanced cytolytic activity." The Journal of Immunology 148.9 (1992): 2918-2922.
Stevenson, G. T., A. Pindar, and C. J. Slade. "A chimeric antibody with dual Fc regions (bisFabFc) prepared by manipulations at the IgG hinge" Anti-cancer drug design 3.4 (1989): 219-230.

(56) References Cited

OTHER PUBLICATIONS

Steward, M. W., C. M. Stanley, and O. E. Obeid. "A mimotope from a solid-phase peptide library induces a measles virus-neutralizing and protective antibody response." Journal of virology 69.12 (1995): 7668-7673.

Sui et al., "Structural and functional bases for broad-spectrum neutralization of avian and human influenza A viruses," Nature Structural and Molecular Biology, vol. 16, No. 3, Mar. 1, 2009, pp. 265-273.

Sui, Jianhua, et al. "Wide prevalence of heterosubtypic broadly neutralizing human anti-influenza A antibodies." Clinical Infectious Diseases 52.8 (2011): 1003-1009.

Thomson, Christy Ann, et al. "Pandemic H1N1 influenza infection and vaccination in humans induces cross-protective antibodies that target the hemagglutinin stem." Frontiers in immunology 3 (2012): 87.

Throsby et al., "Heterosubtypic neutralizing monoclonal antibodies cross-protective against H5N1 and H1 N1 recovered from human lgM+ memory B cells," PLOS One, vol. 3, No. 12, Jan. 1, 2008, 15 pages.

Throsby, Mark, et al. "Heterosubtypic neutralizing monoclonal antibodies cross-protective against H5N1 and H1N1 recovered from human lgM+ memory B cells." PloS one 3.12 (2008): e3942.

Vitetta, Ellen S., et al. "Redesigning nature's poisons to create anti-tumor reagents." Science 238.4830 (1987) 1098-1104.

Whittle, James RR, et al. "Broadly neutralizing human antibody that recognizes the receptor-binding pocket of influenza virus hemagglutinin." Proceedings of the National Academy of Sciences 108.34 (2011): 14216-14221.

Wilkinson, The Scientist, Philadelphia, PA., vol. 14, No. 8 (Apr. 17, 2000), pp. 25-28.

Wrammert, Jens, et al. "Broadly cross-reactive antibodies dominate the human B cell response against 2009 pandemic H1N1 influenza virus infection." Journal of Experimental Medicine (2011): jem-20101352.

Yang, Yiping, et al. "Cellular and humoral immune responses to viral antigens create barriers to lung-directed gene therapy with recombinant adenoviruses." Journal of virology 69.4 (1995): 2004-2015.

\* cited by examiner

|  | FR1 | CDR-H1 | FR2 | CDR-H2 | FR3 | CDR-H4 | CDR-H3 |
|---|---|---|---|---|---|---|---|
|  |  |  |  | 52a |  | 74 | 98 |
|  | 24 26 | 33 34 | 52 54 | 57 58 | 73 76 92 | 97 99 | 101 |

```
IGHV1-69*01    A-GGTFSSYA-I-IIP##GTA-N-ESTS-CAR
F10 (1)        S-E#TFSSFA-I-I#P##GTP-N-#STR-CARSPS##ICSGGTCVF----DHW
CR6343 (2)     A-G#TFSYYA-M-I#P##GTT-T-DSTS-CARSSN##DSV#--------DYW
CR6262 (2)     V-G##FSGSA-I-I#P##GTT-N-#STN-CARGPK##SE#M--------DVW
CR9114 (5)     S-GGT#NNYA-I-I#P##GST-A-I##N-CARHGN######SGM-----DVW
A66 (1)        A-GG#FSMTA-F-I#P##RTP-#-ESTN-CARTLSS#QPNNDAF-----AIW
FE43 (6)       A-GG#FSGFA-I-I###GTA-T-##TS-CARSGG#LPQNNWI-------DPW
CR6332 (2)     A-GG#FRNFA-I-II###GTT-#-DSTN-CARGPH##SS#M--------DVW
CR6329 (2)     A-GG#FRSNS-I-IF###GTT-D-ESST-CARGSG#TTRN#F-------DYW
CR6344 (2)     A-GS#FRNYA-M-II###GTP-#-ESTS-CARIPH#NFGSGS#F-----DYW
70-1F02 (7)    A-GG#FRSNA-I-II###GTA-N-ESTS-CARGP###GNSHL-------DFW
FC41 (6)       A-GG#FSPYA-I-II###GTT-N-KSTT-CARGGR##VD#F--------DYW
70-5B03 (7)    A-GGTF#NFA-#-TI###GTA-#-FSTR-CASSSGS##GD#F-------DYW
CR6327 (2)     A-GGTF#THA-I-I###GTA-N-ESTS-CARGSG#HISTPF--------DNW
CR6331 (2)     A-GGTFSSYA-I-II###GTA-N-E#TS-CARGN###ESSL--------DYW
kashyap#1 (4)* T-GGTFSSYA-#-II###GTT-N-E#TS-CARGS###ETTL--------DYW
D8 (1)         A-GGTFSAYA-F-IT###GTA-N-E#TS-CARGL###ESSL--------DYW
CR6323 (2)     A-GGTFSSYG-I-II###GST-N-ESTS-CARSSG###PA#L-------PHW
V3-2G6 (8)     T-GGTFSSFA-F-II###GTT-S-ESTS-CARGKK###HDTL-------DYW
CR6334 (8)     S-GS#FRSNA-#-II###GSP-S-ESTN-CARGPT###SS#M-------DVW
G17 (1)        T-G#TFSSYA-I-II###GVP-#-KPTS-CAREPG##VGKNGF------DVW
V3-3D2 (8)     A-G#EFNAYA-M-IT###HTA-T-ESTS-CARGPK##HS#M--------DVW
CR6261 (2)     A-GG#FRSYA-I-IIP##GTT-#-D#AG-CAKHMG#QVRETM-------DVW
D7 (1)         A-GG#FNTNA-F-VIP##RTA-S-ESTN-CARSSG#HFRSHF-------DSW
I4-128 (8)     A-GGTFSTYG-#-IIP##ETA-#-ESST-CARPNT#G#ILP--------VYW
V3-2C3 (8)     A-GGTFNNYA-#-IIP##GTA-N-ESTS-CARVCSF#GSGS##NVF---CYW
FC6 (6)        A-GGTFNSHA-I-IIP##GTN-N-##PT-CARGQR##DRDGM-------DVW
I8-1B6 (8)     T-GG#FSNFA-#-ILS##RTT-N-ESTS-CARSITNL####M-------DVW
FB79 (6)       A-GG#FISQA-I-IIP##GAT-N-KSTN-CARLGGSS#HNGPNWF----DPW
FE53 (6)       A-G#T#SNYP-I-VLP##GVT-N-KSTN-CARGKRPG#CSGGVCSS---DYW
V3-1G10 (8)    A-G#TFNHYT-#-II P##GTA-D-RSTG-CARSGTTKTR#NWF----DPW
FB54 (6)       A-G#TFSMYT-I-IIP##GTA-N-TSTN-CARAGTTLTR FNWF-----DPW
FB139 (6)      S-G#TFSMYA-#-IIP##GTT-T-TSTN-CARAGTTVTRFNWF-----DPW
1009-3E06 (7)  A-GMT#NSLA-I-IIP##ETP-#-KSTN-CATSAGGIVN#SLSF-----NIW
1009-3B05 (7)  T-GGT#NNYP-I-SIP##NTP-#-TSTS-CATSAGGIVN#FLLF-----DIW
09-2A06 (9)    A-GGSFTSFV-I-VIP##ATP-#-KSTN-CASPDLTMVFVPHTGPL---DFW
CR6342 (2)     A-GG#FSSYA-I-VIP##RTA-N-E#TS-CARLN##HDSGT##NAPRGWFDPW
CR6325 (2)     A-GGTFSFYS-M-IIP#GTT-N-ESTS-CARGDKGI#####M-------DVW
I5-24 (8)      A-GGTFSRYT-#-FIP##GMT-N-KSTT-CARHDSSG#HPL--------DYW
```

*-The kashyap#1 Ab is a representative of 61 clonally related Abs.

B

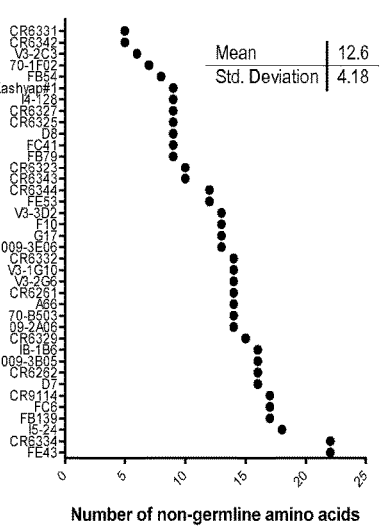

| | |
|---|---|
| Mean | 12.6 |
| Std. Deviation | 4.18 |

Number of non-germline amino acids

C

| AA substitution | IGHV1-69- Ab dataset (n =287) (%) | HV1-69- sBnAb dataset (n =37) (%) | $P^a$ |
|---|---|---|---|
| FR1 | | | |
| A24S | 0.4% | 11% | 0.0047 |
| CDR-H1 | | | |
| G27V | 0.7% | 24% | <0.0001 |
| T28I | 1.7% | 24% | <0.0001 |
| T28P | 1.1% | 14% | 0.0065 |
| F29S | 0.4% | 11% | 0.004 |
| S30R | 4.2% | 22% | 0.0057 |
| FR2 | | | |
| I34V | 6.3% | 22% | 0.0185 |
| CDR-H2 | | | |
| I52S | 0.4% | 16% | 0.0001 |
| P52aG | 0.7% | 22% | <0.0001 |
| P52aA | 1.1% | 22% | <0.0001 |
| FR3 | | | |
| N58K | 7.7% | 27% | 0.0153 |
| CDR-H4 | | | |
| E73Q | 0.4% | 11% | 0.0067 |
| S74F | 1.7% | 14% | 0.0222 | a – p-values obtained by Fisher's exact test with Bonferroni adjustment

D

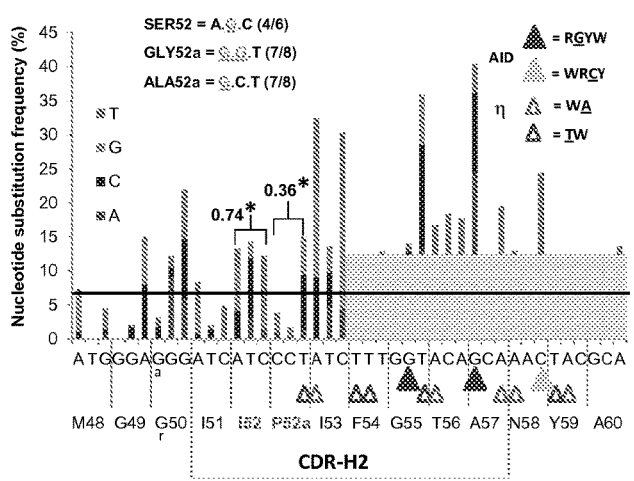

Figure 6.

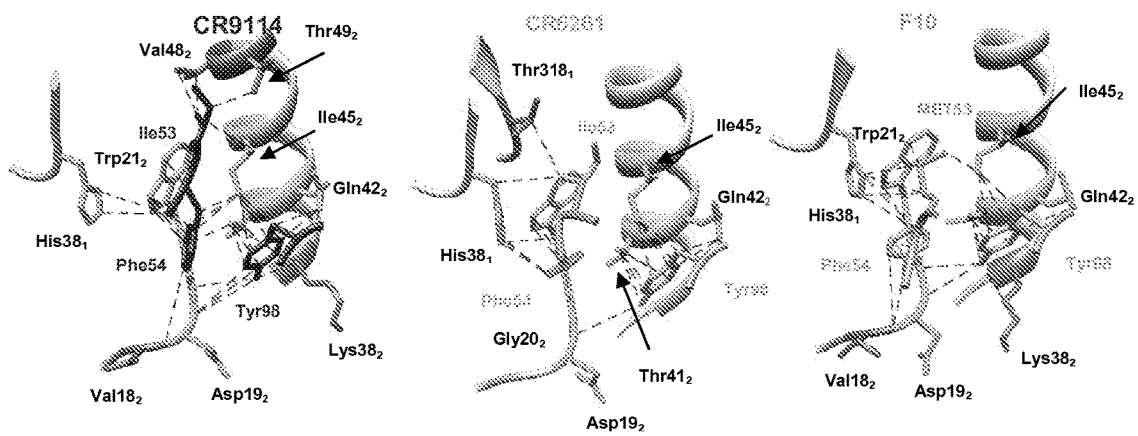

†From the respective PDB files of F10 (3fku), CR6261 (3gbm), and CR9114 (4fqi) the HA complex composed of chain A and chain B was chosen, along with the corresponding heavy chain. ‡ In the solved structure of CR9114 HIS38 and LYS38 are characterized by two side chain rotamers (1/1 ratio). Rotamer A was chosen for VDW contact analysis and presentation purposes. * HA-fp = HA2 fusion peptide domain, HA2-αA = HA2 α-helix domain A.

| CR9114‡ | | | |
|---|---|---|---|
| Ab residue† | HA- residue | HA domain* | # of VDW contacts |
| ILE53 | Ile45 | HA2-αA | 1 |
| | Val48 | HA2-αA | 2 |
| | Thr49 | HA2-αA | 1 |
| PHE54 | Val18 | HA2-fp | 1 |
| | Gly20 | HA2-fp | 4 |
| | Trp21 | HA2-fp | 7 |
| | His38 | HA1 | 2 |
| TYR98 | Asp19 | HA2-fp | 3 |
| | Gly20 | HA2-fp | 1 |
| | Lys38 | HA2-αA | 3 |
| | Thr41 | HA2-αA | 5 |
| | Gln42 | HA2-αA | 3 |
| | Ile45 | HA2-αA | 4 |

| CR6261 | | | |
|---|---|---|---|
| Ab residue† | HA- residue | HA domain* | # of VDW contacts |
| ILE53 | Trp21 | HA2-fp | 2 |
| | Thr318 | HA1 | 1 |
| | His38 | HA1 | 1 |
| PHE54 | Gly20 | HA2-fp | 2 |
| | Trp21 | HA2-fp | 2 |
| | His 38 | HA1 | 4 |
| TYR98 | Asp19 | HA2-fp | 1 |
| | Thr41 | HA2-αA | 5 |
| | Gln42 | HA2-αA | 3 |
| | Ile45 | HA2-αA | 4 |

| F10 | | | |
|---|---|---|---|
| Ab residue† | HA- residue | HA domain* | # of VDW contacts |
| MET53 | Trp21 | HA2-fp | 1 |
| | His38 | HA1 | 5 |
| | Ile45 | HA2-αA | 1 |
| PHE54 | Val18 | HA2-fp | 3 |
| | Gly20 | HA2-fp | 5 |
| | Trp21 | HA2-fp | 2 |
| TYR98 | Asp19 | HA2-fp | 1 |
| | Gly20 | HA2-fp | 1 |
| | Lys38 | HA2-αA | 1 |
| | Thr41 | HA2-αA | 4 |
| | Gln42 | HA2-αA | 2 |
| | Ile45 | HA2-αA | 3 |

A

Ranking according to f1/f0 (light purple)

| AA substitution | f0 | f1 | f1/f0 | Ranking |
|---|---|---|---|---|
| I34V | 6.3 | 21.6 | 3.4 | 13 |
| N58K | 7.7 | 27.0 | 3.5 | 12 |
| S30R | 4.2 | 21.6 | 5.2 | 11 |
| S74F | 1.7 | 13.5 | 7.8 | 10 |
| T28P | 1.1 | 13.5 | 12.9 | 9 |
| T28I | 1.7 | 24.3 | 14.0 | 8 |
| P52aA | 1.1 | 21.6 | 20.6 | 7 |
| A24S | 0.4 | 10.8 | 30.9 | 6 |
| F29S | 0.4 | 10.8 | 30.9 | 5 |
| E73Q | 0.4 | 10.8 | 30.9 | 4 |
| P52aG | 0.7 | 21.6 | 30.9 | 3 |
| G27V | 0.7 | 24.3 | 34.7 | 2 |
| I52S | 0.4 | 16.2 | 46.3 | 1 |

B

Ranking according to f1-f0 (maroon)

| AA substitution | f0 | f1 | f1-f0 | Ranking |
|---|---|---|---|---|
| A24S | 0.4 | 10.8 | 10.5 | 13 |
| F29S | 0.4 | 10.8 | 10.5 | 12 |
| E73Q | 0.4 | 10.8 | 10.5 | 11 |
| S74F | 1.7 | 13.5 | 11.8 | 10 |
| T28P | 1.1 | 13.5 | 12.5 | 9 |
| I34V | 6.3 | 21.6 | 15.4 | 8 |
| I52S | 0.4 | 16.2 | 15.9 | 7 |
| S30R | 4.2 | 21.6 | 17.4 | 6 |
| N58K | 7.7 | 27.0 | 19.4 | 5 |
| P52aA | 1.1 | 21.6 | 20.6 | 4 |
| P52aG | 0.7 | 21.6 | 20.9 | 3 |
| T28I | 1.7 | 24.3 | 22.6 | 2 |
| G27V | 0.7 | 24.3 | 23.6 | 1 |

C

A

|   | CDR-H1 | | | CDR-H2 | | | | CDR-H4 | | | | J | |
|---|---|---|---|---|---|---|---|---|---|---|---|---|---|
|   | Gly27 | Thr28 | Ser30 | Ile52 | Pro52a | Ile53 | Phe54 | Glu73 | Ser74 | Ser76 | Ala78 | PheF100 | Val102 |
| A |   |   |   | 1.4% | 10.0% |   |   |   | 2.3% |   | 81.68% |   |   |
| C |   |   |   |   |   |   |   |   |   |   |   |   |   |
| D |   |   |   |   |   |   |   | 2.3% |   |   |   |   |   |
| E |   |   |   |   |   |   |   | 60.5% |   |   |   |   |   |
| F |   |   |   |   |   | 4.6% | 95.0% |   | 5.0% |   |   | 70.0% |   |
| G | 90.0% |   |   |   | 10.0% |   |   |   |   | 2.5% |   |   |   |
| H |   |   |   |   |   |   |   |   |   |   |   |   |   |
| I |   | 10.0% |   | 71.1% |   | 53.3% |   |   |   |   |   |   |   |
| K |   |   |   |   |   |   |   | 27.8% |   |   |   |   |   |
| L |   |   |   | 1.4% |   | 8.15% | 5.0% |   |   |   |   |   | 13.3% |
| M |   |   |   | 1.4% |   | 10.6% |   |   |   |   |   | 15.0% |   |
| N |   |   |   | 1.4% |   | 8.2% |   |   |   | 11.0% |   |   |   |
| P |   | 10.0% |   |   | 71.6% |   |   |   |   |   |   |   |   |
| Q |   |   |   |   |   |   |   | 5.0% |   |   |   |   | 13.3% |
| R |   |   | 10.0% |   |   |   |   | 2.3% |   | 5.4% |   |   |   |
| S |   |   | 90.0% | 10.0% | 1.1% | 2.3% |   |   | 92.7% | 75.7% | 1.8% |   |   |
| T |   | 80.0% |   | 8.4% | 7.2% | 2.3% |   | 2.3% |   | 5.4% | 1.8% |   |   |
| V | 10.0% |   |   | 4.8% |   | 10.6% |   |   |   |   | 14.7% |   | 60.0% |
| W |   |   |   |   |   |   |   |   |   |   |   |   |   |
| Y |   |   |   |   |   |   |   |   |   |   |   | 15.0% | 13.3% |

Values are rounded to the nearest tenth.

Anti-H5VN04 phage-Abs

```
           CDR-H1         CDR-H2      CDR-H4              CDR-H3                Heterosubtypic
  KABAT   26        33  51 52a 54  57 73       78 92                       101   binding activity
  IGHV1-69*01 GG TF SSYA- I IP IFG TA- ES TS TA- CAR
  11B5       GV TF RSYA- IS AM FG TA- KS TN TA- CARGRGXDPSVGG-----FDVW ⎫
  11A11      GG TF SSYA- I IP IFG TA- ES TN TA- CARGEEAX----------YDLW │
⊛ 9H3        GG IF SSYA- IS P IFG TA- ES TN TA- CARSGGXXDYGVG-----YDQW │
  8A1        GG PF SSYA- IS PLFG TA- ES TS TA- CARAPTXXASRDSYN---FDYW │
⊛ 5B9        GV TF SSYA- IS PM FG TA- ES TN TA- CARGRGXAPDALTN----FDVW ⎬ H1CA0409/H2SIN57
⊛ 5A8        GG TF SSYA- IS P IFG TA- ES TS TV- CARGPGXHPAGASGQF--FDLW │
  5A6        GG TF SSYA- IS P IFG TA- QS TS TA- CARGGGVGRIWIAGYG--FDQW │
  2C4        GG TF SSYA- IS P IFG TA- KS TS TV- CARGARXXAGGY------FDVW │
  9A1        GG TF SSYA- IS P IFG TA- KS TS TA- CARGRYXXTVGV------YDVW ⎭
  11F8       GV TF SSYA- IS PM FG TA- QS TN TA- CARGGTXSPGGTY-----FDVW ⎫
  9C1        GV TF SSYA- IS P IFG TA- KS TS TV- CARGGGXSADGGAGNNTIFDVW │
  8D6        GG TF SSYA- IS PLFG TA- ES TN TA- CARASGXFTGWGT-----FDYW │
⊛ 6F3        GG PF SSYA- IS PM FG TA- ES TS TV- CARGYSXXPGGGGGRN--FDYW │
  6C2        GV TF SSYA- IS PLFG TA- KS TS TA- CARGDAXXVGGGARP---FDLW │
  6A2        GV TF SSYA- I TPM FG TA- KS TS TV- CARGRGXIAVAGD-----MDVW ⎬ H1CA0409
  4G5        GG PF SSYA- IS G IFG TA- ES TS TA- CARGDRFXVGER------FDVW │
⊛ 4F5        GV TF RSYA- IS G IFG TA- ES TS TA- CARSPAXXFGPN------MDVW │
⊛ 4C4        GG TF SSYA- IS PM FG TA- KS TS TA- CAREGGXSPGGVD-----FDYW │
  4E5        GV TF SSYA- IS P IFG TA- ES TN TV- CARGTTXSTARY------FDVW ⎭
  2D3        GV TF SSYA- IS P IFG TA- QS TN TV- CARDSGNXDGYGPGSR--FDVW ⎫ H2SIN57
  9D11       GV TF SSYA- IS PLFG TA- ES TS TA- CARERGXTVGGGG-----MDVW ⎭
  11E9       GG TF SSYA- I TPM FG TA- KS TS TT- CARGPGXXPDSNN-----YDLW ⎫
  11C6       GG TF SSYA- I IP IFG TA- DS TS TA- CARDSTPSVTSSLYRIPAFDVW │
  11A6       GG TF SSYA- I TPM FG TA- KS TS TA- CARGTSXLPGRSG-----FDVW │
  10D4       GG TF SSYA- IS P IFG TA- RS TS TA- CARGPGXXDPSSLRG---FDVW │
  9H4        GG TF SSYA- I TPIFG TA- ES TS TA- CARSGGXSPSIGG-----FDVW │
  9E7        GG TF SSYA- IS PM FG TA- KS TS TA- CARESGXSGTGQ------FDVW │
  9E4        GV TF SSYA- IS P IFG TA- KS TN TV- CAREYLGDDYSSGSY---FDVW │
  8C1        GV TF SSYA- IS PM FG TA- KS TN TA- CARDTTXIAGGH------FDVW ⎬ H5VN04 alone
  4G3        GG TF SSYA- IS PM FG TA- KS TS TA- CARSSRXAPSDSTN----FDQW │
  2H5        GG TF SSYA- IS P IFG TA- TS TS TA- CARSRRXWADGG------FDYW │
  2H4        GG TF SSYA- IS P IFG TA- KS TS TA- CARELGXLAGSPSPG---FDYW │
  2E1        GV TF SSYA- IS PLFG TA- KS TS TV- CARSRTXADGRT------FDVW │
  2D9        GV TF SSYA- IM PM FG TA- KS TS TA- CARERGSWSFGY------FDVW │
  2B8        GG IF SSYA- IS P IFG TA- KS TN TA- CARGRGAXMGPS------MDVW │
  1C2        GG PF SSYA- IS PM FG TA- KS TS TA- CARDDGXAPSGGLRE---FDVW ⎭
```

Figure 16B.

| | Library design scheme | Anti-H5VN04 phage-Abs | Ratio | P[a] |
|---|---|---|---|---|
| HV1-69-sBnAb distinctive amino acid substitutions* | | | | |
| CDR-H1 | | | | |
| G27V | 10% | 39% | 3.9 | 0.0005 |
| CDR-H2 | | | | |
| Ser52 | 10% | 81% | 8.1 | 0.0035 |
| Non-HV1-69-sBnAb distinctive amino acid substitutions | | | | |
| CDR-H2 | | | | |
| I53M | 11% | 36% | 3.4 | 0.007 |
| CDR-H4 | | | | |
| S76N | 11% | 31% | 2.8 | 0.004 |
| CDR-H3 | | | | |
| G97 | 19% | 53% | 2.8 | 0.01 |
| Y98 | 11% | 78% | 7.1 | 0.01 |
| Y99 | 12% | 33% | 2.7 | 0.03 |
| P100 | 4% | 34% | 8.1 | 0.01 |
| G100B | 13% | 43% | 3.3 | 0.01 | a - P-values were obtained by Monte-Carlo simulations.
*- See Figure 2B.

Figure 16C.

| | Library deign scheme | Heterosubtypic subset CDR-H3 (n = 16) | Non-heterosubtypic subset CDR-H3 (n = 8) |
|---|---|---|---|
| Y98 | 11% | 100% (16) * | 100% (8) * |
| Y99 | 12% | 44%*(7)* | 0% |
| P100 | 4% | 38%* (6)* | 38%(3) † |
| G100B | 13% | 63%*(10)* | 50% (4) † |

*- Significant change from the library design scheme. P < 0.05 as determined by Monte-Carlo simulations.
† Non-significant change from the library design scheme.

Figure 16D.

Anti-H1CA0409 phage-Abs

```
                 CDR-H1           CDR-H2         CDR-H4              CDR-H3              Heterosubtypic
      KABAT     26         33  51 52a 54   57  73         78  92                      101  binding activity
   IGHV1-69*01 G G T F S S Y A - I I P I F G T A - E S T S T A - C A R
●  9H3         G G I F S S Y A - I S P I F G T A - E S T N T A - C A R S G G Y Y D Y G V G - - - - - Y D Q W  ┐
●  5B9         G V T F S S Y A - I S P M F G T A - E S T N T A - C A R G R G Y A P D A L T N - - - - F D V W  │
●  5A8         G G T F S S Y A - I S P I F G T A - E S T S T V - C A R G P G Y H P A G A S G Q F - - F D L W  │
   2E12        G V T F S S Y A - I S P M F G T A - E S T N T A - C A R G G Y Y P A G V G R - - - - Y D V W    │
   1H2         G G P F R S Y A - I I P I F G T A - E S T S T A - C A R G G V Y S - - - - - - - - - - F D V W  ├ H5VN04/H2SIN57
   1F5         G G T F S S Y A - I S P I F G T A - E S T S T A - C A R D Q G G T R G N Y - - - - - - F D V W  │
   1F3         G V I F S S Y A - I S P I F G T A - E S T S T A - C A R S R G Y A P G T S F H - - - - Y D V W  │
   1F1         G G T F S S Y A - I S A I F G T A - E S T R T A - C A R G S G Y Y V A A S G A - - - - F D V W  │
   1E6         G V T F S S Y A - I S P I F G T A - E S T S T A - C A R G R E Y Y A S N G D S - - - - F D V W  ┘
●  6F3         G G P F S S Y A - I S P M F G T A - E S T S T V - C A R G Y S Y Y P G G G G G R N - - F D Y W  ┐
●  4F5         G V T F R S Y A - I S G I F G T A - E S T S T A - C A R S P A Y Y F G P N - - - - - - M D V W  │
●  4C4         G G T F S S Y A - I S P M F G T A - K S T S T A - C A R E G G Y S P G G V D - - - - - F D Y W  │
   2G4         G G T F S S Y A - I S P M F G T A - E S T S T V - C A R S R G Y N V A A S F G - - - - F D V W  │
   2E1         G G I F R S Y A - I I P M F G T A - E S T T T V - C A R G A G S T - - - - - - - - - - F D V W  │
   2B6         G G P F S S Y A - I S P I F G T A - K S T N T A - C A R G R S Y I V S V S P G - - - - F D V W  ├ H5VN04
●  2A12        G G T F S S Y A - I V P L F G T A - E S T S T A - C A R G L G L Y - - - - - - - - - - F D V W  │
   2A11        G V T F S S Y A - I S P V F G T A - D S T N T A - C A R S R G Y T V S S L A G R Y - - F D Q W  │
   2A1         G V I F S S Y A - I I P I F G T A - K S T S T A - C A R G G S G S - - - - - - - - - - F D V W  │
   1H8         G V T F S S Y A - I S P M F G T A - E S T N T V - C A R G R A Y L S V R G S - - - - - F D V W  │
   1H4         G V P F S S Y A - I S P L F G T A - Q S T S T V - C A R G L G T Y Y S P S L Y P R G - - M D V W ┘
   2F1         G G T F S S Y A - I T P L F G T A - D S T S T A - C A R G P T L Y S P P V - - - - - - F D V W  ┤ H2SIN57
   2H4         G V T F S S Y A - I T P I F G T A - Q S T S T A - C A R G G G V - - - - - - - - - - - F D V W  ┐
   2H3         G G P F S S Y A - I I P I F G T A - E S T S T A - C A R G T D Y S G Y R G - - - - - - F D V W  │
   2G3         G G T F R S Y A - I M P I F G T A - E S T T T V - C A R G A G V S A G P S W P - - - - F D V W  │
   2E11        G G T F S S Y A - I N P I F G T A - E S T S T A - C A R G E S A Y Y S R N - - - - - - Y D V W  │
   2C1         G G I F S S Y A - I S A I F G T A - E S T S T A - C A R D S G I A S G Y T A Y - - - - M D Y W  ├ H1CA0409 alone
   1F12        G G I F S S Y A - I T P I F G T A - E S T R T A - C A R D L S R D S L N L P G S S P G Y D L W  │
   1F6         G G T F S S Y A - I I T I F G T A - E S T S T A - C A R G G G G R - - - - - - - - - - F D V W  │
   1D9         G G T F S S Y A - I I T I F G T A - K S T S T A - C A R G A T G F - - - - - - - - - - Y D V W  │
●  2B11        G G T F S S Y A - I I P I F G T A - E S T N T A - C A R V R G G Y G P Y G D - - - - - F D V W  ┘
```

Figure 16E.

| | Library design scheme | Anti-H1CA0409 phage-Abs | Ratio | $P^a$ |
|---|---|---|---|---|
| HV1-69-sBnAb distinctive amino acid substitutions* | | | | |
| CDR-H1 | | | | |
| G27V | 10% | 33% | 3.3 | 0.002 |
| CDR-H2 | | | | |
| Ser52 | 10% | 57% | 5.7 | 0.0035 |
| Non-HV1-69-sBnAb distinctive amino acid substitutions | | | | |
| CDR-H4 | | | | |
| S76N | 11% | 30% | 2.7 | 0.014 |
| CDR-H3 | | | | |
| G97 | 19% | 60% | 3.1 | 0.01 |
| Y98 | 11% | 53% | 4.9 | 0.01 | a - P-values were obtained by Monte-Carlo simulations.
*- See Figure 2B.

_US 11,104,722 B2_

SEQUENCE LISTING

<160> NUMBER OF SEQ ID NOS: 1277

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Pro Phe Ser Ser Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Ile Phe Ser Ser Tyr Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Thr Phe Ser Ser Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Val Thr Phe Ser Ser Tyr Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Val Thr Phe Ser Ser Tyr Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic

```
                      peptide

<400> SEQUENCE: 6

Gly Val Thr Phe Ser Ser Tyr Ala
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Thr Phe Ser Ser Tyr Ala
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Thr Phe Ser Ser Tyr Ala
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Thr Phe Ser Ser Tyr Ala
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Val Thr Phe Ser Ser Tyr Ala
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Val Thr Phe Arg Ser Tyr Ala
1               5

<210> SEQ ID NO 12
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Thr Phe Ser Ser Tyr Ala
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Pro Phe Ser Ser Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Thr Phe Ser Ser Tyr Ala
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Thr Phe Ser Ser Tyr Ala
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Val Thr Phe Ser Ser Tyr Ala
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17
```

```
Gly Val Thr Phe Ser Ser Tyr Ala
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Val Thr Phe Ser Ser Tyr Ala
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Pro Phe Ser Ser Tyr Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Pro Phe Ser Ser Tyr Ala
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Val Thr Phe Ser Ser Tyr Ala
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Thr Phe Ser Ser Tyr Ala
1               5

<210> SEQ ID NO 23
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 23

Gly Gly Thr Phe Ser Ser Tyr Ala
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Val Thr Phe Ser Ser Tyr Ala
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Val Thr Phe Ser Ser Tyr Ala
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Val Thr Phe Ser Ser Tyr Ala
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Thr Phe Ser Ser Tyr Ala
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Ile Phe Ser Ser Tyr Ala
1               5
```

```
<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Thr Phe Ser Ser Tyr Ala
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Thr Phe Ser Ser Tyr Ala
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Thr Phe Ser Ser Tyr Ala
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Thr Phe Ser Ser Tyr Ala
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Val Thr Phe Arg Ser Tyr Ala
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34
```

```
Gly Gly Thr Phe Ser Ser Tyr Ala
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Thr Phe Ser Ser Tyr Ala
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Val Thr Phe Ser Ser Tyr Ala
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ile Ser Pro Met Phe Gly Thr Ala
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Ser Pro Ile Phe Gly Thr Ala
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Ser Pro Ile Phe Gly Thr Ala
1               5

<210> SEQ ID NO 40
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 40

Ile Ser Pro Ile Phe Gly Thr Ala
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Met Pro Met Phe Gly Thr Ala
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Ser Pro Leu Phe Gly Thr Ala
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Ser Pro Ile Phe Gly Thr Ala
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ser Pro Ile Phe Gly Thr Ala
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ile Ser Pro Met Phe Gly Thr Ala
1               5
```

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Ser Pro Ile Phe Gly Thr Ala
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Ser Gly Ile Phe Gly Thr Ala
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ile Ser Pro Met Phe Gly Thr Ala
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Ser Gly Ile Phe Gly Thr Ala
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Ser Pro Ile Phe Gly Thr Ala
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 51

Ile Ser Pro Ile Phe Gly Thr Ala
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ile Ser Pro Met Phe Gly Thr Ala
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ile Thr Pro Met Phe Gly Thr Ala
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Ser Pro Leu Phe Gly Thr Ala
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ile Ser Pro Met Phe Gly Thr Ala
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Ser Pro Leu Phe Gly Thr Ala
1               5

<210> SEQ ID NO 57
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 57

Ile Ser Pro Met Phe Gly Thr Ala
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ile Ser Pro Leu Phe Gly Thr Ala
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ile Ser Pro Ile Phe Gly Thr Ala
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ile Ser Pro Ile Phe Gly Thr Ala
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Ser Pro Leu Phe Gly Thr Ala
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ile Ser Pro Ile Phe Gly Thr Ala
1               5
```

```
<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ile Ser Pro Met Phe Gly Thr Ala
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Ser Pro Ile Phe Gly Thr Ala
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ile Thr Pro Ile Phe Gly Thr Ala
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ile Ser Pro Ile Phe Gly Thr Ala
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ile Ile Pro Ile Phe Gly Thr Ala
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 68

Ile Thr Pro Met Phe Gly Thr Ala
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ile Ser Ala Met Phe Gly Thr Ala
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Ile Pro Ile Phe Gly Thr Ala
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Thr Pro Met Phe Gly Thr Ala
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Ser Pro Met Phe Gly Thr Ala
1               5

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Arg Asp Asp Gly Tyr Ala Pro Ser Gly Gly Leu Arg Glu Phe Asp
1               5                   10                  15

Val
```

```
<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Arg Gly Arg Gly Ala Tyr Met Gly Pro Ser Met Asp Val
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Arg Gly Ala Arg Tyr Tyr Ala Gly Gly Tyr Phe Asp Val
1               5                   10

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Arg Asp Ser Gly Asn Tyr Asp Gly Tyr Gly Pro Gly Ser Arg Phe
1               5                   10                  15

Asp Val

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Arg Glu Arg Gly Ser Trp Ser Phe Gly Tyr Phe Asp Val
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Arg Ser Arg Thr Tyr Ala Asp Gly Arg Thr Phe Asp Val
1               5                   10

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 79

Ala Arg Glu Leu Gly Tyr Leu Ala Gly Ser Pro Ser Pro Gly Phe Asp
1               5                   10                  15

Tyr

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Arg Ser Arg Arg Tyr Trp Ala Asp Gly Gly Phe Asp Tyr
1               5                   10

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Arg Glu Gly Gly Tyr Ser Pro Gly Gly Val Asp Phe Asp Tyr
1               5                   10                  15

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Arg Gly Thr Thr Tyr Ser Thr Ala Arg Tyr Phe Asp Val
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Arg Ser Pro Ala Tyr Tyr Phe Gly Pro Asn Met Asp Val
1               5                   10

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Arg Ser Ser Arg Tyr Ala Pro Ser Asp Ser Thr Asn Phe Asp Gln
1               5                   10                  15

```
<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Arg Gly Asp Arg Phe Tyr Val Gly Glu Arg Phe Asp Val
1               5                   10

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Arg Gly Gly Gly Val Gly Arg Ile Trp Ile Ala Gly Tyr Gly Phe
1               5                   10                  15

Asp Gln

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Arg Gly Pro Gly Tyr His Pro Ala Gly Ala Ser Gly Gln Phe Phe
1               5                   10                  15

Asp Leu

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Arg Gly Arg Gly Tyr Ala Pro Asp Ala Leu Thr Asn Phe Asp Val
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Arg Gly Arg Gly Tyr Ile Ala Val Ala Gly Asp Met Asp Val
1               5                   10                  15

<210> SEQ ID NO 90
<211> LENGTH: 17
<212> TYPE: PRT
<213> ORGANISM: Artificial Sequence
<220> FEATURE:
```

<223> OTHER INFORMATION: Description of Artificial Sequence: Synthetic
       peptide

<400> SEQUENCE: 90

Ala Arg Gly Asp Ala Tyr Tyr Val Gly Gly Gly Ala Arg Pro Phe Asp
1               5                   10                  15

Leu

<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 91

Ala Arg Gly Tyr Ser Tyr Tyr Pro Gly Gly Gly Gly Arg Asn Phe
1               5                   10                  15

Asp Tyr

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 92

Ala Arg Ala Pro Thr Tyr Tyr Ala Ser Arg Asp Ser Tyr Asn Phe Asp
1               5                   10                  15

Tyr

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 93

Ala Arg Asp Thr Thr Tyr Ile Ala Gly Gly His Phe Asp Val
1               5                   10

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 94

Ala Arg Ala Ser Gly Tyr Phe Thr Gly Trp Gly Thr Phe Asp Tyr
1               5                   10                  15

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

```
<400> SEQUENCE: 95

Ala Arg Gly Arg Tyr Tyr Tyr Thr Val Gly Val Tyr Asp Val
1               5                   10

<210> SEQ ID NO 96
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Arg Gly Gly Gly Tyr Ser Ala Asp Gly Gly Ala Gly Asn Asn Thr
1               5                   10                  15

Ile Phe Asp Val
            20

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Arg Glu Arg Gly Tyr Thr Val Gly Gly Gly Gly Met Asp Val
1               5                   10                  15

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Arg Glu Tyr Leu Gly Asp Asp Tyr Ser Ser Gly Ser Tyr Phe Asp
1               5                   10                  15

Val

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Arg Glu Ser Gly Tyr Ser Gly Thr Gly Gln Phe Asp Val
1               5                   10

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Arg Ser Gly Gly Tyr Tyr Asp Tyr Gly Val Gly Tyr Asp Gln
1               5                   10                  15
```

```
<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Arg Ser Gly Gly Tyr Ser Pro Ser Ile Gly Gly Phe Asp Val
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Arg Gly Pro Gly Tyr Asp Pro Ser Ser Leu Arg Gly Phe Asp Val
1               5                   10                  15

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Arg Gly Glu Glu Ala Tyr Tyr Asp Leu
1               5                   10

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ala Arg Gly Thr Ser Tyr Leu Pro Gly Arg Ser Gly Phe Asp Val
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Arg Gly Arg Gly Tyr Asp Pro Ser Val Gly Gly Phe Asp Val
1               5                   10                  15

<210> SEQ ID NO 106
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 106

Ala Arg Asp Ser Thr Pro Ser Val Thr Ser Ser Leu Tyr Arg Ile Pro
1               5                   10                  15

Ala Phe Asp Val
            20

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Arg Gly Pro Gly Tyr Tyr Pro Asp Ser Asn Asn Tyr Asp Leu
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Arg Gly Gly Thr Tyr Ser Pro Gly Gly Thr Tyr Phe Asp Val
1               5                   10                  15

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Ser Val Leu Tyr Ser Ser Asn Asn Lys Asn Tyr
1               5                   10

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asn Ile Gly Ser Lys Ser
1               5

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Thr Val Ser Asn Tyr
1               5
```

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ser Ser Asn Ile Gly Ser Asn Thr
1               5

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

His Ile Gly Ser Lys Ser
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ser Ser Asp Val Gly Gly Tyr Asn His
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ser Ser Asp Val Gly Gly Tyr Asn Tyr
1               5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Ser Asn Met Gly Arg Asn Thr
1               5

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 117

Ser Gly Ser Ile Ala Ser Thr Tyr
1               5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ser Gly Ser Ile Ala Ser Asn Tyr
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Ser Asn Ile Gly Ala Gly Tyr Asp
1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ser Gly Ser Ile Ala Ser Asn Tyr
1               5

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Ile Gly Ser Lys Ser
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Gly Ser Val Ser Thr Ser Asn Tyr
1               5

<210> SEQ ID NO 123
<211> LENGTH: 8
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 123

Ser Asn Asn Val Gly Asn Gln Gly
1               5

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Ser Leu Phe Asp Ser Ser Asp Asn Lys Asn Tyr
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Ser Val Leu Tyr Ser Ser Asn Asn Lys Asn Tyr
1               5                   10

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ser Ser Asn Ile Gly Val Asn Tyr
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ser Ser Asn Ile Gly Ser Asn Thr
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gln Ser Val Asp Arg Gly Tyr
1               5

```
<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Ser Asp Ile Gly Ala Tyr Asn Tyr
1               5

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ala Leu Pro Lys Gln Tyr
1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Asp Asn Val Gly Asn Gln Gly
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asn Asn Asn Val Gly Asn Gln Gly
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Ser Asp Val Gly Ala His Asn Phe
1               5

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 134

Gln Ser Val Asp Ser His
1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Thr Ser Asn Val Gly Arg Asn Thr
1               5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Arg Ser Asn Ile Gly Ser Asn Thr
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Arg Ser Asn Ile Gly Arg Asn Thr
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ser Asn Asn Val Gly Asn Gln Gly
1               5

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gln Ser Val Ser Ser Phe
1               5

<210> SEQ ID NO 140
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Leu Pro Lys Gln Tyr
1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ser Gly Ser Ile Ala Ser Asn Tyr
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asn Gly Pro Ser Asn Tyr Ile
1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gln Ser Val Ser Ser Tyr
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ser Ser Asn Ile Gly Val Ser Phe
1               5

<210> SEQ ID NO 145
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Trp Ala Ser
```

```
<210> SEQ ID NO 146
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asp Asp Ser
1

<210> SEQ ID NO 147
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Ala Ser
1

<210> SEQ ID NO 148
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Asn Asn
1

<210> SEQ ID NO 149
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Asp Thr
1

<210> SEQ ID NO 150
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp Val Ser
1

<210> SEQ ID NO 151
<211> LENGTH: 3
<212> TYPE: PRT
<213> ORGANISM: Artificial Sequence
<220> FEATURE:
<223> OTHER INFORMATION: Description of Artificial Sequence: Synthetic
```

```
                                      peptide

<400> SEQUENCE: 151

Glu Val Thr
 1

<210> SEQ ID NO 152
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Asn Asp
 1

<210> SEQ ID NO 153
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Glu Asp His
 1

<210> SEQ ID NO 154
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Glu Asp Asn
 1

<210> SEQ ID NO 155
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Asn Ser
 1

<210> SEQ ID NO 156
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Glu Asp Asn
 1

<210> SEQ ID NO 157
```

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asp Asp Ile
1

<210> SEQ ID NO 158
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Thr Asn
1

<210> SEQ ID NO 159
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Arg Asn Asn
1

<210> SEQ ID NO 160
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Trp Ala Ser
1

<210> SEQ ID NO 161
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Trp Ala Ser
1

<210> SEQ ID NO 162
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162
```

Arg Asn Asn
1

<210> SEQ ID NO 163
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ser Asn Asn
1

<210> SEQ ID NO 164
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Ala Ser
1

<210> SEQ ID NO 165
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Glu Val Ser
1

<210> SEQ ID NO 166
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Lys Asp Ser
1

<210> SEQ ID NO 167
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Asp Asn
1

<210> SEQ ID NO 168
<211> LENGTH: 3
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 168

Arg Asn Asn
1

<210> SEQ ID NO 169
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Glu Val Asn
1

<210> SEQ ID NO 170
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Ala Ser
1

<210> SEQ ID NO 171
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asn Asp Asn
1

<210> SEQ ID NO 172
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Asn Asn
1

<210> SEQ ID NO 173
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Asn Asn
1

```
<210> SEQ ID NO 174
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Lys Asn Asn
1

<210> SEQ ID NO 175
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asp Ala Ser
1

<210> SEQ ID NO 176
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Lys Asp Thr
1

<210> SEQ ID NO 177
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Glu Asp Asn
1

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Leu Asn Ser Asp Gly Ser His
1               5

<210> SEQ ID NO 179
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179
```

Gly Ala Ser
1

<210> SEQ ID NO 180
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Asp Asp
1

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gln Gln Tyr Tyr Ser Gly Ser Trp Thr
1               5

<210> SEQ ID NO 182
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gln Val Trp Asp Arg Ser Ser Asp His Val Val
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gln Gln Tyr Asp Asn Leu Pro Pro Val Thr
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ser Ala Trp Asp Asp Ser Leu Gly Gly Glu Val
1               5                   10

<210> SEQ ID NO 185
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 185

Gln Val Trp Asp Ser Ser Asn Asp His Pro Val
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Thr Ser Tyr Ala Gly Ser Asn Ser Leu Val
1               5                   10

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Ser Tyr Ala Gly Gly Lys Trp Val
1               5

<210> SEQ ID NO 188
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ala Ala Trp Asp Asp Ser Leu Asn Gly Pro Val
1               5                   10

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln Ser Phe Asp Ala Ser Thr Leu Val
1               5

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gln Ser Tyr Asp Ser Asp Asn His Glu Val Ile
1               5                   10
```

<210> SEQ ID NO 191
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gln Ser Tyr Asp Ser Ser Leu Ser Val Val Val
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gln Ser Tyr Asp Thr Ser Asn Arg Lys Val
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gln Val Trp Asp Thr Asn Ser Asp Pro Val Phe Val
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Val Leu Tyr Met Gly Ser Gly Ile Ser Met
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ser Ala Trp Asp Ser Ser Leu Ser Ala Trp Val
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 196

Gln Gln Tyr Phe Ser Ser Pro Pro Ile Phe Thr
1               5                   10

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gln Gln Tyr Tyr Ser Thr Pro Pro Thr
1               5

<210> SEQ ID NO 198
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Val Trp Asp Asp Ser Leu Asn Gly His Trp Val
1               5                   10

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ala Ala Trp Asp Asp Ser Leu Lys Gly Arg Val
1               5                   10

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gln Gln Tyr Gly Ser Ser Arg Leu Ser
1               5

<210> SEQ ID NO 201
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ser Ser Tyr Ala Gly Ser Asn Asn Val Val
1               5                   10

<210> SEQ ID NO 202
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 202

Gln Ala Trp Asp Ser Ser Thr Ala Val
1               5

<210> SEQ ID NO 203
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ser Ala Trp Asp Ser Ser Leu Thr Ala Val Val
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ser Ala Trp Asp Ser Ser Leu Ser Ala Trp Val
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Ala Trp Asp Asp Ser Leu Asp Gly Pro Val
1               5                   10

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gln Gln Arg Ser Met Trp Pro Leu Thr
1               5

<210> SEQ ID NO 207
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Ser Trp Asp Asp Asp Leu Asn Gly Pro Val
1               5                   10

```
<210> SEQ ID NO 208
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gln Ser Tyr Asp Ser Ser Val Val
1               5

<210> SEQ ID NO 209
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ala Ala Trp Asp Val Ser Leu Asn Gly Gln Val
1               5                   10

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ser Ala Trp Asp Ser Ser Leu Ser Asp Trp Val
1               5                   10

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gln Gln Arg Phe Asn Trp Pro Pro Thr
1               5

<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gln Ser Ala Asp Ala Ser Glu Asn Ser Val
1               5                   10

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 213

Gln Ser Tyr Asp Thr Ser Asn Leu Val
1               5

<210> SEQ ID NO 214
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Glu Thr Trp Asp Ser Asn Thr His Val Val
1               5                   10

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gln Gln Val Asn Ser Phe Pro Arg Thr
1               5

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Ala Trp Asp Glu Ser Leu Ser Ser Val Leu
1               5                   10

<210> SEQ ID NO 217
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Gly Gly Thr Phe Ser Ser Tyr Ala
1               5

<210> SEQ ID NO 218
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Val Thr Phe Ser Ser Tyr Ala
1               5

<210> SEQ ID NO 219
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gly Gly Thr Phe Ser Ser Tyr Ala
1               5

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Gly Ile Phe Ser Ser Tyr Ala
1               5

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Val Ile Phe Ser Ser Tyr Ala
1               5

<210> SEQ ID NO 222
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Gly Thr Phe Ser Ser Tyr Ala
1               5

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Gly Thr Phe Ser Ser Tyr Ala
1               5

<210> SEQ ID NO 224
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Gly Pro Phe Arg Ser Tyr Ala
```

```
1               5

<210> SEQ ID NO 225
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Val Pro Phe Ser Ser Tyr Ala
1               5

<210> SEQ ID NO 226
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Val Thr Phe Ser Ser Tyr Ala
1               5

<210> SEQ ID NO 227
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Val Ile Phe Ser Ser Tyr Ala
1               5

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Val Thr Phe Ser Ser Tyr Ala
1               5

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Gly Thr Phe Ser Ser Tyr Ala
1               5

<210> SEQ ID NO 230
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 230

Gly Gly Thr Phe Ser Ser Tyr Ala
1               5

<210> SEQ ID NO 231
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Gly Gly Pro Phe Ser Ser Tyr Ala
1               5

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Gly Ile Phe Ser Ser Tyr Ala
1               5

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gly Gly Ile Phe Arg Ser Tyr Ala
1               5

<210> SEQ ID NO 234
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Gly Thr Phe Ser Ser Tyr Ala
1               5

<210> SEQ ID NO 235
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Val Thr Phe Ser Ser Tyr Ala
1               5

<210> SEQ ID NO 236

```
<210> SEQ ID NO 236
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Gly Thr Phe Ser Ser Tyr Ala
1               5

<210> SEQ ID NO 237
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Gly Thr Phe Arg Ser Tyr Ala
1               5

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Gly Thr Phe Ser Ser Tyr Ala
1               5

<210> SEQ ID NO 239
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Gly Pro Phe Ser Ser Tyr Ala
1               5

<210> SEQ ID NO 240
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Val Thr Phe Ser Ser Tyr Ala
1               5

<210> SEQ ID NO 241
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241
```

```
Gly Gly Thr Phe Ser Ser Tyr Ala
1               5

<210> SEQ ID NO 242
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Val Thr Phe Arg Ser Tyr Ala
1               5

<210> SEQ ID NO 243
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gly Gly Thr Phe Ser Ser Tyr Ala
1               5

<210> SEQ ID NO 244
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gly Val Thr Phe Ser Ser Tyr Ala
1               5

<210> SEQ ID NO 245
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gly Gly Pro Phe Ser Ser Tyr Ala
1               5

<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Gly Ile Phe Ser Ser Tyr Ala
1               5

<210> SEQ ID NO 247
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 247

Ile Ile Thr Ile Phe Gly Thr Ala
1               5

<210> SEQ ID NO 248
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ile Ser Pro Ile Phe Gly Thr Ala
1               5

<210> SEQ ID NO 249
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ile Ser Ala Ile Phe Gly Thr Ala
1               5

<210> SEQ ID NO 250
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ile Thr Pro Ile Phe Gly Thr Ala
1               5

<210> SEQ ID NO 251
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ile Ser Pro Ile Phe Gly Thr Ala
1               5

<210> SEQ ID NO 252
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ile Ser Pro Ile Phe Gly Thr Ala
1               5
```

-continued

```
<210> SEQ ID NO 253
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ile Ile Thr Ile Phe Gly Thr Ala
1               5

<210> SEQ ID NO 254
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ile Ile Pro Ile Phe Gly Thr Ala
1               5

<210> SEQ ID NO 255
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ile Ser Pro Leu Phe Gly Thr Ala
1               5

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ile Ser Pro Met Phe Gly Thr Ala
1               5

<210> SEQ ID NO 257
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Ile Ile Pro Ile Phe Gly Thr Ala
1               5

<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258
```

```
Ile Ser Pro Val Phe Gly Thr Ala
1               5

<210> SEQ ID NO 259
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ile Val Pro Leu Phe Gly Thr Ala
1               5

<210> SEQ ID NO 260
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Ile Ile Pro Ile Phe Gly Thr Ala
1               5

<210> SEQ ID NO 261
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ile Ser Pro Ile Phe Gly Thr Ala
1               5

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ile Ser Ala Ile Phe Gly Thr Ala
1               5

<210> SEQ ID NO 263
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ile Ile Pro Met Phe Gly Thr Ala
1               5

<210> SEQ ID NO 264
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 264

Ile Asn Pro Ile Phe Gly Thr Ala
1               5

<210> SEQ ID NO 265
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Ile Ser Pro Met Phe Gly Thr Ala
1               5

<210> SEQ ID NO 266
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ile Thr Pro Leu Phe Gly Thr Ala
1               5

<210> SEQ ID NO 267
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ile Met Pro Ile Phe Gly Thr Ala
1               5

<210> SEQ ID NO 268
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ile Ser Pro Met Phe Gly Thr Ala
1               5

<210> SEQ ID NO 269
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ile Ile Pro Ile Phe Gly Thr Ala
1               5
```

```
<210> SEQ ID NO 270
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ile Thr Pro Ile Phe Gly Thr Ala
1               5

<210> SEQ ID NO 271
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ile Ser Pro Met Phe Gly Thr Ala
1               5

<210> SEQ ID NO 272
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ile Ser Gly Ile Phe Gly Thr Ala
1               5

<210> SEQ ID NO 273
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ile Ser Pro Ile Phe Gly Thr Ala
1               5

<210> SEQ ID NO 274
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Ile Ser Pro Met Phe Gly Thr Ala
1               5

<210> SEQ ID NO 275
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 275

Ile Ser Pro Met Phe Gly Thr Ala
1               5

<210> SEQ ID NO 276
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Ile Ser Pro Ile Phe Gly Thr Ala
1               5

<210> SEQ ID NO 277
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Ala Arg Gly Ala Thr Gly Phe Tyr Asp Val
1               5                   10

<210> SEQ ID NO 278
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ala Arg Gly Arg Glu Tyr Tyr Ala Ser Asn Gly Asp Ser Phe Asp Val
1               5                   10                  15

<210> SEQ ID NO 279
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Ala Arg Gly Ser Gly Tyr Tyr Val Ala Ala Ser Gly Ala Phe Asp Val
1               5                   10                  15

<210> SEQ ID NO 280
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ala Arg Asp Leu Ser Arg Asp Ser Leu Asn Leu Pro Gly Ser Ser Pro
1               5                   10                  15

Gly Tyr Asp Leu
            20
```

```
<210> SEQ ID NO 281
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ala Arg Ser Arg Gly Tyr Ala Pro Gly Thr Ser Phe His Tyr Asp Val
1               5                   10                  15

<210> SEQ ID NO 282
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Ala Arg Asp Gln Gly Gly Thr Arg Gly Asn Tyr Phe Asp Val
1               5                   10

<210> SEQ ID NO 283
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ala Arg Gly Gly Gly Gly Arg Phe Asp Val
1               5                   10

<210> SEQ ID NO 284
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Ala Arg Gly Gly Val Tyr Ser Phe Asp Val
1               5                   10

<210> SEQ ID NO 285
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ala Arg Gly Leu Gly Thr Tyr Ser Pro Ser Leu Tyr Pro Arg Gly Met
1               5                   10                  15

Asp Val

<210> SEQ ID NO 286
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 286

Ala Arg Gly Arg Ala Tyr Leu Ser Val Arg Gly Ser Phe Asp Val
1               5                   10                  15

<210> SEQ ID NO 287
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ala Arg Gly Gly Ser Gly Ser Phe Asp Val
1               5                   10

<210> SEQ ID NO 288
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ala Arg Ser Arg Gly Tyr Thr Val Ser Ser Leu Ala Gly Arg Tyr Phe
1               5                   10                  15

Asp Gln

<210> SEQ ID NO 289
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ala Arg Gly Leu Gly Leu Tyr Phe Asp Val
1               5                   10

<210> SEQ ID NO 290
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ala Arg Val Arg Gly Gly Tyr Gly Pro Tyr Gly Asp Phe Asp Val
1               5                   10                  15

<210> SEQ ID NO 291
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ala Arg Gly Arg Ser Tyr Ile Val Ser Val Ser Pro Gly Phe Asp Val
1               5                   10                  15

-continued

```
<210> SEQ ID NO 292
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Ala Arg Asp Ser Gly Ile Ala Ser Gly Tyr Thr Ala Tyr Met Asp Tyr
1               5                   10                  15

<210> SEQ ID NO 293
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ala Arg Gly Ala Gly Ser Thr Phe Asp Val
1               5                   10

<210> SEQ ID NO 294
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ala Arg Gly Glu Ser Ala Tyr Tyr Ser Arg Asn Tyr Asp Val
1               5                   10

<210> SEQ ID NO 295
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ala Arg Gly Gly Gly Tyr Tyr Pro Ala Gly Val Gly Arg Tyr Asp Val
1               5                   10                  15

<210> SEQ ID NO 296
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Ala Arg Gly Pro Thr Leu Tyr Ser Pro Pro Val Phe Asp Val
1               5                   10

<210> SEQ ID NO 297
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297
```

```
Ala Arg Gly Ala Gly Val Ser Ala Gly Pro Ser Trp Pro Phe Asp Val
1               5                   10                  15

<210> SEQ ID NO 298
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Ala Arg Ser Arg Gly Tyr Asn Val Ala Ala Ser Phe Gly Phe Asp Val
1               5                   10                  15

<210> SEQ ID NO 299
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Ala Arg Gly Thr Asp Tyr Ser Gly Tyr Arg Gly Phe Asp Val
1               5                   10

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Ala Arg Gly Gly Gly Val Phe Asp Val
1               5

<210> SEQ ID NO 301
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Ala Arg Glu Gly Gly Tyr Ser Pro Gly Gly Val Asp Phe Asp Tyr
1               5                   10                  15

<210> SEQ ID NO 302
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Ala Arg Ser Pro Ala Tyr Tyr Phe Gly Pro Asn Met Asp Val
1               5                   10

<210> SEQ ID NO 303
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 303

Ala Arg Gly Pro Gly Tyr His Pro Ala Gly Ala Ser Gly Gln Phe Phe
1               5                   10                  15

Asp Leu

<210> SEQ ID NO 304
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ala Arg Gly Arg Gly Tyr Ala Pro Asp Ala Leu Thr Asn Phe Asp Val
1               5                   10                  15

<210> SEQ ID NO 305
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ala Arg Gly Tyr Ser Tyr Tyr Pro Gly Gly Gly Gly Gly Arg Asn Phe
1               5                   10                  15

Asp Tyr

<210> SEQ ID NO 306
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Ala Arg Ser Gly Gly Tyr Tyr Asp Tyr Gly Val Gly Tyr Asp Gln
1               5                   10                  15

<210> SEQ ID NO 307
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Ser Ser Asn Ile Gly Ser Asn Thr
1               5

<210> SEQ ID NO 308
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308
```

Asn Ile Ala Thr Lys Ser
1               5

<210> SEQ ID NO 309
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ile Asn Asn Val Gly Asp Gln Gly
1               5

<210> SEQ ID NO 310
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Gln Ser Val Ser Ser Asn
1               5

<210> SEQ ID NO 311
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Asn Ile Gly Ser Lys Ser
1               5

<210> SEQ ID NO 312
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Ser Asn Asn Val Gly Asn Gln Gly
1               5

<210> SEQ ID NO 313
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Thr Ser Asn Ile Gly Asn Asn Ala
1               5

<210> SEQ ID NO 314
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 314

Gly Ser Asn Val Gly Ser Asn Val
1               5

<210> SEQ ID NO 315
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Ser Ser Asn Ile Gly Arg Asn Asp
1               5

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Ser Ser Asn Ile Gly Ser Asn Thr
1               5

<210> SEQ ID NO 317
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Ser Ser Asn Leu Gly Ser Asn Tyr
1               5

<210> SEQ ID NO 318
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Glu Ser Leu Cys Ser Thr Cys
1               5

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Thr Gly Ala Val Thr Ser Gly Tyr Tyr
1               5
```

```
<210> SEQ ID NO 320
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Ser Ser Asn Ile Gly Ser His Ser
1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Ser Ser Asp Val Gly Gly Tyr Asn Tyr
1               5

<210> SEQ ID NO 322
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Ser Leu Arg Thr Ser Tyr
1               5

<210> SEQ ID NO 323
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Ser Ser Asn Ile Gly Ser Asn Thr
1               5

<210> SEQ ID NO 324
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Ser Ser Asn Val Gly Asn Gln Gly
1               5

<210> SEQ ID NO 325
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 325

Gln Asn Val Leu Tyr Ser Ser Asn Asn Lys Asn Asn
1               5                   10

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Ser Gly Ser Val Ser Thr Thr Asn Tyr
1               5

<210> SEQ ID NO 327
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Ser Asn Asn Val Gly Lys Gln Gly
1               5

<210> SEQ ID NO 328
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gln Tyr Ile Asp Arg Ser
1               5

<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Ser Gly Ser Val Ser Ser Phe Asn Tyr
1               5

<210> SEQ ID NO 330
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ser Ser Asn Ile Gly Asn Asn Ala
1               5

<210> SEQ ID NO 331
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 331

Ser Gly Ser Ile Ala Ser Thr Tyr
1               5

<210> SEQ ID NO 332
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Ser Ser Asn Ile Gly Ala Gly Tyr Asp
1               5

<210> SEQ ID NO 333
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Ser Asn Asn Val Gly Asn Gln Gly
1               5

<210> SEQ ID NO 334
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Arg Ser Leu Phe Asp Ser Ser Asp Asn Lys Asn Tyr
1               5                   10

<210> SEQ ID NO 335
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Ser Ser Asn Ile Gly Ser Asn Thr
1               5

<210> SEQ ID NO 336
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Arg Ser Asn Ile Gly Ser Asn Thr
1               5
```

<210> SEQ ID NO 337
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Ser Asn Asn
1

<210> SEQ ID NO 338
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

His Asp Ser
1

<210> SEQ ID NO 339
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Arg Asn Ser
1

<210> SEQ ID NO 340
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gly Ala Ser
1

<210> SEQ ID NO 341
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Tyr Asp Ser
1

<210> SEQ ID NO 342
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 342

Arg Asn Asn
1

<210> SEQ ID NO 343
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Ser Leu Asn
1

<210> SEQ ID NO 344
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Arg Asn Asn
1

<210> SEQ ID NO 345
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gly Arg Asp
1

<210> SEQ ID NO 346
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Ser Asn Asn
1

<210> SEQ ID NO 347
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Arg Asn Ser
1

<210> SEQ ID NO 348
<211> LENGTH: 3
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Gly Ala Thr
1

<210> SEQ ID NO 349
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Ser Thr Ser
1

<210> SEQ ID NO 350
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Gly Asn Ser
1

<210> SEQ ID NO 351
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Glu Val Ser
1

<210> SEQ ID NO 352
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Gln Ser Thr
1

<210> SEQ ID NO 353
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ser Asn Asn
```

<210> SEQ ID NO 354
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Arg Asn Asp
1

<210> SEQ ID NO 355
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Trp Ala Ser
1

<210> SEQ ID NO 356
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Asn Thr Asn
1

<210> SEQ ID NO 357
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Arg Asn Asn
1

<210> SEQ ID NO 358
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Tyr Ala Ser
1

<210> SEQ ID NO 359
<211> LENGTH: 3
<212> TYPE: PRT
<213> ORGANISM: Artificial Sequence
<220> FEATURE:
<223> OTHER INFORMATION: Description of Artificial Sequence: Synthetic

```
                             peptide

<400> SEQUENCE: 359

Asn Thr Asn
1

<210> SEQ ID NO 360
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Tyr Asp Asp
1

<210> SEQ ID NO 361
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Glu Asp His
1

<210> SEQ ID NO 362
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Asp Asn Ser
1

<210> SEQ ID NO 363
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Arg Asn Asn
1

<210> SEQ ID NO 364
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Trp Ala Ser
1

<210> SEQ ID NO 365
```

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ser Asn Asn
1

<210> SEQ ID NO 366
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ser Asn Asn
1

<210> SEQ ID NO 367
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Ala Ala Trp Asp Asp Ser Leu Asn Gly Pro Val
1               5                   10

<210> SEQ ID NO 368
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Ala Ala Trp Asp Asp Ser Leu Ser Gly Pro Trp Val
1               5                   10

<210> SEQ ID NO 369
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ser Ala Trp Asp Ser Ser Leu Ser Asp Trp Val
1               5                   10

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370
```

Gln Gln Tyr Ser Ser Ser Pro Tyr Thr
1               5

<210> SEQ ID NO 371
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Gln Leu Trp Asp His Thr Asn Ser His Val Val
1               5                   10

<210> SEQ ID NO 372
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Ser Ala Trp Asp Asn Thr Val Ser Gly Trp Val
1               5                   10

<210> SEQ ID NO 373
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Glu Ala Trp Asp Asp Ser Leu Ser Gly Pro Val
1               5                   10

<210> SEQ ID NO 374
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Ala Ala Trp Asp Asp Arg Leu Asn Gly Phe Val
1               5                   10

<210> SEQ ID NO 375
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Ala Ala Trp Asp Ala Ser Leu Met Ile Tyr Val
1               5                   10

<210> SEQ ID NO 376
<211> LENGTH: 11
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 376

Ala Ala Trp Asp Asp Ser Leu Asn Gly Tyr Val
1               5                   10

<210> SEQ ID NO 377
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Ala Ala Trp Asp Asp Ser Leu Asn Gly Val Val
1               5                   10

<210> SEQ ID NO 378
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Gln Gln Tyr Gly Ser Ser Pro Gln Thr
1               5

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Leu Leu Tyr Tyr Gly Gly Pro Trp Val
1               5

<210> SEQ ID NO 380
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Ala Ala Trp Asp Asp Gly Leu Ser Gly Trp Val
1               5                   10

<210> SEQ ID NO 381
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Ala Ser Trp Asp Asp Ser Leu Asn Ala Tyr Val
1               5                   10
```

```
<210> SEQ ID NO 382
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Asn Ser Arg Gly Ser Gly Gly Asn Pro Tyr Val
1               5                   10

<210> SEQ ID NO 383
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Ala Ala Trp Asp Asp Ser Leu Asn Gly Arg Val
1               5                   10

<210> SEQ ID NO 384
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Ser Ala Trp Asp Asn Ser Leu Ser Ala Trp Val
1               5                   10

<210> SEQ ID NO 385
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Gln Gln Tyr Tyr Gly Lys Pro Phe Thr
1               5

<210> SEQ ID NO 386
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Val Leu Tyr Met Gly Arg Gly Ile Tyr Val
1               5                   10

<210> SEQ ID NO 387
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387
```

```
Ser Ala Trp Asp Ser Ser Leu Ser Val Trp Val
1               5                   10
```

<210> SEQ ID NO 388
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

```
His Gln Thr Ser Ser Leu Pro Trp Thr
1               5
```

<210> SEQ ID NO 389
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

```
Ala Leu Tyr Val Gly Gly Gly Ile Ser Val
1               5                   10
```

<210> SEQ ID NO 390
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

```
Ala Ala Trp Asp Asp Ser Leu Ser Gly Pro Val
1               5                   10
```

<210> SEQ ID NO 391
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

```
Gln Ser Phe Asp Ala Ser Thr Leu Val
1               5
```

<210> SEQ ID NO 392
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

```
Gln Ser Tyr Asp Ser Ser Leu Ser Val Val Val
1               5                   10
```

<210> SEQ ID NO 393
<211> LENGTH: 11
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 393

Ser Ala Trp Asp Ser Ser Leu Ser Ala Trp Val
1               5                   10

<210> SEQ ID NO 394
<211> LENGTH: 11
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 394

Gln Gln Tyr Phe Ser Ser Pro Pro Ile Phe Thr
1               5                   10

<210> SEQ ID NO 395
<211> LENGTH: 11
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 395

Ala Ala Trp Asp Asp Ser Leu Lys Gly Arg Val
1               5                   10

<210> SEQ ID NO 396
<211> LENGTH: 8
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 396

Gln Ser Tyr Asp Ser Ser Val Val
1               5

<210> SEQ ID NO 397
<211> LENGTH: 372
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 397
caggttcaat tagtgcagtc tggtgctgaa gtgaaaaagc ccggctcaag tgttaaagta      60
agctgtaagg cgagcggtgg cccattcagc tcatacgcca ttagctgggt gcgacaggct     120
cctggtcagg gcctcgaatg gatgggcggc attagcccaa tgtttggcac tgcaaattat     180
gcccagaaat tcagggtag agtcacaatt accgcagaca agagcacctc aaccgcctac     240
atggaactga gtagcctgcg ttccgaagat acagctgtgt attactgtgc gcgcgacgac     300
ggttacgctc ctagtggtgg tctgcgtgag tttgacgttt ggggccaggg gaccttagtc     360
actgtgtcta gc                                                         372

<210> SEQ ID NO 398
<211> LENGTH: 340

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 398
gacatccaga tgacccagtc tccagactcc ctggctgtgt ctctgggcga gagggccacc    60
atcaactgca agtccagccg gagtgtttta tacagctcca acaacaagaa ctacttagct   120
tggtaccaac aaaaaccggg acagcctcct aagttgctca tttattgggc ttctacccgg   180
gaatccgggg tccctgaccg attcagtggc agcgggtctg ggacagattt cactctcacc   240
atcagcagcc tgcaggctga agatgtggcg gtttattact gtcagcaata ttatagtggt   300
tcctggacat tcggccaagg gaccaaggtg gaaatcaaac                         340

<210> SEQ ID NO 399
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 399
caggttcaat tagtgcagtc tggtgctgaa gtgaaaaagc ccggctcaag tgttaaagta    60
agctgtaagg cgagcggagg catctttagc tcatacgcca ttagctgggt gcgacaggct   120
cctggtcagg gcctcgaatg gatgggcggc attagcccta tctttggcac tgcaaattat   180
gcccagaaat tcagggtag agtcacaatt accgcagata aaagcacgaa taccgcctac   240
atggaactga gtagcctgcg ttccgaagat acagctgtgt attactgtgc gcgcggtcgt   300
ggtgcttaca tgggtcctag tatggatgtg tggggccagg ggaccttagt cactgtgtct   360
agc                                                                 363

<210> SEQ ID NO 400
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 400
cagcctgtgc tgactcagcc accctcggtg tcagtggccc caggacagac ggccaggatt    60
acctgtgggg gaaacaacat tggaagtaaa agtgtgcact ggtaccagca gaagccaggc   120 caggccctg tgctggtcgt ctatgatgat agcgaccggc cctcaggat ccctgagcga    180 ttctctggct ccaactctgg gaacacggcc accctgacca tcagcagggt cgaggccggg   240
gatgaggccg actactactg tcaggtgtgg gataggagta tgatcatgt ggtgttcggc    300 ggagggacca agctgaccgt cctag                                         325

<210> SEQ ID NO 401
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 401
```

```
caggttcaat tagtgcagtc tggtgctgaa gtgaaaaagc ccggctcaag tgttaaagta      60
agctgtaagg cgagcggagg taccttcagc tcatacgcca ttagctgggt gcgacaggct     120
cctggtcagg gcctcgaatg gatgggcggc atcagcccaa tctttggcac tgcaaattat     180
gcccagaaat ttcagggtag agtcacaatt accgcagata aaagcacgtc aactgtgtat     240
atggaactga gtagcctgcg ttccgaagat acagctgtgt attactgtgc gcgcggtgct     300
cgttactacg ctggtggtta cttcgatgtg tggggccagg ggaccttagt cactgtgtct     360
agc                                                                   363

<210> SEQ ID NO 402
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 402
gaaattgtgc tgactcagtc tccaggcacc ctgtctttgt ctccagggga agagccacc      60 ctctcctgca gggccagtca gactgttagc aactacttag cctggtatca gcagagacct    120
ggccaggctc ccaggctcct catctacgct gcatccacgc gggccactgg tgtcccagcc    180
aggttcagtg gcagcgggtc tgggacagag ttcactctca ccatcagcag cctgcaatct    240
gaagattttg caatttatta ctgtcaacag tatgataact gcctccggt cactttcggc    300 cctgggacca cagtggatat caaac                                          325

<210> SEQ ID NO 403
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 403
caggttcaat tagtgcagtc tggtgctgaa gtgaaaaagc ccggctcaag tgttaaagta     60
agctgtaagg cgagcggtgt tacctttagc tcatacgcca ttagctgggt gcgacaggct    120
cctggtcagg gcctcgaatg gatgggcggc atcagcccaa tcttcggtac tgcaaattat    180
gcccagaaat ttcagggtag agtcacaatt accgcagatc agagtaccaa cactgtctac    240
atggaactga gtagcctgcg ttccgaagat acagctgtgt attactgtgc gcgcgacagt    300
ggtaattacg acggttacgg tcctggtagt cgtttcgacg tgtggggcca ggggacctta    360
gtcactgtgt ctagc                                                    375

<210> SEQ ID NO 404
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 404
cagcctgggc tgactcagcc accctcagcg tctgggaccc ccgggcagag ggtcaccatc     60
tcttgttctg gaagcagctc caacatcgga agtaatactg taaactggta ccagcagctc    120
ccaggaacgg cccccaaact cctcatctat agtaataatc agcggccctc agggggtccct   180
```

```
gaccgattct ctggctccaa gtctggcacc tcagcctccc tggccatcag tgggctccag    240
tctgaggatg aggctgatta tttctgttca gcttgggatg acagcctggg tggcgaggtc    300
ttcggaactg ggaccaaggt caacgtccta g                                   331
```

```
<210> SEQ ID NO 405
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 405
```

```
caggttcaat tagtgcagtc tggtgctgaa gtgaaaaagc ccggctcaag tgttaaagta     60
agctgtaagg cgagcggagt gacctttagt tcttacgcca ttagctgggt gcgacaggct    120
cctggtcagg gcctcgaatg gatgggcggc attatgccta tgttcggcac tgcaaattat    180
gcccagaaat ttcagggtag agtcacaatt accgcagata gagtacgag cactgcctat    240 atggaactga gtagcctgcg ttccgaagat acagctgtgt attactgtgc gcgcgagcgt    300
ggtagttgga gtttcggtta ctttgatgtg tggggccagg ggaccttagt cactgtgtct    360
agc                                                                  363
```

```
<210> SEQ ID NO 406
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 406
```

```
ctgcctgtgc tgactcagcc accctcgatg tcagcggccc caggacagac ggccaggatt     60
acctgtgggg gagaccacat tggaagtaaa agtgtgcact ggtaccagcg gaagccgggc    120
caggcccctg tgctggtcat ctattctgac accgaccggc cctcagggat ccctgagcgg    180
ttctctggct ccaactctgg gaacacggcc accctgacca tcagcagggt cgaagccggg    240
gatgaggccg actatttctg tcaggtgtgg gatagtagta atgatcatcc ggtgttcggc    300
ggaggcacca agctgaccgt cctag                                          325
```

```
<210> SEQ ID NO 407
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 407
```

```
caggttcaat tagtgcagtc tggtgctgaa gtgaaaaagc ccggctcaag tgttaaagta     60
agctgtaagg cgagcggagt gacctttagc tcttacgcca ttagctgggt gcgacaggct    120
cctggtcagg gcctcgaatg gatgggcggc atcagccctc tgtttggcac tgcaaattat    180
gcccagaaat ttcagggtag agtcacaatt accgcagaca aaagtacgag caccgtgtat    240
atggaactga gtagcctgcg ttccgaagat acagctgtgt attactgtgc gcgcagtcgt    300
acatacgctg acggtcgtac attcgacgtg tggggccagg ggaccttagt cactgtgtct    360
agc                                                                  363
```

<210> SEQ ID NO 408
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 408

| | | | | | |
|---|---|---|---|---|---|
| cagtctgtgc | tgactcagcc | accctccgcg | tccgggtctc | ctggacagtc | ggtcaccatc | 60 |
| tcctgcactg | gaaccagtag | tgacgttggt | ggttataacc | atgtctcctg | gtaccaacag | 120 |
| cacccaggca | aagcccccaa | agtcctgatt | tatgacgtca | gtaagcggcc | ctcaggggtc | 180 |
| ccagatcgct | tctctggctc | caagtctggc | aacacggcct | ccctgaccgt | ctctgggctc | 240 |
| caggctgagg | atgaggctga | ttattactgc | acctcatatg | caggcagcaa | cagtttggtc | 300 |
| ttcggaactg | ggaccgaggt | caccgtccta | g | | | 331 |

<210> SEQ ID NO 409
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 409

| | | | | | |
|---|---|---|---|---|---|
| caggttcaat | tagtgcagtc | tggtgctgaa | gtgaaaaagc | ccggctcaag | tgttaaagta | 60 |
| agctgtaagg | cgagcggtgg | cactttcagt | tcatacgcca | ttagctgggt | gcgacaggct | 120 |
| cctggtcagg | gcctcgaatg | gatgggcggc | atcagcccaa | tctttggtac | tgcaaattat | 180 |
| gcccagaaat | tcagggtag | agtcacaatt | accgcagaca | agagcacgag | cactgcctac | 240 |
| atggaactga | gtagcctgcg | ttccgaagat | acagctgtgt | attactgtgc | gcgcgagctg | 300 |
| ggttacctgg | ctggtagtcc | tagtcctggt | ttcgattact | ggggccaggg | gaccttagtc | 360 |
| actgtgtcta | gc | | | | | 372 |

<210> SEQ ID NO 410
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 410

| | | | | | |
|---|---|---|---|---|---|
| cagtctgtgc | tgactcagcc | accctccgcg | tccgggtctc | ctggacagtc | agtcaccatc | 60 |
| tcctgcactg | gaaccagcag | tgacgttggt | ggttataact | atgtctcctg | gtaccaacag | 120 |
| cacccaggca | aagcccccaa | actcatcatt | tatgaggtca | ctaagcggcc | ctcaggggtc | 180 |
| cctgatcgct | tctctggctc | caagtctggc | aacacggcct | ccctgaccgt | cgctgggctc | 240 |
| caggctgagg | atgaggctga | ttattactgc | agctcgtatg | caggcggcaa | gtgggtcttc | 300 |
| ggaactggga | ccaaggtcac | cgtcctag | | | | 328 |

<210> SEQ ID NO 411
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 411

```
caggttcaat tagtgcagtc tggtgctgaa gtgaaaaagc ccggctcaag tgttaaagta      60
agctgtaagg cgagcggagg cactttttagc tcttacgcca ttagctgggt gcgacaggct    120
cctggtcagg gcctcgaatg gatgggcggc attagcccaa tcttcggcac tgcaaattat    180
gcccagaaat ttcagggtag agtcacaatt accgcagaca ccagcacctc aaccgcctac    240
atggaactga gtagcctgcg ttccgaagat acagctgtgt attactgtgc gcgcagtcgt    300
cgttactggg ctgacggtgg tttcgattat tggggccagg ggaccttagt cactgtgtct    360
agc                                                                   363
```

<210> SEQ ID NO 412
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 412

```
ctgcctgtgc tgactcagcc accctcagcg tctgggaccc ccgggcagag ggtcaccatc      60
tcttgttctg gaagcagctc caacatggga agaaataccg tcaactggta ccggcacctc    120
ccagggacgg cccccgaact cctcatctat gataatgatg agcgtccctc aggggtccct    180
gaccgattct ctggctccaa gtctggcacc tcagcctccc tggccatcag tgggctccag    240
tctgaagatg agggtcatta ttactgtgct gcgtgggatg acagcctgaa tggtccggtg    300
ttcggcggag ggaccaagct gaccgtcctg g                                    331
```

<210> SEQ ID NO 413
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 413

```
caggttcaat tagtgcagtc tggtgctgaa gtgaaaaagc ccggctcaag tgttaaagta      60
agctgtaagg cgagcggagg tacttttagt tcttacgcca ttagctgggt gcgacaggct    120
cctggtcagg gcctcgaatg gatgggcggc attagcccta tgttcggtac tgcaaattat    180
gcccagaaat ttcagggtag agtcacaatt accgcagaca aaagtaccag cactgcctac    240
atggaactga gtagcctgcg ttccgaagat acagctgtgt attactgtgc gcgcgagggt    300
ggttacagtc ctggtggtgt tgacttcgac tactggggcc aggggacctt agtcactgtg    360
tctagc                                                                366
```

<210> SEQ ID NO 414
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 414

```
aattttatgc tgactcagcc ccactctgtg tcggagtctc cggggaagac ggtaaccatc      60
tcctgcaccc gcagcagtgg cagcattgcc agcacctatg tgcagtggta ccggcagcgc    120
```

```
ccgggcagtg cccccaccac tgtgatctat gaggatcatc agagaccctc tggggtccct      180
gatcggttct ccggctccct cgacagctcc tccaactctg cctccctcac catctctgga      240
ctgaggactg aggacgcggc aacctactac tgtcagtctt ttgatgccag cactctggtg      300
ttcggcggcg ggaccaagct gaccgtcctc g                                     331

<210> SEQ ID NO 415
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 415
caggttcaat tagtgcagtc tggtgctgaa gtgaaaaagc ccggctcaag tgttaaagta       60
agctgtaagg cgagcggtgt tactttagt tcttacgcca ttagctgggt gcgacaggct      120
cctggtcagg gcctcgaatg gatgggcggc atcagcccaa tctttggtac tgcaaattat      180
gcccagaaat ttcagggtag agtcacaatt accgcagacg aaagtacgaa tactgtgtat      240
atggaactga gtagcctgcg ttccgaagat acagctgtgt attactgtgc gcgcggtaca      300
acatacagta cagctcgtta cttcgacgtt tggggccagg gaccttagt cactgtgtct      360 agc                                                                    363

<210> SEQ ID NO 416
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 416
aattttatgc tgactcagcc ccactctgtg tcggagtctc cggggaagac ggtaaccatc       60
tcctgcaccc gcagaagtgg cagcattgcc agcaactatg tgcagtggta ccagcagcgc      120
ccgggcagtg cccccaccac tgtgatctat gaggataacc aaagaccctc tggggtccct      180
gatcgcttct ctggctccat cgacaggtcc tccaactctg cctccctcac catctctgga      240
ctgaagactg aggacgaggc tgactactac tgtcagtctt atgacagcga caatcatgaa      300
gtgatattcg gcggagggac caagctgacc gtcctag                               337

<210> SEQ ID NO 417
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 417
caggttcaat tagtgcagtc tggtgctgaa gtgaaaaagc ccggctcaag tgttaaagta       60
agctgtaagg cgagcggagt gactttcgt tcatacgcca ttagctgggt gcgacaggct      120
cctggtcagg gcctcgaatg gatgggcggc atcagcggta tctttggtac tgcaaattat      180
gcccagaaat ttcagggtag agtcacaatt accgcagatg agagcacgtc aaccgcatat      240
atggaactga gtagcctgcg ttccgaagat acagctgtgt attactgtgc gcgcagtcct      300
gcttactact tcggtcctaa tatggacgtg tggggccagg ggaccttagt cactgtgtct      360
``` agc                                                                    363

<210> SEQ ID NO 418
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 418
cagtctgtgc tgactcagcc accctcagtg tctggggccc cagggcagag ggtcaccatc      60
tcctgcactg ggagcagctc caacatcggg gcaggttatg atgtacactg gtaccagcaa     120
cttccaggaa cagtcccaa actcatcatc tatgataata gcaatcggcc ctcaggggtc      180
cctgcccgat tctctggctc caagtctggc acctcagcct ccctggccat cagtgggctc     240
cagtctgagg atgaggccgc atattattgc cagtcgtatg acagcagcct gagtgttgtg     300
gtattcggcg gtgggaccaa gctgtccgtc ctag                                 334

<210> SEQ ID NO 419
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 419
caggttcaat tagtgcagtc tggtgctgaa gtgaaaaagc ccggctcaag tgttaaagta      60
agctgtaagg cgagcggagg cacttttagt tcttacgcca ttagctgggt gcgacaggct     120
cctggtcagg gcctcgaatg gatgggcggc atcagcccta tgtttggtac tgcaaattat     180
gcccagaaat ttcagggtag agtcacaatt accgcagaca aaagtacgag cactgcctac     240
atggaactga gtagcctgcg ttccgaagat acagctgtgt attactgtgc gcgcagtagt     300
cgttacgctc ctagtgacag tacaaatttt gatcaatggg gccaggggac cttagtcact     360
gtgtctagc                                                             369

<210> SEQ ID NO 420
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 420
aattttatgc tgactcagcc ccactctgtg tcggagtctc cggggaagac ggtaaccatc      60
tcctgcaccg gcagcagtgg cagcattgcc agcaactatg tgcagtggta ccagcagcgc     120
ccgggcagtg cccccaccac tgtgatctat gaggataacc aaagaccctc tggggtccct     180
gatcggttct ctggctccat cgacagctcc tccaactctg cctccctcac catctctgga     240
ctgaagactg aggacgaggc tgactactac tgtcagtctt atgataccag caatcggaag     300
gttttcggcg gagggaccaa gctgaccgtc ctag                                 334

<210> SEQ ID NO 421
<211> LENGTH: 363
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 421
caggttcaat tagtgcagtc tggtgctgaa gtgaaaaagc ccggctcaag tgttaaagta      60
agctgtaagg cgagcggtgg cccatttagt tcatacgcca ttagctgggt gcgacaggct     120
cctggtcagg gcctcgaatg gatgggcggc attagcggta tctttggcac tgcaaattat     180
gcccagaaat ttcagggtag agtcacaatt accgcagatg agagcacgtc aaccgcatat     240
atggaactga gtagcctgcg ttccgaagat acagctgtgt attactgtgc gcgcggtgac     300
cgtttctacg ttggtgagcg tttcgatgtg tggggccagg ggaccttagt cactgtgtct     360
agc                                                                   363

<210> SEQ ID NO 422
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 422
cagtctgtgc tgactcagcc accctcggtg tcagtggccc caggacagac ggccagaatt      60
acctgtgggg gaaatgacat tggaagtaaa agtgtccact ggtaccagca gaagccaggc     120
caggcccctg tgctggtcgt ctatgatgat atcgaccggc cctcagggat ccctgagcga     180
ttctctggct ccaactatgg ggacacggcc accctgacca tcagctgggt cgaggccggg     240
gatgaggccg actattactg tcaggtgtgg gatactaata gtgatcccgt ctttgtcttc     300
ggaagtggga ccaaggtcac cgtccttg                                        328

<210> SEQ ID NO 423
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 423
caggttcaat tagtgcagtc tggtgctgaa gtgaaaaagc ccggctcaag tgttaaagta      60
agctgtaagg cgagcggtgg caccttcagc tcttacgcca ttagctgggt gcgacaggct     120
cctggtcagg gcctcgaatg gatgggcggc attagcccaa tcttcggtac tgcaaattat     180
gcccagaaat ttcagggtag agtcacaatt accgcagacc agagcacgag cactgcctac     240
atggaactga gtagcctgcg ttccgaagat acagctgtgt attactgtgc gcgcggtggt     300
ggtgttggtc gtatctggat cgctggttac ggtttcgatc agtggggcca ggggacctta     360
gtcactgtgt ctagc                                                      375

<210> SEQ ID NO 424
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 424
```

```
cagactgtgg tgactcagga gccatcgttc tcagtgtccc ctggagggac agttaccctc    60
acttgtggct tgagctctgg ctcagtctcc actagtaact accccagctg gtaccagcag   120
accccaggcc agcctccacg cacgctcatc tacagcacaa acactcgctc ttctggggtc   180
cctgatcgct tctctggctc catccttggg aacaaagctg ccctcaccat cacgggggcc   240
caggcagatg atgaatctga ttattactgt gtcctatata tgggtagtgg catttcgatg   300
ttcggcggag ggaccaagtt gaccgtccta g                                  331
```

<210> SEQ ID NO 425
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 425

```
caggttcaat tagtgcagtc tggtgctgaa gtgaaaaagc ccggctcaag tgttaaagta    60
agctgtaagg cgagcggtgg tactttagt tcatacgcca ttagctgggt gcgacaggct    120
cctggtcagg gcctcgaatg gatgggcggc attagcccaa tctttggtac tgcaaattat   180
gcccagaaat ttcagggtag agtcacaatt accgcagacg aaagcaccag cactgtgtac   240
atggaactga gtagcctgcg ttccgaagat acagctgtgt attactgtgc gcgcggtcct   300
ggttaccacc ctgctggtgc tagtggtcaa ttctttgatc tttggggcca ggggaccttg   360
gtcactgtgt ctagc                                                    375
```

<210> SEQ ID NO 426
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 426

```
tcctatgagc tgactcagcc accctcggtg tccaaggact tgagacagac cgccacactc    60
acctgcactg ggaacagcaa caatgttggc aaccaaggag cagcttggct gcagcagcac   120
cagggccacc ctcccaaact cctatcctac aggaataacc accggccctc agggatctca   180
gacagatcat ctgcatccag gtcaggagac acagcctccc tgaccattac tggactccag   240
cctgaggacg aggctgacta ttactgctca gcatgggaca gcagcctcag tgcttgggtg   300
ttcggcggag ggaccaagct gaccgtccta g                                  331
```

<210> SEQ ID NO 427
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 427

```
caggttcaat tagtgcagtc tggtgctgaa gtgaaaaagc ccggctcaag tgttaaagta    60
agctgtaagg cgagcggtgt gaccttcagc tcatacgcca ttagctgggt gcgacaggct   120
cctggtcagg gcctcgaatg gatgggcggc attagcccta tgtttggtac tgcaaattat   180
gcccagaaat ttcagggtag agtcacaatt accgcagatg aaagcaccaa caccgcctat   240
```

```
atggaactga gtagcctgcg ttccgaagat acagctgtgt attactgtgc gcgcggtcgt      300
ggttacgctc ctgacgctct gacaaatttt gacgtttggg gccaggggac cttagtcact      360
gtgtctagc                                                              369

<210> SEQ ID NO 428
<211> LENGTH: 346
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 428
gaaattgtgc tgactcagtc tccagactcc ctggctatgt ctctgggcga gagggccacc       60
gtcaactgca gtccagccg gagtctttc gacagctccg acaataagaa ctacttagct      120
tggtaccaga gaaaccagg acagcctcct caattgctca tttactgggc atctacccga      180
caatccgggg tccctgaccg attcagtggc agcgggtctg ggacagattt cactctcacc      240
atcagcagcc tgcaggctga agatgtggca gtttattact gtcagcaata ttttagtagt      300
cctcccatat tcaccttcgg ccctgggacc aaagtggaga tcaaac                    346

<210> SEQ ID NO 429
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 429
caggttcaat tagtgcagtc tggtgctgaa gtgaaaaagc ccggctcaag tgttaaagta       60
agctgtaagg cgagcggagt gacttttagc tcatacgcca ttagctgggt gcgacaggct      120
cctggtcagg gcctcgaatg gatgggcggc attacccta tgtttggtac tgcaaattat      180
gcccagaaat ttcagggtag agtcacaatt accgcagata aaagtacgag caccgtctat      240
atggaactga gtagcctgcg ttccgaagat acagctgtgt attactgtgc gcgcggtcgt      300
ggttacatcg ctgttgctgg tgacatggac gtgtggggcc aggggacctt agtcactgtg      360
tctagc                                                                366

<210> SEQ ID NO 430
<211> LENGTH: 340
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 430
gacatccaga tgacccagtc tccagactcc ctggctgtgt ctctgggcga gagggccacc       60
atcaactgca gtccagtcg gagtgtttta tacagctcca acaataagaa ctacttagct      120
tggtaccagc agaaagcagg acagcctcct aagctgctca tttactgggc atctacccgg      180
gaatccgggg tccctgaccg attcagtggc agcgggtctg ggacagattt cactctcacc      240
atcagcagcc tgcaggctga agatgtggca gtttattact gtcagcaata ttatagtact      300
cctccgacgt tcggccaagg gaccaaggtg gaaatcaaac                           340

<210> SEQ ID NO 431
```

<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 431
caggttcaat tagtgcagtc tggtgctgaa gtgaaaaagc ccggctcaag tgttaaagta      60
agctgtaagg cgagcggtgt taccttcagt tcatacgcca ttagctgggt gcgacaggct     120
cctggtcagg gcctcgaatg gatgggcggc attagcccac tgttcggtac tgcaaattat    180
gcccagaaat tcagggtag agtcacaatt accgcagata agagcacgag cactgcctac     240
atggaactga gtagcctgcg ttccgaagat acagctgtgt attactgtgc gcgcggtgac    300
gcttactacg ttggtggtgg tgctcgtcct tttgacctct ggggccaggg gaccttagtc    360
actgtgtcta gc                                                        372

<210> SEQ ID NO 432
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 432
tcctatgagc tgactcagcc accctcagtg tctgagaccc ccgggcagaa cgtcattatc      60
tcttgttctg gaggcagctc caacatcgga gttaattatg tatactggta tcaggtggtc    120
ccaggagcgg ccccccaaact cctcatctat aggaataatc agcggccctc agggtccct    180 gaccgattct ctggctccaa gtctggcacc tcagcctccc tggccatcag tggactccag    240
tctgaggatg aggctgacta ttactgtgga gtatgggatg acagcctgaa tggtcattgg    300
gtgttcggcg agggaccga cctgaccgtc ctgg                                 334

<210> SEQ ID NO 433
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 433
caggttcaat tagtgcagtc tggtgctgaa gtgaaaaagc ccggctcaag tgttaaagta      60
agctgtaagg cgagcggtgg tccatttagc tcatacgcca ttagctgggt gcgacaggct    120
cctggtcagg gcctcgaatg gatgggcggc attagcccta tgtttggtac tgcaaattat    180
gcccagaaat tcagggtag agtcacaatt accgcagatg aaagcacgtc aaccgtgtac     240
atggaactga gtagcctgcg ttccgaagat acagctgtgt attactgtgc gcgcggttac    300
agttactacc ctggtggtgg tggtggtcgt aatttcgact actggggcca ggggacctta    360
gtcactgtgt ctagc                                                     375

<210> SEQ ID NO 434
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 434

| ctgcctgtgc tgactcagcc accctcagcg tctgggaccc ccgggcagag ggtcaccatc | 60 |
| tcttgttctg gaagcagctc caacatcgga agtaatactg taaactggta ccagcagctc | 120 |
| ccaggaacgg cccccaaact cctcatctat agtaataatc agcggccctc aggggtccct | 180 |
| gaccgattct ctggctccaa gtctggcacc tcagcctccc tggccatcag tgggctccag | 240 |
| tctgagggtg aggctgatta ttactgtgca gcatgggatg acagcctgaa aggtcgggtg | 300 |
| ttcggcggag ggaccaaggt gaccgtccta g | 331 |

<210> SEQ ID NO 435
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 435

| caggttcaat tagtgcagtc tggtgctgaa gtgaaaaagc ccggctcaag tgttaaagta | 60 |
| agctgtaagg cgagcggagg tccattcagt tcttacgcca ttagctgggt gcgacaggct | 120 |
| cctggtcagg gcctcgaatg gatgggcggc atcagccctc tgtttggtac tgcaaattat | 180 |
| gcccagaaat ttcagggtag agtcacaatt accgcagatg aaagcacgtc aaccgcctac | 240 |
| atggaactga gtagcctgcg ttccgaagat acagctgtgt attactgtgc gcgcgctcct | 300 |
| acatactacg ctagtcgtga cagttacaat ttcgattatt ggggccaggg gaccttagtc | 360 |
| actgtgtcta gc | 372 |

<210> SEQ ID NO 436
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 436

| gaaacgacac tcacgcagtc tccagccacc ctgtctgtgt ctccagggga aagagccacc | 60 |
| ctctcctgca gggccagtca gagtgttgac agaggctact tagcctggta tcagcagaag | 120 |
| cctggccagg ctcccaggct cctcatctat ggtgcatccc acagggccgc tggcatccca | 180 |
| gacaggttca gtggcagtgg gtctgggaca gacttcactc tcaccatcag cagactggag | 240 |
| cctgaggatt ttgcagtata tttctgtcag cagtatggta gttcacgcct ctctttcggc | 300 |
| ggagggacca aggtggagat ccaac | 325 |

<210> SEQ ID NO 437
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 437

| caggttcaat tagtgcagtc tggtgctgaa gtgaaaaagc ccggctcaag tgttaaagta | 60 |
| agctgtaagg cgagcggtgt gactttcagt tcttacgcca ttagctgggt gcgacaggct | 120 |
| cctggtcagg gcctcgaatg gatgggcggc attagcccta tgttcggtac tgcaaattat | 180 | gcccagaaat tcagggtag agtcacaatt accgcagaca agagcacgaa tactgcatat      240 atggaactga gtagcctgcg ttccgaagat acagctgtgt attactgtgc gcgcgacaca      300 acatacatcg ctggtggtca cttcgacgtt tggggccagg ggaccttagt cactgtgtct      360 agc                                                                    363

<210> SEQ ID NO 438
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 438
cagtctgtgc tgactcagcc accctccgcg tccgggtctc ctggacagtc agtcaccatc       60
tcctgcactg gaaccagcag tgacattggt gcttataact atgtctcctg gtaccaacaa      120
cacccagaca aagcccccaa gctcatcatt tatgaggtca gtaagcggcc ctcagggggtc     180 cctgatcgct tctctggctc caagtctggc aacacggcct ccctgaccgt ctctgggctc      240
caggctgagg atgaggctga ttattactgc agctcctatg caggcagcaa caatgtggta      300
ttcggcggag ggaccaagct gaccgtccta g                                     331

<210> SEQ ID NO 439
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 439
caggttcaat tagtgcagtc tggtgctgaa gtgaaaaagc ccggctcaag tgttaaagta       60
agctgtaagg cgagcggtgg taccttcagc tcatacgcca ttagctgggt gcgacaggct      120
cctggtcagg gcctcgaatg gatgggcggc atcagccctc tgtttggcac tgcaaattat      180
gcccagaaat tcagggtag agtcacaatt accgcagatg agagtaccaa tactgcctat       240
atggaactga gtagcctgcg ttccgaagat acagctgtgt attactgtgc gcgcgctagt      300
ggttacttca caggttgggg tacattcgac tactggggcc aggggaccttt agtcactgtg     360 tctagc                                                                 366

<210> SEQ ID NO 440
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 440
tcctatgagc tgactcagcc accctcggtg tcagtgtccc caggacagac ggccaggatc       60
acctgctctg gagatgcatt gccaaagcaa tatgcttatt ggtaccagca gaagccaggc      120
caggcccctg tgctggtgat atataaagac agtgagaggc cctcagggat ccctgagcga      180
ttctctggct ccaactctgg gaacacagcc actctgacca tcagcgggac ccaggctttg      240
gatgaggctg actattactg tcaggcgtgg gacagcagca ctgctgtctt cggaactggg      300
accaaggtca ccgtcctag                                                   319

<210> SEQ ID NO 441
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 441
caggttcaat tagtgcagtc tggtgctgaa gtgaaaaagc ccggctcaag tgttaaagta     60
agctgtaagg cgagcggagg tactttagt tcttacgcca ttagctgggt gcgacaggct    120
cctggtcagg gcctcgaatg gatgggcggc atcagcccta tctttggtac tgcaaattat    180
gcccagaaat ttcagggtag agtcacaatt accgcagaca agagcacgag caccgcctac    240
atggaactga gtagcctgcg ttccgaagat acagctgtgt attactgtgc gcgcggtcgt    300
tactactaca cagttggtgt ttatgacgtt tggggccagg ggaccttagt cactgtgtct    360
agc                                                                 363

<210> SEQ ID NO 442
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 442
tcctatgagc tgactcagcc accctcggtg tccaagggct tgagacagac cgccaccctc     60
acctgcattg gggacagcga caatgttggc aaccaaggag taggttggct gcagcagcac    120
cagggccacc ctcccaaact cctgtcctac agggataaca cccggccctc aggcatctca    180
gagagattct ctgcatccag gtcaggaaac acagcctccc tgaccattac tggactccag    240
cctgaggacg aggctgacta ttactgctca gcatgggaca gcagcctcac tgccgtggtg    300
ttcggcggag ggaccaagct ggccgtccta g                                   331

<210> SEQ ID NO 443
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 443
caggttcaat tagtgcagtc tggtgctgaa gtgaaaaagc ccggctcaag tgttaaagta     60
agctgtaagg cgagcggtgt taccttcagt tcttacgcca ttagctgggt gcgacaggct    120
cctggtcagg gcctcgaatg gatgggcggc attagcccta tctttggcac tgcaaattat    180
gcccagaaat ttcagggtag agtcacaatt accgcagata aaagtacctc aaccgtctac    240
atggaactga gtagcctgcg ttccgaagat acagctgtgt attactgtgc gcgcggtggt    300
ggttacagtg ctgacggtgg tgctggtaat aatacaatct tcgacgtttg gggccagggg    360
accttagtca ctgtgtctag c                                              381

<210> SEQ ID NO 444
<211> LENGTH: 331
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 444
cagcctgtgc tgactcagcc accctcggtg tccaagggct tgagacagac cgccacactc      60
acctgtactg ggaacaacaa caatgttggc aaccaaggag cagcctggct gcagcagcac     120
cagggccacc ctcccaaact cctatccgac aggaataaca accggccctc agggatctca     180
gagagattat ctgcatccag gtcaggaaat acagcctccc tgaccattac tggactccag     240
gctgaggacg aggctgacta ttactgctca gcatgggaca gcagcctcag tgcttgggtg     300
ttcggcggag ggaccaagct gaccgtccta a                                     331

<210> SEQ ID NO 445
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 445
caggttcaat tagtgcagtc tggtgctgaa gtgaaaaagc ccggctcaag tgttaaagta      60
agctgtaagg cgagcggagt tactttagc tcttacgcca ttagctgggt gcgacaggct     120
cctggtcagg gcctcgaatg gatgggcggc attagccctc tgtttggtac tgcaaattat     180
gcccagaaat ttcagggtag agtcacaatt accgcagatg agagtacctc aactgcatat     240
atggaactga gtagcctgcg ttccgaagat acagctgtgt attactgtgc gcgcgagcgt     300
ggttacacag ttggtggtgg tggtatggac gtgtggggcc aggggacctt agtcactgtg     360
tctagc                                                                366

<210> SEQ ID NO 446
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 446
cagtctgccc tgactcagcc tccctccgcg tccgggtctc ctggacagtc agtcaccatc      60
tcctgcactg gaaccagcag tgacgttggt gctcacaact tgtctcctg gtaccaacaa     120 cacccagaca aagcccccaa actcatcatt tatgaggtca ataggcggcc ctcagggtc     180 cctgatcgct tctctggctc caagtctggc acctcagcct ccctggccat cagtggtctc     240
cagtctgacg atgaggctga ctattactgt gcagcatggg acgacagtct cgatggtccg     300
gtgttcggcg gagggaccaa gctgaccgtc ctag                                  334

<210> SEQ ID NO 447
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 447
caggttcaat tagtgcagtc tggtgctgaa gtgaaaaagc ccggctcaag tgttaaagta      60
```

```
agctgtaagg cgagcggagt tacttttagc tcatacgcca ttagctgggt gcgacaggct      120
cctggtcagg gcctcgaatg gatgggcggc atcagcccaa tctttggtac tgcaaattat      180
gcccagaaat tcagggtag agtcacaatt accgcagaca agagcacgaa cactgtgtac        240
atggaactga gtagcctgcg ttccgaagat acagctgtgt attactgtgc gcgcgagtac      300
ctgggtgacg actacagtag tggtagttac ttcgatgtgt ggggccaggg gaccttagtc      360
actgtgtcta gc                                                          372
```

<210> SEQ ID NO 448
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 448

```
gaaacgacac tcacgcagtc tccaggcaca ctgtctttgt ctccagggga aacagccatc       60
ctctcctgta gggccagtca gagtgttgat agtcacttag cctggtacca acaaaaaggt      120
ggccaggctc ccaggctcct catctatggt gcatccacca gggccactgg tatcccagcc      180
aggttcagtg gcagtgggtc tgggacagac ttcactctca ccatcaatgg cctagagcct      240
gaggattttg caatttattt ctgtcagcag cgcagcatgt ggccccctcac tttcggcgga     300 gggaccaagg tggagatcaa ac                                               322
```

<210> SEQ ID NO 449
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 449

```
caggttcaat tagtgcagtc tggtgctgaa gtgaaaaagc ccggctcaag tgttaaagta       60
agctgtaagg cgagcggagg tactttcagt tcatacgcca ttagctgggt gcgacaggct      120
cctggtcagg gcctcgaatg gatgggcggc attagcccta tgtttggtac tgcaaattat      180
gcccagaaat tcagggtag agtcacaatt accgcagaca aaagtacctc aactgcatat       240
atggaactga gtagcctgcg ttccgaagat acagctgtgt attactgtgc gcgcgagagt      300
ggttacagtg gtacaggtca atttgacgtg tggggccagg ggaccttagt cactgtgtct      360
agc                                                                    363
```

<210> SEQ ID NO 450
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 450

```
cagtctgtgc tgactcagcc accctcagcg tctgggaccg ccgggcagag ggtcacaatc       60
tcctgttttg ggagaaccct caacgtcgga cgaaacactg ttaactggta ccaacaattg      120
cccggagcgg cccccaagat cctcattttt aacgataatc aacggccctc ggggtccct       180 gaccgcttct ctggctccaa gtctggcacc gccgcctccc tgaccataag taggctccag      240
```

```
tccgcggatg aggctgatta ctattgttca tcatgggatg acgacctgaa cggtccggtc    300
ttcggcggag ggaccaagct gagcgtcgta g                                  331

<210> SEQ ID NO 451
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 451
caggttcaat tagtgcagtc tggtgctgaa gtgaaaaagc ccggctcaag tgttaaagta    60
agctgtaagg cgagcggagg tatctttagt tcttacgcca ttagctgggt gcgacaggct   120
cctggtcagg gcctcgaatg gatgggcggc attagcccaa tcttcggtac tgcaaattat   180
gcccagaaat ttcagggtag agtcacaatt accgcagatg agagcacgaa caccgcctat   240
atggaactga gtagcctgcg ttccgaagat acagctgtgt attactgtgc gcgcagtggt   300
ggttactacg actacggtgt tggttacgac caatggggcc aggggacctt agtcactgtg   360
tctagc                                                              366

<210> SEQ ID NO 452
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 452
cagcctgtgc tgactcagcc accctcagcg tctgggaccc ccgggcagag ggtcaccatc    60
tcttgttctg gaggcaggtc aacatcgga agtaatactg ttaactggta ccagcagctc   120
ccaggaacgg cccccaaact cctcatctat agtaataatc accggccctc aggggtccct   180
gatcgcttct ctggctccaa gtctggcaac acggcctccc tgaccatctc tgggctccag   240
gcggaggatg aggctgatta ttactgccag tcctatgaca gcagcgttgt attcggcgga   300
gggaccaagc tgaccgtcct ag                                            322

<210> SEQ ID NO 453
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 453
caggttcaat tagtgcagtc tggtgctgaa gtgaaaaagc ccggctcaag tgttaaagta    60
agctgtaagg cgagcggtgg taccttcagc tcttacgcca ttagctgggt gcgacaggct   120
cctggtcagg gcctcgaatg gatgggcggc attacccccta tctttggcac tgcaaattat   180
gcccagaaat ttcagggtag agtcacaatt accgcagacg agagtaccag cactgcctac   240
atggaactga gtagcctgcg ttccgaagat acagctgtgt attactgtgc gcgcagtggt   300
ggttacagtc ctagtatcgg tggtttcgac gtttggggcc aggggacctt agtcactgtg   360
tctagc                                                              366

<210> SEQ ID NO 454
```

```
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 454
cagcctgggc tgactcagcc accctcagcg tctgggaccc ccgggcagag ggtcaccatc    60
tcttgttctg gaagcaggtc caatatcgga agaaatactg taaactggta ccagcaactc   120
ccaggaacgg cccccaaact cctcatctat agtaacaatc agcggccctc aggggtccct   180
gaccgagtct ctggctccaa gtctggcacc tcagcctccc tggccatcag tgggctccag   240
tctgaggatg aggctgatta ttactgtgca gcatgggatg tgagcctgaa tggtcaggtc   300
ttcggaactg ggaccaaggt caccgtccta g                                  331

<210> SEQ ID NO 455
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 455
caggttcaat tagtgcagtc tggtgctgaa gtgaaaaagc ccggctcaag tgttaaagta    60
agctgtaagg cgagcggagg tacctttagt tcatacgcca ttagctgggt gcgacaggct   120
cctggtcagg gcctcgaatg gatgggcggc atcagcccaa tctttggtac tgcaaattat   180
gcccagaaat ttcagggtag agtcacaatt accgcagatc gcagtacgag caccgcctac   240
atggaactga gtagcctgcg ttccgaagat acagctgtgt attactgtgc gcgcggtcct   300
ggttacgacc ctagtagtct cgtggttttt gacgtttggg gccagggggac cttagtcact   360 gtgtctagc                                                           369

<210> SEQ ID NO 456
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 456
tcctatgagc tgactcagcc accctcggtg tccaaggact gagacagac cgccacactc    60 acctgcactg ggaacagcaa caatgttggc aaccaaggag cagcttggct gcagcagcac   120
cagggccacc ctcccaaact cctattctac aagaataaca accggccctc agggatttca   180
gagagattat ctgcatccag gtcaggaaac acagcctccc tgaccattac tggactccag   240
cctgaggacg aggctgacta ttactgctca gcatgggaca gcagcctcag tgattgggtg   300
ttcggcggag ggaccaagct gaccgtccta                                    330

<210> SEQ ID NO 457
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 457
```

```
caggttcaat tagtgcagtc tggtgctgaa gtgaaaaagc ccggctcaag tgttaaagta      60
agctgtaagg cgagcggtgg cacttttagc tcttacgcca ttagctgggt gcgacaggct     120
cctggtcagg gcctcgaatg gatgggcggc atcattccaa tctttggtac tgcaaattat     180
gcccagaaat ttcagggtag agtcacaatt accgcagatg agagcacgaa tactgcctac     240
atggaactga gtagcctgcg ttccgaagat acagctgtgt attactgtgc gcgcggtgag     300
gaggcttact acgacctttg gggccagggg accttagtca ctgtgtctag c              351
```

<210> SEQ ID NO 458
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 458

```
gaaattgtgt tgacgcagtc tccaggcacc ctgtctttgt ctccagggga aagagccacc      60
ctctcctgct gggccagtca gagtgttagc agcttcttag cctggtacca acacaaacct     120
ggccaggttc ccaggctcct catctatgat gcatccaata gggccactgg catcccagcc     180
aggttctctg gcagtgggtc tgggacacac ttcactctca ctatcagcag cctagagcct     240
gaagattttg cagtttatta ctgtcagcag cgtttcaatt ggcctccgac gttcggccaa     300
gggaccaagg tggaaagcaa ac                                              322
```

<210> SEQ ID NO 459
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 459

```
caggttcaat tagtgcagtc tggtgctgaa gtgaaaaagc ccggctcaag tgttaaagta      60
agctgtaagg cgagcggagg tacttttagt tcatacgcca ttagctgggt gcgacaggct     120
cctggtcagg gcctcgaatg gatgggcggc atcacccctc tgttcggcac tgcaaattat     180
gcccagaaat ttcagggtag agtcacaatt accgcagaca aaagtacgag caccgcctat     240
atggaactga gtagcctgcg ttccgaagat acagctgtgt attactgtgc gcgcggtaca     300
agttacctgc ctggtcgtag tggttttgat gtttggggcc aggggacctt agtcactgtg     360
tctagc                                                                366
```

<210> SEQ ID NO 460
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 460

```
cagcctgggc tgactcagcc accctcggtg tcagtgtccc caggacagac ggccaggatc      60
acctgctctg cagatgcatt gccaaagcaa tatgcttatt ggtaccagca gaggccaggc     120
caggcccctg tgttgctgat atataaagac actgagaggc cccagggat ccctgagcga      180 ttctctggct ccagctcagg gacaacagtc acgttgacca tcagtggagt ccaggcagaa     240
```

```
gacgaggctg actactattg tcaatcagca gacgctagtg aaaattctgt cttcggaggt    300
gggaccaagg tcaccgtcct ag                                             322
```

<210> SEQ ID NO 461
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 461

```
caggttcaat tagtgcagtc tggtgctgaa gtgaaaaagc ccggctcaag tgttaaagta    60
agctgtaagg cgagcggtgt tactttcgt tcatacgcca ttagctgggt gcgacaggct    120
cctggtcagg gcctcgaatg gatgggcggc atcagcgcaa tgtttggtac tgcaaattat   180
gcccagaaat ttcagggtag agtcacaatt accgcagaca agagtacgaa caccgcatat   240
atggaactga gtagcctgcg ttccgaagat acagctgtgt attactgtgc gcgcggtcgt   300
ggttacgacc ctagtgttgg tggttttgat gtgtggggcc aggggaccttt agtcactgtg   360 tctagc                                                              366
```

<210> SEQ ID NO 462
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 462

```
aattttatgc tgactcagcc ccactctgtg tcggagtctc cggggaagac ggtcagcatc    60
tcctgcaccg gcagcagtgg cagcattgcc agcaactatg tgcagtggta ccagcagcgc   120
ccgggcagtg cccccgccac tgtgatctat gaggataacc aaagaccctc tggggtccct   180
gatcggttct ctggctccat cgacagctcc tccaactctg cctccctcac catctctgga   240
ctgaagactg aggacgaggc tgactactac tgtcagtctt atgataccag caatctggta   300
ttcggcgtag ggaccaagct gaccgtccta g                                  331
```

<210> SEQ ID NO 463
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 463

```
caggttcaat tagtgcagtc tggtgctgaa gtgaaaaagc ccggctcaag tgttaaagta    60
agctgtaagg cgagcggtgg taccttagt tcatacgcca ttagctgggt gcgacaggct   120
cctggtcagg gcctcgaatg gatgggcggc attattccta tcttcggtac tgcaaattat   180
gcccagaaat ttcagggtag agtcacaatt accgcagacg atagcacgtc aaccgcatac   240
atggaactga gtagcctgcg ttccgaagat acagctgtgt attactgtgc gcgcgacagt   300
acacctagtg ttacaagtag tctgtaccgt atccctgctt tgatgtgtg gggccagggg   360 accttagtca ctgtgtctag c                                             381
```

<210> SEQ ID NO 464
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 464

```
ctgcctgtgc tgactcaatc atcctctgcc tctgcttccc tgggatcctc ggtcaagctc      60
acctgcagtc tgaccaatgg gcccagtaac tacatcatcg catggcatca gcagcagcca     120
gagaagggcc ctcggtactt gatgaagctt aacagtgatg gcagccacag caagggggac     180
gggatccctg atcgcttctc aggctccagc tctggggctg agcgctacct caccatctcc     240
aaccttaagt ctgaggatga ggctgattat tactgtgaga cctgggacag taacactcat     300
gtggtattcg gcggagggac caagctgacc gtcctag                              337
```

<210> SEQ ID NO 465
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 465

```
caggttcaat tagtgcagtc tggtgctgaa gtgaaaaagc ccggctcaag tgttaaagta      60
agctgtaagg cgagcggagg tacctttagt tcatacgcca ttagctgggt gcgacaggct     120
cctggtcagg gcctcgaatg gatgggcggc attaccccaa tgtttggtac tgcaaattat     180
gcccagaaat ttcagggtag agtcacaatt accgcagaca agagcacgtc aactacatac     240
atggaactga gtagcctgcg ttccgaagat acagctgtgt attactgtgc gcgcggtcct     300
ggttactacc ctgacagtaa taattatgat ctctggggcc aggggacctt agtcactgtg     360
tctagc                                                                366
```

<210> SEQ ID NO 466
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 466

```
gaaacgacac tcacgcagtc tccaggcacc ctgtctttgt ctccagggga aagagccacc      60
ctctcctgca gggccagtca gagtgttagt agcagctact tagcctggta ccagcagaaa     120
cctggccagg ctcccaggct cctcatctat ggtgcatcaa gtagggccac tggcatccca     180
gacaggttca gtggcagtgg gtctgggaca gacttcactc tcaccatcag cagactggag     240
cctgaagatt ttgcaaccta ctattgtcaa caggttaaca gcttccctcg aacttttggc     300 cagggggacca agctggagat gaaac                                          325
```

<210> SEQ ID NO 467
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 467
caggttcaat tagtgcagtc tggtgctgaa gtgaaaaagc ccggctcaag tgttaaagta    60
agctgtaagg cgagcggtgt gacctttagc tcatacgcca ttagctgggt gcgacaggct   120
cctggtcagg gcctcgaatg gatgggcggc attagcccaa tgtttggcac tgcaaattat   180
gcccagaaat ttcagggtag agtcacaatt accgcagacc agagcacgaa caccgcctat   240
atggaactga gtagcctgcg ttccgaagat acagctgtgt attactgtgc gcgcggtggt   300
acatacagtc ctggtggtac atactttgat gtttggggcc aggggacctt agtcactgtg   360
tctagc                                                              366

<210> SEQ ID NO 468
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 468
cagcctgtgc tgactcagcc accctcagcg tctgcgaccc ccggacagac ggtgaccatc    60
tcttgttctg gcagcagttc caacatcggc gtgagctttg tctactggta tcaacaattt   120
ccaggaacgg cccccaagct cctcatttac agggatgata tgaggcagtc aggggtccct   180
gaccgatttt ctggcttcaa gtctggctcc tcagcctccc tgaccatctc tgggctccag   240
tccgaagatg aggccactta ttattgttcc gcgtgggatg agagcctgag tagtgtgttg   300
ttcggcggag ggaccaaggt caccgtccta g                                  331

<210> SEQ ID NO 469
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 469

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Met Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ala Pro Ser Gly Gly Leu Arg Glu Phe Asp
            100                 105                 110

Val Trp Gly Gln Gly Thr Leu Val Thr Val Ser Ser
        115                 120

<210> SEQ ID NO 470
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 470

Asp Ile Gln Met Thr Gln Ser Pro Asp Ser Leu Ala Val Ser Leu Gly
1               5                   10                  15

Glu Arg Ala Thr Ile Asn Cys Lys Ser Ser Arg Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
65                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Gly Ser Trp Thr Phe Gly Gln Gly Thr Lys Val Glu Ile
            100                 105                 110

Lys

<210> SEQ ID NO 471
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gly Ala Tyr Met Gly Pro Ser Met Asp Val Trp Gly
            100                 105                 110

Gln Gly Thr Leu Val Thr Val Ser Ser
        115                 120

<210> SEQ ID NO 472
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472

Gln Pro Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val

```
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Arg Ser Ser Asp His
                85                  90                  95

Val Val Phe Gly Gly Gly Thr Lys Leu Thr Val Leu
            100                 105

<210> SEQ ID NO 473
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 473

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Arg Tyr Tyr Ala Gly Gly Tyr Phe Asp Val Trp Gly
            100                 105                 110

Gln Gly Thr Leu Val Thr Val Ser Ser
        115                 120

<210> SEQ ID NO 474
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Asn Tyr
            20                  25                  30

Leu Ala Trp Tyr Gln Gln Arg Pro Gly Gln Ala Pro Arg Leu Leu Ile
        35                  40                  45

Tyr Ala Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys Gln Gln Tyr Asp Asn Leu Pro Pro
```

```
                    85                  90                  95

Val Thr Phe Gly Pro Gly Thr Thr Val Asp Ile Lys
                100                 105

<210> SEQ ID NO 475
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ser Pro Ile Phe Gly Thr Ala Asn Tyr Ala Gln Lys Phe
        50                  55                  60

Gln Gly Arg Val Thr Ile Thr Ala Asp Gln Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Gly Asn Tyr Asp Gly Tyr Gly Pro Gly Ser Arg Phe
                100                 105                 110

Asp Val Trp Gly Gln Gly Thr Leu Val Thr Val Ser Ser
            115                 120                 125

<210> SEQ ID NO 476
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Gln Pro Gly Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ser Ala Trp Asp Asp Ser Leu
                85                  90                  95

Gly Gly Glu Val Phe Gly Thr Gly Thr Lys Val Asn Val Leu
                100                 105                 110

<210> SEQ ID NO 477
<211> LENGTH: 121
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 477

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Met Pro Met Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Gly Ser Trp Ser Phe Gly Tyr Phe Asp Val Trp Gly
            100                 105                 110

Gln Gly Thr Leu Val Thr Val Ser Ser
        115                 120

<210> SEQ ID NO 478
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 478

Leu Pro Val Leu Thr Gln Pro Pro Ser Met Ser Ala Ala Pro Gly Gln
1               5                   10                  15

Thr Ala Arg Ile Thr Cys Gly Gly Asp His Ile Gly Ser Lys Ser Val
            20                  25                  30

His Trp Tyr Gln Arg Lys Pro Gly Gln Ala Pro Val Leu Val Ile Tyr
        35                  40                  45

Ser Asp Thr Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Phe Cys Gln Val Trp Asp Ser Ser Asn Asp His
                85                  90                  95

Pro Val Phe Gly Gly Gly Thr Lys Leu Thr Val Leu
            100                 105

<210> SEQ ID NO 479
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 479

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

```
Gly Gly Ile Ser Pro Leu Phe Gly Thr Ala Asn Tyr Ala Gln Lys Phe
        50                  55                  60

Gln Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Thr Tyr Ala Asp Gly Arg Thr Phe Asp Val Trp Gly
            100                 105                 110

Gln Gly Thr Leu Val Thr Val Ser Ser
        115                 120

<210> SEQ ID NO 480
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 480

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Leu Phe Gly Thr Ala Asn Tyr Ala Gln Lys Phe
    50                  55                  60

Gln Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Thr Tyr Ala Asp Gly Arg Thr Phe Asp Val Trp Gly
            100                 105                 110

Gln Gly Thr Leu Val Thr Val Ser Ser
        115                 120

<210> SEQ ID NO 481
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 481

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Glu Leu Gly Tyr Leu Ala Gly Ser Pro Ser Pro Gly Phe Asp
            100                 105                 110

Tyr Trp Gly Gln Gly Thr Leu Val Thr Val Ser Ser
        115                 120

<210> SEQ ID NO 482
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 482

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Ile Ile Tyr Glu Val Thr Lys Arg Pro Ser Gly Val Pro Asp Arg Phe
    50                  55                  60

Ser Gly Ser Lys Ser Gly Asn Thr Ala Ser Leu Thr Val Ala Gly Leu
65                  70                  75                  80

Gln Ala Glu Asp Glu Ala Asp Tyr Tyr Cys Ser Ser Tyr Ala Gly Gly
                85                  90                  95

Lys Trp Val Phe Gly Thr Gly Thr Lys Val Thr Val Leu
            100                 105

<210> SEQ ID NO 483
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Arg Tyr Trp Ala Asp Gly Gly Phe Asp Tyr Trp Gly
            100                 105                 110

Gln Gly Thr Leu Val Thr Val Ser Ser
        115                 120

<210> SEQ ID NO 484
<211> LENGTH: 110
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 484

Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Met Gly Arg Asn
                20                  25                  30

Thr Val Asn Trp Tyr Arg His Leu Pro Gly Thr Ala Pro Glu Leu Leu
            35                  40                  45

Ile Tyr Asp Asn Asp Glu Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Gly His Tyr Tyr Cys Ala Ala Trp Asp Asp Ser Leu
                85                  90                  95

Asn Gly Pro Val Phe Gly Gly Gly Thr Lys Leu Thr Val Leu
                100                 105                 110

<210> SEQ ID NO 485
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 485

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ser Pro Met Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Tyr Ser Pro Gly Gly Val Asp Phe Asp Tyr Trp
                100                 105                 110

Gly Gln Gly Thr Leu Val Thr Val Ser Ser
            115                 120

<210> SEQ ID NO 486
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 486

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Thr
                20                  25                  30
```

Tyr Val Gln Trp Tyr Arg Gln Arg Pro Gly Ser Ala Pro Thr Thr Val
                35                  40                  45

Ile Tyr Glu Asp His Gln Arg Pro Ser Gly Val Pro Asp Arg Phe Ser
 50                  55                  60

Gly Ser Leu Asp Ser Ser Asn Ser Ala Ser Leu Thr Ile Ser Gly
 65                  70                  75                  80

Leu Arg Thr Glu Asp Ala Ala Thr Tyr Tyr Cys Gln Ser Phe Asp Ala
                 85                  90                  95

Ser Thr Leu Val Phe Gly Gly Gly Thr Lys Leu Thr Val Leu
            100                 105                 110

<210> SEQ ID NO 487
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 487

Gln Val Gln Leu Val Gln Ser Gly Ala Glu Val Lys Lys Pro Gly Ser
 1               5                   10                  15

Ser Val Lys Val Ser Cys Lys Ala Ser Gly Val Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ser Pro Ile Phe Gly Thr Ala Asn Tyr Ala Gln Lys Phe
 50                  55                  60

Gln Gly Arg Val Thr Ile Thr Ala Asp Glu Ser Thr Asn Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Thr Thr Tyr Ser Thr Ala Arg Tyr Phe Asp Val Trp Gly
             100                 105                 110

Gln Gly Thr Leu Val Thr Val Ser Ser
         115                 120

<210> SEQ ID NO 488
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 488

Asn Phe Met Leu Thr Gln Pro His Ser Val Ser Glu Ser Pro Gly Lys
 1               5                   10                  15

Thr Val Thr Ile Ser Cys Thr Arg Arg Ser Gly Ser Ile Ala Ser Asn
                 20                  25                  30

Tyr Val Gln Trp Tyr Gln Gln Arg Pro Gly Ser Ala Pro Thr Thr Val
             35                  40                  45

Ile Tyr Glu Asp Asn Gln Arg Pro Ser Gly Val Pro Asp Arg Phe Ser
 50                  55                  60

Gly Ser Ile Asp Arg Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Asp Asn His Glu Val Ile Phe Gly Gly Gly Thr Lys Leu Thr Val Leu
            100                 105                 110

<210> SEQ ID NO 489
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 489

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Arg Ser Tyr
            20                  25                  30

Ala Ile Ser Trp Val Arg Gln Ala Pro Gly Gln Gly Leu Glu Trp Met
        35                  40                  45

Gly Gly Ile Ser Gly Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Ala Tyr Tyr Phe Gly Pro Asn Met Asp Val Trp Gly
            100                 105                 110

Gln Gly Thr Leu Val Thr Val Ser Ser
        115                 120

<210> SEQ ID NO 490
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Val Pro Lys Leu
        35                  40                  45

Ile Ile Tyr Asp Asn Ser Asn Arg Pro Ser Gly Val Pro Ala Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Ala Tyr Tyr Cys Gln Ser Tyr Asp Ser Ser
                85                  90                  95

Leu Ser Val Val Val Phe Gly Gly Gly Thr Lys Leu Ser Val Leu
            100                 105                 110

<210> SEQ ID NO 491
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 491

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Met Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Arg Tyr Ala Pro Ser Asp Ser Thr Asn Phe Asp Gln
            100                 105                 110

Trp Gly Gln Gly Thr Leu Val Thr Val Ser Ser
        115                 120

<210> SEQ ID NO 492
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 492

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Thr
                85                  90                  95

Ser Asn Arg Lys Val Phe Gly Gly Gly Thr Lys Leu Thr Val Leu
            100                 105                 110

<210> SEQ ID NO 493
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 493

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Gly Ile Phe Gly Thr Ala Asn Tyr Ala Gln Lys Phe

```
                    50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Gly Asp Arg Phe Tyr Val Gly Arg Phe Asp Val Trp Gly
                100                 105                 110

Gln Gly Thr Leu Val Thr Val Ser Ser
            115                 120
```

<210> SEQ ID NO 494
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 494

```
Gln Ser Val Leu Thr Gln Pro Pro Ser Val Ser Val Ala Pro Gly Gln
 1               5                  10                  15

Thr Ala Arg Ile Thr Cys Gly Gly Asn Asp Ile Gly Ser Lys Ser Val
                20                  25                  30

His Trp Tyr Gln Gln Lys Pro Gly Gln Ala Pro Val Leu Val Val Tyr
             35                  40                  45

Asp Asp Ile Asp Arg Pro Ser Gly Ile Pro Glu Arg Phe Ser Gly Ser
 50                  55                  60

Asn Tyr Gly Asp Thr Ala Thr Leu Thr Ile Ser Trp Val Glu Ala Gly
 65                  70                  75                  80

Asp Glu Ala Asp Tyr Tyr Cys Gln Val Trp Asp Thr Asn Ser Asp Pro
                 85                  90                  95

Val Phe Val Phe Gly Ser Gly Thr Lys Val Thr Val Leu
                100                 105
```

<210> SEQ ID NO 495
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 495

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
             35                  40                  45

Gly Gly Ile Ser Pro Ile Phe Gly Thr Ala Asn Tyr Ala Gln Lys Phe
         50                  55                  60

Gln Gly Arg Val Thr Ile Thr Ala Asp Gln Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Gly Gly Gly Val Gly Arg Ile Trp Ile Ala Gly Tyr Gly Phe
                100                 105                 110

Asp Gln Trp Gly Gln Gly Thr Leu Val Thr Val Ser Ser
```

<210> SEQ ID NO 496
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 496

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Asn Tyr Pro Ser Trp Tyr Gln Gln Thr Pro Gly Gln Pro Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Ser Met Phe Gly Gly Gly Thr Lys Leu Thr Val Leu
            100                 105                 110

<210> SEQ ID NO 497
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 497

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Pro Gly Tyr His Pro Ala Gly Ala Ser Gly Gln Phe Phe
            100                 105                 110

Asp Leu Trp Gly Gln Gly Thr Leu Val Thr Val Ser Ser
        115                 120                 125

<210> SEQ ID NO 498
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 498

```
Ser Tyr Glu Leu Thr Gln Pro Pro Ser Val Ser Lys Asp Leu Arg Gln
1               5                   10                  15

Thr Ala Thr Leu Thr Cys Thr Gly Asn Ser Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn His Arg Pro Ser Gly Ile Ser Asp Arg Ser Ser
50                      55                  60

Ala Ser Arg Ser Gly Asp Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Ala Trp Val Phe Gly Gly Gly Thr Lys Leu Thr Val Leu
            100                 105                 110
```

<210> SEQ ID NO 499
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 499

```
Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Met Phe Gly Thr Ala Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gly Tyr Ala Pro Asp Ala Leu Thr Asn Phe Asp Val
            100                 105                 110

Trp Gly Gln Gly Thr Leu Val Thr Val Ser Ser
        115                 120
```

<210> SEQ ID NO 500
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 500

```
Glu Ile Val Leu Thr Gln Ser Pro Asp Ser Leu Ala Met Ser Leu Gly
1               5                   10                  15

Glu Arg Ala Thr Val Asn Cys Lys Ser Ser Arg Ser Leu Phe Asp Ser
            20                  25                  30

Ser Asp Asn Lys Asn Tyr Leu Ala Trp Tyr Gln Lys Lys Pro Gly Gln
        35                  40                  45

Pro Pro Gln Leu Leu Ile Tyr Trp Ala Ser Thr Arg Gln Ser Gly Val
    50                  55                  60
```

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Ser Pro Pro Ile Phe Thr Phe Gly Pro Gly Thr Lys Val
            100                 105                 110

Glu Ile Lys
        115

<210> SEQ ID NO 501
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 501

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Thr Pro Met Phe Gly Thr Ala Asn Tyr Ala Gln Lys Phe
    50                  55                  60

Gln Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Arg Gly Tyr Ile Ala Val Ala Gly Asp Met Asp Val Trp
            100                 105                 110

Gly Gln Gly Thr Leu Val Thr Val Ser Ser
        115                 120

<210> SEQ ID NO 502
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 502

Asp Ile Gln Met Thr Gln Ser Pro Asp Ser Leu Ala Val Ser Leu Gly
1               5                   10                  15

Glu Arg Ala Thr Ile Asn Cys Lys Ser Ser Arg Ser Val Leu Tyr Ser
            20                  25                  30

Ser Asn Asn Lys Asn Tyr Leu Ala Trp Tyr Gln Gln Lys Ala Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
            100                 105                 110

Lys

<210> SEQ ID NO 503
<211> LENGTH: 124
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 503

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Leu Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Ala Tyr Tyr Val Gly Gly Ala Arg Pro Phe Asp
            100                 105                 110

Leu Trp Gly Gln Gly Thr Leu Val Thr Val Ser Ser
        115                 120

<210> SEQ ID NO 504
<211> LENGTH: 111
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 504

Ser Tyr Glu Leu Thr Gln Pro Pro Ser Val Ser Glu Thr Pro Gly Gln
1               5                   10                  15

Asn Val Ile Ile Ser Cys Ser Gly Gly Ser Ser Asn Ile Gly Val Asn
            20                  25                  30

Tyr Val Tyr Trp Tyr Gln Val Val Pro Gly Ala Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gly Val Trp Asp Asp Ser Leu
                85                  90                  95

Asn Gly His Trp Val Phe Gly Gly Gly Thr Asp Leu Thr Val Leu
            100                 105                 110

<210> SEQ ID NO 505
<211> LENGTH: 125
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 505

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Met Phe Gly Thr Ala Asn Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Tyr Pro Gly Gly Gly Gly Arg Asn Phe
            100                 105                 110

Asp Tyr Trp Gly Gln Gly Thr Leu Val Thr Val Ser Ser
        115                 120                 125

<210> SEQ ID NO 506
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 506

Leu Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Gly Glu Ala Asp Tyr Tyr Cys Ala Ala Trp Asp Asp Ser Leu
                85                  90                  95

Lys Gly Arg Val Phe Gly Gly Gly Thr Lys Val Thr Val Leu
            100                 105                 110

<210> SEQ ID NO 507
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Leu Phe Gly Thr Ala Asn Tyr Ala Gln Lys Phe

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Pro Thr Tyr Tyr Ala Ser Arg Asp Ser Tyr Asn Phe Asp
            100                 105                 110

Tyr Trp Gly Gln Gly Thr Leu Val Thr Val Ser Ser
        115                 120
```

<210> SEQ ID NO 508
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 508

```
Glu Thr Thr Leu Thr Gln Ser Pro Ala Thr Leu Ser Val Ser Pro Gly
  1               5                  10                  15

Glu Arg Ala Thr Leu Ser Cys Arg Ala Ser Gln Ser Val Asp Arg Gly
             20                  25                  30

Tyr Leu Ala Trp Tyr Gln Gln Lys Pro Gly Gln Ala Pro Arg Leu Leu
         35                  40                  45

Ile Tyr Gly Ala Ser His Arg Ala Ala Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Phe Cys Gln Gln Tyr Gly Ser Ser Arg
                 85                  90                  95

Leu Ser Phe Gly Gly Gly Thr Lys Val Glu Ile Gln
            100                 105
```

<210> SEQ ID NO 509
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 509

```
Gln Val Gln Leu Val Gln Ser Gly Ala Glu Val Lys Lys Pro Gly Ser
  1               5                  10                  15

Ser Val Lys Val Ser Cys Lys Ala Ser Gly Val Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ser Pro Met Phe Gly Thr Ala Asn Tyr Ala Gln Lys Phe
     50                  55                  60

Gln Gly Arg Val Thr Ile Thr Ala Asp Lys Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Thr Thr Tyr Ile Ala Gly Gly His Phe Asp Val Trp Gly
            100                 105                 110

Gln Gly Thr Leu Val Thr Val Ser Ser
        115                 120
```

<210> SEQ ID NO 510
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 510

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Ala Tyr
            20                  25                  30

Asn Tyr Val Ser Trp Tyr Gln Gln His Pro Asp Lys Ala Pro Lys Leu
        35                  40                  45

Ile Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Val Val Phe Gly Gly Gly Thr Lys Leu Thr Val Leu
            100                 105                 110

<210> SEQ ID NO 511
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Leu Phe Gly Thr Ala Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Gly Tyr Phe Thr Gly Trp Gly Thr Phe Asp Tyr Trp
            100                 105                 110

Gly Gln Gly Thr Leu Val Thr Val Ser Ser
        115                 120

<210> SEQ ID NO 512
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 512

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Asp Ser Ser Thr Ala Val
                85                  90                  95

Phe Gly Thr Gly Thr Lys Val Thr Val Leu
            100                 105
```

<210> SEQ ID NO 513
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 513

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Tyr Tyr Tyr Thr Val Gly Val Tyr Asp Val Trp Gly
            100                 105                 110

Gln Gly Thr Leu Val Thr Val Ser Ser
        115                 120
```

<210> SEQ ID NO 514
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 514

```
Ser Tyr Glu Leu Thr Gln Pro Pro Ser Val Ser Lys Gly Leu Arg Gln
1               5                   10                  15

Thr Ala Thr Leu Thr Cys Ile Gly Asp Ser Asp Asn Val Gly Asn Gln
            20                  25                  30

Gly Val Gly Trp Leu Gln Gln His Gln Gly His Pro Pro Lys Leu Leu
        35                  40                  45

Ser Tyr Arg Asp Asn Thr Arg Pro Ser Gly Ile Ser Glu Arg Phe Ser
50                  55                  60
```

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Thr Ala Val Val Phe Gly Gly Gly Thr Lys Leu Ala Val Leu
            100                 105                 110

<210> SEQ ID NO 515
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 515

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Tyr Ser Ala Asp Gly Ala Gly Asn Asn Thr
            100                 105                 110

Ile Phe Asp Val Trp Gly Gln Gly Thr Leu Val Thr Val Ser Ser
        115                 120                 125

<210> SEQ ID NO 516
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 516

Gln Pro Val Leu Thr Gln Pro Pro Ser Val Ser Lys Gly Leu Arg Gln
1               5                   10                  15

Thr Ala Thr Leu Thr Cys Thr Gly Asn Asn Asn Val Gly Asn Gln
            20                  25                  30

Gly Ala Ala Trp Leu Gln Gln His Gln Gly His Pro Lys Leu Leu
        35                  40                  45

Ser Asp Arg Asn Asn Asn Arg Pro Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Ala Glu Asp Glu Ala Asp Tyr Tyr Cys Ser Ala Trp Asp Ser Ser Leu
                85                  90                  95

Ser Ala Trp Val Phe Gly Gly Gly Thr Lys Leu Thr Val Leu
            100                 105                 110

<210> SEQ ID NO 517

<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 517

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Leu Phe Gly Thr Ala Asn Tyr Ala Gln Lys Phe
    50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Gly Tyr Thr Val Gly Gly Gly Met Asp Val Trp
            100                 105                 110

Gly Gln Gly Thr Leu Val Thr Val Ser Ser
        115                 120

<210> SEQ ID NO 518
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 518

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala His
            20                  25                  30

Asn Phe Val Ser Trp Tyr Gln Gln His Pro Asp Lys Ala Pro Lys Leu
        35                  40                  45

Ile Ile Tyr Glu Val Asn Arg Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Asp Asp Glu Ala Asp Tyr Tyr Cys Ala Ala Trp Asp Ser
                85                  90                  95

Leu Asp Gly Pro Val Phe Gly Gly Gly Thr Lys Leu Thr Val Leu
            100                 105                 110

<210> SEQ ID NO 519
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 519

Gln Val Gln Leu Val Gln Ser Gly Ala Glu Val Lys Lys Pro Gly Ser
1               5                   10                  15

-continued

```
Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Lys Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Arg Glu Tyr Leu Gly Asp Asp Tyr Ser Ser Gly Tyr Phe Asp
            100                 105                 110

Val Trp Gly Gln Gly Thr Leu Val Thr Val Ser Ser
        115                 120
```

<210> SEQ ID NO 520
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 520

```
Glu Thr Thr Leu Thr Gln Ser Pro Gly Thr Leu Ser Leu Ser Pro Gly
1               5                   10                  15

Glu Thr Ala Ile Leu Ser Cys Arg Ala Ser Gln Ser Val Asp Ser His
            20                  25                  30

Leu Ala Trp Tyr Gln Gln Lys Gly Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Asn Gly Leu Glu Pro
65                  70                  75                  80

Glu Asp Phe Ala Ile Tyr Phe Cys Gln Gln Arg Ser Met Trp Pro Leu
                85                  90                  95

Thr Phe Gly Gly Gly Thr Lys Val Glu Ile Lys
            100                 105
```

<210> SEQ ID NO 521
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 521

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Met Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Glu Ser Gly Tyr Ser Gly Thr Gly Gln Phe Asp Val Trp Gly
            100                 105                 110

Gln Gly Thr Leu Val Thr Val Ser Ser
        115                 120

<210> SEQ ID NO 522
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 522

Gln Ser Val Leu Thr Gln Pro Pro Ser Ala Ser Gly Thr Ala Gly Gln
1               5                   10                  15

Arg Val Thr Ile Ser Cys Phe Gly Arg Thr Ser Asn Val Gly Arg Asn
            20                  25                  30

Thr Val Asn Trp Tyr Gln Gln Leu Pro Gly Ala Ala Pro Lys Ile Leu
        35                  40                  45

Ile Phe Asn Asp Asn Gln Arg Pro Ser Gly Val Pro Asp Arg Phe Ser
50                  55                  60

Gly Ser Lys Ser Gly Thr Ala Ala Ser Leu Thr Ile Ser Arg Leu Gln
65                  70                  75                  80

Ser Ala Asp Glu Ala Asp Tyr Tyr Cys Ser Ser Trp Asp Asp Ser Leu
                85                  90                  95

Asn Gly Pro Val Phe Gly Gly Gly Thr Lys Leu Ser Val Val
            100                 105                 110

<210> SEQ ID NO 523
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 523

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Tyr Tyr Asp Tyr Gly Val Gly Tyr Asp Gln Trp
            100                 105                 110

Gly Gln Gly Thr Leu Val Thr Val Ser Ser
        115                 120

<210> SEQ ID NO 524
<211> LENGTH: 107
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 524

Gln Pro Val Leu Thr Gln Pro Pro Ser Ala Ser Gly Thr Pro Gly Gln
1               5                   10                  15

Arg Val Thr Ile Ser Cys Ser Gly Gly Arg Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn His Arg Pro Ser Gly Val Pro Asp Arg Phe Ser
    50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Gln Ser Tyr Asp Ser Ser Val
                85                  90                  95

Val Phe Gly Gly Gly Thr Lys Leu Thr Val Leu
            100                 105

<210> SEQ ID NO 525
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 525

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Thr Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Tyr Ser Pro Ser Ile Gly Gly Phe Asp Val Trp
            100                 105                 110

Gly Gln Gly Thr Leu Val Thr Val Ser Ser
        115                 120

<210> SEQ ID NO 526
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 526

Gln Pro Gly Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Arg Asn
```

```
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Val Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Val Ser Leu
                85                  90                  95

Asn Gly Gln Val Phe Gly Thr Gly Thr Lys Val Thr Val Leu
            100                 105                 110

<210> SEQ ID NO 527
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 527

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Gly Tyr Asp Pro Ser Ser Leu Arg Gly Phe Asp Val
            100                 105                 110

Trp Gly Gln Gly Thr Leu Val Thr Val Ser Ser
        115                 120

<210> SEQ ID NO 528
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 528

Ser Tyr Glu Leu Thr Gln Pro Pro Ser Val Ser Lys Asp Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Phe Tyr Lys Asn Asn Asn Arg Pro Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
```

```
                85                  90                  95
Ser Asp Trp Val Phe Gly Gly Gly Thr Lys Leu Thr Val Leu
            100                 105                 110

<210> SEQ ID NO 529
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 529

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Glu Ala Tyr Tyr Asp Leu Trp Gly Gln Gly Thr Leu
            100                 105                 110

Val Thr Val Ser Ser
        115

<210> SEQ ID NO 530
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 530

Glu Ile Val Leu Thr Gln Ser Pro Gly Thr Leu Ser Leu Ser Pro Gly
1               5                   10                  15

Glu Arg Ala Thr Leu Ser Cys Trp Ala Ser Gln Ser Val Ser Ser Phe
            20                  25                  30

Leu Ala Trp Tyr Gln His Lys Pro Gly Gln Val Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr His Phe Thr Leu Thr Ile Ser Ser Leu Glu Pro
65                  70                  75                  80

Glu Asp Phe Ala Val Tyr Tyr Cys Gln Gln Arg Phe Asn Trp Pro Pro
                85                  90                  95

Thr Phe Gly Gln Gly Thr Lys Val Glu Ser Lys
            100                 105

<210> SEQ ID NO 531
<211> LENGTH: 122
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 531

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Thr Pro Met Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Ser Tyr Leu Pro Gly Arg Ser Gly Phe Asp Val Trp
            100                 105                 110

Gly Gln Gly Thr Leu Val Thr Val Ser Ser
        115                 120

<210> SEQ ID NO 532
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 532

Gln Pro Gly Leu Thr Gln Pro Pro Ser Val Ser Val Ser Pro Gly Gln
1               5                   10                  15

Thr Ala Arg Ile Thr Cys Ser Ala Asp Ala Leu Pro Lys Gln Tyr Ala
            20                  25                  30

Tyr Trp Tyr Gln Gln Arg Pro Gly Gln Ala Pro Val Leu Leu Ile Tyr
        35                  40                  45

Lys Asp Thr Glu Arg Pro Pro Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ala Ser Glu Asn Ser
                85                  90                  95

Val Phe Gly Gly Gly Thr Lys Val Thr Val Leu
            100                 105

<210> SEQ ID NO 533
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 533

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Arg Ser Tyr
            20                  25                  30

Ala Ile Ser Trp Val Arg Gln Ala Pro Gly Gln Gly Leu Glu Trp Met
        35                  40                  45

Gly Ile Ser Ala Met Phe Gly Thr Ala Asn Tyr Ala Gln Lys Phe
            50                  55                  60

Gln Gly Arg Val Thr Ile Thr Ala Asp Lys Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Arg Gly Tyr Asp Pro Ser Val Gly Gly Phe Asp Val Trp
                100                 105                 110

Gly Gln Gly Thr Leu Val Thr Val Ser Ser
            115                 120

<210> SEQ ID NO 534
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 534

Asn Phe Met Leu Thr Gln Pro His Ser Val Ser Glu Ser Pro Gly Lys
 1               5                  10                  15

Thr Val Ser Ile Ser Cys Thr Gly Ser Ser Gly Ser Ile Ala Ser Asn
             20                  25                  30

Tyr Val Gln Trp Tyr Gln Gln Arg Pro Gly Ser Ala Pro Ala Thr Val
         35                  40                  45

Ile Tyr Glu Asp Asn Gln Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Thr
                 85                  90                  95

Ser Asn Leu Val Phe Gly Val Gly Thr Lys Leu Thr Val Leu
                100                 105                 110

<210> SEQ ID NO 535
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 535

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Asp Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ser Thr Pro Ser Val Thr Ser Ser Leu Tyr Arg Ile Pro
                100                 105                 110

-continued

Ala Phe Asp Val Trp Gly Gln Gly Thr Leu Val Thr Val Ser Ser
        115                 120                 125

<210> SEQ ID NO 536
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 536

Leu Pro Val Leu Thr Gln Ser Ser Ala Ser Ala Ser Leu Gly Ser
1               5                   10                  15

Ser Val Lys Leu Thr Cys Ser Leu Thr Asn Gly Pro Ser Asn Tyr Ile
            20                  25                  30

Ile Ala Trp His Gln Gln Pro Glu Lys Gly Pro Arg Tyr Leu Met
        35                  40                  45

Lys Leu Asn Ser Asp Gly Ser His Ser Lys Gly Asp Gly Ile Pro Asp
50                  55                  60

Arg Phe Ser Gly Ser Ser Ser Gly Ala Glu Arg Tyr Leu Thr Ile Ser
65                  70                  75                  80

Asn Leu Lys Ser Glu Asp Glu Ala Asp Tyr Tyr Cys Glu Thr Trp Asp
                85                  90                  95

Ser Asn Thr His Val Val Phe Gly Gly Thr Lys Leu Thr Val Leu
            100                 105                 110

<210> SEQ ID NO 537
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 537

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Thr Pro Met Phe Gly Thr Ala Asn Tyr Ala Gln Lys Phe
50                  55                  60

Gln Gly Arg Val Thr Ile Thr Ala Asp Lys Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Arg Gly Pro Gly Tyr Tyr Pro Asp Ser Asn Asn Tyr Asp Leu Trp
            100                 105                 110

Gly Gln Gly Thr Leu Val Thr Val Ser Ser
        115                 120

<210> SEQ ID NO 538
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 538

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys Gln Gln Val Asn Ser Phe Pro
                85                  90                  95

Arg Thr Phe Gly Gln Gly Thr Lys Leu Glu Met Lys
            100                 105

<210> SEQ ID NO 539
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 539

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Met Phe Gly Thr Ala Asn Tyr Ala Gln Lys Phe
    50                  55                  60

Gln Gly Arg Val Thr Ile Thr Ala Asp Gln Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Tyr Ser Gly Gly Tyr Phe Asp Val Trp
            100                 105                 110

Gly Gln Gly Thr Leu Val Thr Val Ser Ser
        115                 120

<210> SEQ ID NO 540
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 540

Gln Pro Val Leu Thr Gln Pro Pro Ser Ala Ser Ala Thr Pro Gly Gln
1               5                   10                  15

Thr Val Thr Ile Ser Cys Ser Gly Ser Ser Ser Asn Ile Gly Val Ser
            20                  25                  30

Phe Val Tyr Trp Tyr Gln Gln Phe Pro Gly Thr Ala Pro Lys Leu Leu
        35                  40                  45

Ile Tyr Arg Asp Asp Met Arg Gln Ser Gly Val Pro Asp Arg Phe Ser
 50                  55                  60

Gly Phe Lys Ser Gly Ser Ser Ala Ser Leu Thr Ile Ser Gly Leu Gln
 65                  70                  75                  80

Ser Glu Asp Glu Ala Thr Tyr Tyr Cys Ser Ala Trp Asp Glu Ser Leu
                 85                  90                  95

Ser Ser Val Leu Phe Gly Gly Gly Thr Lys Val Thr Val Leu
            100                 105                 110

<210> SEQ ID NO 541
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 541
caggttcaat tagtgcagtc tggtgctgaa gtgaaaaagc ccggctcaag tgttaaagta      60
agctgtaagg cgagcggagg tactttagc tcatacgcca ttagctgggt gcgacaggct     120
cctggtcagg gcctcgaatg gatgggcggc attatcacaa tctttggtac tgcaaattat    180
gcccagaaat ttcagggtag agtcacaatt accgcagaca aaagtacctc aaccgcatac    240
atggaactga gtagcctgcg ttccgaagat acagctgtgt attactgtgc gcgcggtgct    300
acaggtttct acgacgtttg gggccagggg accttagtca ctgtgtctag c            351

<210> SEQ ID NO 542
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 542
ctgcctgtgc tgactcagcc accctcagcg tctgggaccc ccgggcagag ggtcaccatc     60
tcttgttctg gaagcagctc aacatcgga agtaatactg taaactggta ccagcagctc    120
ccaggaacgg ccccccaaact cctcatctat agtaataatc agcggccctc aggggtccct    180
gaccgattct ctggctccaa gtctggcacc tcagcctccc tggccatcag tgggctccag    240
tctgaggatg aggctgatta ttactgtgca gcatgggatg acagcctgaa tggtccggta    300
ttcggcggag ggaccaagct gaccgtccta g                                  331

<210> SEQ ID NO 543
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 543
caggttcaat tagtgcagtc tggtgctgaa gtgaaaaagc ccggctcaag tgttaaagta      60
agctgtaagg cgagcggagt tactttcagc tcatacgcca ttagctgggt gcgacaggct    120
cctggtcagg gcctcgaatg gatgggcggc attagcccta tcttcggcac tgcaaattat    180
gcccagaaat ttcagggtag agtcacaatt accgcagatg aaagcacgtc aactgcatac    240
atggaactga gtagcctgcg ttccgaagat acagctgtgt attactgtgc gcgcggtcgt    300
gagtactacg ctagtaatgg tgacagtttc gatgtttggg gccaggggac cttagtcact    360
gtgtctagc    369

<210> SEQ ID NO 544
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 544
cagcctgtgc tgactcagcc accctcggtg tcagtggccc caggaaagac ggccagcatt    60
tcctgtgagg gaaacaacat tgcgactaaa agtgtgcact ggtaccagca gaagtcaggc    120 cacgccoctg tggtggtcgt ctatcatgat agcgaccggc cctcagggt ccctgaccga    180 ttctctggct ccaagtctgg cacctcagcc tccctggcca tcagtgggct ccggtccgag    240
gatgaggctg attattactg tgcagcatgg gatgacagcc tgagtggtcc ttgggtgttc    300
ggcggaggga ccaagctgac cgtcctag    328

<210> SEQ ID NO 545
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 545
caggttcaat tagtgcagtc tggtgctgaa gtgaaaaagc ccggctcaag tgttaaagta    60
agctgtaagg cgagcggagg tacctttagt tcatacgcca ttagctgggt gcgacaggct    120
cctggtcagg gcctcgaatg gatgggcggc attagcgcaa tcttcggcac tgcaaattat    180
gcccagaaat tcagggtag agtcacaatt accgcagatg agagcacgcg caccgcatac    240
atggaactga gtagcctgcg ttccgaagat acagctgtgt attactgtgc gcgcggtagt    300
ggttactacg ttgctgctag tggtgctttc gacgtgtggg gccaggggac cttagtcact    360
gtgtctagc    369

<210> SEQ ID NO 546
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 546
cagcctgggc tgactcagcc accctcggtg tcaagggct tgagacagac cgccacactc    60
acctgcactg gaacatcaa caatgttggc gaccaaggag caggttggct gcagcagcac    120
cagggccgcc ctcccaaact cctgtcgtac aggaatagca accggccctc aggtgtctca    180
gagagattct ctgcatccag gtcaggaaat acagcctccc tgaccattac tggactccag    240
cctgaggacg aggctgacta ttactgctca gcatgggaca gcagcctcag tgattgggtg    300
ttcggcggag ggaccaagct gaccgtccta g    331

<210> SEQ ID NO 547
<211> LENGTH: 381
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 547
caggttcaat tagtgcagtc tggtgctgaa gtgaaaaagc ccggctcaag tgttaaagta      60
agctgtaagg cgagcggtgg catcttcagc tcatacgcca ttagctgggt gcgacaggct     120
cctggtcagg gcctcgaatg gatgggcggc atcacccaa tcttcggcac tgcaaattat     180
gcccagaaat ttcagggtag agtcacaatt accgcagacg aaagcacgcg taccgcatat     240
atggaactga gtagcctgcg ttccgaagat acagctgtgt attactgtgc gcgcgacctg     300
agtcgtgaca gtctgaatct gcctggtagt agtcctggtt acgatctctg gggccagggg     360
accttagtca ctgtgtctag c                                                381

<210> SEQ ID NO 548
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 548
gaaacgacac tcacgcagtc tccaggcacc ctgtctttgt ctccaggaga aagagccacc      60
ctctcctgca gggccagtca gagtgttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtgtatta ctgtcagcag tatagtagtt ctccctacac ttttggccag     300
gggaccaaac tggagatcaa ac                                               322

<210> SEQ ID NO 549
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 549
caggttcaat tagtgcagtc tggtgctgaa gtgaaaaagc ccggctcaag tgttaaagta      60
agctgtaagg cgagcggagt gattttcagc tcatacgcca ttagctgggt gcgacaggct     120
cctggtcagg gcctcgaatg gatgggcggc attagcccta tcttcggcac tgcaaattat     180
gcccagaaat ttcagggtag agtcacaatt accgcagatg agagcacgtc aaccgcatat     240
atggaactga gtagcctgcg ttccgaagat acagctgtgt attactgtgc gcgcagtcgt     300
ggttacgctc ctggtacaag tttccactac gatgtgtggg gccaggggac cttagtcact     360
gtgtctagc                                                              369

<210> SEQ ID NO 550
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 550
```

```
ctgcctgtgc tgactcaggc accctcaatg tcagtggccc caggaaagac ggccagtatt    60
acctgtgggg gagacaacat tggaagtaaa agtgtgcact ggtaccagca gaagccaggc   120
caggcccctg tgctggtcat gtattatgat agcgaccggc cctcagggat ccctgagcga   180
ttctctggct ccaactctgg gaacacggcc accctgacca tcagcagggt cgaggccggg   240
gatgaggccg actatttctg ccagctgtgg gatcatacta attctcatgt ggtcttcggc   300
ggaaggacca aactgaccgt cctag                                         325
```

<210> SEQ ID NO 551
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 551

```
caggttcaat tagtgcagtc tggtgctgaa gtgaaaaagc ccggctcaag tgttaaagta    60
agctgtaagg cgagcggtgg cacctttagt tcttacgcca ttagctgggt gcgacaggct   120
cctggtcagg gcctcgaatg gatgggcggc attagcccaa tctttggcac tgcaaattat   180
gcccagaaat ttcagggtag agtcacaatt acctcagatg agagtaccag cactgcatac   240
atggaactga gtagcctgcg ttccgaagat acagctgtgt attactgtgc gcgcgaccaa   300
ggtggtacac gtggtaatta cttcgacgtt tggggccagg ggaccttagt cactgtgtct   360
agc                                                                 363
```

<210> SEQ ID NO 552
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 552

```
cagcctgtgc tgactcagcc accctcggtg tccaagggct tgagacagac cgccacagtc    60
acctgcactg gaacagcaa caatgttggc aaccaaggag cagcttggct gcagcagcac   120
cagggccacc ctcccaaact cctatcctac aggaataaca accggccctc agggatttca   180
gagagattat ctgcatccag gtcaggaaac acagcctccc tgaccattgc tggactccag   240
cctgaggacg aggctgacta ttactgctca gcatgggaca caccgtcag tggttgggtg   300 ttcggcggag ggaccagggt gaccgtccta g                                  331
```

<210> SEQ ID NO 553
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 553

```
caggttcaat tagtgcagtc tggtgctgaa gtgaaaaagc ccggctcaag tgttaaagta    60
agctgtaagg cgagcggtgg tactttcagt tcatacgcca ttagctgggt gcgacaggct   120
cctggtcagg gcctcgaatg gatgggcggc attatcacaa tcttcggtac tgcaaattat   180
gcccagaaat ttcagggtag agtcacaatt accgcagatg agagcacgaa caccgcctac   240
```

```
atggaactga gtagcctgcg ttccgaagat acagctgtgt attactgtgc gcgcggtggt    300
ggtggtcgtt ttgacgtttg gggccagggg accttagtca ctgtgtctag c             351

<210> SEQ ID NO 554
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 554
tcctatgagc tgactcagcc accctcagtg tctgggaccc ccgggcagag ggtcaccatc     60
tcttgttctg gaagcacctc caacatcgga ataatgctc taaactgta ccagaaactc     120 ccagggacgg cccccaaact cctcatctat agtcttaatc agcgtccctc agggtccct     180 gaccgattct ctggctccaa gtctggcacc tcagcctccc tggccatcag tgggctccag    240
tctgaggatg aggctgatta ttactgtgaa gcatgggatg acagcctgag tggtccggtg    300
ttcggcggag ggaccaaggt gaccgtccta g                                   331

<210> SEQ ID NO 555
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 555
caggttcaat tagtgcagtc tggtgctgaa gtgaaaaagc ccggctcaag tgttaaagta     60
agctgtaagg cgagcggagg tccatttcgc tcatacgcca ttagctgggt gcgacaggct    120
cctggtcagg gcctcgaatg gatgggcggc attatcccaa tcttcggcac tgcaaattat    180
gcccagaaat tcagggtag agtcacaatt accgcagatg aaagtacgtc aactgcatac    240
atggaactga gtagcctgcg ttccgaagat acagctgtgt attactgtgc gcgcggtggt    300
gtttacagtt ttgatgtgtg gggccagggg accttagtca ctgtgtctag c             351

<210> SEQ ID NO 556
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 556
cagtctgggc tgactcagcc accctcagcg tctgggaccc ccgggcagag ggtcaccatt     60
tcttgttctg gaagcggctc caacgtcgga agtaatgttg taaattggta ccagcatctc    120
ccaggaacgg cccccaaact cctcatctat cgtaataatc agcggccctc agggtccct     180 gaccgattct ctggctccaa gtctggcacc tcagcctccc tggccatcag tgggctccag    240
tctgaggatg aggctgatta ttattgtgca gcatgggatg acagactgaa tggctttgtc    300
tttggtactg ggacgaaggt caccgtcctg a                                   331

<210> SEQ ID NO 557
<211> LENGTH: 375
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 557
caggttcaat tagtgcagtc tggtgctgaa gtgaaaaagc ccggctcaag tgttaaagta    60
agctgtaagg cgagcggtgt tcctttcagt tcttacgcca ttagctgggt gcgacaggct   120
cctggtcagg gcctcgaatg gatgggcggc atcagcccac tgtttggtac tgcaaattat   180
gcccagaaat ttcagggtag agtcacaatt accgcagacc agagcacgtc aaccgtctac   240
atggaactga gtagcctgcg ttccgaagat acagctgtgt attactgtgc gcgcggtctg   300
ggtacataca gtcctagtct gtaccctcgt ggtatggacg tttggggcca ggggaccttg    360
gtcactgtgt ctagc                                                   375

<210> SEQ ID NO 558
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 558
ctgcctgtgc tgactcagcc accctcagcg tctgggaccc ccggacagag tgtcaccatc    60
tcttgttctg gaagcagctc caacatcggc agaaatgatg ttaactggta ccagcaattc   120
ccgggaaggg ccccccaaact cctcatctat ggtcgtgatg agcggccctt cggggtccct   180
gcccgattct ctggctccaa gtctggcacc tcagcctccc tggccatcag tgggctccag   240
tctgaggatg aggctgatta ttactgtgct catgggatg ccagtctgat gatctatgtc    300
ttcggaactg ggaccacggt caccgtcctg g                                  331

<210> SEQ ID NO 559
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 559
caggttcaat tagtgcagtc tggtgctgaa gtgaaaaagc ccggctcaag tgttaaagta    60
agctgtaagg cgagcggagt gacctttagt tcatacgcca ttagctgggt gcgacaggct   120
cctggtcagg gcctcgaatg gatgggcggc atcagcccta tgttcggcac tgcaaattat   180
gcccagaaat ttcagggtag agtcacaatt accgcagacg aaagtacgaa tactgtctat   240
atggaactga gtagcctgcg ttccgaagat acagctgtgt attactgtgc gcgcggtcgt   300
gcttacctga gtgttcgtgg tagtttcgac gtgtggggcc aggggacctt agtcactgtg   360
tctagc                                                              366

<210> SEQ ID NO 560
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 560

```
tcctatgagc tgactcagcc accctcagtg tctgggaccc ccgggcagag ggtcaccatc    60
tcttgttctg gaagcagctc caacatcgga agtaacactg taaactggta ccagcagctc   120
ccaggaacgg cccccaaact cctcatctat agtaataatc agcggccctc agggggtccct  180 gaccgattct ctggctccaa gtctggcacc tcagcctccc tggccatcag tgggctccag   240
tctgaggatg aggctgatta ttactgtgca gcatgggatg acagcctgaa tggttatgtc   300
ttcggaactg ggaccaaggt caccgtccta g                                   331

<210> SEQ ID NO 561
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 561
caggttcaat tagtgcagtc tggtgctgaa gtgaaaaagc ccggctcaag tgttaaagta    60
agctgtaagg cgagcggtgt gatttttcagt tcttacgcca ttagctgggt gcgacaggct  120
cctggtcagg gcctcgaatg gatgggcggc atcatcccaa tctttggcac tgcaaattat   180
gcccagaaat ttcagggtag agtcacaatt accgcagata aaagtacgtc aactgcctat   240
atggaactga gtagcctgcg ttccgaagat acagctgtgt attactgtgc gcgcggtggt   300
agtggtagtt tcgacgtttg gggccagggg accttagtca ctgtgtctag c            351

<210> SEQ ID NO 562
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 562
cagcctgggc tgactcagcc accctcagcg tctgggaccc ccgggcagag ggtcaccatc    60
tcttgttctg gaagcagttc caacctcgga agtaattatg tcttctggta ccagcaccto   120 ccaggagcgg cccccaaact cctcatctat agaaatagtc agcggccctc tggggtccct   180
gaccgattct ctggctccaa gtctggcacc tcagcctccc tggccatcag tgggctccag   240
tctgaggatg aggctgatta ttactgtgca gcatgggatg acagcctgaa tggtgtggta   300
ttcggcggag ggaccaagct gaccgtccta g                                   331

<210> SEQ ID NO 563
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 563
caggttcaat tagtgcagtc tggtgctgaa gtgaaaaagc ccggctcaag tgttaaagta    60
agctgtaagg cgagcggagt gactttcagc tcttacgcca ttagctgggt gcgacaggct  120
cctggtcagg gcctcgaatg gatgggcggc atcagccctg tgtttggtac tgcaaattat   180
gcccagaaat ttcagggtag agtcacaatt accgcagatg atagtacgaa taccgcctac   240
atggaactga gtagcctgcg ttccgaagat acagctgtgt attactgtgc gcgcagtcgt   300
```

```
ggttacacag ttagtagtct ggctggtcgt tacttcgacc agtggggcca ggggacctta      360
gtcactgtgt ctagc                                                       375
```

<210> SEQ ID NO 564
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 564

```
gaaacgacac tcacgcagtc tccaggcacc ctgtccttgt ctccagggga aagagcctcc      60
ctctcctgca aggccagtga gagtctttgc agcacttgct tggcctggta ccagcagaaa     120
cctggccagg ctcccaggct catcgtctat ggtgcaacca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctca gacgttcggc     300
caagggacca aggtggaaat caaac                                           325
```

<210> SEQ ID NO 565
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 565

```
caggttcaat tagtgcagtc tggtgctgaa gtgaaaaagc ccggctcaag tgttaaagta      60
agctgtaagg cgagcggagg cacttttagc tcatacgcca ttagctgggt gcgacaggct     120
cctggtcagg gcctcgaatg gatgggcggc atcgtgccac tgtttggcac tgcaaattat     180
gcccagaaat ttcagggtag agtcacaatt accgcagacg aaagtaccag cactgcatat     240
atggaactga gtagcctgcg ttccgaagat acagctgtgt attactgtgc gcgcggtctg     300
ggtctgtact ttgacgtgtg gggccagggg accttagtca ctgtgtctag c              351
```

<210> SEQ ID NO 566
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 566

```
cagactgtgg tgactcagga gccctcactg actgtgtccc caggagagac agtcactctc      60
acctgtgctt ccagcactgg agcagtcacc agtggttact atccaaactg gttccagcag     120
aaacctggac aagcacccag gcactgatt tatagtacaa gcaacaaaca ctcctggacc     180
cctgcccggt tctcaggctc cctccttggg gcaaagctg ccctgacact gtcaggtgtg     240
cagcctgagg acgaggctga gtattattgt ctgctctact atggtggtcc ttgggtgttc     300
ggcggaggga ccaagttgac cgtcctgg                                        328
```

<210> SEQ ID NO 567
<211> LENGTH: 366
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 567

| caggttcaat tagtgcagtc tggtgctgaa gtgaaaaagc ccggctcaag tgttaaagta | 60 |
| agctgtaagg cgagcggtgg tactttcagc tcatacgcca ttagctgggt gcgacaggct | 120 |
| cctggtcagg gcctcgaatg gatgggcggc attatcccaa tcttcggtac tgcaaattat | 180 |
| gcccagaaat ttcagggtag agtcacaatt accgcagacg aaagcacgaa caccgcctac | 240 |
| atggaactga gtagcctgcg ttccgaagat acagctgtgt attactgtgc gcgcgttcgt | 300 |
| ggtggttacg gtccttacgg tgactttgac gtttggggcc aggggacctt agtcactgtg | 360 |
| tctagc | 366 |

<210> SEQ ID NO 568
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 568

| cagcctgggc tgactcagcc accctcagcg tctgggaccc ccgggcagag ggtcaccatc | 60 |
| tcttgttctg gaagcagctc caacatcgga agtcattctg tgaactggta ccggcagctc | 120 |
| ccaggaacgg cccccccaact cctcatctat ggtaacagca atcggccctc aggggtccct | 180 |
| gaccgattct ctggctccaa gtctggcacc tcagcgtccc tggccatcag tgggctccag | 240 |
| tctgaggatg aggctgatta tttctgtgcg gcatgggatg acggcctgag tggttgggtg | 300 |
| ttcggcggag ggaccaaatt gaccgtccta g | 331 |

<210> SEQ ID NO 569
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 569

| caggttcaat tagtgcagtc tggtgctgaa gtgaaaaagc ccggctcaag tgttaaagta | 60 |
| agctgtaagg cgagcggtgg ccctttttagc tcatacgcca ttagctgggt gcgacaggct | 120 |
| cctggtcagg gcctcgaatg gatgggcggc attagcccaa tcttcggcac tgcaaattat | 180 |
| gcccagaaat ttcagggtag agtcacaatt accgcagata agagtacgaa caccgcatac | 240 |
| atggaactga gtagcctgcg ttccgaagat acagctgtgt attactgtgc gcgcggtcgt | 300 |
| agttacatcg ttagtgttag tcctggtttt gacgtgtggg gccaggggac cttagtcact | 360 |
| gtgtctagc | 369 |

<210> SEQ ID NO 570
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 570

| cagtctgtgc tgactcagcc accctccgcg tccgggtctc ctggacagtc agtcaccatc | 60 |

```
tcctgcactg gaaccagcag tgacgttggt ggttataact atgtctcctg gtaccaacag    120
tacccaggca aagcccccaa actcatgatt tatgaggtca gtaagcggcc ctcagggggtc   180 cctgatcgtt tctctggctc caagtctggc acctcagcct ccctggccat cagtgagctc    240
caatctgagg atgaggctga ttattactgt gcatcatggg atgacagcct gaatgcttat    300
gtcttcggaa gtgggaccaa ggtcaccgtc ctgg                                334

<210> SEQ ID NO 571
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 571
caggttcaat tagtgcagtc tggtgctgaa gtgaaaaagc ccggctcaag tgttaaagta     60
agctgtaagg cgagcggagg catttttcagt tcatacgcca ttagctgggt gcgacaggct   120
cctggtcagg gcctcgaatg gatgggcggc atcagcgcaa tctttggtac tgcaaattat    180
gcccagaaat tcagggtag agtcacaatt accgcagatg agagtaccag caccgcatat     240
atggaactga gtagcctgcg ttccgaagat acagctgtgt attactgtgc gcgcgacagt    300
ggtatcgcta tggttacac agcttacatg gattattggg gccaggggac cttagtcact    360
gtgtctagc                                                            369

<210> SEQ ID NO 572
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 572
tcttctgagc tgactcagga ccctgctgtg tctgtggcct tgggacagac agtcaggatc     60
acatgccaag gagacagcct cagaacctct tacgcaagct ggtaccagca gaagccaggc   120
cagtcccctg tactggtcat ctatcaaagt actaagcggc cctcagggat ccctgagcga    180
ttctctgcct ccagctcagg aaacacagct tccctgacca tcactgggggc tcaggcggaa   240 gatgaggctg actattactg taactcccgg ggcagcgggg gtaacccccta tgtcttcgga   300 actgggacca aggtcaccgt ccttg                                          325

<210> SEQ ID NO 573
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 573
caggttcaat tagtgcagtc tggtgctgaa gtgaaaaagc ccggctcaag tgttaaagta     60
agctgtaagg cgagcggtgg catttttccgt tcatacgcca ttagctgggt gcgacaggct  120
cctggtcagg gcctcgaatg gatgggcggc attatcccaa tgttcggtac tgcaaattat    180
gcccagaaat tcagggtag agtcacaatt accgcagatg agagtacgac tactgtctat     240
atggaactga gtagcctgcg ttccgaagat acagctgtgt attactgtgc gcgcggtgct    300
```

<210> SEQ ID NO 574
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 574

```
cagtctgtgc tgactcagcc accctcagcg tctgggaccc ccgggcagag ggtcaccatc      60
tcttgttctg gaagcagctc caacatcgga agtaatactg taaactggta ccagcagctc     120
ccaggaacgg cccccagact cctcatctat agtaataatc agcggccctc agggtccct     180 gaccgattct ctggctccaa gtctggcacc tcagcctccc tggccatcag tgggctccag     240
tctgaggatg aggctgatta ttactgtgca gcatgggatg acagcctgaa tggtcgggtg     300
ttcggcggag gaccaagct gaccgtccta g                                    331
```

<210> SEQ ID NO 575
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 575

```
caggttcaat tagtgcagtc tggtgctgaa gtgaaaaagc ccggctcaag tgttaaagta      60
agctgtaagg cgagcggtgg taccttcagc tcatacgcca ttagctgggt gcgacaggct     120
cctggtcagg gcctcgaatg gatgggcggc attaaccta tctttggtac tgcaaattat     180
gcccagaaat ttcagggtag agtcacaatt accgcagatg agagcacgaa tactgcctac     240
atggaactga gtagcctgcg ttccgaagat acagctgtgt attactgtgc gcgcggtgag     300
agtgcttact acagtcgtaa ttacgatgtg tggggccagg ggaccttagt cactgtgtct     360
agc                                                                  363
```

<210> SEQ ID NO 576
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 576

```
tcctatgagc tgactcagcc accctcggtg tccaagggct tgagacagac cgccacactc      60
acctgcactg ggaacagcag caatgttggc aaccaaggag catcttggct gcagcagcac     120
cagggccacc ctcccaaact cctatcctac aggaatgaca accggccctc agggatctca     180
gagagattct ctgcatccag gtcaggaaat acagcctccc tgaccattac tggactccag     240
cctgaggacg aggctgacta ttactgctca gcatgggaca cagcctcag tgcttgggtg     300 ttcggtggag gaccaagct gaccgtccta g                                    331
```

<210> SEQ ID NO 577
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 577
caggttcaat tagtgcagtc tggtgctgaa gtgaaaaagc ccggctcaag tgttaaagta      60
agctgtaagg cgagcggtgt gacttttagc tcatacgcca ttagctgggt gcgacaggct     120
cctggtcagg gcctcgaatg gatgggcggc atcagcccaa tgttcggcac tgcaaattat     180
gcccagaaat ttcagggtag agtcacaatt accgcagatg agagcacgaa taccgcatat     240
atggaactga gtagcctgcg ttccgaagat acagctgtgt attactgtgc gcgcggtggt     300
ggttactacc ctgctggtgt tggtcgttat gatgtttggg gccaggggac cttagtcact     360
gtgtctagc                                                             369

<210> SEQ ID NO 578
<211> LENGTH: 340
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 578
gacatcgtga tgacccagtc tccagactcc ctggctgtgt ctctgggcga gagggccacc      60
atcaactgca gtccagcca gaatgtttta tacagctcca acaataagaa taacttagct     120
tggtaccaac aaagaccagg acagcctcct aaagtgctcc tttattgggc atctacccgg     180
gcatccgggg tccctgaccg attcagtggc agcgggtctg ggacagattt cactctcacc     240
atcaacagcc ttcaggctga agatgtggca ctttattact gtcaacaata ttatggtaaa     300 ccccttcactt tcggccctgg gaccaaagtg gagatcaaac                          340

<210> SEQ ID NO 579
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 579
caggttcaat tagtgcagtc tggtgctgaa gtgaaaaagc ccggctcaag tgttaaagta      60
agctgtaagg cgagcggagg tacctttagc tcatacgcca ttagctgggt gcgacaggct     120
cctggtcagg gcctcgaatg gatgggcggc attacccctc tgttcggcac tgcaaattat     180
gcccagaaat ttcagggtag agtcacaatt accgcagacg atagtacgtc aactgcatat     240
atggaactga gtagcctgcg ttccgaagat acagctgtgt attactgtgc gcgcggtcct     300
acactgtaca gtcctcctgt ttttgatgtg tggggccagg ggaccttagt cactgtgtct     360
agc                                                                   363

<210> SEQ ID NO 580
<211> LENGTH: 331
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 580

```
cagactgtgg tgactcagga gccatcgttc tcagtgtccc ctggagggac aatcaccctc    60
acttgtggct tgagttctgg ctcagtctct actactaatt atcccagctg gtaccagcag   120
accccaggcc gaactccacg cacgctcatc tacaacacaa acactcgctc ttctggggtc   180
cctgatcgct tctctggctc catccttggg aacaaagctg ccctcaccat cacggggcc    240 caggcaggtg atgaatctga ttattactgt gttttatata tgggtcgtgg catttatgtc   300
ttcggaagtg ggaccaaggt ctccgtcctg g                                 331
```

<210> SEQ ID NO 581
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 581

```
caggttcaat tagtgcagtc tggtgctgaa gtgaaaaagc ccggctcaag tgttaaagta    60
agctgtaagg cgagcggagg cacttttcgc tcttacgcca ttagctgggt gcgacaggct   120
cctggtcagg gcctcgaatg gatgggcggc atcatgccaa tctttggtac tgcaaattat   180
gcccagaaat ttcagggtag agtcacaatt accgcagacg agagtacgac aaccgtgtac   240
atggaactga gtagcctgcg ttccgaagat acagctgtgt attactgtgc gcgcggtgct   300
ggtgttagtg ctggtcctag ttggccttt gacgtttggg gccaggggac cttagtcact   360
gtgtctagc                                                          369
```

<210> SEQ ID NO 582
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 582

```
cagcctgggc tgactcagcc accctcggtg tccaaggact tgaggcagac cgccacactc    60
acctgcactg gaacagcaa caatgttggc aaacaaggag ctacttggct gcagcagcac   120
cagggccacc ctcccaaact cctatcctac aggaataaca accggccctc agggatctca   180
gagagattct ctgcatccag gtcaggagac acagcctccc tgaccattac tggcctccag   240
cctgaggacg aggctgacta ttactgctca gcatgggaca gcagcctcag tgtatgggtg   300
ttcggcggag ggaccaagct gaccgtccta g                                 331
```

<210> SEQ ID NO 583
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 583

```
caggttcaat tagtgcagtc tggtgctgaa gtgaaaaagc ccggctcaag tgttaaagta    60
agctgtaagg cgagcggtgg taccttcagc tcatacgcca ttagctgggt gcgacaggct   120
cctggtcagg gcctcgaatg gatgggcggc attagcccta tgtttggtac tgcaaattat   180
gcccagaaat ttcagggtag agtcacaatt accgcagatg agagcacgtc aaccgtgtac   240
```

```
atggaactga gtagcctgcg ttccgaagat acagctgtgt attactgtgc gcgcagtcgt    300
ggttacaatg ttgctgctag tttcggtttc gatgtgtggg gccaggggac cttagtcact    360
gtgtctagc                                                            369

<210> SEQ ID NO 584
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 584
gaaattgtgt tgacgcagtc tccatccttc ctgtctgcat ctgtaggaga cagagtcacc     60
atcacttgcc gggccagtca gtacattgat cgtagcttac actggtacca gcagaaacca    120
gatcagtctc caaagctcct catcaagtat gcttctcagt ccatctcagg gtcccctcg    180 aggttcagtg gcagtggatc tgggacagat ttcagcctca ccatcaatag cctggaaact    240
gaagatgctg caacctatta ctgccatcag accagtagtt tgccgtggac attcggccaa    300
gggaccacgg tggaaatcaa ac                                             322

<210> SEQ ID NO 585
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 585
caggttcaat tagtgcagtc tggtgctgaa gtgaaaaagc ccggctcaag tgttaaagta     60
agctgtaagg cgagcggtgg cccatttagc tcatacgcca ttagctgggt gcgacaggct    120
cctggtcagg gcctcgaatg gatgggcggc atcatcccta tcttcggcac tgcaaattat    180
gcccagaaat ttcagggtag agtcacaatt accgcagatg aaagtacgtc aaccgcctat    240
atggaactga gtagcctgcg ttccgaagat acagctgtgt attactgtgc gcgcggtaca    300
gactacagtg gttaccgtgg ttttgacgtt tggggccagg ggaccttagt cactgtgtct    360
agc                                                                  363

<210> SEQ ID NO 586
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 586
cagactgtgg tgactcagga gccatcgttc tcagtgtccc ctggagggac agtcacactc     60
acctgtgctt tgagttctgg ctcagtctcc agttttaact acgccagctg gtaccagcag    120
accccaggcc aggcgccacg cacactcatc tccaacacaa acactcgctc ttctggggtc    180
cctgatcgct tctctggctc catccttggg aacaaagcta ccctcaccat cacggggcc    240 caggcagatg atgaatctca ttattactgt gcactgtatg tgggtggtgg catttccgtg    300
ttcggcggag ggaccaagtt gaccgtccta g                                   331

<210> SEQ ID NO 587
```

-continued

```
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 587
caggttcaat tagtgcagtc tggtgctgaa gtgaaaaagc ccggctcaag tgttaaagta      60
agctgtaagg cgagcggtgt tactttagc tcatacgcca ttagctgggt gcgacaggct     120
cctggtcagg gcctcgaatg gatgggcggc atcacccccaa tctttggcac tgcaaattat   180
gcccagaaat ttcagggtag agtcacaatt accgcagatc agagtacgag cactgcatac    240
atggaactga gtagcctgcg ttccgaagat acagctgtgt attactgtgc gcgcggtggt    300
ggtgttttcg acgtttgggg ccaggggacc ttagtcactg tgtctagc                 348

<210> SEQ ID NO 588
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 588
tcctatgagc tgactcagcc accctcggtg tctggagccc ccgacagag ggtcaccatc      60 tcctgttctg gaagcagctc caacatcgga ataatgctg taaactggta ccagcagctc    120
ccaggaaagg ctcccaaact cctcatctat tatgatgata tgctgccctc aggggtctct    180
gaccgattct ctggctccaa gtctggctcc tcagcctccc tggccatcag tgggctccag   240
tctgaggatg aggctgacta ttattgtgca gcatgggatg acagcctgag cggtccggtt    300
ttcggcggag ggaccaacct gaccgtccta g                                   331

<210> SEQ ID NO 589
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 589
caggttcaat tagtgcagtc tggtgctgaa gtgaaaaagc ccggctcaag tgttaaagta      60
agctgtaagg cgagcggagg tactttagt tcttacgcca ttagctgggt gcgacaggct    120
cctggtcagg gcctcgaatg gatgggcggc attagcccta tgttcggtac tgcaaattat   180
gcccagaaat ttcagggtag agtcacaatt accgcagaca aaagtaccag cactgcctac   240
atggaactga gtagcctgcg ttccgaagat acagctgtgt attactgtgc gcgcgagggt   300
ggttacagtc ctggtggtgt tgacttcgac tactggggcc aggggacctt agtcactgtg   360
tctagc                                                               366

<210> SEQ ID NO 590
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 590
```

```
aattttatgc tgactcagcc ccactctgtg tcggagtctc cggggaagac ggtaaccatc    60
tcctgcaccc gcagcagtgg cagcattgcc agcacctatg tgcagtggta ccggcagcgc   120
ccgggcagtg cccccaccac tgtgatctat gaggatcatc agagaccctc tggggtccct   180
gatcggttct ccggctccct cgacagctcc tccaactctg cctccctcac catctctgga   240
ctgaggactg aggacgcggc aacctactac tgtcagtctt ttgatgccag cactctggtg   300
ttcggcggcg ggaccaagct gaccgtcctc g                                  331
```

```
<210> SEQ ID NO 591
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 591
caggttcaat tagtgcagtc tggtgctgaa gtgaaaaagc ccggctcaag tgttaaagta    60
agctgtaagg cgagcggagt gacttttcgt tcatacgcca ttagctgggt gcgacaggct   120
cctggtcagg gcctcgaatg gatgggcggc atcagcggta tctttggtac tgcaaattat   180
gcccagaaat ttcagggtag agtcacaatt accgcagatg agagcacgtc aaccgcatat   240
atggaactga gtagcctgcg ttccgaagat acagctgtgt attactgtgc gcgcagtcct   300
gcttactact tcggtcctaa tatggacgtg tggggccagg ggaccttagt cactgtgtct   360
agc                                                                 363
```

```
<210> SEQ ID NO 592
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 592
cagtctgtgc tgactcagcc accctcagtg tctggggccc cagggcagag ggtcaccatc    60
tcctgcactg ggagcagctc caacatcggg gcaggttatg atgtacactg gtaccagcaa   120
cttccaggaa cagtccccaa actcatcatc tatgataata gcaatcggcc ctcaggggtc   180
cctgcccgat tctctggctc caagtctggc acctcagcct ccctggccat cagtgggctc   240
cagtctgagg atgaggccgc atattattgc cagtcgtatg acagcagcct gagtgttgtg   300
gtattcggcg gtgggaccaa gctgtccgtc ctag                               334
```

```
<210> SEQ ID NO 593
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 593
caggttcaat tagtgcagtc tggtgctgaa gtgaaaaagc ccggctcaag tgttaaagta    60
agctgtaagg cgagcggtgg tactttttagt tcatacgcca ttagctgggt gcgacaggct   120
cctggtcagg gcctcgaatg gatgggcggc attagcccaa tctttggtac tgcaaattat   180
gcccagaaat ttcagggtag agtcacaatt accgcagacg aaagcaccag cactgtgtac   240
```

```
atggaactga gtagcctgcg ttccgaagat acagctgtgt attactgtgc gcgcggtcct    300
ggttaccacc ctgctggtgc tagtggtcaa ttctttgatc tttggggcca ggggaccttta   360 gtcactgtgt ctagc                                                     375
```

<210> SEQ ID NO 594
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 594

```
tcctatgagc tgactcagcc accctcggtg tccaaggact tgagacagac cgccacactc    60
acctgcactg ggaacagcaa caatgttggc aaccaaggag cagcttggct gcagcagcac    120
cagggccacc ctcccaaact cctatcctac aggaataacc accggccctc agggatctca    180
gacagatcat ctgcatccag gtcaggagac acagcctccc tgaccattac tggactccag    240
cctgaggacg aggctgacta ttactgctca gcatgggaca gcagcctcag tgcttgggtg    300
ttcggcggag ggaccaagct gaccgtccta g                                   331
```

<210> SEQ ID NO 595
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 595

```
caggttcaat tagtgcagtc tggtgctgaa gtgaaaaagc ccggctcaag tgttaaagta    60
agctgtaagg cgagcggtgt gaccttcagc tcatacgcca ttagctgggt gcgacaggct    120
cctggtcagg gcctcgaatg gatgggcggc attagcccta tgtttggtac tgcaaattat    180
gcccagaaat tcagggtag agtcacaatt accgcagatg aaagcaccaa caccgcctat    240
atggaactga gtagcctgcg ttccgaagat acagctgtgt attactgtgc gcgcggtcgt    300
ggttacgctc ctgacgctct gacaaatttt gacgtttggg gccaggggac cttagtcact    360
gtgtctagc                                                            369
```

<210> SEQ ID NO 596
<211> LENGTH: 346
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 596

```
gaaattgtgc tgactcagtc tccagactcc ctggctatgt ctctgggcga gagggccacc    60
gtcaactgca gtccagccg gagtcttttc gacagctccg acaataagaa ctacttagct    120
tggtaccaga gaaaaccagg acagcctcct caattgctca tttactgggc atctacccga    180
caatccgggg tccctgaccg attcagtggc agcgggtctg ggacagattt cactctcacc    240
atcagcagcc tgcaggctga agatgtggca gtttattact gtcagcaata ttttagtagt    300
cctcccatat tcaccttcgg ccctgggacc aaagtggaga tcaaac                   346
```

```
<210> SEQ ID NO 597
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 597
caggttcaat tagtgcagtc tggtgctgaa gtgaaaaagc ccggctcaag tgttaaagta      60
agctgtaagg cgagcggtgg tccatttagc tcatacgcca ttagctgggt gcgacaggct     120
cctggtcagg gcctcgaatg gatgggcggc attagcccta tgtttggtac tgcaaattat     180
gcccagaaat ttcagggtag agtcacaatt accgcagatg aaagcacgtc aaccgtgtac     240
atggaactga gtagcctgcg ttccgaagat acagctgtgt attactgtgc gcgcggttac     300
agttactacc ctggtggtgg tggtggtcgt aatttcgact actggggcca ggggaccttg     360
gtcactgtgt ctagc                                                      375

<210> SEQ ID NO 598
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 598
ctgcctgtgc tgactcagcc accctcagcg tctgggaccc ccgggcagag ggtcaccatc      60
tcttgttctg gaagcagctc caacatcgga agtaatactg taaactggta ccagcagctc     120
ccaggaacgg cccccaaact cctcatctat agtaataatc agcggccctc agggggtccct    180 gaccgattct ctggctccaa gtctggcacc tcagcctccc tggccatcag tgggctccag     240
tctgagggtg aggctgatta ttactgtgca gcatgggatg acagcctgaa aggtcgggtg     300
ttcggcggag ggaccaaggt gaccgtccta g                                    331

<210> SEQ ID NO 599
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 599
caggttcaat tagtgcagtc tggtgctgaa gtgaaaaagc ccggctcaag tgttaaagta      60
agctgtaagg cgagcggagg tatctttagt tcttacgcca ttagctgggt gcgacaggct     120
cctggtcagg gcctcgaatg gatgggcggc attagcccaa tcttcggtac tgcaaattat     180
gcccagaaat ttcagggtag agtcacaatt accgcagatg agagcacgaa caccgcctat     240
atggaactga gtagcctgcg ttccgaagat acagctgtgt attactgtgc gcgcagtggt     300
ggttactacg actacggtgt tggttacgac caatggggcc aggggacctt agtcactgtg     360
tctagc                                                                366

<210> SEQ ID NO 600
<211> LENGTH: 322
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 600

```
cagcctgtgc tgactcagcc accctcagcg tctgggaccc ccgggcagag ggtcaccatc      60
tcttgttctg gaggcaggtc caacatcgga agtaatactg ttaactggta ccagcagctc     120
ccaggaacgg cccccaaact cctcatctat agtaataatc accggccctc aggggtccct     180
gatcgcttct ctggctccaa gtctggcaac acggcctccc tgaccatctc tgggctccag     240
gcggaggatg aggctgatta ttactgccag tcctatgaca gcagcgttgt attcggcgga     300
gggaccaagc tgaccgtcct ag                                              322
```

<210> SEQ ID NO 601
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 601

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Thr Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Thr Gly Phe Tyr Asp Val Trp Gly Gln Gly Thr Leu
            100                 105                 110

Val Thr Val Ser Ser
        115
```

<210> SEQ ID NO 602
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 602

```
Leu Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95
```

```
Asn Gly Pro Val Phe Gly Gly Gly Thr Lys Leu Thr Val Leu
            100                 105                 110
```

<210> SEQ ID NO 603
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 603

```
Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Glu Tyr Tyr Ala Ser Asn Gly Asp Ser Phe Asp Val
            100                 105                 110

Trp Gly Gln Gly Thr Leu Val Thr Val Ser Ser
        115                 120
```

<210> SEQ ID NO 604
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 604

```
Gln Pro Val Leu Thr Gln Pro Pro Ser Val Ser Val Ala Pro Gly Lys
1               5                   10                  15

Thr Ala Ser Ile Ser Cys Glu Gly Asn Asn Ile Ala Thr Lys Ser Val
            20                  25                  30

His Trp Tyr Gln Gln Lys Ser Gly His Ala Pro Val Val Val Val Tyr
        35                  40                  45

His Asp Ser Asp Arg Pro Ser Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Ala Ala Trp Asp Asp Ser Leu Ser Gly
                85                  90                  95

Pro Trp Val Phe Gly Gly Gly Thr Lys Leu Thr Val Leu
            100                 105
```

<210> SEQ ID NO 605
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 605

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Ala Ile Phe Gly Thr Ala Asn Tyr Ala Gln Lys Phe
    50                  55                  60

Gln Gly Arg Val Thr Ile Thr Ala Asp Glu Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Gly Tyr Tyr Val Ala Ala Ser Gly Ala Phe Asp Val
            100                 105                 110

Trp Gly Gln Gly Thr Leu Val Thr Val Ser Ser
        115                 120

<210> SEQ ID NO 606
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 606

Gln Pro Gly Leu Thr Gln Pro Pro Ser Val Ser Lys Gly Leu Arg Gln
1               5                   10                  15

Thr Ala Thr Leu Thr Cys Thr Gly Asn Ile Asn Asn Val Gly Asp Gln
            20                  25                  30

Gly Ala Gly Trp Leu Gln Gln His Gln Gly Arg Pro Pro Lys Leu Leu
        35                  40                  45

Ser Tyr Arg Asn Ser Asn Arg Pro Ser Gly Val Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Asp Trp Val Phe Gly Gly Gly Thr Lys Leu Thr Val Leu
            100                 105                 110

<210> SEQ ID NO 607
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 607

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Ser Tyr
            20                  25                  30

Ala Ile Ser Trp Val Arg Gln Ala Pro Gly Gln Gly Leu Glu Trp Met
        35                  40                  45

```
Gly Gly Ile Thr Pro Ile Phe Gly Thr Ala Asn Tyr Ala Gln Lys Phe
         50                  55                  60

Gln Gly Arg Val Thr Ile Thr Ala Asp Glu Ser Thr Arg Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Leu Ser Arg Asp Ser Leu Asn Leu Pro Gly Ser Ser Pro
             100                 105                 110

Gly Tyr Asp Leu Trp Gly Gln Gly Thr Leu Val Thr Val Ser Ser
             115                 120                 125

<210> SEQ ID NO 608
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 608

Glu Thr Thr Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Ser Ser Ser Pro Tyr
                 85                  90                  95

Thr Phe Gly Gln Gly Thr Lys Leu Glu Ile Lys
             100                 105

<210> SEQ ID NO 609
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 609

Gln Val Gln Leu Val Gln Ser Gly Ala Glu Val Lys Lys Pro Gly Ser
 1               5                  10                  15

Ser Val Lys Val Ser Cys Lys Ala Ser Gly Val Ile Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ser Pro Ile Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Arg Gly Tyr Ala Pro Gly Thr Ser Phe His Tyr Asp Val
             100                 105                 110
```

```
Trp Gly Gln Gly Thr Leu Val Thr Val Ser Ser
        115                 120
```

<210> SEQ ID NO 610
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 610

```
Leu Pro Val Leu Thr Gln Ala Pro Ser Met Ser Val Ala Pro Gly Lys
1               5                   10                  15

Thr Ala Ser Ile Thr Cys Gly Gly Asp Asn Ile Gly Ser Lys Ser Val
            20                  25                  30

His Trp Tyr Gln Gln Lys Pro Gly Gln Ala Pro Val Leu Val Met Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Phe Cys Gln Leu Trp Asp His Thr Asn Ser His
                85                  90                  95

Val Val Phe Gly Gly Arg Thr Lys Leu Thr Val Leu
            100                 105
```

<210> SEQ ID NO 611
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 611

```
Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ser Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Gly Gly Thr Arg Gly Asn Tyr Phe Asp Val Trp Gly
            100                 105                 110

Gln Gly Thr Leu Val Thr Val Ser Ser
        115                 120
```

<210> SEQ ID NO 612
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 612

Gln Pro Val Leu Thr Gln Pro Ser Val Ser Lys Gly Leu Arg Gln
1               5                   10                  15

Thr Ala Thr Val Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Leu Ser
    50                  55                  60

Ala Ser Arg Ser Gly Asn Thr Ala Ser Leu Thr Ile Ala Gly Leu Gln
65                  70                  75                  80

Pro Glu Asp Glu Ala Asp Tyr Tyr Cys Ser Ala Trp Asp Asn Thr Val
                85                  90                  95

Ser Gly Trp Val Phe Gly Gly Gly Thr Arg Val Thr Val Leu
            100                 105                 110

<210> SEQ ID NO 613
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 613

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Thr Ile Phe Gly Thr Ala Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Gly Arg Phe Asp Val Trp Gly Gln Gly Thr Leu
            100                 105                 110

Val Thr Val Ser Ser
        115

<210> SEQ ID NO 614
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 614

Ser Tyr Glu Leu Thr Gln Pro Pro Ser Val Ser Gly Thr Pro Gly Gln
1               5                   10                  15

Arg Val Thr Ile Ser Cys Ser Gly Ser Thr Ser Asn Ile Gly Asn Asn
            20                  25                  30

Ala Leu Asn Trp Tyr Gln Lys Leu Pro Gly Thr Ala Pro Lys Leu Leu
        35                  40                  45

Ile Tyr Ser Leu Asn Gln Arg Pro Ser Gly Val Pro Asp Arg Phe Ser
```

```
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Glu Ala Trp Asp Asp Ser Leu
                 85                  90                  95

Ser Gly Pro Val Phe Gly Gly Gly Thr Lys Val Thr Val Leu
            100                 105                 110
```

<210> SEQ ID NO 615
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 615

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Pro Phe Arg Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Val Tyr Ser Phe Asp Val Trp Gly Gln Gly Thr Leu
            100                 105                 110

Val Thr Val Ser Ser
        115
```

<210> SEQ ID NO 616
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 616

```
Gln Ser Gly Leu Thr Gln Pro Pro Ser Ala Ser Gly Thr Pro Gly Gln
 1               5                  10                  15

Arg Val Thr Ile Ser Cys Ser Gly Ser Gly Ser Asn Val Gly Ser Asn
                20                  25                  30

Val Val Asn Trp Tyr Gln His Leu Pro Gly Thr Ala Pro Lys Leu Leu
            35                  40                  45

Ile Tyr Arg Asn Asn Gln Arg Pro Ser Gly Val Pro Asp Arg Phe Ser
     50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Arg Leu
                 85                  90                  95

Asn Gly Phe Val Phe Gly Thr Gly Thr Lys Val Thr Val Leu
            100                 105                 110
```

```
<210> SEQ ID NO 617
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 617

Gln Val Gln Leu Val Gln Ser Gly Ala Glu Val Lys Lys Pro Gly Ser
1               5                   10                  15

Ser Val Lys Val Ser Cys Lys Ala Ser Gly Val Pro Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Leu Phe Gly Thr Ala Asn Tyr Ala Gln Lys Phe
    50                  55                  60

Gln Gly Arg Val Thr Ile Thr Ala Asp Gln Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Thr Tyr Ser Pro Ser Leu Tyr Pro Arg Gly Met
            100                 105                 110

Asp Val Trp Gly Gln Gly Thr Leu Val Thr Val Ser Ser
        115                 120                 125

<210> SEQ ID NO 618
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 618

Leu Pro Val Leu Thr Gln Pro Pro Ser Ala Ser Gly Thr Pro Gly Gln
1               5                   10                  15

Ser Val Thr Ile Ser Cys Ser Gly Ser Ser Ser Asn Ile Gly Arg Asn
            20                  25                  30

Asp Val Asn Trp Tyr Gln Gln Phe Pro Gly Arg Ala Pro Lys Leu Leu
        35                  40                  45

Ile Tyr Gly Arg Asp Glu Arg Pro Phe Gly Val Pro Ala Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Ala Ser Leu
                85                  90                  95

Met Ile Tyr Val Phe Gly Thr Gly Thr Thr Val Thr Val Leu
            100                 105                 110

<210> SEQ ID NO 619
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 619

Gln Val Gln Leu Val Gln Ser Gly Ala Glu Val Lys Lys Pro Gly Ser
1               5                   10                  15
```

-continued

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ser Pro Met Phe Gly Thr Ala Asn Tyr Ala Gln Lys Phe
 50                  55                  60

Gln Gly Arg Val Thr Ile Thr Ala Asp Glu Ser Thr Asn Thr Val Tyr
 65                  70                  75                  80

Met Glu Leu Ser Ser Leu Arg Ser Glu Asp Thr Ala Val Tyr Tyr Cys
            85                  90                  95

Ala Arg Gly Arg Ala Tyr Leu Ser Val Arg Gly Ser Phe Asp Val Trp
            100                 105                 110

Gly Gln Gly Thr Leu Val Thr Val Ser Ser
            115                 120

<210> SEQ ID NO 620
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 620

Ser Tyr Glu Leu Thr Gln Pro Pro Ser Val Ser Gly Thr Pro Gly Gln
 1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
            85                  90                  95

Asn Gly Tyr Val Phe Gly Thr Gly Thr Lys Val Thr Val Leu
            100                 105                 110

<210> SEQ ID NO 621
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 621

Gln Val Gln Leu Val Gln Ser Gly Ala Glu Val Lys Lys Pro Gly Ser
 1               5                   10                  15

Ser Val Lys Val Ser Cys Lys Ala Ser Gly Val Ile Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

```
Met Glu Leu Ser Ser Leu Arg Ser Glu Asp Thr Ala Val Tyr Tyr Cys
                 85                  90                  95

Ala Arg Gly Gly Ser Gly Ser Phe Asp Val Trp Gly Gln Gly Thr Leu
            100                 105                 110

Val Thr Val Ser Ser
        115

<210> SEQ ID NO 622
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 622

Gln Pro Gly Leu Thr Gln Pro Pro Ser Ala Ser Gly Thr Pro Gly Gln
1               5                   10                  15

Arg Val Thr Ile Ser Cys Ser Gly Ser Ser Ser Asn Leu Gly Ser Asn
            20                  25                  30

Tyr Val Phe Trp Tyr Gln His Leu Pro Gly Ala Ala Pro Lys Leu Leu
        35                  40                  45

Ile Tyr Arg Asn Ser Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 623
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 623

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Val Phe Gly Thr Ala Asn Tyr Ala Gln Lys Phe
    50                  55                  60

Gln Gly Arg Val Thr Ile Thr Ala Asp Asp Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Gly Tyr Thr Val Ser Ser Leu Ala Gly Arg Tyr Phe
            100                 105                 110

Asp Gln Trp Gly Gln Gly Thr Leu Val Thr Val Ser Ser
        115                 120                 125

<210> SEQ ID NO 624
```

```
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 624
```

Glu Thr Thr Leu Thr Gln Ser Pro Gly Thr Leu Ser Leu Ser Pro Gly
1               5                   10                  15

Glu Arg Ala Ser Leu Ser Cys Lys Ala Ser Glu Ser Leu Cys Ser Thr
            20                  25                  30

Cys Leu Ala Trp Tyr Gln Gln Lys Pro Gly Gln Ala Pro Arg Leu Ile
        35                  40                  45

Val Tyr Gly Ala Thr Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Gln Thr Phe Gly Gln Gly Thr Lys Val Glu Ile Lys
            100                 105

```
<210> SEQ ID NO 625
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 625
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Val Pro Leu Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Leu Tyr Phe Asp Val Trp Gly Gln Gly Thr Leu
            100                 105                 110

Val Thr Val Ser Ser
        115

```
<210> SEQ ID NO 626
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 626
```

Gln Thr Val Val Thr Gln Glu Pro Ser Leu Thr Val Ser Pro Gly Glu
1               5                   10                  15

Thr Val Thr Leu Thr Cys Ala Ser Ser Thr Gly Ala Val Thr Ser Gly
            20                  25                  30

Tyr Tyr Pro Asn Trp Phe Gln Gln Lys Pro Gly Gln Ala Pro Arg Ala
            35                  40                  45

Leu Ile Tyr Ser Thr Ser Asn Lys His Ser Trp Thr Pro Ala Arg Phe
        50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Tyr Tyr Gly Gly
                85                  90                  95

Pro Trp Val Phe Gly Gly Gly Thr Lys Leu Thr Val Leu
            100                 105

<210> SEQ ID NO 627
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 627

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Val Arg Gly Gly Tyr Gly Pro Tyr Gly Asp Phe Asp Val Trp
            100                 105                 110

Gly Gln Gly Thr Leu Val Thr Val Ser Ser
        115                 120

<210> SEQ ID NO 628
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 628

Gln Pro Gly Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser His
            20                  25                  30

Ser Val Asn Trp Tyr Arg Gln Leu Pro Gly Thr Ala Pro Gln Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

```
Ser Glu Asp Glu Ala Asp Tyr Phe Cys Ala Ala Trp Asp Asp Gly Leu
                85                  90                  95

Ser Gly Trp Val Phe Gly Gly Gly Thr Lys Leu Thr Val Leu
            100                 105                 110

<210> SEQ ID NO 629
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 629

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Thr Ala Asn Tyr Ala Gln Lys Phe
    50                  55                  60

Gln Gly Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Ser Tyr Ile Val Ser Val Ser Pro Gly Phe Asp Val
            100                 105                 110

Trp Gly Gln Gly Thr Leu Val Thr Val Ser Ser
        115                 120

<210> SEQ ID NO 630
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 630

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln Tyr Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Thr Ser Ala Ser Leu Ala Ile Ser Glu Leu
65                  70                  75                  80

Gln Ser Glu Asp Glu Ala Asp Tyr Tyr Cys Ala Ser Trp Asp Asp Ser
                85                  90                  95

Leu Asn Ala Tyr Val Phe Gly Ser Gly Thr Lys Val Thr Val Leu
            100                 105                 110

<210> SEQ ID NO 631
<211> LENGTH: 123
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 631

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ser Ala Ile Phe Gly Thr Ala Asn Tyr Ala Gln Lys Phe
50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Gly Ile Ala Ser Gly Tyr Thr Ala Tyr Met Asp Tyr
                100                 105                 110

Trp Gly Gln Gly Thr Leu Val Thr Val Ser Ser
            115                 120

<210> SEQ ID NO 632
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 632

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Ser Tyr Ala
                20                  25                  30

Ser Trp Tyr Gln Gln Lys Pro Gly Gln Ser Pro Val Leu Val Ile Tyr
            35                  40                  45

Gln Ser Thr Lys Arg Pro Ser Gly Ile Pro Glu Arg Phe Ser Ala Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Gly Ser Gly Asn Pro
                85                  90                  95

Tyr Val Phe Gly Thr Gly Thr Lys Val Thr Val Leu
                100                 105

<210> SEQ ID NO 633
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 633

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Arg Ser Tyr
                20                  25                  30

Ala Ile Ser Trp Val Arg Gln Ala Pro Gly Gln Gly Leu Glu Trp Met
```

```
                35                  40                  45
Gly Gly Ile Ile Pro Met Phe Gly Thr Ala Asn Tyr Ala Gln Lys Phe
         50                  55                  60

Gln Gly Arg Val Thr Ile Thr Ala Asp Glu Ser Thr Thr Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Ala Gly Ser Thr Phe Asp Val Trp Gly Gln Gly Thr Leu
            100                 105                 110

Val Thr Val Ser Ser
            115

<210> SEQ ID NO 634
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 634

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
             20                  25                  30

Thr Val Asn Trp Tyr Gln Gln Leu Pro Gly Thr Ala Pro Arg Leu Leu
         35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Arg Val Phe Gly Gly Gly Thr Lys Leu Thr Val Leu
            100                 105                 110

<210> SEQ ID NO 635
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 635

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Asn Pro Ile Phe Gly Thr Ala Asn Tyr Ala Gln Lys Phe
 50                  55                  60

Gln Gly Arg Val Thr Ile Thr Ala Asp Glu Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Glu Ser Ala Tyr Tyr Ser Arg Asn Tyr Asp Val Trp Gly
```

```
              100                 105                 110

Gln Gly Thr Leu Val Thr Val Ser Ser
            115                 120

<210> SEQ ID NO 636
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 636

Ser Tyr Glu Leu Thr Gln Pro Pro Ser Val Ser Lys Gly Leu Arg Gln
1               5                   10                  15

Thr Ala Thr Leu Thr Cys Thr Gly Asn Ser Ser Asn Val Gly Asn Gln
            20                  25                  30

Gly Ala Ser Trp Leu Gln Gln His Gln Gly His Pro Pro Lys Leu Leu
        35                  40                  45

Ser Tyr Arg Asn Asp Asn Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Asn Ser Leu
                85                  90                  95

Ser Ala Trp Val Phe Gly Gly Gly Thr Lys Leu Thr Val Leu
            100                 105                 110

<210> SEQ ID NO 637
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 637

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Met Phe Gly Thr Ala Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Tyr Tyr Pro Ala Gly Val Gly Arg Tyr Asp Val
            100                 105                 110

Trp Gly Gln Gly Thr Leu Val Thr Val Ser Ser
            115                 120

<210> SEQ ID NO 638
<211> LENGTH: 113
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 638

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Val Leu Tyr Ser
            20                  25                  30

Ser Asn Asn Lys Asn Asn Leu Ala Trp Tyr Gln Gln Arg Pro Gly Gln
        35                  40                  45

Pro Pro Lys Val Leu Leu Tyr Trp Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Leu Tyr Tyr Cys Gln Gln
                85                  90                  95

Tyr Tyr Gly Lys Pro Phe Thr Phe Gly Pro Gly Thr Lys Val Glu Ile
            100                 105                 110

Lys

<210> SEQ ID NO 639
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 639

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Thr Pro Leu Phe Gly Thr Ala Asn Tyr Ala Gln Lys Phe
    50                  55                  60

Gln Gly Arg Val Thr Ile Thr Ala Asp Asp Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Thr Leu Tyr Ser Pro Pro Val Phe Asp Val Trp Gly
            100                 105                 110

Gln Gly Thr Leu Val Thr Val Ser Ser
        115                 120

<210> SEQ ID NO 640
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 640

Gln Thr Val Val Thr Gln Glu Pro Ser Phe Ser Val Ser Pro Gly Gly
1               5                   10                  15

Thr Ile Thr Leu Thr Cys Gly Leu Ser Ser Gly Ser Val Ser Thr Thr
            20                  25                  30

Asn Tyr Pro Ser Trp Tyr Gln Gln Thr Pro Gly Arg Thr Pro Arg Thr
            35                  40                  45

Leu Ile Tyr Asn Thr Asn Thr Arg Ser Ser Gly Val Pro Asp Arg Phe
 50                  55                  60

Ser Gly Ser Ile Leu Gly Asn Lys Ala Ala Leu Thr Ile Thr Gly Ala
 65                  70                  75                  80

Gln Ala Gly Asp Glu Ser Asp Tyr Tyr Cys Val Leu Tyr Met Gly Arg
                 85                  90                  95

Gly Ile Tyr Val Phe Gly Ser Gly Thr Lys Val Ser Val Leu
            100                 105                 110

<210> SEQ ID NO 641
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 641

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Arg Ser Tyr
                 20                  25                  30

Ala Ile Ser Trp Val Arg Gln Ala Pro Gly Gln Gly Leu Glu Trp Met
             35                  40                  45

Gly Gly Ile Met Pro Ile Phe Gly Thr Ala Asn Tyr Ala Gln Lys Phe
         50                  55                  60

Gln Gly Arg Val Thr Ile Thr Ala Asp Glu Ser Thr Thr Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Ala Gly Val Ser Ala Gly Pro Ser Trp Pro Phe Asp Val
            100                 105                 110

Trp Gly Gln Gly Thr Leu Val Thr Val Ser Ser
        115                 120

<210> SEQ ID NO 642
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 642

Gln Pro Gly Leu Thr Gln Pro Pro Ser Val Ser Lys Asp Leu Arg Gln
 1               5                  10                  15

Thr Ala Thr Leu Thr Cys Thr Gly Asn Ser Asn Asn Val Gly Lys Gln
                 20                  25                  30

Gly Ala Thr Trp Leu Gln Gln His Gln Gly His Pro Pro Lys Leu Leu
             35                  40                  45

Ser Tyr Arg Asn Asn Asn Arg Pro Ser Gly Ile Ser Glu Arg Phe Ser
 50                  55                  60

Ala Ser Arg Ser Gly Asp Thr Ala Ser Leu Thr Ile Thr Gly Leu Gln
 65                  70                  75                  80

Pro Glu Asp Glu Ala Asp Tyr Tyr Cys Ser Ala Trp Asp Ser Ser Leu
                 85                  90                  95

-continued

Ser Val Trp Val Phe Gly Gly Gly Thr Lys Leu Thr Val Leu
            100                 105                 110

<210> SEQ ID NO 643
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 643

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Met Phe Gly Thr Ala Asn Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Gly Tyr Asn Val Ala Ala Ser Phe Gly Phe Asp Val
            100                 105                 110

Trp Gly Gln Gly Thr Leu Val Thr Val Ser Ser
        115                 120

<210> SEQ ID NO 644
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 644

Glu Ile Val Leu Thr Gln Ser Pro Ser Phe Leu Ser Ala Ser Val Gly
1               5                   10                  15

Asp Arg Val Thr Ile Thr Cys Arg Ala Ser Gln Tyr Ile Asp Arg Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Glu Thr
65                  70                  75                  80

Glu Asp Ala Ala Thr Tyr Tyr Cys His Gln Thr Ser Ser Leu Pro Trp
                85                  90                  95

Thr Phe Gly Gln Gly Thr Thr Val Glu Ile Lys
            100                 105

<210> SEQ ID NO 645
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 645

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Asp Tyr Ser Gly Tyr Arg Gly Phe Asp Val Trp Gly
            100                 105                 110

Gln Gly Thr Leu Val Thr Val Ser Ser
        115                 120

<210> SEQ ID NO 646
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 646

Gln Thr Val Val Thr Gln Glu Pro Ser Phe Ser Val Ser Pro Gly Gly
1               5                   10                  15

Thr Val Thr Leu Thr Cys Ala Leu Ser Ser Gly Ser Val Ser Ser Phe
            20                  25                  30

Asn Tyr Ala Ser Trp Tyr Gln Gln Thr Pro Gly Gln Ala Pro Arg Thr
        35                  40                  45

Leu Ile Ser Asn Thr Asn Thr Arg Ser Ser Gly Val Pro Asp Arg Phe
    50                  55                  60

Ser Gly Ser Ile Leu Gly Asn Lys Ala Thr Leu Thr Ile Thr Gly Ala
65                  70                  75                  80

Gln Ala Asp Asp Glu Ser His Tyr Tyr Cys Ala Leu Tyr Val Gly Gly
                85                  90                  95

Gly Ile Ser Val Phe Gly Gly Gly Thr Lys Leu Thr Val Leu
            100                 105                 110

<210> SEQ ID NO 647
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 647

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Thr Pro Ile Phe Gly Thr Ala Asn Tyr Ala Gln Lys Phe

```
                    50                  55                  60
Gln Gly Arg Val Thr Ile Thr Ala Asp Gln Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Gly Gly Gly Val Phe Asp Val Trp Gly Gln Gly Thr Leu Val
                100                 105                 110

Thr Val Ser Ser
            115

<210> SEQ ID NO 648
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 648

Ser Tyr Glu Leu Thr Gln Pro Pro Ser Val Ser Gly Ala Pro Arg Gln
  1               5                  10                  15

Arg Val Thr Ile Ser Cys Ser Gly Ser Ser Ser Asn Ile Gly Asn Asn
                 20                  25                  30

Ala Val Asn Trp Tyr Gln Gln Leu Pro Gly Lys Ala Pro Lys Leu Leu
             35                  40                  45

Ile Tyr Tyr Asp Asp Met Leu Pro Ser Gly Val Ser Asp Arg Phe Ser
         50                  55                  60

Gly Ser Lys Ser Gly Ser Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Ser Gly Pro Val Phe Gly Gly Gly Thr Asn Leu Thr Val Leu
                100                 105                 110

<210> SEQ ID NO 649
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 649

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ser Pro Met Phe Gly Thr Ala Asn Tyr Ala Gln Lys Phe
         50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Gly Tyr Ser Pro Gly Gly Val Asp Phe Asp Tyr Trp
                100                 105                 110

Gly Gln Gly Thr Leu Val Thr Val Ser Ser
```

115                 120

<210> SEQ ID NO 650
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 650

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Thr
            20                  25                  30

Tyr Val Gln Trp Tyr Arg Gln Arg Pro Gly Ser Ala Pro Thr Thr Val
        35                  40                  45

Ile Tyr Glu Asp His Gln Arg Pro Ser Gly Val Pro Asp Arg Phe Ser
    50                  55                  60

Gly Ser Leu Asp Ser Ser Ser Asn Ser Ala Ser Leu Thr Ile Ser Gly
65                  70                  75                  80

Leu Arg Thr Glu Asp Ala Ala Thr Tyr Tyr Cys Gln Ser Phe Asp Ala
                85                  90                  95

Ser Thr Leu Val Phe Gly Gly Gly Thr Lys Leu Thr Val Leu
            100                 105                 110

<210> SEQ ID NO 651
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 651

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Arg Ser Tyr
            20                  25                  30

Ala Ile Ser Trp Val Arg Gln Ala Pro Gly Gln Gly Leu Glu Trp Met
        35                  40                  45

Gly Gly Ile Ser Gly Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Ala Tyr Tyr Phe Gly Pro Asn Met Asp Val Trp Gly
            100                 105                 110

Gln Gly Thr Leu Val Thr Val Ser Ser
        115                 120

<210> SEQ ID NO 652
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 652

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Val Pro Lys Leu
            35                  40                  45

Ile Ile Tyr Asp Asn Ser Asn Arg Pro Ser Gly Val Pro Ala Arg Phe
50                      55                  60

Ser Gly Ser Lys Ser Gly Thr Ser Ala Ser Leu Ala Ile Ser Gly Leu
65                  70                  75                  80

Gln Ser Glu Asp Glu Ala Ala Tyr Tyr Cys Gln Ser Tyr Asp Ser Ser
                85                  90                  95

Leu Ser Val Val Val Phe Gly Gly Gly Thr Lys Leu Ser Val Leu
            100                 105                 110

<210> SEQ ID NO 653
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 653

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ser Pro Ile Phe Gly Thr Ala Asn Tyr Ala Gln Lys Phe
        50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Pro Gly Tyr His Pro Ala Gly Ala Ser Gly Gln Phe Phe
            100                 105                 110

Asp Leu Trp Gly Gln Gly Thr Leu Val Thr Val Ser Ser
            115                 120                 125

<210> SEQ ID NO 654
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 654

Ser Tyr Glu Leu Thr Gln Pro Pro Ser Val Ser Lys Asp Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
            35                  40                  45

Ser Tyr Arg Asn Asn His Arg Pro Ser Gly Ile Ser Asp Arg Ser Ser
50                  55                  60

```
Ala Ser Arg Ser Gly Asp Thr Ala Ser Leu Thr Ile Thr Gly Leu Gln
 65                  70                  75                  80

Pro Glu Asp Glu Ala Asp Tyr Tyr Cys Ser Ala Trp Asp Ser Ser Leu
                 85                  90                  95

Ser Ala Trp Val Phe Gly Gly Gly Thr Lys Leu Thr Val Leu
            100                 105                 110

<210> SEQ ID NO 655
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 655

Gln Val Gln Leu Val Gln Ser Gly Ala Glu Val Lys Lys Pro Gly Ser
 1               5                  10                  15

Ser Val Lys Val Ser Cys Lys Ala Ser Gly Val Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ser Pro Met Phe Gly Thr Ala Asn Tyr Ala Gln Lys Phe
     50                  55                  60

Gln Gly Arg Val Thr Ile Thr Ala Asp Glu Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Arg Gly Tyr Ala Pro Asp Ala Leu Thr Asn Phe Asp Val
            100                 105                 110

Trp Gly Gln Gly Thr Leu Val Thr Val Ser Ser
        115                 120

<210> SEQ ID NO 656
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 656

Glu Ile Val Leu Thr Gln Ser Pro Asp Ser Leu Ala Met Ser Leu Gly
 1               5                  10                  15

Glu Arg Ala Thr Val Asn Cys Lys Ser Ser Arg Ser Leu Phe Asp Ser
             20                  25                  30

Ser Asp Asn Lys Asn Tyr Leu Ala Trp Tyr Gln Lys Pro Gly Gln
         35                  40                  45

Pro Pro Gln Leu Leu Ile Tyr Trp Ala Ser Thr Arg Gln Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Phe Ser Ser Pro Pro Ile Phe Thr Phe Gly Pro Gly Thr Lys Val
            100                 105                 110

Glu Ile Lys
        115
```

<210> SEQ ID NO 657
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 657

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ser Pro Met Phe Gly Thr Ala Asn Tyr Ala Gln Lys Phe
        50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Tyr Tyr Pro Gly Gly Gly Gly Arg Asn Phe
            100                 105                 110

Asp Tyr Trp Gly Gln Gly Thr Leu Val Thr Val Ser Ser
            115                 120                 125

<210> SEQ ID NO 658
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 658

Leu Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Gly Glu Ala Asp Tyr Tyr Cys Ala Ala Trp Asp Asp Ser Leu
                85                  90                  95

Lys Gly Arg Val Phe Gly Gly Gly Thr Lys Val Thr Val Leu
            100                 105                 110

<210> SEQ ID NO 659
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 659

```
Gln Val Gln Leu Val Gln Ser Gly Ala Glu Val Lys Lys Pro Gly Ser
1               5                   10                  15

Ser Val Lys Val Ser Cys Lys Ala Ser Gly Ile Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ser Pro Ile Phe Gly Thr Ala Asn Tyr Ala Gln Lys Phe
50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Gly Gly Tyr Tyr Asp Tyr Gly Val Gly Tyr Asp Gln Trp
            100                 105                 110

Gly Gln Gly Thr Leu Val Thr Val Ser Ser
            115                 120
```

```
<210> SEQ ID NO 660
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 660

Gln Pro Val Leu Thr Gln Pro Pro Ser Ala Ser Gly Thr Pro Gly Gln
1               5                   10                  15

Arg Val Thr Ile Ser Cys Ser Gly Gly Arg Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn His Arg Pro Ser Gly Val Pro Asp Arg Phe Ser
50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Gln Ser Tyr Asp Ser Ser Val
            85                  90                  95

Val Phe Gly Gly Gly Thr Lys Leu Thr Val Leu
            100                 105
```

```
<210> SEQ ID NO 661
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 661

Cys Ala Arg Xaa Xaa Gly Tyr Xaa Pro
1               5
```

```
<210> SEQ ID NO 662
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(6)
<223> OTHER INFORMATION: Any amino acid

<400> SEQUENCE: 662

Cys Ala Arg Xaa Xaa Xaa Tyr Tyr
1               5

<210> SEQ ID NO 663
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 663
tggacaaggg cttgagtgga t                                             21

<210> SEQ ID NO 664
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 664
ccctggaact tctgtgcgta gt                                            22

<210> SEQ ID NO 665
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 665
cctatccttg gtatagca                                                 18

<210> SEQ ID NO 666
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 666
tggacaaggg cttgagtgga t                                             21

<210> SEQ ID NO 667
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 667
```

```
ccctggaact tctgtgcgta gt                                              22
```

<210> SEQ ID NO 668
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668

```
ccctatcttt ggtacagc                                                   18
```

<210> SEQ ID NO 669
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669

Trp Gly Gln Gly Thr Leu Val Thr Val Ser Ser
1               5                   10

<210> SEQ ID NO 670
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

Tyr Tyr Tyr Tyr Tyr Gly Met Asp Val Trp Gly Gln Gly Thr Thr Val
1               5                   10                  15

Thr Val Ser Ser
            20

<210> SEQ ID NO 671
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Phe Asp Val Trp Gly Gln Gly Thr Leu Val Thr Val Ser Ser
1               5                   10

<210> SEQ ID NO 672
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Gly Gly Gly Ser Gly Gly Gly Ser Gly Gly Gly Ser Gly Gly Gly Ser
1               5                   10                  15

<210> SEQ ID NO 673
<211> LENGTH: 8
<212> TYPE: PRT

<213> ORGANISM: Artificial Sequence
<220> FEATURE:
<223> OTHER INFORMATION: Description of Artificial Sequence: Synthetic peptide

<400> SEQUENCE: 673

Ile Ile Pro Ile Phe Gly Thr Ala
1               5

<210> SEQ ID NO 674
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 674

Ile Ser Pro Ile Phe Gly Thr Ala
1               5

<210> SEQ ID NO 675
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 675

Ile Ile Pro Met Phe Gly Thr Ala
1               5

<210> SEQ ID NO 676
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 676

Ile Ile Pro Ile Phe Arg Thr Ala
1               5

<210> SEQ ID NO 677

<400> SEQUENCE: 677

000

<210> SEQ ID NO 678
<211> LENGTH: 872
<212> TYPE: DNA
<213> ORGANISM: Homo sapiens

<400> SEQUENCE: 678

```
gcaggattta gggcttggtc tctcagcatc ccacacttgt acagctgatg tggcatctgt      60
gttttctttc tcatcgtaga tcaggctttg agctgtgaaa tacccctgcct catgcatatg    120 caaataacct gaggtcttct gagataaata tagatatatt ggtgccctga gagcatcaca    180
taacaaccac attcctcctc taaagaagcc cctgggagca cagctcatca ccatggactg    240
gacctggagg ttcctctttg tggtggcagc agctacaggt aagggggcttc ctagtcctaa    300 ggctgaggaa gggatcctgg tttagttaaa gaggatttta ttcacccctg tgtcctctcc    360
```

```
acaggtgtcc agtcccaggt gcagctggtg cagtctgggg ctgaggtgaa gaagcctggg      420
tcctcggtga aggtctcctg caaggcttct ggaggcacct tcagcagcta tgctatcagc      480
tgggtgcgac aggcccctgg acaagggctt gagtggatgg gagggatcat ccctatcttt      540
ggtacagcaa actacgcaca gaagttccag gcagagtca cgattaccgc ggacgaatcc       600
acgagcacag cctacatgga gctgagcagc ctgagatctg aggacacggc cgtgtattac      660
tgtgcgagag acacagtgtg aaaacccaca tcctgagagt gtcagaaacc ctgagggaga     720
aggcagctgt gccgggctga ggagatgaca gggtttatta ggtttaaggc tgtttacaaa      780
atgggttata tatttgagaa aaaaagaaca gtagaaacaa gtacatactc ctctaatttt     840
aagataatta ttccattcaa gagtcgtaat at                                   872
```

<210> SEQ ID NO 679
<211> LENGTH: 407
<212> TYPE: DNA
<213> ORGANISM: Homo sapiens

<400> SEQUENCE: 679

```
ctggaggttc ctctttgtgg tggcagcagc tacaggtaag gggtttccta gtcctaaggc      60
tgaggaaggg atcctggttt agttaaagag gattttattc acccctgtgt cctctccaga     120
ggtgtccact cccaggtgca gctggtgcag tctgggctg aggtgaagaa gcctgggtcc      180
tcggtgaagg tctcctgcaa ggcttctgga ggcaccttca gcagctatgc tatcagctgg     240
gtgcgacagg cccctggaca agggcttgag tggatgggag gatcatccc tatctttggt      300 acagcaaact acgcacagaa gttccagggc agagtcacga ttaccgcgga cgaatccacg     360
agcacagcct acatggagct gagcagcctg agatctgatg acacggc                   407
```

<210> SEQ ID NO 680
<211> LENGTH: 294
<212> TYPE: DNA
<213> ORGANISM: Homo sapiens

<400> SEQUENCE: 680

```
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac      180
gcacagaagt tccagggcag agtcacgatt accacggacg aatccacgag cacagcctac     240
atggagctga gcagcctgag atctgaggac acggccgtgt attactgtgc gaga           294
```

<210> SEQ ID NO 681
<211> LENGTH: 869
<212> TYPE: DNA
<213> ORGANISM: Homo sapiens

<400> SEQUENCE: 681

```
gcaggattta gggcttggtc tctcagcatc ccacacttgt acagctgatg tggcatctgt      60
gttttctttc tcatcctaga tcaggctttg agctgtgaaa taccctgcct catgcatatg     120
caaataacct gaggtcttct gagataaata tagatatatt ggtgccctga gagcatcaca     180
taacaaccac attcctcctc tgaagaagcc cctgggagca cagctcatca ccatggactg     240
gacctggagg ttcctctttg tggtggcagc agctacaggt aagggcttc ctagtcctaa     300 ggctgaggaa gggatcctgg tttagttaaa gaggatttta ttcacccctg tgtcctctcc     360
acaggtgtcc agtcccaggt gcagctggtg cagtctgggg ctgaggtgaa gaagcctggg    420
```

```
tcctcggtga aggtctcctg caaggcttct ggaggcacct tcagcagcta tgctatcagc      480
tgggtgcgac aggcccctgg acaagggctt gagtggatgg gagggatcat ccctatcttt      540
ggtacagcaa actacgcaca gaagttccag gcagagtca cgattaccgc ggacaaatcc       600
acgagcacag cctacatgga gctgagcagc ctgagatctg aggacacggc cgtgtattac      660
tgtgcgagag acacagtgtg aaaacccaca tcctgagagt gtcagaaacc ctgagggaga      720
aggcagctgt gccgggctga ggagatgaca ggggttatta ggtttaaggc tgtttacaaa      780
atgggttata tatttgagaa aaaaagaaca gtagaaacaa gtacatactc taattttaag      840
ataaatattc cattcaagag tcgtaatat                                        869
```

<210> SEQ ID NO 682
<211> LENGTH: 233
<212> TYPE: DNA
<213> ORGANISM: Homo sapiens

<400> SEQUENCE: 682

```
agaagcctgg gtcctcggtg aaggtctcct gcaaggcttc tggaggcacc ttcagcagct       60
atgctatcag ctgggtgcga caggcccctg gacaagggct tgagtggatg gaaggatca      120 tccctatctt tggtacagca aactacgcac agaagttcca gggcagagtc acgattaccg     180
cggacgaatc cacgagcaca gcctacatgg agctgagcag cctgagatct gag            233
```

<210> SEQ ID NO 683
<211> LENGTH: 392
<212> TYPE: DNA
<213> ORGANISM: Homo sapiens

<400> SEQUENCE: 683

```
taagggcttt cctagtccta aggctgagga agggatcctg gtttagttaa agaggatttt       60
attcacccct gtgtcctctc cacaggtgtc cagtcccagg tccagctggt gcagtctggg      120
gctgaggtga agaagcctgg gtcctcggtg aaggtctcct gcaaggcttc tggaggcacc      180
ttcagcagct atgctatcag ctgggtgcga caggcccctg gacaagggct tgagtggatg      240
ggagggatca tccctatctt tggtacagca aactacgcac agaagttcca gggcagagtc      300
acgattaccg cggacgaatc cacgagcaca gcctacatgg agctgagcag cctgagatct      360
gaggacacgg ccgtgtatta ctgtgcgaga ga                                    392
```

<210> SEQ ID NO 684
<211> LENGTH: 360
<212> TYPE: DNA
<213> ORGANISM: Homo sapiens

<400> SEQUENCE: 684

```
atggactgga cctggagggt cctctttgtg gtggcagcta caggtgtcca gtcccaggtc       60
cagctggtgc agtctggggc tgaggtgaag aagcctgggt cctcagtgaa ggtctcctgc      120
aaggcttctg gaggcacctt cagcagctat gctatcagct gggtgcgaca ggcccctgga      180
caagggcttg agtggatggg aggatcatc cctatctttg gtacagcaaa ctacgcacag       240
aagttccagg gcagagtcac gattaccgcg gacgaatcca cgagcacagc ctacatggag      300
ctgagcagcc tgagatctga ggacacggcc gtgtattact gtgcgagaga cacagtgtga      360
```

<210> SEQ ID NO 685
<211> LENGTH: 294
<212> TYPE: DNA

-continued

<213> ORGANISM: Homo sapiens

<400> SEQUENCE: 685

```
caggtccagc tggtgcaatc tggggctgag gtgaagaagc ctgggtcctc ggtgaaggtc      60
tcctgcaagg cttctggagg caccttcagc agctatacta tcagctgggt gcgacaggcc     120
cctggacaag ggcttgagtg gatgggaagg atcatcccta tccttggtat agcaaactac     180
gcacagaagt tccagggcag agtcacgatt accgcggaca atccacgag cacagcctac      240
atggagctga gcagcctgag atctgaggac acggccgtgt attactgtgc gaga           294
```

<210> SEQ ID NO 686
<211> LENGTH: 779
<212> TYPE: DNA
<213> ORGANISM: Homo sapiens

<400> SEQUENCE: 686

```
agaaatgggg cagggatgc gtttcctcag gcaggattta gggcttggtc tctcagcatc       60
ccacacttgt acagctgatg tggcatctgt gttttctttc tcatcctaga tcaagctttg     120
agctgtgaaa taccctgcct catgaatatg caaataatct gaggtcttct gagataaata     180
tagatatatt ggtgccctga gagcatcaca taacaaccag attcctcctc taaagaagcc     240
cctgggagca cagctcatca ccatggactg gacctggagg ttcctctttg tggtggcagc     300
agctacaggt aaggggcttc ctagtcctaa ggctgaggaa gggatcctgg tttagttaaa     360
gaggatttta ttcacccctg tgtcctctcc acaggtgtcc agtcccaggt ccagctggtg     420
cagtctgggg ctgaggtgaa gaagcctggg tcctcggtga aggtctcctg caaggcttct     480
ggaggcacct tcagcagcta tgctatcagc tgggtgcgac aggcccctgg acaagggctt     540
gagtggatgg gaaggatcat ccctatcctt ggtatagcaa actacgcaca gaagttccag     600
ggcagagtca cgattaccgc ggacaaatcc acgagcacag cctacatgga gctgagcagc     660
ctgagatctg aggacacggc cgtgtattac tgtgcgagag acacagtgtg aaaacccaca     720
tcctgagagt gtcagaaacc ctgagggaga aggcagctgt gccgggctga ggagatgac      779
```

<210> SEQ ID NO 687
<211> LENGTH: 392
<212> TYPE: DNA
<213> ORGANISM: Homo sapiens

<400> SEQUENCE: 687

```
taagggcttt cctagtccta aggctgagga agggatcctg gtttagttaa agaggatttt      60
attcacccct gtgtcctctc cacaggtgtc cagtcccagg tccagctggt gcaatctggg     120
gctgaggtga agaagcctgg gtcctcggtg aaggtctcct gcaaggcttc tggaggcacc     180
ttcagcagct atactatcag ctgggtgcga caggcccctg acaagggct tgagtggatg      240
ggaaggatca tccctatcct tggtacagca aactacgcac agaagttcca ggcagagtc      300
acgattaccg cggacaaatc cacgagcaca gcctacatgg agctgagcag cctgagatct     360
gaggacacgg ccgtgtatta ctgtgcgaga ga                                   392
```

<210> SEQ ID NO 688
<211> LENGTH: 392
<212> TYPE: DNA
<213> ORGANISM: Homo sapiens

<400> SEQUENCE: 688

```
taagggcttt cctagtccta aggctgagga agggatcctg gtttagttaa agaggatttt      60
```

```
attcacccct gtgtcctctc cacaggtgtc cagtcccagg tgcagctggt gcagtctggg    120
gctgaggtga agaagcctgg gtcctcggtg aaggtctcct gcaaggcttc tggaggcacc    180
ttcagcagct atgctatcag ctgggtgcga caggcccctg gacaagggct tgagtggatg    240
ggaaggatca tccctatcct tggtatagca aactacgcac agaagttcca gggcagagtc    300
acgattaccg cggacaaatc cacgagcaca gcctacatgg agctgagcag cctgagatct    360
gaggacacgg ccgtgtatta ctgtgcgaga ga                                  392
```

<210> SEQ ID NO 689
<211> LENGTH: 392
<212> TYPE: DNA
<213> ORGANISM: Homo sapiens

<400> SEQUENCE: 689

```
taagggcttt cctagtccta aggctgagga agggatcctg gtttagttaa agaggatttt     60
attcacccct gtgtcctgtc cacaggtgtc cagtcccagg tccagctggt gcagtctggg    120
gctgaggtga agaagcctgg gtcctcagtg aaggtctcct gcaaggcttc tggaggcacc    180
ttcagcagct atgctatcag ctgggtgcga caggcccctg gacaagggct tgagtggatg    240
ggagggatca tccctatcct tggtatagca aactacgcac agaagttcca gggcagagtc    300
acgattaccg cggacaaatc cacgagcaca gcctacatgg agctgagcag cctgagatct    360
gaggacacgg ccgtgtatta ctgtgcgaga ga                                  392
```

<210> SEQ ID NO 690
<211> LENGTH: 392
<212> TYPE: DNA
<213> ORGANISM: Homo sapiens

<400> SEQUENCE: 690

```
taagggcttt cctagtccta aggctgagga agggatcctg gtttagttaa agaggatttt     60
attcacccct gtgtcctctc cacaggtgtc cagtcccagg tccagctggt gcagtctggg    120
gctgaggtga agaagcctgg gtcctcggtg aaggtctcct gcaaggcttc tggaggcacc    180
ttcagcagct atgctatcag ctgggtgcga caggcccctg gacaagggct tgagtggatg    240
ggaaggatca tccctatcct tggtacagca aactacgcac agaagttcca gggcagagtc    300
acgattaccg cggacgaatc cacgagcaca gcctacatgg agctgagcag cctgagatct    360
gaggacacgg ccgtgtatta ctgtgcgaga ga                                  392
```

<210> SEQ ID NO 691
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 691

Arg Gly Tyr Trp
1

<210> SEQ ID NO 692
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 692

Trp Arg Cys Tyr
1

<210> SEQ ID NO 693
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 693

Gly Gly Thr Phe Ser Ser Tyr Ala
1               5

<210> SEQ ID NO 694
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 694

Ile Ile Pro Ile Phe Gly Thr Ala
1               5

<210> SEQ ID NO 695
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 695

Glu Ser Thr Ser
1

<210> SEQ ID NO 696
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 696

Glu Val Thr Phe Ser Ser Phe Ala
1               5

<210> SEQ ID NO 697
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 697

Ile Ser Pro Met Phe Gly Thr Pro
1               5

<210> SEQ ID NO 698
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 698

Gln Ser Thr Arg
1

<210> SEQ ID NO 699
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 699

Cys Ala Arg Ser Pro Ser Tyr Ile Cys Ser Gly Gly Thr Cys Val Phe
1               5                   10                  15

Asp His Trp

<210> SEQ ID NO 700
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 700

Gly Gly Thr Ser Asn Asn Tyr Ala
1               5

<210> SEQ ID NO 701
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 701

Ile Ser Pro Ile Phe Gly Ser Thr
1               5

<210> SEQ ID NO 702
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 702

Ile Phe Ser Asn
1

<210> SEQ ID NO 703
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 703
```

Cys Ala Arg His Gly Asn Tyr Tyr Tyr Ser Gly Met Asp Val Trp
1               5                   10                  15

<210> SEQ ID NO 704
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 704

Gly Gly Pro Phe Arg Ser Tyr Ala
1               5

<210> SEQ ID NO 705
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 705

Ile Ile Pro Ile Phe Gly Thr Thr
1               5

<210> SEQ ID NO 706
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 706

Asp Phe Ala Gly
1

<210> SEQ ID NO 707
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 707

Cys Ala Lys His Met Gly Tyr Gln Val Arg Glu Thr Met Asp Val Trp
1               5                   10                  15

<210> SEQ ID NO 708
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 708

Ala Gly Gly Thr Phe Ser Ser Tyr Ala Ile
1               5                   10

<210> SEQ ID NO 709
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 709

Ile Ile Pro Ile Phe Gly Thr Ala Asn
1               5

<210> SEQ ID NO 710
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 710

Glu Ser Thr Ser
1

<210> SEQ ID NO 711
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 711

Ser Glu Val Thr Phe Ser Ser Phe Ala Ile
1               5                   10

<210> SEQ ID NO 712
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 712

Ile Ser Pro Met Phe Gly Thr Pro Asn
1               5

<210> SEQ ID NO 713
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 713

Gln Ser Thr Arg
1

<210> SEQ ID NO 714
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 714

Cys Ala Arg Ser Pro Ser Tyr Ile Cys Ser Gly Gly Thr Cys Val Phe
1               5                   10                  15
```

Asp His Trp

<210> SEQ ID NO 715
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 715

Ala Gly Val Thr Phe Ser Tyr Tyr Ala Met
1               5                   10

<210> SEQ ID NO 716
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 716

Ile Ser Pro Met Phe Gly Thr Thr Thr
1               5

<210> SEQ ID NO 717
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 717

Asp Ser Thr Ser
1

<210> SEQ ID NO 718
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 718

Cys Ala Arg Ser Ser Asn Tyr Tyr Asp Ser Val Tyr Asp Tyr Trp
1               5                   10                  15

<210> SEQ ID NO 719
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 719

Val Gly Val Ile Phe Ser Gly Ser Ala Ile
1               5                   10

<210> SEQ ID NO 720
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 720

Ile Ser Pro Leu Phe Gly Thr Thr Asn
1               5

<210> SEQ ID NO 721
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 721

Gln Ser Thr Asn
1

<210> SEQ ID NO 722
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 722

Cys Ala Arg Gly Pro Lys Tyr Tyr Ser Glu Tyr Met Asp Val Trp
1               5                   10                  15

<210> SEQ ID NO 723
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 723

Ser Gly Gly Thr Ser Asn Asn Tyr Ala Ile
1               5                   10

<210> SEQ ID NO 724
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 724

Ile Ser Pro Ile Phe Gly Ser Thr Ala
1               5

<210> SEQ ID NO 725
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 725

Ile Phe Ser Asn
1

<210> SEQ ID NO 726

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 726

Cys Ala Arg His Gly Asn Tyr Tyr Tyr Ser Gly Met Asp Val Trp
1               5                   10                  15

<210> SEQ ID NO 727
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 727

Ala Gly Gly Pro Phe Ser Met Thr Ala Phe
1               5                   10

<210> SEQ ID NO 728
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 728

Ile Ser Pro Ile Phe Arg Thr Pro Lys
1               5

<210> SEQ ID NO 729
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 729

Glu Ser Thr Asn
1

<210> SEQ ID NO 730
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 730

Cys Ala Arg Thr Leu Ser Ser Tyr Gln Pro Asn Asn Asp Ala Phe Ala
1               5                   10                  15

Ile Trp

<210> SEQ ID NO 731
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 731

Ala Gly Gly Pro Phe Ser Gly Phe Ala Ile
1               5                   10

<210> SEQ ID NO 732
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 732

Ile Ser Ala Val Phe Gly Thr Ala Thr
1               5

<210> SEQ ID NO 733
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 733

Gln Phe Thr Ser
1

<210> SEQ ID NO 734
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 734

Cys Ala Arg Ser Gly Gly Tyr Leu Pro Gln Asn Asn Trp Ile Asp Pro
1               5                   10                  15

Trp

<210> SEQ ID NO 735
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 735

Ala Gly Gly Pro Phe Arg Asn Phe Ala Ile
1               5                   10

<210> SEQ ID NO 736
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 736

Ile Ile Ala Val Phe Gly Thr Thr Lys
1               5

<210> SEQ ID NO 737
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 737

Asp Ser Thr Asn
1

<210> SEQ ID NO 738
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 738

Cys Ala Arg Gly Pro His Tyr Tyr Ser Ser Tyr Met Asp Val Trp
1               5                   10                  15

<210> SEQ ID NO 739
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 739

Ala Gly Gly Ile Phe Arg Ser Asn Ser Ile
1               5                   10

<210> SEQ ID NO 740
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 740

Ile Phe Ala Leu Phe Gly Thr Thr Asp
1               5

<210> SEQ ID NO 741
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 741

Glu Ser Ser Thr
1

<210> SEQ ID NO 742
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 742
```

```
Cys Ala Arg Gly Ser Gly Tyr Thr Thr Arg Asn Tyr Phe Asp Tyr Trp
1               5                   10                  15

<210> SEQ ID NO 743
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 743

Ala Gly Ser Ile Phe Arg Asn Tyr Ala Met
1               5                   10

<210> SEQ ID NO 744
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 744

Ile Ile Ala Ile Phe Gly Thr Pro Lys
1               5

<210> SEQ ID NO 745
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 745

Glu Ser Thr Ser
1

<210> SEQ ID NO 746
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 746

Cys Ala Arg Ile Pro His Tyr Asn Phe Gly Ser Gly Ser Tyr Phe Asp
1               5                   10                  15

Tyr Trp

<210> SEQ ID NO 747
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 747

Ala Gly Gly Ile Phe Arg Ser Asn Ala Ile
1               5                   10

<210> SEQ ID NO 748
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 748

Ile Ile Ala Val Phe Gly Thr Ala Asn
1               5

<210> SEQ ID NO 749
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 749

Glu Ser Thr Ser
1

<210> SEQ ID NO 750
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 750

Cys Ala Arg Gly Pro Tyr Tyr Tyr Gly Asn Ser His Leu Asp Phe Trp
1               5                   10                  15

<210> SEQ ID NO 751
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 751

Ala Gly Gly Ile Phe Ser Pro Tyr Ala Ile
1               5                   10

<210> SEQ ID NO 752
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 752

Ile Ile Ala Ile Phe Gly Thr Thr Asn
1               5

<210> SEQ ID NO 753
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 753

Lys Ser Thr Thr
1
```

<210> SEQ ID NO 754
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 754

Cys Ala Arg Gly Gly Arg Tyr Tyr Val Asp Tyr Phe Asp Tyr Trp
1               5                   10                  15

<210> SEQ ID NO 755
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 755

Ala Gly Gly Thr Phe Arg Asn Phe Ala Val
1               5                   10

<210> SEQ ID NO 756
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 756

Ile Ile Ala Ile Phe Gly Thr Ala Lys
1               5

<210> SEQ ID NO 757
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 757

Glu Ser Thr Arg
1

<210> SEQ ID NO 758
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 758

Cys Ala Ser Ser Ser Gly Ser Tyr Tyr Gly Asp Tyr Phe Asp Tyr Trp
1               5                   10                  15

<210> SEQ ID NO 759
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 759

Ala Gly Gly Thr Phe Arg Thr His Ala Ile
1               5                   10

<210> SEQ ID NO 760
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 760

Ile Ile Ala Ile Phe Gly Thr Ala Asn
1               5

<210> SEQ ID NO 761
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 761

Glu Ser Thr Ser
1

<210> SEQ ID NO 762
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 762

Cys Ala Arg Gly Ser Gly Tyr His Ile Ser Thr Pro Phe Asp Asn Trp
1               5                   10                  15

<210> SEQ ID NO 763
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 763

Ala Gly Gly Thr Phe Ser Ser Tyr Ala Ile
1               5                   10

<210> SEQ ID NO 764
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 764

Ile Ile Gly Met Phe Gly Thr Ala Asn
1               5

<210> SEQ ID NO 765
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 765

Glu Phe Thr Ser
1

<210> SEQ ID NO 766
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 766

Cys Ala Arg Gly Asn Tyr Tyr Glu Ser Ser Leu Asp Tyr Trp
1               5                   10                  15

<210> SEQ ID NO 767
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 767

Thr Gly Gly Thr Phe Ser Ser Tyr Ala Val
1               5                   10

<210> SEQ ID NO 768
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 768

Ile Ile Gly Met Phe Gly Thr Thr Asn
1               5

<210> SEQ ID NO 769
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 769

Glu Met Thr Ser
1

<210> SEQ ID NO 770
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 770

Cys Ala Arg Gly Ser Tyr Tyr Tyr Glu Thr Thr Leu Asp Tyr Trp
```

```
                 1               5                  10                  15

<210> SEQ ID NO 771
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 771

Ala Gly Gly Thr Phe Ser Ala Tyr Ala Phe
1               5                  10

<210> SEQ ID NO 772
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 772

Ile Thr Gly Met Phe Gly Thr Ala Asn
1               5

<210> SEQ ID NO 773
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 773

Glu Leu Thr Ser
1

<210> SEQ ID NO 774
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 774

Cys Ala Arg Gly Leu Tyr Tyr Tyr Glu Ser Ser Leu Asp Tyr Trp
1               5                  10                  15

<210> SEQ ID NO 775
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 775

Ala Gly Gly Thr Phe Ser Ser Tyr Gly Ile
1               5                  10

<210> SEQ ID NO 776
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 776

Ile Ile Gly Met Phe Gly Ser Thr Asn
1               5

<210> SEQ ID NO 777
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 777

Glu Ser Thr Ser
1

<210> SEQ ID NO 778
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 778

Cys Ala Arg Ser Ser Gly Tyr Tyr Pro Ala Tyr Leu Pro His Trp
1               5                   10                  15

<210> SEQ ID NO 779
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 779

Thr Gly Gly Thr Phe Ser Ser Phe Ala Phe
1               5                   10

<210> SEQ ID NO 780
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 780

Ile Ile Gly Met Phe Gly Thr Thr Ser
1               5

<210> SEQ ID NO 781
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 781

Glu Ser Thr Ser
1

<210> SEQ ID NO 782

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 782

Cys Ala Arg Gly Lys Lys Tyr Tyr His Asp Thr Leu Asp Tyr Trp
1               5                   10                  15

<210> SEQ ID NO 783
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 783

Ser Gly Ser Pro Phe Arg Ser Asn Ala Val
1               5                   10

<210> SEQ ID NO 784
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 784

Ile Leu Gly Val Phe Gly Ser Pro Ser
1               5

<210> SEQ ID NO 785
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 785

Glu Ser Thr Asn
1

<210> SEQ ID NO 786
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 786

Cys Ala Arg Gly Pro Thr Tyr Tyr Tyr Ser Tyr Met Asp Val Trp
1               5                   10                  15

<210> SEQ ID NO 787
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 787
```

Thr Gly Val Thr Phe Ser Ser Tyr Ala Ile
1               5                   10

<210> SEQ ID NO 788
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 788

Ile Ile Gly Val Phe Gly Val Pro Lys
1               5

<210> SEQ ID NO 789
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 789

Lys Pro Thr Ser
1

<210> SEQ ID NO 790
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 790

Cys Ala Arg Glu Pro Gly Tyr Tyr Val Gly Lys Asn Gly Phe Asp Val
1               5                   10                  15

Trp

<210> SEQ ID NO 791
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 791

Ala Gly Val Ile Phe Asn Ala Tyr Ala Met
1               5                   10

<210> SEQ ID NO 792
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 792

Ile Thr Gly Val Phe His Thr Ala Thr
1               5

<210> SEQ ID NO 793
<211> LENGTH: 4
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 793

Glu Ser Thr Ser
1

<210> SEQ ID NO 794
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 794

Cys Ala Arg Gly Pro Lys Tyr Tyr His Ser Tyr Met Asp Val Trp
1               5                   10                  15

<210> SEQ ID NO 795
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 795

Ala Gly Gly Pro Phe Arg Ser Tyr Ala Ile
1               5                   10

<210> SEQ ID NO 796
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 796

Ile Ile Pro Ile Phe Gly Thr Thr Lys
1               5

<210> SEQ ID NO 797
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 797

Asp Phe Ala Gly
1

<210> SEQ ID NO 798
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 798

Cys Ala Lys His Met Gly Tyr Gln Val Arg Glu Thr Met Asp Val Trp
1               5                   10                  15
```

<210> SEQ ID NO 799
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 799

Ala Gly Gly Ile Phe Asn Thr Asn Ala Phe
1               5                   10

<210> SEQ ID NO 800
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 800

Val Ile Pro Leu Phe Arg Thr Ala Ser
1               5

<210> SEQ ID NO 801
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 801

Glu Ser Thr Asn
1

<210> SEQ ID NO 802
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 802

Cys Ala Arg Ser Ser Gly Tyr His Phe Arg Ser His Phe Asp Ser Trp
1               5                   10                  15

<210> SEQ ID NO 803
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 803

Ala Gly Gly Thr Phe Ser Thr Tyr Gly Val
1               5                   10

<210> SEQ ID NO 804
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 804

Ile Ile Pro Ile Phe Gly Thr Ala Lys
1               5

<210> SEQ ID NO 805
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 805

Glu Ser Ser Thr
1

<210> SEQ ID NO 806
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 806

Cys Ala Arg Pro Asn Thr Tyr Gly Tyr Ile Leu Pro Val Tyr Trp
1               5                   10                  15

<210> SEQ ID NO 807
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 807

Ala Gly Gly Thr Phe Asn Asn Tyr Ala Val
1               5                   10

<210> SEQ ID NO 808
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 808

Ile Ile Pro Ile Phe Gly Thr Ala Asn
1               5

<210> SEQ ID NO 809
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 809

Glu Ser Thr Ser
1

<210> SEQ ID NO 810
<211> LENGTH: 20

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 810

Cys Ala Arg Val Cys Ser Phe Tyr Gly Ser Gly Ser Tyr Tyr Asn Val
1               5                   10                  15

Phe Cys Tyr Trp
            20

<210> SEQ ID NO 811
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 811

Thr Gly Gly Thr Phe Asn Ser His Ala Ile
1               5                   10

<210> SEQ ID NO 812
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 812

Ile Ile Pro Met Phe Gly Thr Thr Asn
1               5

<210> SEQ ID NO 813
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 813

Gln Leu Pro Thr
1

<210> SEQ ID NO 814
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 814

Cys Ala Arg Gly Gln Arg Tyr Tyr Tyr Asp Arg Asp Gly Met Asp Val
1               5                   10                  15

Trp

<210> SEQ ID NO 815
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 815

Thr Gly Gly Ile Phe Ser Asn Phe Ala Val
1               5                   10

<210> SEQ ID NO 816
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 816

Ile Leu Ser Ile Phe Arg Thr Thr Asn
1               5

<210> SEQ ID NO 817
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 817

Glu Ser Thr Ser
1

<210> SEQ ID NO 818
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 818

Cys Ala Arg Ser Ile Thr Asn Leu Tyr Tyr Tyr Tyr Met Asp Val Trp
1               5                   10                  15

<210> SEQ ID NO 819
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 819

Ala Gly Gly Ile Phe Ile Ser Gln Ala Ile
1               5                   10

<210> SEQ ID NO 820
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 820

Ile Ile Pro Met Phe Gly Ala Thr Asn
1               5

<210> SEQ ID NO 821

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 821

Lys Ser Thr Asn
1

<210> SEQ ID NO 822
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 822

Cys Ala Arg Leu Gly Ser Gly Ser Tyr His Asn Gly Pro Asn Trp Phe
1               5                   10                  15

Asp Pro Trp

<210> SEQ ID NO 823
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 823

Ala Gly Val Thr Ser Ser Asn Tyr Pro Ile
1               5                   10

<210> SEQ ID NO 824
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 824

Val Leu Pro Leu Phe Gly Val Thr Asn
1               5

<210> SEQ ID NO 825
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 825

Lys Ser Thr Asn
1

<210> SEQ ID NO 826
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 826

Cys Ala Arg Gly Lys Arg Pro Gly Tyr Cys Ser Gly Gly Val Cys Ser
1               5                   10                  15

Ser Asp Tyr Trp
            20

<210> SEQ ID NO 827
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 827

Ala Gly Val Thr Phe Asn His Tyr Thr Val
1               5                   10

<210> SEQ ID NO 828
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 828

Ile Ile Pro Leu Phe Gly Thr Ala Asp
1               5

<210> SEQ ID NO 829
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 829

Arg Ser Thr Gly
1

<210> SEQ ID NO 830
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 830

Cys Ala Arg Ser Gly Thr Thr Lys Thr Arg Tyr Asn Trp Phe Asp Pro
1               5                   10                  15

Trp

<210> SEQ ID NO 831
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 831

Ala Gly Val Thr Phe Ser Met Tyr Thr Ile
1               5                   10
```

```
<210> SEQ ID NO 832
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 832

Ile Ile Pro Leu Phe Gly Thr Ala Asn
1               5

<210> SEQ ID NO 833
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 833

Thr Ser Thr Asn
1

<210> SEQ ID NO 834
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 834

Cys Ala Arg Ala Gly Thr Thr Leu Thr Arg Phe Asn Trp Phe Asp Pro
1               5                   10                  15

Trp

<210> SEQ ID NO 835
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 835

Ser Gly Val Thr Phe Ser Met Tyr Ala Val
1               5                   10

<210> SEQ ID NO 836
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 836

Ile Ile Pro Leu Phe Gly Thr Thr Thr
1               5

<210> SEQ ID NO 837
<211> LENGTH: 4
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 837

Thr Ser Thr Asn
1

<210> SEQ ID NO 838
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 838

Cys Ala Arg Ala Gly Thr Thr Val Thr Arg Phe Asn Trp Phe Asp Pro
1               5                   10                  15

Trp

<210> SEQ ID NO 839
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 839

Ala Gly Met Thr Ser Asn Ser Leu Ala Ile
1               5                   10

<210> SEQ ID NO 840
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 840

Ile Ile Pro Val Phe Glu Thr Pro Lys
1               5

<210> SEQ ID NO 841
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 841

Lys Ser Thr Asn
1

<210> SEQ ID NO 842
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 842

Cys Ala Thr Ser Ala Gly Gly Ile Val Asn Tyr Tyr Leu Ser Phe Asn
1               5                   10                  15

Ile Trp

<210> SEQ ID NO 843
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 843

Thr Gly Gly Thr Ser Asn Asn Tyr Pro Ile
1               5                   10

<210> SEQ ID NO 844
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 844

Ser Ile Pro Ile Phe Asn Thr Pro Lys
1               5

<210> SEQ ID NO 845
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 845

Thr Ser Thr Ser
1

<210> SEQ ID NO 846
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 846

Cys Ala Thr Ser Ala Gly Gly Ile Val Asn Tyr Phe Leu Leu Phe Asp
1               5                   10                  15

Ile Trp

<210> SEQ ID NO 847
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 847

Ala Gly Gly Ser Phe Thr Ser Phe Val Ile
1               5                   10

<210> SEQ ID NO 848
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 848

Val Ile Pro Ile Phe Ala Thr Pro Lys
1               5

<210> SEQ ID NO 849
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 849

Lys Ser Thr Asn
1

<210> SEQ ID NO 850
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 850

Cys Ala Ser Pro Asp Leu Thr Met Val Phe Val Pro His Thr Gly Pro
1               5                   10                  15

Leu Asp Phe Trp
            20

<210> SEQ ID NO 851
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 851

Ala Gly Gly Phe Phe Ser Ser Tyr Ala Ile
1               5                   10

<210> SEQ ID NO 852
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 852

Val Ile Pro Ile Phe Arg Thr Ala Asn
1               5

<210> SEQ ID NO 853
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 853

```
Glu Phe Thr Ser
1

<210> SEQ ID NO 854
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 854

Cys Ala Arg Leu Asn Tyr His Asp Ser Gly Thr Tyr Tyr Asn Ala Pro
1               5                   10                  15

Arg Gly Trp Phe Asp Pro Trp
            20

<210> SEQ ID NO 855
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 855

Ala Gly Gly Thr Phe Ser Phe Tyr Ser Met
1               5                   10

<210> SEQ ID NO 856
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 856

Ile Ile Pro Met Phe Gly Thr Thr Asn
1               5

<210> SEQ ID NO 857
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 857

Glu Ser Thr Ser
1

<210> SEQ ID NO 858
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 858

Cys Ala Arg Gly Asp Lys Gly Ile Tyr Tyr Tyr Met Asp Val Trp
1               5                   10                  15

<210> SEQ ID NO 859
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 859

Ala Gly Gly Thr Phe Ser Arg Tyr Thr Val
1               5                   10

<210> SEQ ID NO 860
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 860

Phe Ile Pro Leu Leu Gly Met Thr Asn
1               5

<210> SEQ ID NO 861
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 861

Lys Ser Thr Thr
1

<210> SEQ ID NO 862
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 862

Cys Ala Arg His Asp Ser Ser Gly Tyr His Pro Leu Asp Tyr Trp
1               5                   10                  15

<210> SEQ ID NO 863
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 863
atgggaggga tcatccctat ctttggtaca gcaaactacg ca                              42

<210> SEQ ID NO 864
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly or Pro
```

-continued

<400> SEQUENCE: 864

Ile Ile Xaa Met Phe Gly Thr Ala
1               5

<210> SEQ ID NO 865
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly or Pro

<400> SEQUENCE: 865

Ile Ile Xaa Val Phe Gly Val Pro
1               5

<210> SEQ ID NO 866
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly or Pro

<400> SEQUENCE: 866

Ile Thr Xaa Met Phe Gly Thr Ala
1               5

<210> SEQ ID NO 867
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Ile

<400> SEQUENCE: 867

Ile Xaa Pro Ile Phe Arg Thr Pro
1               5

<210> SEQ ID NO 868
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Ile

<400> SEQUENCE: 868

Ile Xaa Pro Met Phe Gly Thr Pro
1               5

```
<210> SEQ ID NO 869
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 869

Ile Ser Pro Met Phe Gly Thr Pro
1               5

<210> SEQ ID NO 870
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 870

Ile Ser Pro Ile Phe Gly Thr Ala
1               5

<210> SEQ ID NO 871
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 871

Ile Ile Pro Met Phe Gly Thr Ala
1               5

<210> SEQ ID NO 872
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 872

Ile Ile Pro Ile Phe Gly Thr Ala
1               5

<210> SEQ ID NO 873
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 873

Ile Ser Pro Ile Phe Arg Thr Pro
1               5

<210> SEQ ID NO 874
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 874
```

Ile Ser Pro Ile Phe Gly Thr Ala
1               5

<210> SEQ ID NO 875
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 875

Ile Ile Pro Ile Phe Arg Thr Ala
1               5

<210> SEQ ID NO 876
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 876

Ile Ile Pro Ile Phe Gly Thr Ala
1               5

<210> SEQ ID NO 877
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 877

Gly Gly Thr Phe Ser Ser Tyr Ala
1               5

<210> SEQ ID NO 878
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 878

Ile Ile Pro Ile Phe Gly Thr Ala
1               5

<210> SEQ ID NO 879
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 879

Glu Ser Thr Ser Thr Ala
1               5

<210> SEQ ID NO 880
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 880

Gly Gly Thr Phe Ser Ser Tyr Ala
1               5

<210> SEQ ID NO 881
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 881

Ile Ile Pro Ile Phe Gly Thr Ala
1               5

<210> SEQ ID NO 882
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 882

Lys Ser Thr Ser Thr Ala
1               5

<210> SEQ ID NO 883
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 883

Gly Gly Pro Phe Ser Ser Tyr Ala
1               5

<210> SEQ ID NO 884
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 884

Ile Ser Pro Leu Phe Gly Thr Ala
1               5

<210> SEQ ID NO 885
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 885

Glu Ser Thr Ser Thr Ala
1               5
```

<210> SEQ ID NO 886
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 886

Cys Ala Arg Ala Pro Thr Tyr Tyr Ala Ser Arg Asp Ser Tyr Asn Phe
1               5                   10                  15

Asp Tyr Trp

<210> SEQ ID NO 887
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 887

Gly Val Thr Phe Arg Ser Tyr Ala
1               5

<210> SEQ ID NO 888
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 888

Ile Ser Gly Ile Phe Gly Thr Ala
1               5

<210> SEQ ID NO 889
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 889

Glu Ser Thr Ser Thr Ala
1               5

<210> SEQ ID NO 890
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 890

Cys Ala Arg Ser Pro Ala Tyr Tyr Phe Gly Pro Asn Met Asp Val Trp
1               5                   10                  15

<210> SEQ ID NO 891
<211> LENGTH: 8
<212> TYPE: PRT
<213> ORGANISM: Artificial Sequence
<220> FEATURE:
<223> OTHER INFORMATION: Description of Artificial Sequence: Synthetic

```
                         peptide

<400> SEQUENCE: 891

Gly Val Thr Phe Ser Ser Tyr Ala
1               5

<210> SEQ ID NO 892
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 892

Ile Ser Pro Ile Phe Gly Thr Ala
1               5

<210> SEQ ID NO 893
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 893

Gln Ser Thr Asn Thr Val
1               5

<210> SEQ ID NO 894
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 894

Cys Ala Arg Asp Ser Gly Asn Tyr Asp Gly Tyr Gly Pro Gly Ser Arg
1               5                   10                  15

Phe Asp Val Trp
            20

<210> SEQ ID NO 895
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 895

Gly Val Thr Phe Ser Ser Tyr Ala
1               5

<210> SEQ ID NO 896
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 896

Ile Ser Pro Ile Phe Gly Thr Ala
1               5
```

<210> SEQ ID NO 897
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 897

Lys Ser Thr Ser Thr Val
1               5

<210> SEQ ID NO 898
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 898

Cys Ala Arg Gly Gly Gly Tyr Ser Ala Asp Gly Gly Ala Gly Asn Asn
1               5                   10                  15

Thr Ile Phe Asp Val Trp
            20

<210> SEQ ID NO 899
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 899

Gly Val Thr Phe Ser Ser Tyr Ala
1               5

<210> SEQ ID NO 900
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 900

Ile Ser Pro Met Phe Gly Thr Ala
1               5

<210> SEQ ID NO 901
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 901

Gln Ser Thr Asn Thr Ala
1               5

<210> SEQ ID NO 902
<211> LENGTH: 17
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 902

Cys Ala Arg Gly Gly Thr Tyr Ser Pro Gly Gly Thr Tyr Phe Asp Val
1               5                   10                  15
Trp

<210> SEQ ID NO 903
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 903

Gly Val Thr Phe Ser Ser Tyr Ala
1               5

<210> SEQ ID NO 904
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 904

Ile Ser Pro Met Phe Gly Thr Ala
1               5

<210> SEQ ID NO 905
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 905

Glu Ser Thr Asn Thr Ala
1               5

<210> SEQ ID NO 906
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 906

Cys Ala Arg Gly Arg Gly Tyr Ala Pro Asp Ala Leu Thr Asn Phe Asp
1               5                   10                  15
Val Trp

<210> SEQ ID NO 907
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 907
```

```
Gly Gly Thr Phe Ser Ser Tyr Ala
1               5
```

<210> SEQ ID NO 908
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 908

```
Ile Ser Pro Met Phe Gly Thr Ala
1               5
```

<210> SEQ ID NO 909
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 909

```
Lys Ser Thr Ser Thr Ala
1               5
```

<210> SEQ ID NO 910
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 910

```
Cys Ala Arg Glu Gly Gly Tyr Ser Pro Gly Gly Val Asp Phe Asp Tyr
1               5                   10                  15

Trp
```

<210> SEQ ID NO 911
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 911

```
Gly Gly Pro Phe Ser Ser Tyr Ala
1               5
```

<210> SEQ ID NO 912
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 912

```
Ile Ser Pro Met Phe Gly Thr Ala
1               5
```

<210> SEQ ID NO 913
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 913

Lys Ser Thr Ser Thr Ala
1               5

<210> SEQ ID NO 914
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 914

Cys Ala Arg Asp Asp Gly Tyr Ala Pro Ser Gly Gly Leu Arg Glu Phe
1               5                   10                  15

Asp Val Trp

<210> SEQ ID NO 915
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 915

Gly Gly Thr Phe Ser Ser Tyr Ala
1               5

<210> SEQ ID NO 916
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 916

Ile Ser Pro Met Phe Gly Thr Ala
1               5

<210> SEQ ID NO 917
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 917

Lys Ser Thr Ser Thr Ala
1               5

<210> SEQ ID NO 918
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 918
```

Cys Ala Arg Ser Ser Arg Tyr Ala Pro Ser Asp Ser Thr Asn Phe Asp
1               5                   10                  15

Gln Trp

<210> SEQ ID NO 919
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 919

Gly Val Thr Phe Ser Ser Tyr Ala
1               5

<210> SEQ ID NO 920
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 920

Ile Thr Pro Met Phe Gly Thr Ala
1               5

<210> SEQ ID NO 921
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 921

Lys Ser Thr Ser Thr Val
1               5

<210> SEQ ID NO 922
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 922

Cys Ala Arg Gly Arg Gly Tyr Ile Ala Val Ala Gly Asp Met Asp Val
1               5                   10                  15

Trp

<210> SEQ ID NO 923
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 923

Gly Gly Thr Phe Ser Ser Tyr Ala
1               5

```
<210> SEQ ID NO 924
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 924

Ile Ile Pro Ile Phe Gly Thr Ala
1               5

<210> SEQ ID NO 925
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 925

Ala Asp Glu Ser Thr Ser
1               5

<210> SEQ ID NO 926
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 926

Gly Gly Thr Phe Ser Ser Tyr Ala
1               5

<210> SEQ ID NO 927
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 927

Ile Ile Pro Ile Phe Gly Thr Ala
1               5

<210> SEQ ID NO 928
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 928

Ala Asp Glu Ser Thr Ser
1               5

<210> SEQ ID NO 929
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 929
```

```
Gly Gly Thr Phe Ser Ser Tyr Ala
1               5

<210> SEQ ID NO 930
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 930

Ile Ile Pro Ile Phe Gly Thr Ala
1               5

<210> SEQ ID NO 931
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 931

Thr Asp Glu Ser Thr Ser
1               5

<210> SEQ ID NO 932
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 932

Gly Gly Thr Phe Ser Ser Tyr Ala
1               5

<210> SEQ ID NO 933
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 933

Ile Ile Pro Ile Phe Gly Thr Ala
1               5

<210> SEQ ID NO 934
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 934

Ala Asp Lys Ser Thr Ser
1               5

<210> SEQ ID NO 935
<211> LENGTH: 8
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 935

Gly Gly Thr Phe Ser Ser Tyr Ala
1               5

<210> SEQ ID NO 936
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 936

Ile Ile Pro Ile Phe Gly Thr Ala
1               5

<210> SEQ ID NO 937
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 937

Ala Asp Glu Ser Thr Ser
1               5

<210> SEQ ID NO 938
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 938

Gly Gly Thr Phe Ser Ser Tyr Ala
1               5

<210> SEQ ID NO 939
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 939

Ile Ile Pro Ile Phe Gly Thr Ala
1               5

<210> SEQ ID NO 940
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 940

Ala Asp Glu Ser Thr Ser
1               5
```

<210> SEQ ID NO 941
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 941

Gly Gly Thr Phe Ser Ser Tyr Ala
1               5

<210> SEQ ID NO 942
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 942

Ile Ile Pro Ile Phe Gly Thr Ala
1               5

<210> SEQ ID NO 943
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 943

Ala Asp Glu Ser Thr Ser
1               5

<210> SEQ ID NO 944
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 944

Gly Gly Thr Phe Ser Ser Tyr Thr
1               5

<210> SEQ ID NO 945
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 945

Ile Ile Pro Ile Leu Gly Ile Ala
1               5

<210> SEQ ID NO 946
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 946

Ala Asp Lys Ser Thr Ser
1               5

<210> SEQ ID NO 947
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 947

Gly Gly Thr Phe Ser Ser Tyr Ala
1               5

<210> SEQ ID NO 948
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 948

Ile Ile Pro Ile Leu Gly Ile Ala
1               5

<210> SEQ ID NO 949
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 949

Ala Asp Lys Ser Thr Ser
1               5

<210> SEQ ID NO 950
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 950

Gly Gly Thr Phe Ser Ser Tyr Thr
1               5

<210> SEQ ID NO 951
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 951

Ile Ile Pro Ile Leu Gly Thr Ala
1               5

<210> SEQ ID NO 952
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 952

Ala Asp Lys Ser Thr Ser
1               5

<210> SEQ ID NO 953
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 953

Gly Gly Thr Phe Ser Ser Tyr Ala
1               5

<210> SEQ ID NO 954
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 954

Ile Ile Pro Ile Leu Gly Ile Ala
1               5

<210> SEQ ID NO 955
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 955

Ala Asp Lys Ser Thr Ser
1               5

<210> SEQ ID NO 956
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 956

Gly Gly Thr Phe Ser Ser Tyr Ala
1               5

<210> SEQ ID NO 957
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 957

Ile Ile Pro Ile Leu Gly Ile Ala
1               5
```

<210> SEQ ID NO 958
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 958

Ala Asp Lys Ser Thr Ser
1               5

<210> SEQ ID NO 959
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 959

Gly Gly Thr Phe Ser Ser Tyr Ala
1               5

<210> SEQ ID NO 960
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 960

Ile Ile Pro Ile Leu Gly Thr Ala
1               5

<210> SEQ ID NO 961
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 961

Ala Asp Glu Ser Thr Ser
1               5

<210> SEQ ID NO 962
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 962
aaggcttctg gaggcacctt cagcagctat gctatcagct gg                          42

<210> SEQ ID NO 963
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 963

Gly Gly Thr Phe Ser Ser Tyr Ala
1               5

<210> SEQ ID NO 964
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 964

Ile Ile Pro Ile Phe Gly Thr Ala
1               5

<210> SEQ ID NO 965
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 965

Glu Ser Thr Ser Thr Ala
1               5

<210> SEQ ID NO 966
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 966

Gly Gly Thr Phe Ser Ser Tyr Ala
1               5

<210> SEQ ID NO 967
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 967

Ile Ile Pro Ile Phe Gly Thr Ala
1               5

<210> SEQ ID NO 968
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 968

Lys Ser Thr Ser Thr Ala
1               5

<210> SEQ ID NO 969
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 969

Gly Gly Thr Phe Ser Ser Tyr Ala
1               5

<210> SEQ ID NO 970
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 970

Ile Ser Pro Ile Phe Gly Thr Ala
1               5

<210> SEQ ID NO 971
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 971

Glu Ser Thr Ser Thr Val
1               5

<210> SEQ ID NO 972
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 972

Cys Ala Arg Gly Pro Gly Tyr His Pro Ala Gly Ala Ser Gly Gln Phe
1               5                   10                  15

Phe Asp Leu Trp
            20

<210> SEQ ID NO 973
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 973

Gly Val Thr Phe Ser Ser Tyr Ala
1               5

<210> SEQ ID NO 974
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 974
```

Ile Ser Pro Met Phe Gly Thr Ala
1               5

<210> SEQ ID NO 975
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 975

Glu Ser Thr Asn Thr Ala
1               5

<210> SEQ ID NO 976
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 976

Cys Ala Arg Gly Arg Gly Tyr Ala Pro Asp Ala Leu Thr Asn Phe Asp
1               5                   10                  15

Val Trp

<210> SEQ ID NO 977
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 977

Gly Gly Thr Phe Ser Ser Tyr Ala
1               5

<210> SEQ ID NO 978
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 978

Ile Ser Pro Met Phe Gly Thr Ala
1               5

<210> SEQ ID NO 979
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 979

Lys Ser Thr Ser Thr Ala
1               5

<210> SEQ ID NO 980
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 980

Cys Ala Arg Glu Gly Gly Tyr Ser Pro Gly Gly Val Asp Phe Asp Tyr
1               5                   10                  15

Trp

<210> SEQ ID NO 981
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 981

Gly Gly Pro Phe Ser Ser Tyr Ala
1               5

<210> SEQ ID NO 982
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 982

Ile Ser Pro Met Phe Gly Thr Ala
1               5

<210> SEQ ID NO 983
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 983

Glu Ser Thr Ser Thr Val
1               5

<210> SEQ ID NO 984
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 984

Cys Ala Arg Gly Tyr Ser Tyr Tyr Pro Gly Gly Gly Gly Arg Asn
1               5                   10                  15

Phe Asp Tyr Trp
            20

<210> SEQ ID NO 985
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                                peptide

<400> SEQUENCE: 985

Gly Gly Ile Phe Ser Ser Tyr Ala
1               5

<210> SEQ ID NO 986
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 986

Ile Ser Pro Ile Phe Gly Thr Ala
1               5

<210> SEQ ID NO 987
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 987

Glu Ser Thr Asn Thr Ala
1               5

<210> SEQ ID NO 988
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 988

Cys Ala Arg Ser Gly Gly Tyr Tyr Asp Tyr Gly Val Gly Tyr Asp Gln
1               5                   10                  15

Trp

<210> SEQ ID NO 989
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 989

Gly Val Thr Phe Arg Ser Tyr Ala
1               5

<210> SEQ ID NO 990
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 990

Ile Ser Gly Ile Phe Gly Thr Ala
1               5
```

```
<210> SEQ ID NO 991
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 991

Glu Ser Thr Ser Thr Ala
1               5

<210> SEQ ID NO 992
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 992

Cys Ala Arg Ser Pro Ala Tyr Tyr Phe Gly Pro Asn Met Asp Val Trp
1               5                   10                  15

<210> SEQ ID NO 993
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 993

Cys Ala Arg Gly Pro Gly Tyr His Pro Ala Gly Ala Ser Gly Gln Phe
1               5                   10                  15

Phe Asp Leu Trp
            20

<210> SEQ ID NO 994
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 994

Cys Ala Arg Gly Arg Gly Tyr Ala Pro Asp Ala Leu Thr Asn Phe Asp
1               5                   10                  15

Val Trp

<210> SEQ ID NO 995
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 995

Cys Ala Arg Glu Gly Gly Tyr Ser Pro Gly Gly Val Asp Phe Asp Tyr
1               5                   10                  15

Trp

<210> SEQ ID NO 996
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 996

Cys Ala Arg Gly Tyr Ser Tyr Tyr Pro Gly Gly Gly Gly Arg Asn
1               5                   10                  15

Phe Asp Tyr Trp
            20

<210> SEQ ID NO 997
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 997

Cys Ala Arg Ser Gly Gly Tyr Tyr Asp Tyr Gly Val Gly Tyr Asp Gln
1               5                   10                  15

Trp

<210> SEQ ID NO 998
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 998

Cys Ala Arg Ser Pro Ala Tyr Tyr Phe Gly Pro Asn Met Asp Val Trp
1               5                   10                  15

<210> SEQ ID NO 999
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 999

Cys Ala Arg Ser Gly Gly Tyr Leu Pro Gln Asn Asn Trp Ile Asp Pro
1               5                   10                  15

Trp

<210> SEQ ID NO 1000
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1000

Cys Ala Arg Glu Gly Gly Tyr Ser Pro Gly Gly Val Asp Phe Asp Tyr
1               5                   10                  15

Trp

<210> SEQ ID NO 1001
```

-continued

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1001

Cys Ala Arg Ser Ser Gly Tyr Tyr Pro Ala Tyr Leu Pro His Trp
1               5                   10                  15

<210> SEQ ID NO 1002
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1002

Cys Ala Arg Ser Gly Gly Tyr Tyr Asp Tyr Gly Val Gly Tyr Asp Gln
1               5                   10                  15

Trp

<210> SEQ ID NO 1003
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1003

Cys Ala Arg Glu Pro Gly Tyr Tyr Val Gly Lys Asn Gly Phe Asp Val
1               5                   10                  15

Trp

<210> SEQ ID NO 1004
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1004

Cys Ala Arg Ser Pro Ala Tyr Tyr Phe Gly Pro Asn Met Asp Val Trp
1               5                   10                  15

<210> SEQ ID NO 1005
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1005

Gly Gly Thr Phe Ser Ser Tyr Ala
1               5

<210> SEQ ID NO 1006
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 1006

Ile Ile Pro Ile Phe Gly Thr Ala
1               5

<210> SEQ ID NO 1007
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1007

Glu Ser Thr Ser Thr Ala
1               5

<210> SEQ ID NO 1008
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1008

Gly Val Thr Phe Arg Ser Tyr Ala
1               5

<210> SEQ ID NO 1009
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1009

Ile Ser Ala Met Phe Gly Thr Ala
1               5

<210> SEQ ID NO 1010
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1010

Lys Ser Thr Asn Thr Ala
1               5

<210> SEQ ID NO 1011
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1011

Cys Ala Arg Gly Arg Gly Tyr Asp Pro Ser Val Gly Gly Phe Asp Val
1               5                   10                  15

Trp

<210> SEQ ID NO 1012
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1012

Gly Gly Thr Phe Ser Ser Tyr Ala
1               5

<210> SEQ ID NO 1013
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1013

Ile Ile Pro Ile Phe Gly Thr Ala
1               5

<210> SEQ ID NO 1014
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1014

Glu Ser Thr Asn Thr Ala
1               5

<210> SEQ ID NO 1015
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1015

Cys Ala Arg Gly Glu Glu Ala Tyr Tyr Asp Leu Trp
1               5                   10

<210> SEQ ID NO 1016
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1016

Gly Gly Ile Phe Ser Ser Tyr Ala
1               5

<210> SEQ ID NO 1017
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1017

Ile Ser Pro Ile Phe Gly Thr Ala
1               5

<210> SEQ ID NO 1018
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1018

Glu Ser Thr Asn Thr Ala
1               5

<210> SEQ ID NO 1019
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1019

Cys Ala Arg Ser Gly Gly Tyr Tyr Asp Tyr Gly Val Gly Tyr Asp Gln
1               5                   10                  15

Trp

<210> SEQ ID NO 1020
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1020

Gly Gly Pro Phe Ser Ser Tyr Ala
1               5

<210> SEQ ID NO 1021
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1021

Ile Ser Pro Leu Phe Gly Thr Ala
1               5

<210> SEQ ID NO 1022
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1022

Glu Ser Thr Ser Thr Ala
1               5

<210> SEQ ID NO 1023
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1023

Cys Ala Arg Ala Pro Thr Tyr Tyr Ala Ser Arg Asp Ser Tyr Asn Phe
1               5                   10                  15

Asp Tyr Trp

<210> SEQ ID NO 1024
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1024

Gly Val Thr Phe Ser Ser Tyr Ala
1               5

<210> SEQ ID NO 1025
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1025

Ile Ser Pro Met Phe Gly Thr Ala
1               5

<210> SEQ ID NO 1026
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1026

Glu Ser Thr Asn Thr Ala
1               5

<210> SEQ ID NO 1027
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1027

Cys Ala Arg Gly Arg Gly Tyr Ala Pro Asp Ala Leu Thr Asn Phe Asp
1               5                   10                  15

Val Trp

<210> SEQ ID NO 1028
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 1028

Gly Gly Thr Phe Ser Ser Tyr Ala
1               5

<210> SEQ ID NO 1029
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1029

Ile Ser Pro Ile Phe Gly Thr Ala
1               5

<210> SEQ ID NO 1030
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1030

Glu Ser Thr Ser Thr Val
1               5

<210> SEQ ID NO 1031
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1031

Cys Ala Arg Gly Pro Gly Tyr His Pro Ala Gly Ala Ser Gly Gln Phe
1               5                   10                  15

Phe Asp Leu Trp
            20

<210> SEQ ID NO 1032
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1032

Gly Gly Thr Phe Ser Ser Tyr Ala
1               5

<210> SEQ ID NO 1033
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1033

Ile Ser Pro Ile Phe Gly Thr Ala
1               5
```

```
<210> SEQ ID NO 1034
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1034

Gln Ser Thr Ser Thr Ala
1               5

<210> SEQ ID NO 1035
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1035

Cys Ala Arg Gly Gly Gly Val Gly Arg Ile Trp Ile Ala Gly Tyr Gly
1               5                   10                  15

Phe Asp Gln Trp
            20

<210> SEQ ID NO 1036
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1036

Gly Gly Thr Phe Ser Ser Tyr Ala
1               5

<210> SEQ ID NO 1037
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1037

Ile Ser Pro Ile Phe Gly Thr Ala
1               5

<210> SEQ ID NO 1038
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1038

Lys Ser Thr Ser Thr Val
1               5

<210> SEQ ID NO 1039
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 1039

Cys Ala Arg Gly Ala Arg Tyr Tyr Ala Gly Gly Tyr Phe Asp Val Trp
1               5                   10                  15

<210> SEQ ID NO 1040
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1040

Gly Gly Thr Phe Ser Ser Tyr Ala
1               5

<210> SEQ ID NO 1041
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1041

Ile Ser Pro Ile Phe Gly Thr Ala
1               5

<210> SEQ ID NO 1042
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1042

Lys Ser Thr Ser Thr Ala
1               5

<210> SEQ ID NO 1043
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1043

Cys Ala Arg Gly Arg Tyr Tyr Tyr Thr Val Gly Val Tyr Asp Val Trp
1               5                   10                  15

<210> SEQ ID NO 1044
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1044

Gly Val Thr Phe Ser Ser Tyr Ala
1               5
```

```
<210> SEQ ID NO 1045
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1045

Ile Ser Pro Met Phe Gly Thr Ala
1               5

<210> SEQ ID NO 1046
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1046

Gln Ser Thr Asn Thr Ala
1               5

<210> SEQ ID NO 1047
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1047

Cys Ala Arg Gly Gly Thr Tyr Ser Pro Gly Gly Thr Tyr Phe Asp Val
1               5                   10                  15

Trp

<210> SEQ ID NO 1048
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1048

Gly Val Thr Phe Ser Ser Tyr Ala
1               5

<210> SEQ ID NO 1049
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1049

Ile Ser Pro Ile Phe Gly Thr Ala
1               5

<210> SEQ ID NO 1050
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 1050

Lys Ser Thr Ser Thr Val
1               5

<210> SEQ ID NO 1051
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1051

Cys Ala Arg Gly Gly Gly Tyr Ser Ala Asp Gly Gly Ala Gly Asn Asn
1               5                   10                  15

Thr Ile Phe Asp Val Trp
            20

<210> SEQ ID NO 1052
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1052

Gly Gly Thr Phe Ser Ser Tyr Ala
1               5

<210> SEQ ID NO 1053
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1053

Ile Ser Pro Leu Phe Gly Thr Ala
1               5

<210> SEQ ID NO 1054
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1054

Glu Ser Thr Asn Thr Ala
1               5

<210> SEQ ID NO 1055
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1055

Cys Ala Arg Ala Ser Gly Tyr Phe Thr Gly Trp Gly Thr Phe Asp Tyr
1               5                   10                  15

Trp

<210> SEQ ID NO 1056
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1056

Gly Gly Pro Phe Ser Ser Tyr Ala
1               5

<210> SEQ ID NO 1057
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1057

Ile Ser Pro Met Phe Gly Thr Ala
1               5

<210> SEQ ID NO 1058
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1058

Glu Ser Thr Ser Thr Val
1               5

<210> SEQ ID NO 1059
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1059

Cys Ala Arg Gly Tyr Ser Tyr Tyr Pro Gly Gly Gly Gly Arg Asn
1               5                   10                  15

Phe Asp Tyr Trp
            20

<210> SEQ ID NO 1060
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1060

Gly Val Thr Phe Ser Ser Tyr Ala
1               5

<210> SEQ ID NO 1061
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1061

Ile Ser Pro Leu Phe Gly Thr Ala
1               5

<210> SEQ ID NO 1062
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1062

Lys Ser Thr Ser Thr Ala
1               5

<210> SEQ ID NO 1063
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1063

Cys Ala Arg Gly Asp Ala Tyr Tyr Val Gly Gly Gly Ala Arg Pro Phe
1               5                   10                  15

Asp Leu Trp

<210> SEQ ID NO 1064
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1064

Gly Val Thr Phe Ser Ser Tyr Ala
1               5

<210> SEQ ID NO 1065
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1065

Ile Thr Pro Met Phe Gly Thr Ala
1               5

<210> SEQ ID NO 1066
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1066
```

```
Lys Ser Thr Ser Thr Val
1               5

<210> SEQ ID NO 1067
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1067

Cys Ala Arg Gly Arg Gly Tyr Ile Ala Val Ala Gly Asp Met Asp Val
1               5                   10                  15

Trp

<210> SEQ ID NO 1068
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1068

Gly Gly Pro Phe Ser Ser Tyr Ala
1               5

<210> SEQ ID NO 1069
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1069

Ile Ser Gly Ile Phe Gly Thr Ala
1               5

<210> SEQ ID NO 1070
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1070

Glu Ser Thr Ser Thr Ala
1               5

<210> SEQ ID NO 1071
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1071

Cys Ala Arg Gly Asp Arg Phe Tyr Val Gly Glu Arg Phe Asp Val Trp
1               5                   10                  15

<210> SEQ ID NO 1072
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1072

Gly Val Thr Phe Arg Ser Tyr Ala
1               5

<210> SEQ ID NO 1073
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1073

Ile Ser Gly Ile Phe Gly Thr Ala
1               5

<210> SEQ ID NO 1074
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1074

Glu Ser Thr Ser Thr Ala
1               5

<210> SEQ ID NO 1075
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1075

Cys Ala Arg Ser Pro Ala Tyr Tyr Phe Gly Pro Asn Met Asp Val Trp
1               5                   10                  15

<210> SEQ ID NO 1076
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1076

Gly Gly Thr Phe Ser Ser Tyr Ala
1               5

<210> SEQ ID NO 1077
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1077

Ile Ser Pro Met Phe Gly Thr Ala
```

```
1               5

<210> SEQ ID NO 1078
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1078

Lys Ser Thr Ser Thr Ala
1               5

<210> SEQ ID NO 1079
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1079

Cys Ala Arg Glu Gly Gly Tyr Ser Pro Gly Gly Val Asp Phe Asp Tyr
1               5                   10                  15

Trp

<210> SEQ ID NO 1080
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1080

Gly Val Thr Phe Ser Ser Tyr Ala
1               5

<210> SEQ ID NO 1081
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1081

Ile Ser Pro Ile Phe Gly Thr Ala
1               5

<210> SEQ ID NO 1082
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1082

Glu Ser Thr Asn Thr Val
1               5

<210> SEQ ID NO 1083
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 1083

Cys Ala Arg Gly Thr Thr Tyr Ser Thr Ala Arg Tyr Phe Asp Val Trp
1               5                   10                  15

<210> SEQ ID NO 1084
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1084

Gly Val Thr Phe Ser Ser Tyr Ala
1               5

<210> SEQ ID NO 1085
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1085

Ile Ser Pro Ile Phe Gly Thr Ala
1               5

<210> SEQ ID NO 1086
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1086

Gln Ser Thr Asn Thr Val
1               5

<210> SEQ ID NO 1087
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1087

Cys Ala Arg Asp Ser Gly Asn Tyr Asp Gly Tyr Gly Pro Gly Ser Arg
1               5                   10                  15

Phe Asp Val Trp
            20

<210> SEQ ID NO 1088
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1088
```

Gly Val Thr Phe Ser Ser Tyr Ala
1               5

<210> SEQ ID NO 1089
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1089

Ile Ser Pro Leu Phe Gly Thr Ala
1               5

<210> SEQ ID NO 1090
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1090

Glu Ser Thr Ser Thr Ala
1               5

<210> SEQ ID NO 1091
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1091

Cys Ala Arg Glu Arg Gly Tyr Thr Val Gly Gly Gly Met Asp Val
1               5                   10                  15

Trp

<210> SEQ ID NO 1092
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1092

Gly Gly Thr Phe Ser Ser Tyr Ala
1               5

<210> SEQ ID NO 1093
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1093

Ile Thr Pro Met Phe Gly Thr Ala
1               5

<210> SEQ ID NO 1094
<211> LENGTH: 6
<212> TYPE: PRT

<210> SEQ ID NO 1094
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1094

Lys Ser Thr Ser Thr Thr
1               5

<210> SEQ ID NO 1095
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1095

Cys Ala Arg Gly Pro Gly Tyr Tyr Pro Asp Ser Asn Asn Tyr Asp Leu
1               5                   10                  15
Trp

<210> SEQ ID NO 1096
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1096

Gly Gly Thr Phe Ser Ser Tyr Ala
1               5

<210> SEQ ID NO 1097
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1097

Ile Ile Pro Ile Phe Gly Thr Ala
1               5

<210> SEQ ID NO 1098
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1098

Asp Ser Thr Ser Thr Ala
1               5

<210> SEQ ID NO 1099
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1099

```
Cys Ala Arg Asp Ser Thr Pro Ser Val Thr Ser Ser Leu Tyr Arg Ile
1               5                   10                  15
Pro Ala Phe Asp Val Trp
            20

<210> SEQ ID NO 1100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1100

Gly Gly Thr Phe Ser Ser Tyr Ala
1               5

<210> SEQ ID NO 1101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1101

Ile Thr Pro Met Phe Gly Thr Ala
1               5

<210> SEQ ID NO 1102
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1102

Lys Ser Thr Ser Thr Ala
1               5

<210> SEQ ID NO 1103
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1103

Cys Ala Arg Gly Thr Ser Tyr Leu Pro Gly Arg Ser Gly Phe Asp Val
1               5                   10                  15
Trp

<210> SEQ ID NO 1104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1104

Gly Gly Thr Phe Ser Ser Tyr Ala
1               5
```

```
<210> SEQ ID NO 1105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1105

Ile Ser Pro Ile Phe Gly Thr Ala
1               5

<210> SEQ ID NO 1106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1106

Arg Ser Thr Ser Thr Ala
1               5

<210> SEQ ID NO 1107
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1107

Cys Ala Arg Gly Pro Gly Tyr Asp Pro Ser Ser Leu Arg Gly Phe Asp
1               5                   10                  15

Val Trp

<210> SEQ ID NO 1108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1108

Gly Gly Thr Phe Ser Ser Tyr Ala
1               5

<210> SEQ ID NO 1109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1109

Ile Thr Pro Ile Phe Gly Thr Ala
1               5

<210> SEQ ID NO 1110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 1110

Glu Ser Thr Ser Thr Ala
1               5

<210> SEQ ID NO 1111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1111

Cys Ala Arg Ser Gly Gly Tyr Ser Pro Ser Ile Gly Gly Phe Asp Val
1               5                   10                  15

Trp

<210> SEQ ID NO 1112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1112

Gly Gly Thr Phe Ser Ser Tyr Ala
1               5

<210> SEQ ID NO 1113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1113

Ile Ser Pro Met Phe Gly Thr Ala
1               5

<210> SEQ ID NO 1114
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1114

Lys Ser Thr Ser Thr Ala
1               5

<210> SEQ ID NO 1115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1115

Cys Ala Arg Glu Ser Gly Tyr Ser Gly Thr Gly Gln Phe Asp Val Trp
1               5                   10                  15
```

```
<210> SEQ ID NO 1116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1116

Gly Val Thr Phe Ser Ser Tyr Ala
1               5

<210> SEQ ID NO 1117
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1117

Ile Ser Pro Ile Phe Gly Thr Ala
1               5

<210> SEQ ID NO 1118
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1118

Lys Ser Thr Asn Thr Val
1               5

<210> SEQ ID NO 1119
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1119

Cys Ala Arg Glu Tyr Leu Gly Asp Asp Tyr Ser Ser Gly Ser Tyr Phe
1               5                   10                  15

Asp Val Trp

<210> SEQ ID NO 1120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1120

Gly Val Thr Phe Ser Ser Tyr Ala
1               5

<210> SEQ ID NO 1121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 1121

Ile Ser Pro Met Phe Gly Thr Ala
1               5

<210> SEQ ID NO 1122
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1122

Lys Ser Thr Asn Thr Ala
1               5

<210> SEQ ID NO 1123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1123

Cys Ala Arg Asp Thr Thr Tyr Ile Ala Gly Gly His Phe Asp Val Trp
1               5                   10                  15

<210> SEQ ID NO 1124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1124

Gly Gly Thr Phe Ser Ser Tyr Ala
1               5

<210> SEQ ID NO 1125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1125

Ile Ser Pro Met Phe Gly Thr Ala
1               5

<210> SEQ ID NO 1126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1126

Lys Ser Thr Ser Thr Ala
1               5

<210> SEQ ID NO 1127
<211> LENGTH: 18

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1127

Cys Ala Arg Ser Ser Arg Tyr Ala Pro Ser Asp Ser Thr Asn Phe Asp
1               5                   10                  15

Gln Trp

<210> SEQ ID NO 1128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1128

Gly Gly Thr Phe Ser Ser Tyr Ala
1               5

<210> SEQ ID NO 1129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1129

Ile Ser Pro Ile Phe Gly Thr Ala
1               5

<210> SEQ ID NO 1130
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1130

Thr Ser Thr Ser Thr Ala
1               5

<210> SEQ ID NO 1131
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1131

Cys Ala Arg Ser Arg Arg Tyr Trp Ala Asp Gly Gly Phe Asp Tyr Trp
1               5                   10                  15

<210> SEQ ID NO 1132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1132
```

Gly Gly Thr Phe Ser Ser Tyr Ala
1               5

<210> SEQ ID NO 1133
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1133

Ile Ser Pro Ile Phe Gly Thr Ala
1               5

<210> SEQ ID NO 1134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1134

Lys Ser Thr Ser Thr Ala
1               5

<210> SEQ ID NO 1135
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1135

Cys Ala Arg Glu Leu Gly Tyr Leu Ala Gly Ser Pro Ser Pro Gly Phe
1               5                   10                  15

Asp Tyr Trp

<210> SEQ ID NO 1136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1136

Gly Val Thr Phe Ser Ser Tyr Ala
1               5

<210> SEQ ID NO 1137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1137

Ile Ser Pro Leu Phe Gly Thr Ala
1               5

<210> SEQ ID NO 1138
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1138

Lys Ser Thr Ser Thr Val
1               5

<210> SEQ ID NO 1139
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1139

Cys Ala Arg Ser Arg Thr Tyr Ala Asp Gly Arg Thr Phe Asp Val Trp
1               5                   10                  15

<210> SEQ ID NO 1140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1140

Gly Val Thr Phe Ser Ser Tyr Ala
1               5

<210> SEQ ID NO 1141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1141

Ile Met Pro Met Phe Gly Thr Ala
1               5

<210> SEQ ID NO 1142
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1142

Lys Ser Thr Ser Thr Ala
1               5

<210> SEQ ID NO 1143
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1143

Cys Ala Arg Glu Arg Gly Ser Trp Ser Phe Gly Tyr Phe Asp Val Trp
```

-continued

```
1               5                   10                  15
```

<210> SEQ ID NO 1144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1144

Gly Gly Ile Phe Ser Ser Tyr Ala
1               5

<210> SEQ ID NO 1145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1145

Ile Ser Pro Ile Phe Gly Thr Ala
1               5

<210> SEQ ID NO 1146
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1146

Lys Ser Thr Asn Thr Ala
1               5

<210> SEQ ID NO 1147
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1147

Cys Ala Arg Gly Arg Gly Ala Tyr Met Gly Pro Ser Met Asp Val Trp
1               5                   10                  15

<210> SEQ ID NO 1148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1148

Gly Gly Pro Phe Ser Ser Tyr Ala
1               5

<210> SEQ ID NO 1149
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1149

Ile Ser Pro Met Phe Gly Thr Ala
1               5

<210> SEQ ID NO 1150
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1150

Lys Ser Thr Ser Thr Ala
1               5

<210> SEQ ID NO 1151
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1151

Cys Ala Arg Asp Asp Gly Tyr Ala Pro Ser Gly Gly Leu Arg Glu Phe
1               5                   10                  15

Asp Val Trp

<210> SEQ ID NO 1152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1152

Gly Gly Thr Phe Ser Ser Tyr Ala
1               5

<210> SEQ ID NO 1153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1153

Ile Ile Pro Ile Phe Gly Thr Ala
1               5

<210> SEQ ID NO 1154
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1154

Glu Ser Thr Ser Thr Ala
1               5

<210> SEQ ID NO 1155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1155

Gly Gly Ile Phe Ser Ser Tyr Ala
1               5

<210> SEQ ID NO 1156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1156

Ile Ser Pro Ile Phe Gly Thr Ala
1               5

<210> SEQ ID NO 1157
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1157

Glu Ser Thr Asn Thr Ala
1               5

<210> SEQ ID NO 1158
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1158

Cys Ala Arg Ser Gly Gly Tyr Tyr Asp Tyr Gly Val Gly Tyr Asp Gln
1               5                   10                  15

Trp

<210> SEQ ID NO 1159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1159

Gly Val Thr Phe Ser Ser Tyr Ala
1               5

<210> SEQ ID NO 1160
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1160

Ile Ser Pro Met Phe Gly Thr Ala
1               5

<210> SEQ ID NO 1161
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1161

Glu Ser Thr Asn Thr Ala
1               5

<210> SEQ ID NO 1162
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1162

Cys Ala Arg Gly Arg Gly Tyr Ala Pro Asp Ala Leu Thr Asn Phe Asp
1               5                   10                  15

Val Trp

<210> SEQ ID NO 1163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1163

Gly Gly Thr Phe Ser Ser Tyr Ala
1               5

<210> SEQ ID NO 1164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1164

Ile Ser Pro Ile Phe Gly Thr Ala
1               5

<210> SEQ ID NO 1165
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1165

Glu Ser Thr Ser Thr Val
1               5

-continued

<210> SEQ ID NO 1166
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1166

Cys Ala Arg Gly Pro Gly Tyr His Pro Ala Gly Ala Ser Gly Gln Phe
1               5                   10                  15

Phe Asp Leu Trp
            20

<210> SEQ ID NO 1167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1167

Gly Val Thr Phe Ser Ser Tyr Ala
1               5

<210> SEQ ID NO 1168
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1168

Ile Ser Pro Met Phe Gly Thr Ala
1               5

<210> SEQ ID NO 1169
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1169

Glu Ser Thr Asn Thr Ala
1               5

<210> SEQ ID NO 1170
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1170

Cys Ala Arg Gly Gly Gly Tyr Tyr Pro Ala Gly Val Gly Arg Tyr Asp
1               5                   10                  15

Val Trp

<210> SEQ ID NO 1171
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 1171

Gly Gly Pro Phe Arg Ser Tyr Ala
1               5

<210> SEQ ID NO 1172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1172

Ile Ile Pro Ile Phe Gly Thr Ala
1               5

<210> SEQ ID NO 1173
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1173

Glu Ser Thr Ser Thr Ala
1               5

<210> SEQ ID NO 1174
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1174

Cys Ala Arg Gly Gly Val Tyr Ser Phe Asp Val Trp
1               5                   10

<210> SEQ ID NO 1175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1175

Gly Gly Thr Phe Ser Ser Tyr Ala
1               5

<210> SEQ ID NO 1176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1176

Ile Ser Pro Ile Phe Gly Thr Ala
1               5
```

```
<210> SEQ ID NO 1177
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1177

Glu Ser Thr Ser Thr Ala
1               5

<210> SEQ ID NO 1178
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1178

Cys Ala Arg Asp Gln Gly Gly Thr Arg Gly Asn Tyr Phe Asp Val Trp
1               5                   10                  15

<210> SEQ ID NO 1179
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1179

Gly Val Ile Phe Ser Ser Tyr Ala
1               5

<210> SEQ ID NO 1180
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1180

Ile Ser Pro Ile Phe Gly Thr Ala
1               5

<210> SEQ ID NO 1181
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1181

Glu Ser Thr Ser Thr Ala
1               5

<210> SEQ ID NO 1182
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 1182

Cys Ala Arg Ser Arg Gly Tyr Ala Pro Gly Thr Ser Phe His Tyr Asp
1               5                   10                  15

Val Trp

<210> SEQ ID NO 1183
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1183

Gly Gly Thr Phe Ser Ser Tyr Ala
1               5

<210> SEQ ID NO 1184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1184

Ile Ser Ala Ile Phe Gly Thr Ala
1               5

<210> SEQ ID NO 1185
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1185

Glu Ser Thr Arg Thr Ala
1               5

<210> SEQ ID NO 1186
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1186

Cys Ala Arg Gly Ser Gly Tyr Tyr Val Ala Ala Ser Gly Ala Phe Asp
1               5                   10                  15

Val Trp

<210> SEQ ID NO 1187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1187

Gly Val Thr Phe Ser Ser Tyr Ala
1               5
```

```
<210> SEQ ID NO 1188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1188

Ile Ser Pro Ile Phe Gly Thr Ala
1               5

<210> SEQ ID NO 1189
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1189

Glu Ser Thr Ser Thr Ala
1               5

<210> SEQ ID NO 1190
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1190

Cys Ala Arg Gly Arg Glu Tyr Tyr Ala Ser Asn Gly Asp Ser Phe Asp
1               5                   10                  15

Val Trp

<210> SEQ ID NO 1191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1191

Gly Gly Pro Phe Ser Ser Tyr Ala
1               5

<210> SEQ ID NO 1192
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1192

Ile Ser Pro Met Phe Gly Thr Ala
1               5

<210> SEQ ID NO 1193
<211> LENGTH: 6
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 1193

Glu Ser Thr Ser Thr Val
1               5

<210> SEQ ID NO 1194
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1194

Cys Ala Arg Gly Tyr Ser Tyr Tyr Pro Gly Gly Gly Gly Arg Asn
1               5                   10                  15

Phe Asp Tyr Trp
            20

<210> SEQ ID NO 1195
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1195

Gly Val Thr Phe Arg Ser Tyr Ala
1               5

<210> SEQ ID NO 1196
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1196

Ile Ser Gly Ile Phe Gly Thr Ala
1               5

<210> SEQ ID NO 1197
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1197

Glu Ser Thr Ser Thr Ala
1               5

<210> SEQ ID NO 1198
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1198

Cys Ala Arg Ser Pro Ala Tyr Tyr Phe Gly Pro Asn Met Asp Val Trp

```
                 1               5                  10                 15
```

<210> SEQ ID NO 1199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1199

```
Gly Gly Thr Phe Ser Ser Tyr Ala
1               5
```

<210> SEQ ID NO 1200
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1200

```
Ile Ser Pro Met Phe Gly Thr Ala
1               5
```

<210> SEQ ID NO 1201
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1201

```
Lys Ser Thr Ser Thr Ala
1               5
```

<210> SEQ ID NO 1202
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1202

```
Cys Ala Arg Glu Gly Gly Tyr Ser Pro Gly Gly Val Asp Phe Asp Tyr
1               5                   10                  15

Trp
```

<210> SEQ ID NO 1203
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1203

```
Gly Gly Thr Phe Ser Ser Tyr Ala
1               5
```

<210> SEQ ID NO 1204
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1204

Ile Ser Pro Met Phe Gly Thr Ala
1               5

<210> SEQ ID NO 1205
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1205

Glu Ser Thr Ser Thr Val
1               5

<210> SEQ ID NO 1206
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1206

Cys Ala Arg Ser Arg Gly Tyr Asn Val Ala Ala Ser Phe Gly Phe Asp
1               5                   10                  15

Val Trp

<210> SEQ ID NO 1207
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1207

Gly Gly Ile Phe Arg Ser Tyr Ala
1               5

<210> SEQ ID NO 1208
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1208

Ile Ile Pro Met Phe Gly Thr Ala
1               5

<210> SEQ ID NO 1209
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1209

Glu Ser Thr Thr Thr Val
```

```
1               5
```

<210> SEQ ID NO 1210
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1210

```
Cys Ala Arg Gly Ala Gly Ser Thr Phe Asp Val Trp
1               5                   10
```

<210> SEQ ID NO 1211
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1211

```
Gly Gly Pro Phe Ser Ser Tyr Ala
1               5
```

<210> SEQ ID NO 1212
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1212

```
Ile Ser Pro Ile Phe Gly Thr Ala
1               5
```

<210> SEQ ID NO 1213
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1213

```
Lys Ser Thr Asn Thr Ala
1               5
```

<210> SEQ ID NO 1214
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1214

```
Cys Ala Arg Gly Arg Ser Tyr Ile Val Ser Val Ser Pro Gly Phe Asp
1               5                   10                  15

Val Trp
```

<210> SEQ ID NO 1215
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1215

Gly Gly Thr Phe Ser Ser Tyr Ala
1               5

<210> SEQ ID NO 1216
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1216

Ile Val Pro Leu Phe Gly Thr Ala
1               5

<210> SEQ ID NO 1217
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1217

Glu Ser Thr Ser Thr Ala
1               5

<210> SEQ ID NO 1218
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1218

Cys Ala Arg Gly Leu Gly Leu Tyr Phe Asp Val Trp
1               5                   10

<210> SEQ ID NO 1219
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1219

Gly Val Thr Phe Ser Ser Tyr Ala
1               5

<210> SEQ ID NO 1220
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1220

Ile Ser Pro Val Phe Gly Thr Ala
1               5
```

<210> SEQ ID NO 1221
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1221

Asp Ser Thr Asn Thr Ala
1               5

<210> SEQ ID NO 1222
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1222

Cys Ala Ser Arg Gly Tyr Thr Val Ser Ser Leu Ala Gly Arg Tyr
1               5                   10                  15

Phe Asp Gln Trp
            20

<210> SEQ ID NO 1223
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1223

Gly Val Ile Phe Ser Ser Tyr Ala
1               5

<210> SEQ ID NO 1224
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1224

Ile Ile Pro Ile Phe Gly Thr Ala
1               5

<210> SEQ ID NO 1225
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1225

Lys Ser Thr Ser Thr Ala
1               5

<210> SEQ ID NO 1226
<211> LENGTH: 12
<212> TYPE: PRT
<213> ORGANISM: Artificial Sequence
<220> FEATURE:

<223> OTHER INFORMATION: Description of Artificial Sequence: Synthetic
    peptide

<400> SEQUENCE: 1226

Cys Ala Arg Gly Gly Ser Gly Ser Phe Asp Val Trp
1               5                   10

<210> SEQ ID NO 1227
<211> LENGTH: 8
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 1227

Gly Val Thr Phe Ser Ser Tyr Ala
1               5

<210> SEQ ID NO 1228
<211> LENGTH: 8
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 1228

Ile Ser Pro Met Phe Gly Thr Ala
1               5

<210> SEQ ID NO 1229
<211> LENGTH: 6
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 1229

Glu Ser Thr Asn Thr Val
1               5

<210> SEQ ID NO 1230
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 1230

Cys Ala Arg Gly Arg Ala Tyr Leu Ser Val Arg Gly Ser Phe Asp Val
1               5                   10                  15

Trp

<210> SEQ ID NO 1231
<211> LENGTH: 8
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 1231

Gly Val Pro Phe Ser Ser Tyr Ala
1               5

```
<210> SEQ ID NO 1232
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1232

Ile Ser Pro Leu Phe Gly Thr Ala
1               5

<210> SEQ ID NO 1233
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1233

Gln Ser Thr Ser Thr Val
1               5

<210> SEQ ID NO 1234
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1234

Cys Ala Arg Gly Leu Gly Thr Tyr Ser Pro Ser Leu Tyr Pro Arg Gly
1               5                   10                  15

Met Asp Val Trp
            20

<210> SEQ ID NO 1235
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1235

Gly Gly Thr Phe Ser Ser Tyr Ala
1               5

<210> SEQ ID NO 1236
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1236

Ile Thr Pro Leu Phe Gly Thr Ala
1               5

<210> SEQ ID NO 1237
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 1237

Asp Ser Thr Ser Thr Ala
1               5

<210> SEQ ID NO 1238
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1238

Cys Ala Arg Gly Pro Thr Leu Tyr Ser Pro Pro Val Phe Asp Val Trp
1               5                   10                  15

<210> SEQ ID NO 1239
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1239

Gly Val Thr Phe Ser Ser Tyr Ala
1               5

<210> SEQ ID NO 1240
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1240

Ile Thr Pro Ile Phe Gly Thr Ala
1               5

<210> SEQ ID NO 1241
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1241

Gln Ser Thr Ser Thr Ala
1               5

<210> SEQ ID NO 1242
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1242

Cys Ala Arg Gly Gly Gly Val Phe Asp Val Trp
1               5                   10
```

<210> SEQ ID NO 1243
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1243

Gly Gly Pro Phe Ser Ser Tyr Ala
1               5

<210> SEQ ID NO 1244
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1244

Ile Ile Pro Ile Phe Gly Thr Ala
1               5

<210> SEQ ID NO 1245
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1245

Glu Ser Thr Ser Thr Ala
1               5

<210> SEQ ID NO 1246
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1246

Cys Ala Arg Gly Thr Asp Tyr Ser Gly Tyr Arg Gly Phe Asp Val Trp
1               5                   10                  15

<210> SEQ ID NO 1247
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1247

Gly Gly Thr Phe Arg Ser Tyr Ala
1               5

<210> SEQ ID NO 1248
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1248

Ile Met Pro Ile Phe Gly Thr Ala
1               5

<210> SEQ ID NO 1249
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1249

Glu Ser Thr Thr Thr Val
1               5

<210> SEQ ID NO 1250
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1250

Cys Ala Arg Gly Ala Gly Val Ser Ala Gly Pro Ser Trp Pro Phe Asp
1               5                   10                  15

Val Trp

<210> SEQ ID NO 1251
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1251

Gly Gly Thr Phe Ser Ser Tyr Ala
1               5

<210> SEQ ID NO 1252
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1252

Ile Asn Pro Ile Phe Gly Thr Ala
1               5

<210> SEQ ID NO 1253
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1253

Glu Ser Thr Asn Thr Ala
1               5

<210> SEQ ID NO 1254
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1254

Cys Ala Arg Gly Glu Ser Ala Tyr Tyr Ser Arg Asn Tyr Asp Val Trp
1               5                   10                  15

<210> SEQ ID NO 1255
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1255

Gly Gly Ile Phe Ser Ser Tyr Ala
1               5

<210> SEQ ID NO 1256
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1256

Ile Ser Ala Ile Phe Gly Thr Ala
1               5

<210> SEQ ID NO 1257
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1257

Glu Ser Thr Ser Thr Ala
1               5

<210> SEQ ID NO 1258
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1258

Cys Ala Arg Asp Ser Gly Ile Ala Ser Gly Tyr Thr Ala Tyr Met Asp
1               5                   10                  15

Tyr Trp

<210> SEQ ID NO 1259
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 1259

Gly Gly Ile Phe Ser Ser Tyr Ala
1               5

<210> SEQ ID NO 1260
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1260

Ile Thr Pro Ile Phe Gly Thr Ala
1               5

<210> SEQ ID NO 1261
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1261

Glu Ser Thr Arg Thr Ala
1               5

<210> SEQ ID NO 1262
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1262

Cys Ala Arg Asp Leu Ser Arg Asp Ser Leu Asn Leu Pro Gly Ser Ser
1               5                   10                  15

Pro Gly Tyr Asp Leu Trp
            20

<210> SEQ ID NO 1263
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1263

Gly Gly Thr Phe Ser Ser Tyr Ala
1               5

<210> SEQ ID NO 1264
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1264

Ile Ile Thr Ile Phe Gly Thr Ala
1               5
```

```
<210> SEQ ID NO 1265
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1265

Glu Ser Thr Asn Thr Ala
1               5

<210> SEQ ID NO 1266
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1266

Cys Ala Arg Gly Gly Gly Gly Arg Phe Asp Val Trp
1               5                   10

<210> SEQ ID NO 1267
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1267

Gly Gly Thr Phe Ser Ser Tyr Ala
1               5

<210> SEQ ID NO 1268
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1268

Ile Ile Thr Ile Phe Gly Thr Ala
1               5

<210> SEQ ID NO 1269
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1269

Lys Ser Thr Ser Thr Ala
1               5

<210> SEQ ID NO 1270
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1270
```

```
Cys Ala Arg Gly Ala Thr Gly Phe Tyr Asp Val Trp
1               5                   10
```

<210> SEQ ID NO 1271
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1271

```
Gly Gly Thr Phe Ser Ser Tyr Ala
1               5
```

<210> SEQ ID NO 1272
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1272

```
Ile Ile Pro Ile Phe Gly Thr Ala
1               5
```

<210> SEQ ID NO 1273
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1273

```
Glu Ser Thr Asn Thr Ala
1               5
```

<210> SEQ ID NO 1274
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1274

```
Cys Ala Arg Val Arg Gly Gly Tyr Gly Pro Tyr Gly Asp Phe Asp Val
1               5                   10                  15

Trp
```

<210> SEQ ID NO 1275
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1275

```
Met Gly Gly Ile Ile Pro Ile Phe Gly Thr Ala Asn Tyr Ala
1               5                   10
```

<210> SEQ ID NO 1276
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1276

Ile Ile Pro Ile Phe Gly Thr Ala
1               5

<210> SEQ ID NO 1277
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1277

Lys Ala Ser Gly Gly Thr Phe Ser Ser Tyr Ala Ile Ser Trp
1               5                   10
```

IMMUNOGENETIC RESTRICTION ON ELICITATION OF ANTIBODIES

CROSS-REFERENCE TO RELATED APPLICATIONS

This application is a divisional application of U.S. Ser. No. 15/127,404, filed on Sep. 19, 2016, which is a national stage application of International Application No. PCT/US2015/021529, filed on Mar. 19, 2015, which claims the benefit of, and priority to, U.S. Ser. No. 61/974,297, filed on Apr. 2, 2014, and U.S. Ser. No. 61/955,678, filed on Mar. 19, 2014, the contents of each which are hereby incorporated by reference in their entireties.

GOVERNMENT INTEREST

This invention was made with government support under AI074518 awarded by the National Institutes of Health and W911NF-10-{1-0266 awarded by the Defense Advanced Research Projects Agency. The United States government has certain rights in the invention.

SEQUENCE LISTING

The instant application contains a Sequence Listing which has been submitted electronically in ASCII format and is hereby incorporated by reference in its entirety. Said ASCII copy, created on Apr. 23, 2019, is named 5031461-030US4_SL.txt and is 479,811 bytes in size.

FIELD OF THE INVENTION

This invention relates generally to influenza neutralizing antibodies, the structural determinants of such antibodies, as well as to methods for use thereof.

BACKGROUND OF THE INVENTION

An influenza pandemic represents one of the greatest acute infectious threats to human health. Vaccination remains the principle means of preventing seasonal and pandemic influenza and its complications. A "universal" influenza vaccine that induces broad immunity against multiple subtypes of influenza viruses has been a long sought goal in medical research. The recent discovery of human broadly neutralizing "heterosubtypic" antibodies binding to a highly conserved hydrophobic pocket on the stem of HA (sBnAb) have reignited efforts to develop such a vaccine. However, only very low concentrations of sBnAbs are detected in the sera of seasonal influenza or H5N1 vaccines, or in commercial intravenous immunoglobulin (IVIG) preparations.

There is continuous effort to produce monoclonal antibodies (mAbs) and drugs for immunotherapies against the influenza virus. Specifically, efforts are directed to development of a therapeutic compound that neutralizes all of the various influenza strais. Currently, only a handful mAbs are reported that are able to achieve this goal. These mAbs were isolated by panning phage antibody libraries and by screening B-cells from vaccinated volunteers. However, an increased understanding of characteristics of broadly neutralizing influenza antibodies may be useful to incorporate certain structural determinants in a more rational design approach for discovery and production of a broad panel of neutralizing influenza antibodies.

Furthermore, current approaches for the assessment of immunogens and vaccine compositions are based on serological studies known as the hemagglutination inhibition assay and the microneutralization assay. While these assays set the standard for judging the efficacy of vaccines, to date there is no approach that can evaluate the ability of influenza vaccines to induce broadly neutralizing "heterosubtypic" antibodies binding to a highly conserved hydrophobic pocket on the stem of HA (HV1-sBnAbs).

Thus, there exists a great need for additional monoclonal antibodies that can broadly neutralize influenza virus and methods for increasing the affinity or efficacy of such antibodies through a rational design approach. Furthermore, there exists a need for methods to evaluate the ability of influenza vaccines to induce broadly neutralizing influenza antibodies in subjects.

SUMMARY OF THE INVENTION

The present invention is based upon the discovery of structural determinants in broadly neutralizing anti-influenza antibodies. These structural determinants are important for high affinity to a broad spectrum of influenza strains via recognition of the stem region of the hemagglutinin (HA) protein of the influenza virus. The present invention is based upon various methods of use and antibodies derived from these studies.

The present invention features isolated humanized antibodies that neutralizes an influenza virus. In one aspect, the antibody binds to the stem region of HA of the influenza virus. The influenza virus is an influenza A virus. For example, the influenza virus is a Group 1 influenza virus. In one aspect, the antibody is a single chain Fv antibody, an $F_{ab}$ fragment, an $F_{ab'}$ fragment, or an $F_{(ab')_2}$ fragment. In another aspect, the antibody is linked to a therapeutic agent. For example, the therapeutic agent is a toxin, a radiolabel, a siRNA, a small molecule, or a cytokine.

The antibodies comprise a heavy chain comprising a CDR1 comprising any one of the amino acid sequences SEQ ID NOs: 1-36 and 217-246; a CDR2 comprising any one of the amino acid sequences SEQ ID NOs: 37-72 and 2-[7-276; and a CDR3 comprising any one of the amino acid sequences SEQ ID NOs: 73-108 and 277-306; and a light chain comprising a CDR1 comprising any one of the amino acid sequences SEQ ID NOs: 109-144 and 307-336; a CDR2 comprising any one of the amino acid sequences SEQ ID NOs: 1-[5-180 and 337-366; and a CDR3 comprising any one of the amino acid sequences SEQ ID NOs: 181-216 and 367-396. In one embodiment, the antibody comprises a $V_H$ amino acid sequence selected from any one of SEQ ID NOS: 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 601, 603, 605, 607, 609, 611, 613, 615, 617, 619, 621, 623, 625, 627, 629, 631, 633, 635, 637, 639, 641, 643, 645, 647, 649, 651, 653, 655, 657, and 659; and a $V_L$ amino acid sequence selected from any one of SEQ ID NOS: 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 602, 604, 606, 608, 610, 612, 614, 616, 618, 620, 622, 624, 626, 628, 630, 632, 634, 636, 638, 640, 642, 644, 646, 648, 650, 652, 654, 656, 658, and 660.

The nucleic acid sequence of the antibodies described herein comprise a nucleic acid sequence selected from SEQ ID NOs: 397-468 and 5-[1-600. The nucleic acid sequence of the antibodies described herein encode a polypeptide comprising an amino acid sequence selected from SEQ ID NOs: 469-540 and 601-660. The polypeptides disclosed herein comprise amino acids sequences selected from SEQ ID NOs: 469-540 and 601-660. The present invention includes a vector containing nucleic acid sequences selected from SEQ ID NOs: 397-468 and 5-[1-600 or encoding an amino acid sequence selected from SEQ ID NOs: 469-540 and 601-660. In another embodiment, the present invention includes a cell containing the vector described above.

The present invention further provides a cell producing any of the antibodies disclosed herein.

The present invention also features a composition comprising any of the antibodies disclosed herein, and a carrier. For example, the carrier is a pharmaceutically-acceptable excipient.

The present invention further provides a method for treating a disease or disorder caused by an influenza virus, by administering to a person at risk of suffering from said disease or disorder, a therapeutically effective amount of any of the monoclonal antibodies described herein.

The present invention also provides a method of improving the neutralization capacity or affinity of antibodies that bind to the HA protein of an influenza virus by mutating at least one amino acid in the VH domain, wherein the at least one mutation is selected from the following: a serine at position 24, a valine at position 27, an isoleucine or proline at position 28, a serine at position 29, an arginine at position 30, a valine at position 34, a serine at position 52, a glycine or an alanine at position 52a, a lysine at position 58, a glutamine at position 73, a phenylalanine at position 74, a methionine, isoleucine or leucine at position 53, a phenylalanine at position 54, a tyrosine at position 98, and a tyrosine at position 99, or any combination thereof.

The present invention further features a method of screening an immunogen or vaccine composition to induce broadly neutralizing influenza antibodies by (a) contacting a population of B-cells having at least one copy of the 51p1 allele with the immunogen or vaccine composition under conditions capable of eliciting antibodies from the B-cells; (b) collecting the antibodies elicited from said B-cells in step (a); and (c) determining the presence or absence of the antibodies from step (b) that are encoded by the VH1-69 germline gene or the 51p1 allele; wherein the presence of antibodies encoded by the VH1-69 germline gene or the 51p1 allele indicates that the immunogen or vaccine composition is capable of inducing broadly neutralizing influenza antibodies. In one aspect, step (c) is performed by measuring the reactivity of the antibodies with a reagent that specifically detects antibodies encoded by the VH1-69 germline gene or the 51p1 allele. For example, the reagent is an anti-idiotype antibody, such as anti-51p1 monoclonal G6 antibody or an antigen-binding fragment thereof.

The present invention further features a method of predicting the efficacy of an influenza vaccine in a subject by (a) obtaining a blood or serum sample from the subject; (b) isolating the genomic DNA from the sample; and (c) determining the copy number of the 51p1 and hv1263 genes; wherein one or more copies of the 51p1 gene indicates that the influenza vaccine will elicit broadly neutralizing influenza antibodies in said subject, and wherein one or more copies of the hv1263 gene without at least one copy of the 51p1 gene indicates that the influenza vaccine will not be efficacious in eliciting broadly neutralizing influenza antibodies in said subject.

The present invention also features a method of predicting the efficacy of an influenza vaccine in a subject by (a) obtaining a blood or serum sample from the subject; (b) isolating the serum-derived immunoglobulins from the sample; and (c) analyzing the reactivity of the serum-derived immunoglobulins to an antibody that specifically recognizes antibodies encoded by the IGVH1-69 germline gene; wherein reactivity to said antibody indicates that the influenza vaccine will elicit broadly neutralizing influenza antibodies in said subject. The antibody that specifically recognizes antibodies encoded by the IGVH1-69 germline gene is, for example, an anti-51p1 monoclonal G6 antibody or an antigen-binding fragment thereof. The step of analyzing the reactivity of the serum-derived immunoglobulins is performed by immunoblotting or ELISA.

The present invention also provides a method of predicting the efficacy of an influenza vaccine in a subject by (a) obtaining a blood sample from the subject; (b) isolating a nucleic acid from the sample; and (c) determining the presence or absence of a broadly-neutralizing antibody molecular signature by nucleic acid analysis; wherein the presence of said broadly-neutralizing antibody molecular signature indicates that the influenza vaccine will be or has been efficacious in eliciting broadly neutralizing antibodies in said subject. The nucleic acid is genomic DNA or RNA. The nucleic acid analysis is next generation sequencing, such as Illumina sequencing.

The broadly-neutralizing antibody molecular signature includes any one of the following: at least one copy of the 51p1 allele; a nucleic acid encoding an immunoglobulin variable heavy chain comprising any one of the following: a serine at position 24, a valine at position 27, an isoleucine or proline at position 28, a serine at position 29, an arginine at position 30, a valine at position 34, a serine at position 52, a glycine or an alanine at position 52a, a lysine at position 58, a glutamine at position 73, a phenylalanine at position 74, a methionine, isoleucine or leucine at position 53, a phenylalanine at position 54, a tyrosine at position 98, and a tyrosine at position 99, or any combination thereof; or a nucleic acid encoding an immunoglobulin variable heavy chain comprising a phenylalanine at position 54, a hydrophobic amino acid at position 53, and a tyrosine at amino acid positions 97, 98, and/or 99. Other antibody molecular signatures include a nucleic acid encoding an immunoglobulin comprising a heavy chain comprising any one of the following: a serine at position 24, a valine at position 27, an isoleucine or proline at position 28, a serine at position 29, an arginine at position 30, a valine at position 34, a serine at position 52, a glycine or an alanine at position 52a, a lysine at position 58, a glutamine at position 73, a phenylalanine at position 74, a methionine, isoleucine, valine or leucine at position 53, or a phenylalanine at position 54; and a tyrosine at positions 97, 98, and/or 99; a nucleic acid encoding an immunoglobulin comprising a heavy chain comprising a glycine at position 52a and a tyrosine at positions 97, 98 or 99, or any combination thereof; a nucleic acid encoding an immunoglobulin comprising a heavy chain comprising a glycine at position 52a and either a methionine at position 53 or a valine and position 52; a nucleic acid encoding an immunoglobulin comprising a heavy chain comprising a valine at position 27, a serine at position 52, and a glutamine at position 73; a nucleic acid encoding an immunoglobulin comprising a heavy chain comprising a serine at position 52 and a glutamine at position 73; a nucleic acid encoding an immunoglobulin comprising a heavy chain comprising a proline at position 28 and an arginine at position 30; a nucleic acid encoding an immunoglobulin comprising a heavy chain comprising a proline at position 28, an arginine at position 30, and an alanine at position 52a; a nucleic acid encoding an immunoglobulin comprising a heavy chain comprising an arginine at position 30 and an alanine at position 52a; a nucleic acid encoding an immunoglobulin comprising a heavy chain comprising an isoleucine at position 28, an arginine at position 30, and an alanine at position 52a; and a nucleic acid encoding an immunoglobulin comprising a heavy chain comprising an isoleucine at position 28 and an arginine at position 30.

The present invention further provides a method of predicting prior immunologic exposure or memory to an influenza virus or responsiveness to an influenza virus by (a) obtaining a blood sample from the subject; (b) isolating a nucleic acid from the sample; and (c) determining the presence or absence of a broadly-neutralizing antibody molecular signature by nucleic acid analysis. In a preferred embodiment, the method of predicting prior immunologic exposure or memory to an influenza virus or antigen responsiveness to vaccine or influenza virus infection includes: (a) obtaining a blood sample from the subject; (b) isolating at least one B cell population from the blood sample; (c) isolating RNA from the at least one B cell population; (e) detecting RNA encoding immunoglobulins; (0 determining the presence of immunoglobulins comprising a broadly-neutralizing antibody molecular signature; and (g) calculating the ratios or absolute frequency of B cell receptor precursors in at least one B cell population comprising the broadly-neutralizing antibody molecular signature; wherein said ratio is used to predict prior exposure or memory to an influenza virus or antigen responsiveness to vaccine or influenza virus infection. The B cell population may be naïve B cells or memory B cells. The immunoglobulins are IgG, IgM, IgA, IgD, or IgE. The present invention also provides methods for selecting a vaccine regimen, wherein subjects with at least one 51p1-like allele or a broadly-neutralizing antibody molecular signature does not receive a vaccine and wherein subjects without a 51p1-like allele, or without a broadly-neutralizing antibody molecular signature would receive a vaccine.

The present invention further provides kits for any of the methods described herein. The kit includes a reagent for detecting the 51p1 and/or the hv1263 allele and instructions for their use. For example, the reagent for detecting the 51p1 allele is an anti-51p1 monoclonal G6 antibody. In another embodiment, the reagent for detecting the 51p1 allele is a primer pair that hybridizes to the 51p1 allele.

The present invention further provides methods for identifying a subject that will be responsive to an influenza vaccine. In one embodiment, a method of identifying a subject that will be responsive to an influenza vaccine comprises: a) obtaining a blood or serum sample from the subject; b) isolating the genomic DNA from the sample; c) determining the copy number of the 51p1 and hv1263 genes; wherein the subject will be responsive to the influenza vaccine if said subject contains one or more copies of the 51p1 gene, and wherein the subject will not be responsive to the influenza vaccine if said subject has one or more copies of the hv1263 gene without at least one copy of the 51p1 gene; and d) administering the influenza vaccine to the subject that is determined to be responsive to the influenza vaccine.

The present invention also provides methods for identifying a subject that will be or has been responsive to an influenza vaccine. In one embodiment, a method of identifying a subject that will be or has been responsive to an influenza vaccine comprises: a) obtaining a blood sample from the subject; b) isolating a nucleic acid from the sample; and c) determining the presence or absence of a broadly-neutralizing antibody molecular signature by nucleic acid analysis; wherein the presence of said broadly-neutralizing antibody molecular signature indicates that the subject will be or has been responsive to the influenza vaccine; and d) administering the influenza vaccine to the subject that is determined to be responsive to the influenza vaccine.

Other features and advantages of the invention will be apparent from and are encompassed by the following detailed description and claims.

BRIEF DESCRIPTION OF THE DRAWINGS

FIG. 1, panel A discloses SEQ ID NOS 693-707, respectively, in order of appearance._B) Left—The location of F10 binding on the HA is shown with HA colored in salmon and HA2 colored in grey. Right panels —The location of the CDR residues identified in a). In light green is the HA2 fusion peptide from $Trp21_2$-to-$Val118_2$. C) Binding kinetics data of F10, CR6261, and the respective variants of F10 F54A, F10 Y98A, CR6261 F54A and CR6261 Y98A, against H5VN04.

FIG. 2. Characterization of HV1-69-sBnAbs VH domain.
A) Alignment of 38 HV1-69-sBnAbs is shown with highlights pointing to hydrophobic residues at position 53, the maintenance of Phe54, the occurrence of CDR-H3-Tyr residues and 13 highlighted unique amino acid substitutions determined to be statistically distinct from a reference IGHV1-6951p1 allele related Ab dataset (C). Other hydrophobic residues in position 74 are highlighted in grey. FIG. 2, panel A discloses SEQ ID NOS 708-862, respectively, in order of appearance._B) Distribution of number of V-segment substitutions for the 38 HV1-69-sBnAbs. D) The IGHV1-6951p1 Ab reference dataset was studied for substitution frequency of codon nucleotides in the CDR-H2 region and for location of AID and polη hotspots. The odds for the distinctive HV1-69-sBnAbs amino acids (red) are significantly less than that observed collectively for the other codon positions (* indicate P<0.05 for the odds value presented). The upper inset shows the common nucleotide substitutions that generate the distinctive amino acid substitutions. (See additional discussions in FIG. 11 description). FIG. 2, panel D discloses SEQ ID NOS 691-692, 863, and 1275, respectively, in order of appearance.

FIG. 3, panel A discloses SEQ ID NOS 672 and 864-868, respectively, in order of appearance. B) Kinetic analysis by BiaCore of F10 and A66 CDR-H2 variants against purified H5VN04.
FIG. 3, panel B discloses SEQ ID NOS 1276 and 869-876, respectively, in order of appearance._C) F10 V-segment germline variants (left) were analyzed for H5VN04 binding in the phage-Ab (5 scFv/phage) format by MSD ELISA (middle) and for their ability to activate B-cell when expressed as B-cell receptors in the presence of H5VN04 (right).

Binding activities against the anti-51p1 mouse anti-idiotypic mAb G6 that is specifically reactive to the 51p1 allelic group was performed using pre-vaccination, 1 month post vaccination, and 4 years post vaccination sera of 20 individuals genotyped to the presence of 51p1 or hv1263 alleles by using a MSD ELISA approach. ELISA assay against H5VN04 b) and against H5VN04 HA c) was performed using the 1-month post vaccination sera. d) The 1-month post vaccination sera were analyzed for their ability to inhibit F10 from binding to H1CA0409 that was coated on MSD plates. The Mann-Whitney T-test was used to generate P values in all serological assays.

FIG. 6. VDW contact analysis of F10, CR6261 and CR9114 common heavy chain anchor residues to H5VN04.

The common anchor amino acids of CDR-H2 Ile53/Met53, Phe54 and CDR-H3 Tyr98 were studied for their respective HA contact residues. This analysis was performed by using Chimera's (31) find contacts function, which declares a contact (dashed lines) when the sum of the VDW radii of two atoms minus the distance between them is greater than or equal to −0.4 Å. In cyan are HA contact residues shared by all three Abs, in green are non-common HA VDW contacts.

Figure 7:
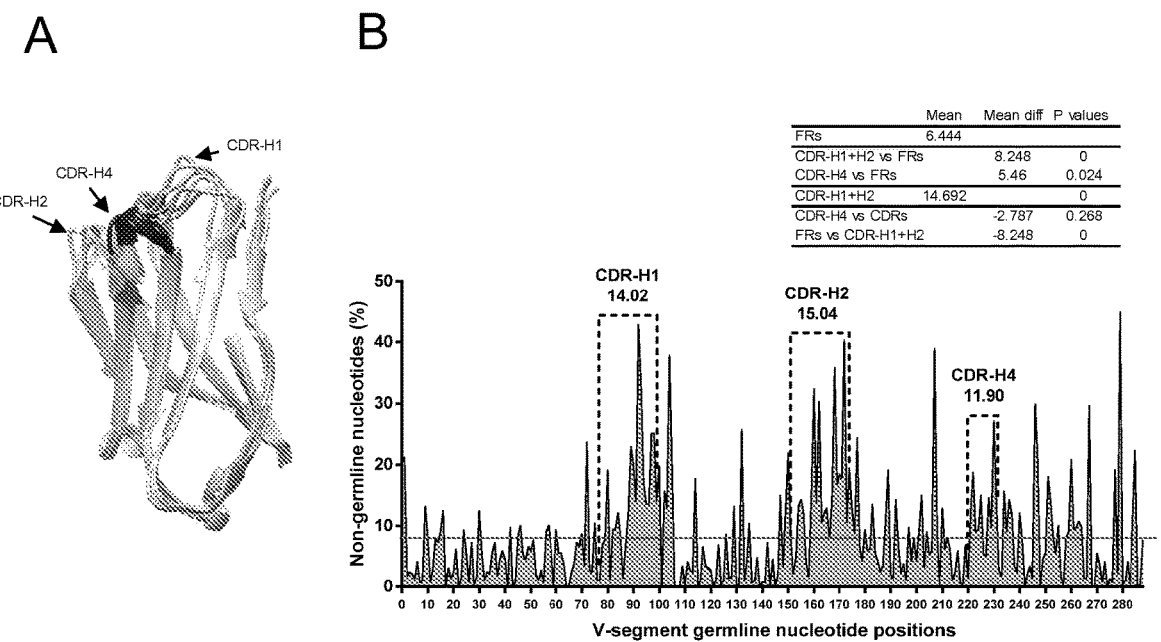

FIG. 7. Defining the CDR-H4 loop in IGHV1-6951p1 allele based Abs.

The existence of a CDR-H4 loop, or hypervariable loop-4 (HV4), has been suggested by several studies (34, 35). However, no formal definition has been given to this loop. In this study the approach for defining the CDR-H4 loop was based on structural alignment, and by studying the overall nucleotide substitution frequency of the structurally defined CDR-H4 region in the reference IGHV1-69-Ab dataset (sees Methods for more details). (A) Structural alignment was performed for 7 non-antigen complexed IGHV1-6951p1 allele related Abs: E51, 47e, 412d, CR9114, 1-69/b3, CR6261 and N12-i2. Six Abs are all characterized by a loop that starts with position 73 and ends with position 76 with the exception of N12-i2. Accordingly, the CDR-H4 loop germline sequence is defined as E.S.T.S. (B) The IGHV1-69-Ab reference dataset was analyzed for non-germline nucleotide substitution frequencies. The red line shows the mean of non-germline nucleotide substitution frequency observed for FR regions of the V-segment and dashed lines point to the CDR areas. The analysis of variance (ANOVA) shows (B—inset) that the mean of non-germline nucleotide substitution frequency of the CDR-H4 area is significantly higher than that of the FRs (p=0.02), but is not significantly different than that of the CDR-H1+H2 (p=0.27).

Figure 1:
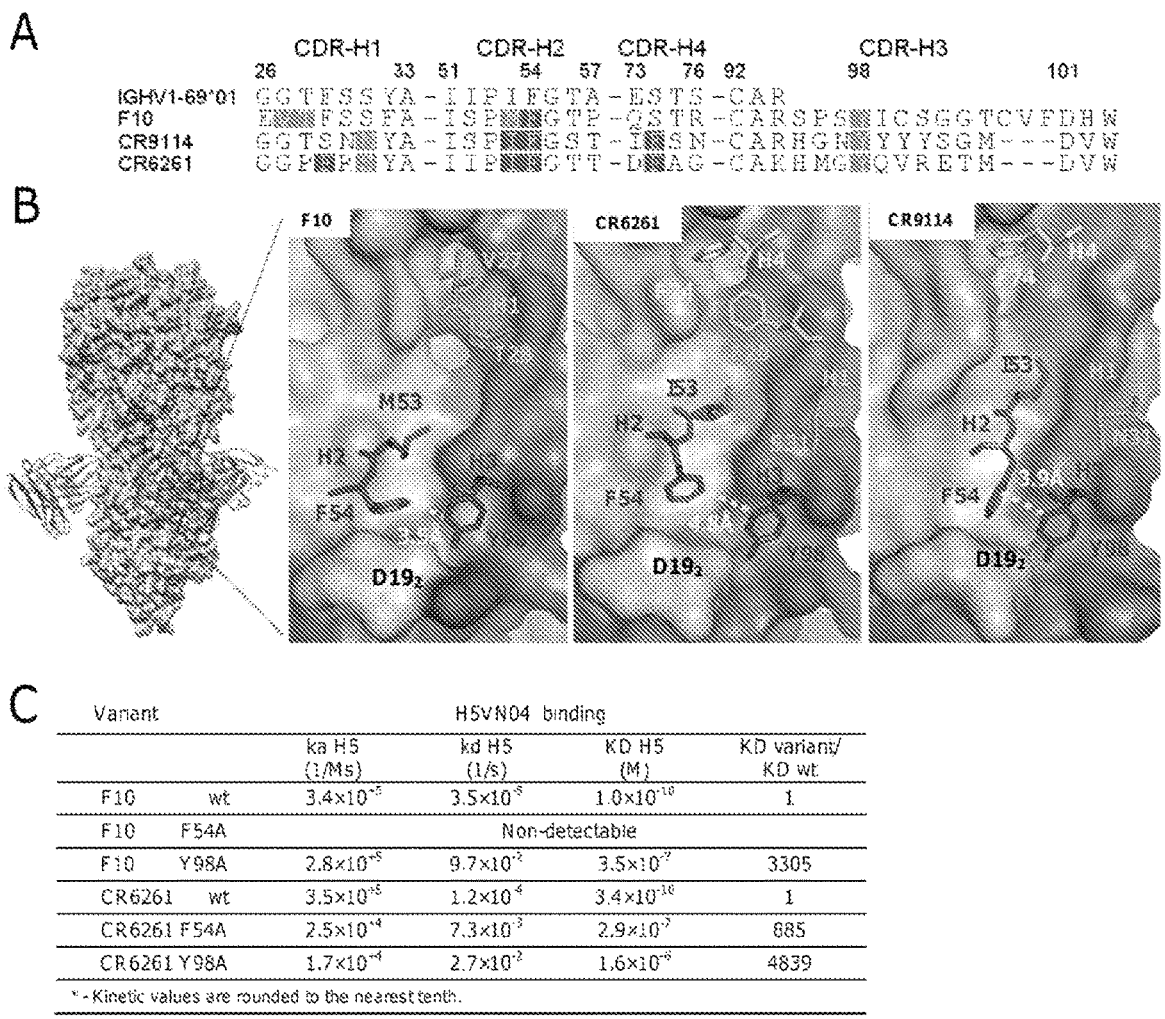
FIG. 1. The structural basis of HV1-69-sBnAb similarity.
A) The ANCHOR web server (17) was used to identify heavy chain CDR residues that make favorable contacts (-1kcal/mol>-3kcal/mol orange) and highly favorable binding contacts (<-3kcal/mol red) in the co-crystal structures of F10 (PDB: 3FKU) CR6261 (PDB: 3GBM), and CR9114 (PDB: 4FQI).
Figure 8:
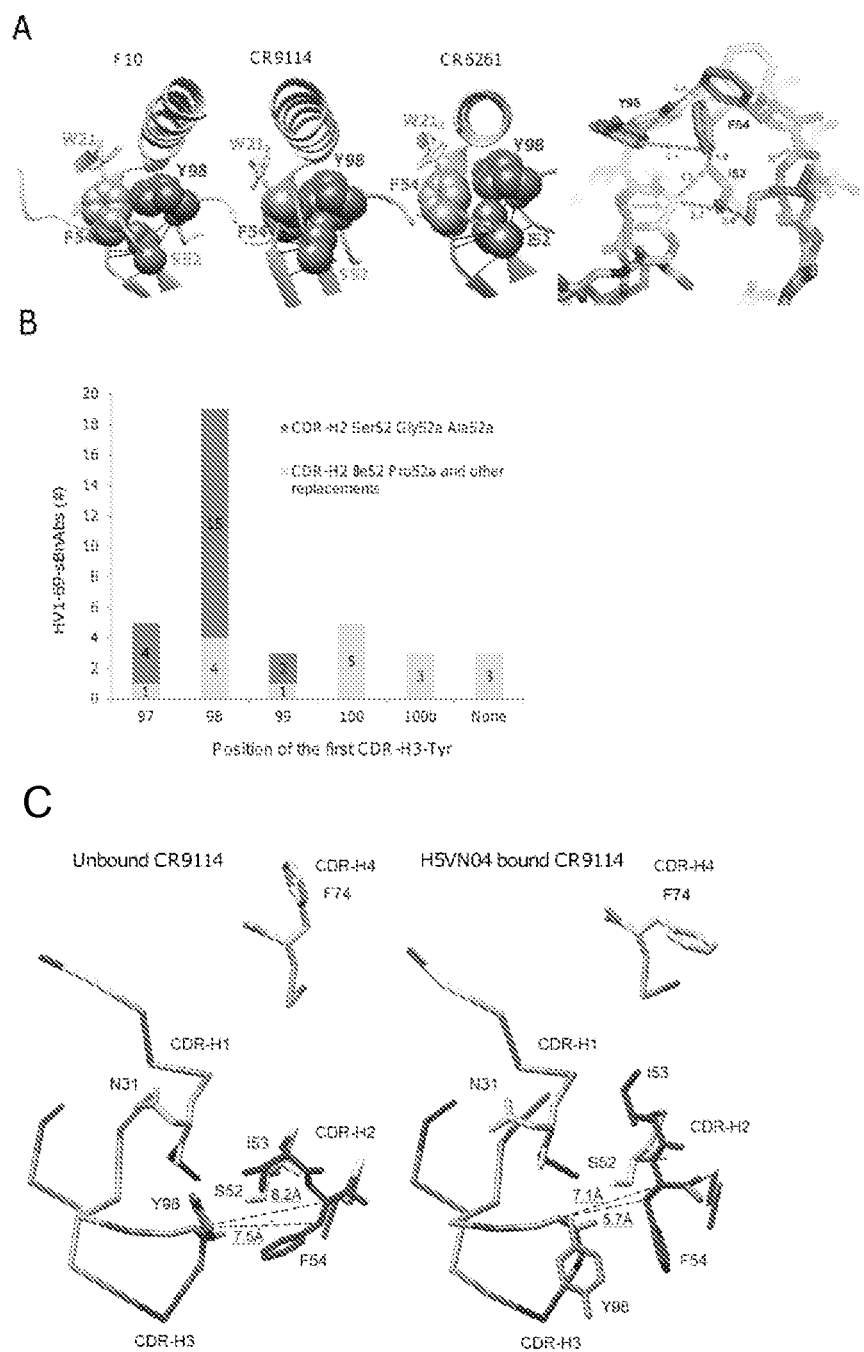

FIG. 8. Understanding the structural role of the distinctive CDR-H2 amino acid substitutions in HV1-69-sBnAbs A) VDW contact analysis (black lines) shows that Ser52 of F10 and CR9114 (orange), and Ile52 of CR6261(gray) make only intramolecular contacts; i.e., do not form contacts with their respective H5VN04s. Antibodies are shown in color; HA is in light gray. At far right, steric consequences of the germline Ile52 and the Ile52Ser substitutions are shown when the Abs are overlaid on their framework residues (RMSD 0.5 Å). Comparing structures of the HV1-69-sBnAbs, centered on Ile52 of CR6261 (green), with F10 (yellow) and CR9114 (cyan), the Ile52Ser mutation in F10 and CR9114 enables the 2 strands to come closer together, as indicated by the yellow and cyan arrows. Distances in red indicate hypothetical steric clashes (<3 Å) that would be created if Ile52 were present in CR9114 and F10. B) The position of the first CDR-H3 TYR that was recorded in the HV1-69-sBnAbs subset characterized by CDR-H2 Ser52, Gly52a and Ala52a versus the HV1-69-sBnAb subset that is devoid of these unique amino acid replacements. The sum of HV1-69-sBnAbs with at least one tyrosine in position 97-to-99 is 27 (71%). C) Comparison between the unbound (PDB 4FQH, left) and H5VN04-bound structures (PDB 4FQI, right) of CR9114, colored according to the magnitude of structural change after superposition on the main-chain of the VH domain (from blue=0 Å, through white=1 Å, to red=1.8 Å). CDRs and side-chains of the major contact residues are shown, as depicted in FIG. 1A. Distances between the Cα and Cβ atoms of Phe54 and the Cα atom of CDR-H3 Tyr98 (shown as dashed lines) are indicated. Large rotations of the side chains of CDR-H3 Tyr98, CDR-H2 Phe54 and CDR-H2 Ile53 are also evident, as previously noted [7].

Figure 9:
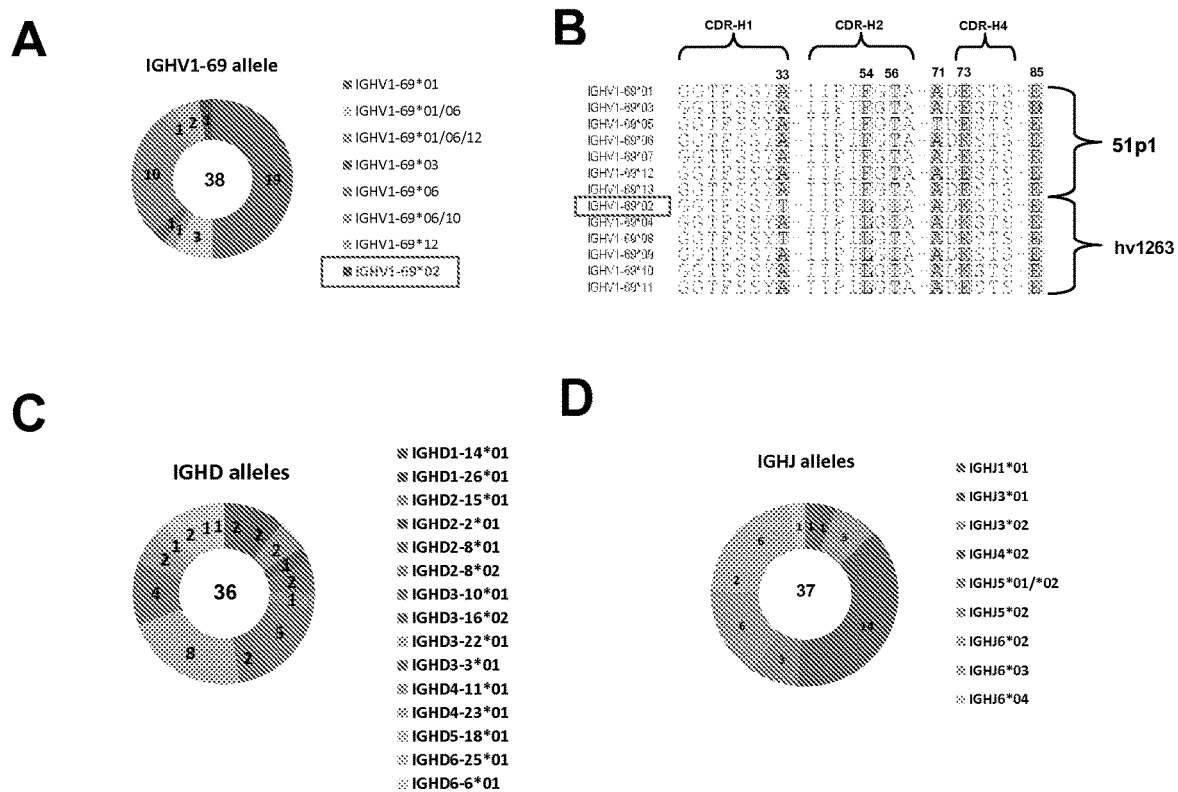

FIG. 9. HV1-69-sBnAbs immunogenetic analysis.

HV1-69-sBnAbs were analyzed for A) V-segment allele usage (n=38), with panel B) showing the 13 known IGHV1-69 alleles and their classification into the 51p1 and hv1263 allele groups. FIG. 9, panel B discloses SEQ ID NOS 923-961, respectively, in order of appearance. Panel C) shows D-segment usage (n=36), and panel D) shows J-segment usage (n=37).

Figure 10:
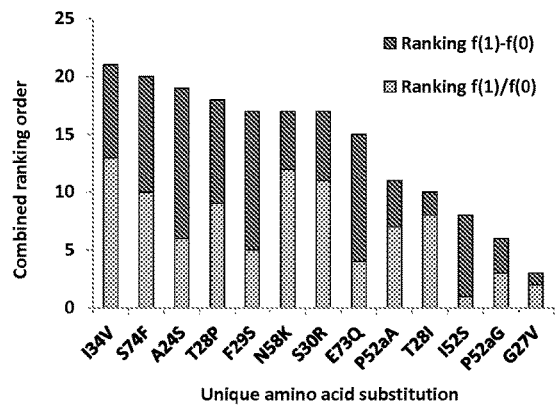

FIG. 10. Ranking of HV1-69-sBnAbs uniquely associated amino acid substitutions.

The frequencies of the 13 HV1-69-sBnAb distinctive amino acid substitutions identified in FIG. 2, panel C (f1), were divided A) or subtracted B) by the respective substitution frequencies observed in the reference IGHV1-69-Ab dataset (f0) and were ranked from lowest to highest product. C) The ranking scores from a) and b) were combined into an overall ranking score. Accordingly, I34V is ranked the lowest while G27V is ranked highest for distinct association with the HV1-69 sBnAbs.

Figure 11:
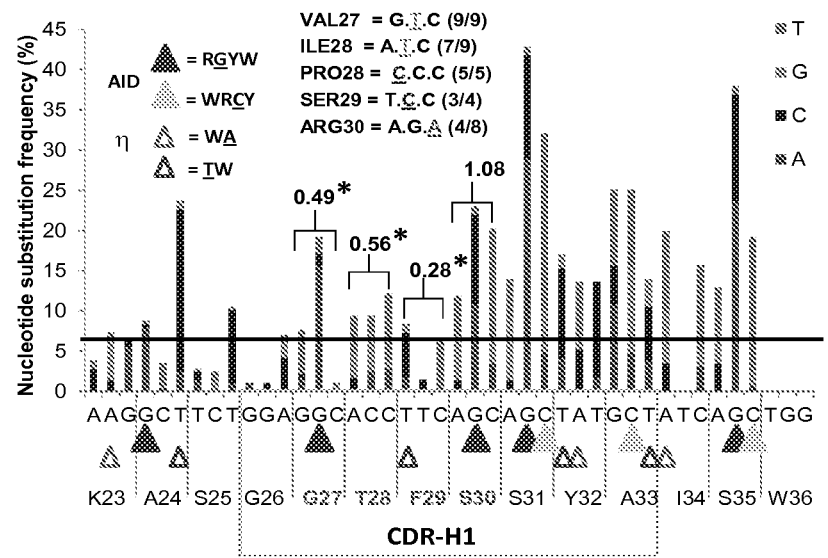

FIG. 11. Nucleotide substitution frequencies observed in the CDR-H1 area of the IGHV1-69 reference dataset.

The IGHV1-6951p1 Ab reference dataset was studied for the substitution frequency of codon nucleotides in the CDR-H1 area and for the location of AID and pol□ hotspots. The odds for nucleotide substitutions in the codons of the distinctive HV1-69-sBnAbs amino acids (red) of G27, T28, F29, but not S30, are significantly lower (*–P<0.05) than that was observed collectively in the codon positions G26, S31 Y32 and A33 that are not unique to HV1-69-sBnAbs. In the upper insert the common nucleotide substitutions that generate the distinctive amino acid substitutions are shown. Similarly to the observation made with the CDR-H2 domain (FIG. 2, panel d), a cluster of SHM hotspots is noticeable towards the 3' end of the loop. It is also observed that the distinctive amino acid substitution of G27V is located under AID hot spot of RGYW (SEQ ID NO: 691). This codon position required transversion of dG-to-dT for generating G27V which occurs at a low frequency of 2.1% as compared to the 15.7% transition of dG-to-dA (G27D). The high frequency of the dG-to-dA transition is expected based on known mechanisms of AID action (22, 36). Accordingly, the RGYW (SEQ ID NO: 691) motifs are characterized by high frequencies of dG-to-dA transition and WRCY (SEQ ID NO: 692) motifs are characterized by high frequencies of dC-to-dT transition. For both FIG. 11 and FIG. 2, panel d, the horizontal black line shows the mean±SD (6.44±7.23) of non-germline nucleotide substitution frequency observed for FR regions to serve as a baseline. The shaded area around the line represents one standard deviation. FIG. 11 also discloses SEQ ID NO: 962 and 1277, respectively, in order of appearance.

Figure 12:
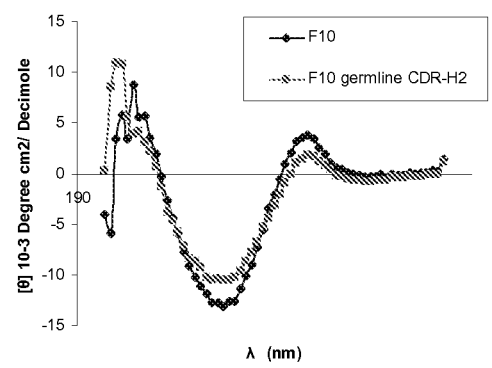

FIG. 12. Circular dichrosim of F10 and a non-H5 reactive F10 variant.

Circular dichorism measurement of F10 and the non-H5 reactive variant characterized by a germline configured CDR-H2 shows a highly similar CD profile for both constructs.

Figure 13:
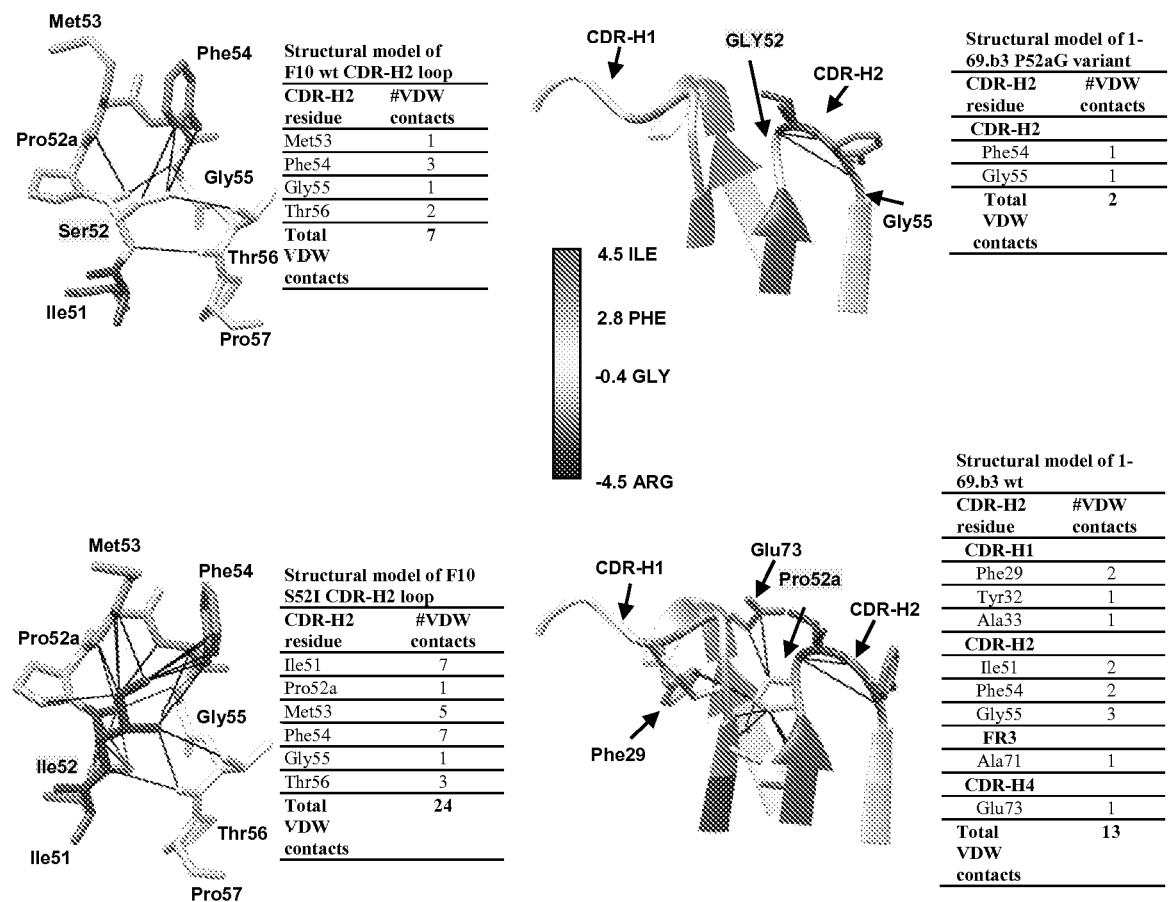

FIG. 13. Understanding the structural role of the HV1-69-sBnAbs distinctive AA substitutions in positions 52 and 52a.

A) In the model of non-HA complexed F10, VDW contacts were analyzed for Ser52 against other CDR-H2 loop residues (upper panel). Ser52 was in-silico mutagenized (32) to Ile52 to show the occurrence of a much higher number of VDW contacts (lower panel). B) Upper panel—Pro52a in 1-69/b3 (mAb characterized by a non-mutated IGHV1-69*01 V-segment) was in-silico mutagenized to Gly52A to show the occurrence of minimal number of VDW contacts as compared to the germline Pro52a as shown in the lower panel.

Figure 14:
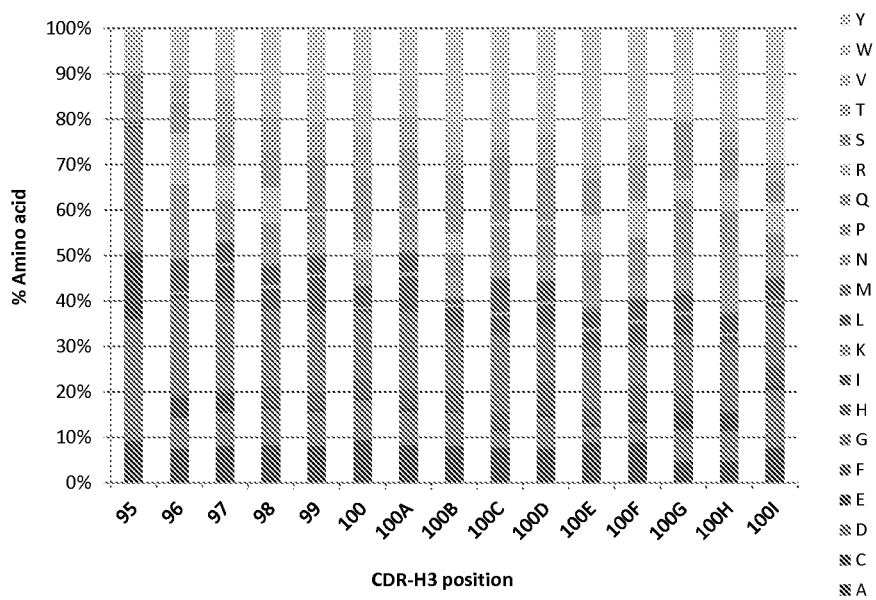

FIG. 14. The design principles of the VH1-69 synthetic library. A)

Diversification plan of the V and J segments. A) Diversification plan of the V and J segments. In grey are amino acids that were elevated beyond their natural observed frequency. B) Diversification scheme for the CDR-H3 domain, which was based on the natural frequency and diversity observed in a reference CDR-H3 alignment made from IGHV1-6951p1 allele based Abs (n=1217).

Figure 15:
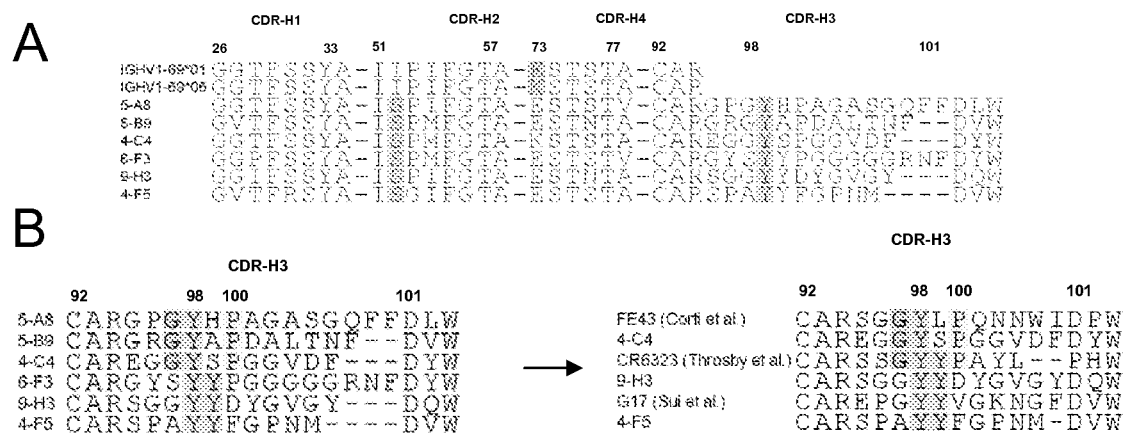

FIG. 15. CDR-H3 similarities with the six common phage-Abs obtained from independent H5VN04 and H1CA0409 panning campaigns.

A) Heavy chain CDR sequences of 6 common clones isolated from the H5VN04 and H1CA0409 panning campaigns (SEQ ID NOS 963-992, respectively, in order of appearance). B) Left, alignment of the six common clones CDR-H3 domain identifies two consensus motifs CARxxGYxP (SEQ ID NO: 661) and CARxxxYY (SEQ ID NO: 662). Right, synthetic CDR-H3s were paired with similar naturally occurring CDR-H3s (SEQ ID NOS 993-1004, respectively, in order of appearance).

FIG. 16A-16E. CDR sequences and binding characteristics of the anti-H5VN04 phage-Ab pool.

FIG. 16A) CDR sequence alignment (SEQ ID NOS 1005-1151, respectively, in order of appearance) of the anti-H5VN04 phage-Ab pool was ordered based on heterosubtypic binding activity as tested against H1CA0409 and H2 SIN 57. Highlights point to the statistically significant enriched residues post selection as discovered by Chi square test in FIG. 16B). FIG. 16C) Heterosubtypic (n=16) and non-heterosubtypic (n=8) anti-H5VN04 phage-Abs that are characterized by Ser52/Tyr98 were analyzed separately by Chi square test for the frequency of enriched amino acids in CDR-H3. FIG. 16D) CDR sequence alignment (SEQ ID NOS 1152-1274, respectively, in order of appearance) of the anti-H1CA0409 phage-Ab pool was ordered based on heterosubtypic binding activity as tested against H5VN04 and H2 SIN 57. Highlights point to the statistically significant enriched residues post selection as discovered by Chi square test in FIG. 16E). Red circles point to the two phage-Abs which did not bind to the stem domain of H1CA0409. Blue circles point to common phage-Ab clones discovered independently from both panning campaigns.

DETAILED DESCRIPTION

The recent discovery of human broadly neutralizing "heterosubtypic" antibodies binding to a highly conserved hydrophobic pocket (1-3) on the stem of HA (sBnAb) has reignited efforts to develop a "universal" influenza virus vaccine. These sBnAbs were identified either by panning phage-Ab libraries (1, 2, 4, 5), or were recovered from B-cells of infected and vaccinated influenza donors (6-9) (Table 9). However, only very low concentrations sBnAbs are detected in the sera of seasonal influenza (6) or H5N1 vaccinees, or in commercial intravenous immunoglobulin (IVIG) preparations (10); with a notable exception being in the response to pdm2009 H1N1 strains (11, 12).

Interestingly, more than 75% of anti-group 1 influenza A virus sBnAbs use the IGHV1-69 germline gene. While the IGVH1-69 germline gene is highly utilized in the population (13), it is unclear what constrains the elicitation of HV1-69-sBnAbs by vaccination or seasonal influenza infection to levels high enough to universally protect the population against group 1 influenza A subtypes. The highly immunogenic globular head (6, 7, 10) and the cryptic nature of the stem on mature virions (14) have been thought as the main impediments for sBnAb elicitation.

Analysis of 38 HV1-69-sBnAbs recovered from 8 laboratories (Table 9), together with mutagenesis studies, structural modeling, and panning of a semi-synthetic IGHV1-69 Ab library against H5/H1 was performed. The results described herein show that there are a limited number of structural solutions for IGHV1-69-encoded antibodies to become HV1-69-sBnAbs, and that a major solution is conveyed by specific mutations at 2 positions within the CDR-H2 loop, in a region sparse in activation-induced cytidine deaminase (AID) and polymerase eta (pol η) consensus binding motifs. These mutated residues do not directly contact HA, rather they act to enhance the flexibility of the CDR-H2 loop, which enables the two key binding residues from adjacent loops, CDR-H2 Phe54 and CDR-H3 Tyr98, to insert their aromatic side-chains into adjacent hydrophobic pockets in the stem. In addition, IGHV1-69 polymorphism plays a role in restricting HV1-69-sBnAb elicitation, as CDR-H2 Phe54 is only present in seven of 13 IGHV1-69 alleles, which belong to the 51p1 allele like group (15) that are lacking in a significant proportion of the general population (16).

The present invention is based upon the discovery of structural determinants found in influenza hemagglutinin (HA) stem-directed broadly-neutralizing antibodies (HV1-69-sBnAbs). These structural determinants can be used for rational design of broadly neutralizing influenza antibodies with higher affinity, and production of a broad, polyclonal panel of HV1-69-sBnAbs.

The present invention provides antibodies produced using a semi-synthetic IGHV1-69 antibody library using the structural determinants disclosed herein to yield novel broadly neutralizing influenza antibodies. The antibodies disclosed herein bind to the hydrophobic pocket on the stem of HA influenza protein. Specifically, the libraries were panned against trimeric HA proteins H5VN04 and H1CA0409. 36/36 and 28/30 unique stem targeted phage-Ab clones were isolated by the panning method. The antibodies isolated from panning against H5VN04 are 1C2, 2B8, 2C4, 2D3, 2D9, 2E1, 2H4, 2H5, 4C4, 4E5, 4F5, 4G3, 4G5, 5A6, 5A8, 5B9, 6A2, 6C2, 6F3, 8A1, 8C1, 8D6, 9A1, 9C1, 9D11, 9E4, 9E7, 9H3, 10D4, 11A11, 11A6, 11B5, 1106, 11E9, and 11F8. The antibodies isolated from panning against H1CA0409 are 1D9, 1E6, 1F1, 1F12, 1F3, 1F5, 1F6, 1H2, 1H4, 2A1, 2A11, 2A12, 2B11, 2B6, 2C1, 2E11, 2E12, 2F1, 2G3, 2H3, 2H4, 4C4, 4F5, 5A8, 5B9, 6F3, and 9H3. Six antibodies were commonly identified in both panning methods, specifically, antibodies 4C4, 4F5, 6F3, 5A8, 5B9, and 9H3. Antibodies 2B11 and 2A2 do not bind to the stem region of HA. The antibodies disclosed herein have heterosubtypic binding activity, as shown in FIGS. 16A and 16D. The nucleic acid sequences and amino acid sequences of each of these antibodies are disclosed herein.

Structural Determinants

The structural determinants identified in the experiments disclosed herein can also be used as a tool to evaluate the efficacy of influenza vaccines, and characterize individual patients and their immunological reaction to influenza vaccines (i.e., the ability to produce high or low titers of HV1-69-sBnAbs).

The present invention provides structural determinants that were found to occur at high frequency in HV1-69-sBnAbs. These structural determinants are found in the variable heavy chain encoded by VH germline genes that belong to the IGHV1-6951p1 allele related group, which is mainly defined by Phe54, wherein the amino acid at position 53 is a hydrophobic amino acid (i.e. methionine, isoleucine, or leucine), position 54 is a phenylalanine, and positions 97, 98, and/or 99 is a tyrosine. Preferably, the amino acid at position 54 and the amino acid at position 98 is a tyrosine.

Structural analysis of known HV1-sBnAbs showed that the common aromatic pair of Phe54 (located in CDR-H2) and Tyr98 (located in CDR-H3) pack closely together to bind to adjacent pockets formed by elements of the HA fusion peptide. Specifically, Tyr98 makes both hydrophobic interactions as well as a strong H-bond with the fusion peptide (the main chain carbonyl of $Asp19_2$), and adopts a single conformation in the 3 known structures. The side-chains of Phe54 converge in one location, packing on top of a prominent loop in the fusion peptide (residues $18_2$-$21_2$), and orthogonally against the $Trp21_2$ side-chain of H5VN04 (FIGS. 1B and 6). In contrast to their side-chains the Cα positions of Phe54 diverge, so that the upstream residues at position 53 adopt distinct locations along a groove formed at the interface between HA1 and HA2 elements of the same H5 subunit. The importance of the two main common anchor residues, CDR-H2 Phe54 and CDR-H3-Tyr, has been shown by alanine substitution mutagenesis assays, which demonstrated that alanines at position 54 or 98 significantly reduce binding to HA. Although these residues do not play a role in directly contacting the HA, they play a critical role in the formation of the structure of the antibody to recognize the HA stem domain with high affinity.

Other amino acids found in the VH domain have also been identified as contributing to the affinity of an anti-influenza antibody to HA. Analysis of a panel of HV1-69-sBnAbs revealed that at least 13 amino acid somatic mutations from the IGHV1-69 germline gene may also contribute to increased affinity of antibodies to influenza HA. These mutations are located in the Framework 1 region: A24S; mutations located in CDR-H1: G27V, T28I, T28P, F29S, and 530R; mutations located in Framework 2 region: I34V; mutations located in CDR-H2: I52S, P52aG, P52aA; mutations located in Framework 3 region: N58K; mutations located in CDR-H4: E73Q and S74F. Mutagenesis analysis revealed that revertant mutations to the germline IGHV1-69 residues resulted in drastic reduction or ablation of binding kinetics and reactivity to influenza HA protein. Therefore, these additional structural determinants may also be utilized for the development or rational design of novel HV1-69-sBnAbs.

The present invention provides methods for utilizing the structural determinants described herein to improve or increase the neutralization capacity or affinity of anti-influenza antibodies. These structural determinants can be introduced into nucleotide sequences that encode anti-influenza HA protein antibodies, or nucleic acid expression vectors containing such sequences, to increase the affinity of the antibodies to influenza HA. For example, the present invention provides a method of improving the neutralization capacity or affinity of antibodies that bind to the HA protein of an influenza virus by any one of the following: mutating the amino acid at position 24 to a serine, mutating the amino acid at position 27 to a valine, mutating the amino acid at position 28 to an isoleucine or proline, mutating the amino acid at position 29 to a serine, mutating the amino acid at position 30 to an arginine, mutating the amino acid at position 34 to a valine, mutating the amino acid at position 52 to a serine, mutating the amino acid at position 52a to a glycine or an alanine, mutating the amino acid at position 58 to a lysine, mutating the amino acid at position 73 to a glutamine, mutating the amino acid at position 74 to a phenylalanine, mutating the amino acid at position 53 to a methionine, isoleucine or leucine, mutating the amino acid at position 54 to a phenylalanine, mutating the amino acid at position 98 to a tyrosine, and mutating the amino acid at position 99 to a tyrosine, or any combination thereof, of the antibody. The numbering of the amino acid sequence of the antibody used herein is the Kabat numbering system (Kabat, E A, et al., Sequences of Protein of immunological interest, Fifth Edition, US Department of Health and Human Services, US Government Printing Office (1991)).

For example, in those embodiments in which the anti-influenza antibody is encoded by the IGHV 1-69 germline gene, the mutations can be any one of the following: A24S, G27V, T28I, T28P, F29S, S30R, I34V, I52S, P52aG, P52aA, N58K, E73Q, and S74F or any combination thereof.

In another embodiment, any of the structural determinants described herein can be introduced to a synthetic antibody library for the rational design of a panel of broadly neutralizing influenza antibodies. For example, the structural determinants include, a serine at position 24, a valine at position 27, an isoleucine or proline at position 28, a serine at position 29, an arginine at position 30, a valine at position 34, a serine at position 52, a glycine or an alanine at position 52a, a lysine at position 58, a glutamine at position 73, a phenylalanine at position 74, a methionine, isoleucine or leucine at position 53, a phenylalanine at position 54, a tyrosine at position 98, and a tyrosine at position 99, or any combination thereof. The substitution or mutations of the germline IGHV 1-69 gene can be readily performed by the ordinarily skilled artisan by recombinant methods known in the art.

Antibody affinity to influenza HA protein can be assayed by ELISA or other immunoassay techniques. Kinetic studies, such as surface plasmon resonance can be used to determine the on and off rates of the antibody to the antigen or epitope.

Neutralization capacity for the identified antibodies to neutralize influenza virus can be assayed using in vitro or in vivo neutralization assays. For example, animal models can be infected with influenza virus (i.e., a lethal dose), administered anti-influenza antibodies, and symptoms can be monitored for alleviation of symptoms with effective neutralizing antibodies. Alternatively, assays can be performed to identify anti-influenza antibodies that recognize HA and inhibit fusion of the viral envelope to the host cell. Additional assays to determine antibody affinity and neutralization capacity are readily known by the ordinarily skilled artisan.

Methods of Evaluating Efficacy of Vaccines

The current approach for the assessment of vaccine efficacy is based on functional studies, which include hemagglutination inhibition assays and microneutralization assays. However, there are no assays that can evaluate the ability of influenza vaccines to specifically induce the broadly neutralizing HA stem-binding HV1-69-sBnAbs, which serve as more universal antibodies. Moreover, there are no assays that can predict vaccine efficacy in a subject prior. The identification of the immunogenetic restrictions, or structural determinants, that are associated with HV1-69-sBnAbs at high frequency serves as a novel tool for the assessment of vaccines to elicit HV1-69-sBnAbs.

As used herein, "vaccine efficacy" is meant the ability of a vaccine to induce or elicit particular anti-influenza antibodies after vaccination, for example, broad neutralizing influenza antibodies that recognize the HA stem domain (HV1-69-sBnAbs). A vaccine is considered efficacious if vaccination or exposure to the vaccine composition results in elicitation HV1-69-sBnAbs, or broadly neutralizing influenza antibodies. In some embodiments, the anti-influenza antibodies that are elicited are derived from the IGHV1-69 germline genes, specifically, the 51p1-like allele group. In some embodiments, the anti-influenza antibodies are characterized by the presence of any one of the following structural determinants, a methionine, isoleucine or leucine at position 53, a phenylalanine at position 54, a tyrosine at position 98, and a tyrosine at position 99, or any combination thereof.

The IGHV1-69 germline gene alleles can be subdivided into two alleles groups, those which belong to the 51p1-like (also known as 51p1-related) allele group and those which belong to the hv1263-like allele group. Sequence analysis studies have shown that HV1-69-sBnAbs arise mainly from the 51p1-like allele group, as the 51p1-like allele group is characterized by a phenylalanine at amino acid position 54 (Phe54) in CDR-H2. In contrast, the hv1263-like allele group is characterized by a leucine at position 54 (Leu54) in CDR-H2. IGHV1-69 gene copy number is variable among individuals due to gene duplication and deletions (24). Moreover, expression of 51p1-like alleles is reported to be proportional to its germline gene copy number. (16). However, the 51p1-like allele does not appear in all individuals, roughly 25% of the population lacks the 51p1-like alleles. As a result, individuals who are devoid of 51p1-like alleles or have a low frequency of B-cells bearing 51p1 allele related B cell receptors (BCRs), may have lower titers of HV1-69-sBnAbs.

51p1-like alleles can be found, for example, in databases readily available such as the global ImMunoGeneTics (IMGT) Web Resource for Immunoglobulins (http://www.imgt.org/IMGTrepertoire/Proteins/taballeles/human/IGH/IGHV/Hu_IGHVall.ht ml). Examples of 51p1-allele-like genes include, but are not limited to those listed in Table A:

TABLE A

51p1-allele like genes and nucleic acid sequences

| IGHV allele name | Accession No. | Sequence |
|---|---|---|
| IGHV1-69*01 | L22582.1 | GCAGGATTTAGGGCTTGGTCTCTCAGCATCCCACACTTGTACA GCTGATGTGGCATCTGTGTTTTCTTTC TCATCGTAGATCAGGCTTTGAGCTGTGAAATACCCTGCCTCAT GCATATGCAAATAACCTGAGGTCTTCT GAGATAAATATAGATATATTGGTGCCCTGAGAGCATCACATA ACAACCACATTCCTCCTCTAAAGAAGCC CCTGGGAGCACAGCTCATCACCATGGACTGGACCTGGAGGTT CCTCTTTGTGGTGGCAGCAGCTACAGGT AAGGGGCTTCCTAGTCCTAAGGCTGAGGAAGGGATCCTGGTT TAGTTAAAGAGGATTTTATTCACCCCTG TGTCCTCTCCACAGGTGTCCAGTCCCAGGTGCAGCTGGTGCA GTCTGGGGCTGAGGTGAAGAAGCCTGGG TCCTCGGTGAAGGTCTCCTGCAAGGCTTCTGGAGGCACCTTC AGCAGCTATGCTATCAGCTGGGTGCGAC AGGCCCCTGGACAAGGGCTTGAGTGGATGGGAGGGATCATCC CTATCTTTGGTACAGCAAACTACGCACA GAAGTTCCAGGGCAGAGTCACGATTACCGCGGACGAATCCAC GAGCACAGCCTACATGGAGCTGAGCAGC CTGAGATCTGAGGACACGGCCGTGTATTACTGTGCGAGAGAC ACAGTGTGAAAACCCACATCCTGAGAGT GTCAGAAACCCTGAGGGAGAAGGCAGCTGTGCCGGGCTGAG GAGATGACAGGGTTTATTAGGTTTAAGGC TGTTTACAAAATGGGTTATATATTTGAGAAAAAAAGAACAGT AGAAACAAGTACATACTCCTCTAATTTT AAGATAATTATTCCATTCAAGAGTCGTAATAT (SEQ ID NO: 678) |
| IGHV1-69*03 | X92340.1 | CTGGAGGTTCCTCTTTGTGGTGGCAGCAGCTACAGGTAAGGG GTTTCCTAGTCCTAAGGCTGAGGAAGGG ATCCTGGTTTAGTTAAAGAGGATTTTATTCACCCCTGTGTCCT CTCCAGAGGTGTCCACTCCCAGGTGCA GCTGGTGCAGTCTGGGGCTGAGGTGAAGAAGCCTGGGTCCTC GGTGAAGGTCTCCTGCAAGGCTTCTGGA |

TABLE A-continued

51p1-allele like genes and nucleic acid sequences

| IGHV allele name | Accession No. | Sequence |
|---|---|---|
| | | GGCACCTTCAGCAGCTATGCTATCAGCTGGGTGCGACAGGCC<br>CCTGGACAAGGGCTTGAGTGGATGGGAG<br>GGATCATCCCTATCTTTGGTACAGCAAACTACGCACAGAAGT<br>TCCAGGGCAGAGTCACGATTACCGCGGA<br>CGAATCCACGAGCACAGCCTACATGGAGCTGAGCAGCCTGAG<br>ATCTGATGACACGGC (SEQ ID NO: 679) |
| IGHV1-69*05 | X67905.1 | CAGGTCCAGCTGGTGCAGTCTGGGGCTGAGGTGAAGAAGCCT<br>GGGTCCTCGGTGAAGGTCTCCTGCAAGG<br>CTTCTGGAGGCACCTTCAGCAGCTATGCTATCAGCTGGGTGC<br>GACAGGCCCCTGGACAAGGGCTTGAGTG<br>GATGGGAGGGATCATCCCTATCTTTGGTACAGCAAACTACGC<br>ACAGAAGTTCCAGGGCAGAGTCACGATT<br>ACCACGGACGAATCCACGAGCACAGCCTACATGGAGCTGAG<br>CAGCCTGAGATCTGAGGACACGGCCGTGT<br>ATTACTGTGCGAGA (SEQ ID NO: 680) |
| IGHV1-69*06 | L22583.1 | GCAGGATTTAGGGCTTGGTCTCTCAGCATCCCACACTTGTACA<br>GCTGATGTGGCATCTGTGTTTTCTTTC<br>TCATCCTAGATCAGGCTTTGAGCTGTGAAATACCCTGCCTCAT<br>GCATATGCAAATAACCTGAGGTCTTCT<br>GAGATAAATATAGATATATTGGTGCCCTGAGAGCATCACATA<br>ACAACCACATTCCTCCTCTGAAGAAGCC<br>CCTGGGAGCACAGCTCATCACCATGGACTGGACCTGGAGGTT<br>CCTCTTTGTGGTGGCAGCAGCTACAGGT<br>AAGGGGCTTCCTAGTCCTAAGGCTGAGGAAGGGATCCTGGTT<br>TAGTTAAAGAGGATTTTATTCACCCCTG<br>TGTCCTCTCCACAGGTGTCCAGTCCCAGGTGCAGCTGGTGCA<br>GTCTGGGGCTGAGGTGAAGAAGCCTGGG<br>TCCTCGGTGAAGGTCTCCTGCAAGGCTTCTGGAGGCACCTTC<br>AGCAGCTATGCTATCAGCTGGGTGCGAC<br>AGGCCCCTGGACAAGGGCTTGAGTGGATGGGAGGGATCATCC<br>CTATCTTTGGTACAGCAAACTACGCACA<br>GAAGTTCCAGGGCAGAGTCACGATTACCGCGGACAAATCCAC<br>GAGCACAGCCTACATGGAGCTGAGCAGC<br>CTGAGATCTGAGGACACGGCCGTGTATTACTGTGCGAGAGAC<br>ACAGTGTGAAAACCCACATCCTGAGAGT<br>GTCAGAAACCCTGAGGGAGAAGGCAGCTGTGCCGGGCTGAG<br>GAGATGACAGGGGTTATTAGGTTTAAGGC<br>TGTTTACAAAATGGGTTATATATTTGAGAAAAAAAGAACAGT<br>AGAAACAAGTACATACTCTAATTTTAAG<br>ATAAATATTCCATTCAAGAGTCGTAATAT<br>(SEQ ID NO: 681) |
| IGHV1-69*07 | Z29978.1 | AGAAGCCTGGGTCCTCGGTGAAGGTCTCCTGCAAGGCTTCTG<br>GAGGCACCTTCAGCAGCTATGCTATCAG<br>CTGGGTGCGACAGGCCCCTGGACAAGGGCTTGAGTGGATGGG<br>AAGGATCATCCCTATCTTTGGTACAGCA<br>AACTACGCACAGAAGTTCCAGGGCAGAGTCACGATTACCGCG<br>GACGAATCCACGAGCACAGCCTACATGG<br>AGCTGAGCAGCCTGAGATCTGAG<br>(SEQ ID NO: 682) |
| IGHV1-69*12 | Z14301.1 | TAAGGGGCTTCCTAGTCCTAAGGCTGAGGAAGGGATCCTGGT<br>TTAGTTAAAGAGGATTTTATTCACCCCT<br>GTGTCCTCTCCACAGGTGTCCAGTCCCAGGTCCAGCTGGTGC<br>AGTCTGGGGCTGAGGTGAAGAAGCCTGG<br>GTCCTCGGTGAAGGTCTCCTGCAAGGCTTCTGGAGGCACCTT<br>CAGCAGCTATGCTATCAGCTGGGTGCGA<br>CAGGCCCCTGGACAAGGGCTTGAGTGGATGGGAGGGATCATC<br>CCTATCTTTGGTACAGCAAACTACGCAC<br>AGAAGTTCCAGGGCAGAGTCACGATTACCGCGGACGAATCCA<br>CGAGCACAGCCTACATGGAGCTGAGCAG<br>CCTGAGATCTGAGGACACGGCCGTGTATTACTGTGCGAGAGA<br>(SEQ ID NO: 683) |
| IGHV1-69*13 | Z14214.1 | ATGGACTGGACCTGGAGGGTCCTCTTTGTGGTGGCAGCTACA<br>GGTGTCCAGTCCCAGGTCCAGCTGGTGC<br>AGTCTGGGGCTGAGGTGAAGAAGCCTGGGTCCTCAGTGAAGG<br>TCTCCTGCAAGGCTTCTGGAGGCACCTT<br>CAGCAGCTATGCTATCAGCTGGGTGCGACAGGCCCCTGGACA<br>AGGGCTTGAGTGGATGGGAGGGATCATC<br>CCTATCTTTGGTACAGCAAACTACGCACAGAAGTTCCAGGGC<br>AGAGTCACGATTACCGCGGACGAATCCA |

TABLE A-continued

51p1-allele like genes and nucleic acid sequences

| IGHV allele name | Accession No. | Sequence |
|---|---|---|
| | | CGAGCACAGCCTACATGGAGCTGAGCAGCCTGAGATCTGAGG<br>ACACGGCCGTGTATTACTGTGCGAGAGA<br>CACAGTGTGA<br>(SEQ ID NO: 684) |

Examples of hv1263 allele-like genes include, but are not limited to those listed in Table B:

TABLE B hv1263 allele-like genes and nucleic acid sequences

| IGHV allele name | Accession No. | Sequence |
|---|---|---|
| IGHV1-69*02 | Z27506.1 | CAGGTCCAGCTGGTGCAATCTGGGGCTGAGGTGAAGAAGCC<br>TGGGTCCTCGGTGAAGGTCTCCTGCAAGG<br>CTTCTGGAGGCACCTTCAGCAGCTATACTATCAGCTGGGTGC<br>GACAGGCCCCTGGACAAGGGCTTGAGTG<br>GATGGGAAGGATCATCCCTATCCTTGGTATAGCAAACTACGC<br>ACAGAAGTTCCAGGGCAGAGTCACGATT<br>ACCGCGGACAAATCCACGAGCACAGCCTACATGGAGCTGAG<br>CAGCCTGAGATCTGAGGACACGGCCGTGT<br>ATTACTGTGCGAGA (SEQ ID NO: 685) |
| IGHV1-69*04 | M83132.1 | AGAAATGGGGCAGGGGATGCGTTTCCTCAGGCAGGATTTAG<br>GGCTTGGTCTCTCAGCATCCCACACTTGT<br>ACAGCTGATGTGGCATCTGTGTTTTCTTTCTCATCCTAGATCA<br>AGCTTTGAGCTGTGAAATACCCTGCCT<br>CATGAATATGCAAATAATCTGAGGTCTTCTGAGATAAATATA<br>GATATATTGGTGCCCTGAGAGCATCACA<br>TAACAACCAGATTCCTCCTCTAAAGAAGCCCCTGGGAGCAC<br>AGCTCATCACCATGGACTGGACCTGGAGG<br>TTCCTCTTTGTGGTGGCAGCAGCTACAGGTAAGGGGCTTCCT<br>AGTCCTAAGGCTGAGGAAGGGATCCTGG<br>TTTAGTTAAAGAGGATTTTATTCACCCCTGTGTCCTCTCCACA<br>GGTGTCCAGTCCCAGGTCCAGCTGGTG<br>CAGTCTGGGGCTGAGGTGAAGAAGCCTGGGTCCTCGGTGAA<br>GGTCTCCTGCAAGGCTTCTGGAGGCACCT<br>TCAGCAGCTATGCTATCAGCTGGGTGCGACAGGCCCCTGGAC<br>AAGGGCTTGAGTGGATGGGAAGGATCAT<br>CCCTATCCTTGGTATAGCAAACTACGCACAGAAGTTCCAGGG<br>CAGAGTCACGATTACCGCGGACAAATCC<br>ACGAGCACAGCCTACATGGAGCTGAGCAGCCTGAGATCTGA<br>GGACACGGCCGTGTATTACTGTGCGAGAG<br>ACACAGTGTGAAAACCCACATCCTGAGAGTGTCAGAAACCC<br>TGAGGGAGAAGGCAGCTGTGCCGGGCTGA<br>GGAGATGAC (SEQ ID NO: 686) |
| IGHV1-69*08 | Z14309.1 | TAAGGGGCTTCCTAGTCCTAAGGCTGAGGAAGGGATCCTGG<br>TTTAGTTAAAGAGGATTTTATTCACCCCT<br>GTGTCCTCTCCACAGGTGTCCAGTCCCAGGTCCAGCTGGTGC<br>AATCTGGGGCTGAGGTGAAGAAGCCTGG<br>GTCCTCGGTGAAGGTCTCCTGCAAGGCTTCTGGAGGCACCTT<br>CAGCAGCTATACTATCAGCTGGGTGCGA<br>CAGGCCCCTGGACAAGGGCTTGAGTGGATGGGAAGGATCAT<br>CCCTATCCTTGGTACAGCAAACTACGCAC<br>AGAAGTTCCAGGGCAGAGTCACGATTACCGCGGACAAATCC<br>ACGAGCACAGCCTACATGGAGCTGAGCAG<br>CCTGAGATCTGAGGACACGGCCGTGTATTACTGTGCGAGAG<br>A (SEQ ID NO: 687) |
| IGHV1-69*09 | Z14307.1 | TAAGGGGCTTCCTAGTCCTAAGGCTGAGGAAGGGATCCTGG<br>TTTAGTTAAAGAGGATTTTATTCACCCCT<br>GTGTCCTCTCCACAGGTGTCCAGTCCCAGGTGCAGCTGGTGC<br>AGTCTGGGGCTGAGGTGAAGAAGCCTGG<br>GTCCTCGGTGAAGGTCTCCTGCAAGGCTTCTGGAGGCACCTT<br>CAGCAGCTATGCTATCAGCTGGGTGCGA<br>CAGGCCCCTGGACAAGGGCTTGAGTGGATGGGAAGGATCAT<br>CCCTATCCTTGGTATAGCAAACTACGCAC |

TABLE B-continued

| hv1263 allele-like genes and nucleic acid sequences | | |
|---|---|---|
| IGHV allele name | Accession No. | Sequence |
| | | AGAAGTTCCAGGGCAGAGTCACGATTACCGCGGACAAATCC ACGAGCACAGCCTACATGGAGCTGAGCAG CCTGAGATCTGAGGACACGGCCGTGTATTACTGTGCGAGAG A (SEQ ID NO: 688) |
| IGHV1-69*10 | Z14300.1 | TAAGGGGCTTCCTAGTCCTAAGGCTGAGGAAGGGATCCTGG TTTAGTTAAAGAGGATTTTATTCACCCCT GTGTCCTGTCCACAGGTGTCCAGTCCCAGGTCCAGCTGGTGC AGTCTGGGGCTGAGGTGAAGAAGCCTGG GTCCTCAGTGAAGGTCTCCTGCAAGGCTTCTGGAGGCACCTT CAGCAGCTATGCTATCAGCTGGGTGCGA CAGGCCCCTGGACAAGGGCTTGAGTGGATGGGAGGGATCAT CCCTATCCTTGGTATAGCAAACTACGCAC AGAAGTTCCAGGGCAGAGTCACGATTACCGCGGACAAATCC ACGAGCACAGCCTACATGGAGCTGAGCAG CCTGAGATCTGAGGACACGGCCGTGTATTACTGTGCGAGAG A (SEQ ID NO: 689) |
| IGHV1-69*11 | Z14296.1 | TAAGGGGCTTCCTAGTCCTAAGGCTGAGGAAGGGATCCTGG TTTAGTTAAAGAGGATTTTATTCACCCCT GTGTCCTCTCCACAGGTGTCCAGTCCCAGGTCCAGCTGGTGC AGTCTGGGGCTGAGGTGAAGAAGCCTGG GTCCTCGGTGAAGGTCTCCTGCAAGGCTTCTGGAGGCACCTT CAGCAGCTATGCTATCAGCTGGGTGCGA CAGGCCCCTGGACAAGGGCTTGAGTGGATGGGAAGGATCAT CCCTATCCTTGGTACAGCAAACTACGCAC AGAAGTTCCAGGGCAGAGTCACGATTACCGCGGACGAATCC ACGAGCACAGCCTACATGGAGCTGAGCAG CCTGAGATCTGAGGACACGGCCGTGTATTACTGTGCGAGAG A (SEQ ID NO: 690) |

The ordinarily skilled artisan could readily identify additional alleles and their nucleic acid sequences using databases or literature available in the art, or methods and techniques known in the art.

Figure 5:
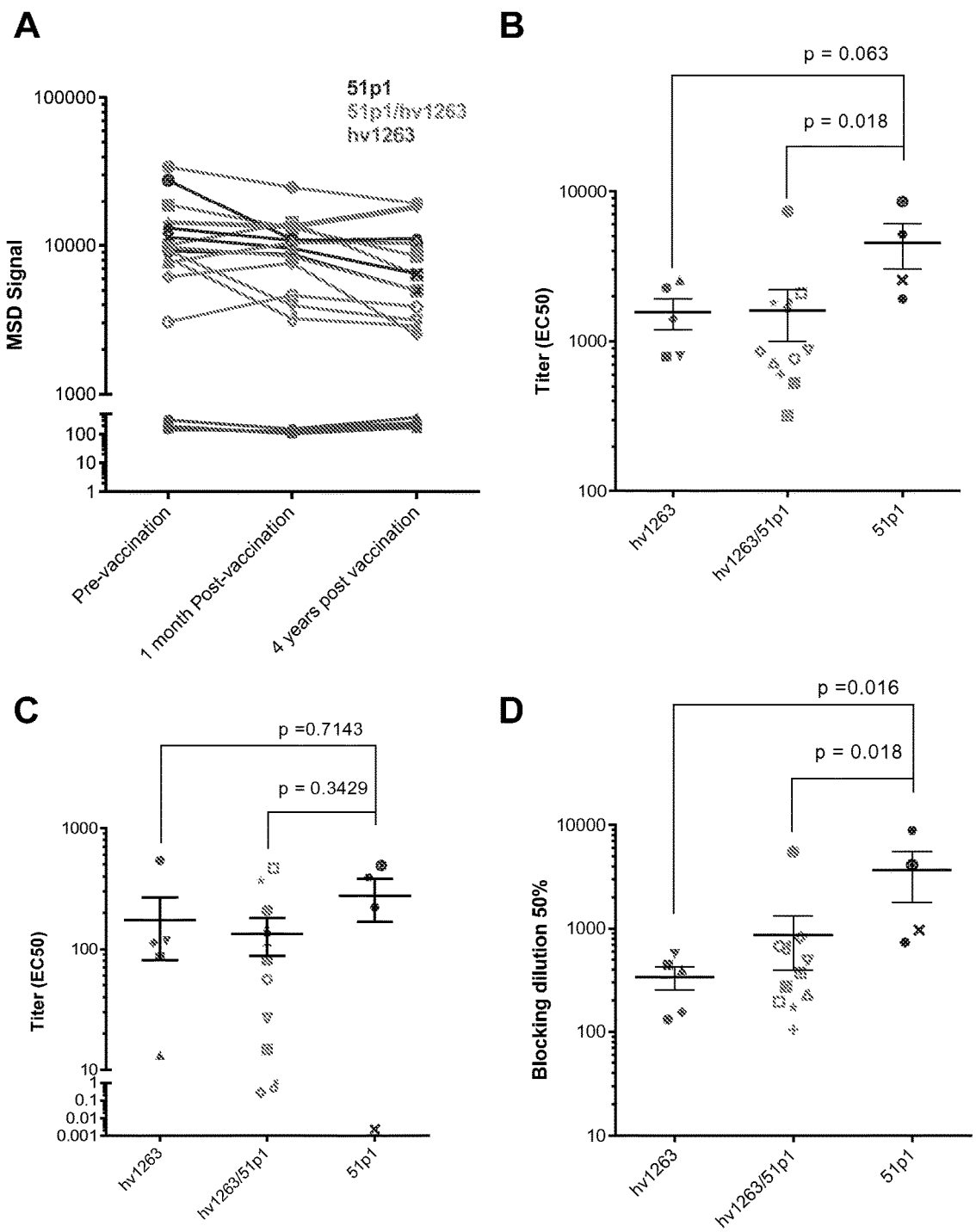
FIG. 5. Serological assays aimed at studying the effect of IGHV1-69 polymorphism.

FIG. 5 shows that individuals homogenous for the 51p1-like allele group are characterized by higher ability of their serum to block F10 binding to H1-CA0409 than the hv1263-like homogenous group.

Utilizing the structural determinants disclosed herein, the present invention provides methods for determining the efficacy of a particular influenza vaccine. The present invention provides methods for analyzing the occurrence or frequency of anti-influenza antibodies elicited in pre-vaccinated and post-vaccinated B-cell samples from subjects to determine the efficacy of a particular influenza vaccine for a particular subject. Specifically, B cell samples from the subject are obtained and prepared using methods known in the art to analyze secreted immunoglobulins before vaccination and after vaccination. The presence or absence, levels, or frequency of anti-influenza antibodies that recognize the HA stem protein or are derived from the IGHV1-69 germline gene can be determined. Preferably, the antibodies are tested for the presence or absence of the structural determinants disclosed herein, for example, Met, Ile or Leu at position 53, Phe at position 54, and Tyr at positions 97, 98 or 99, or any combination thereof in the variable heavy chain (as determined by Kabat numbering). A higher level or frequency of antibodies having one or more structural determinant after vaccination indicates that the vaccine was successful in the elicitation of HV1-69-sBnAbs.

The present invention also provides methods for screening an immunogen or vaccine composition to induce broadly neutralizing influenza virus antibodies that bind to the influenza HA protein by presenting the immunogen or vaccine composition to a population of B cells under conditions for elicitation of antibodies from the B cells, wherein the B cells have at least one copy of a 51p1-like allele or IGHV1-69 germline gene; and determining the presence or absence or level of antibodies secreted from the B cells that recognize the HA stem domain, have the structural determinants of the variable heavy chain as described herein, or are encoded by either a 51p1-like allele or the IGHV1-69 germline gene. These methods may be particularly useful for identifying immunogens or vaccine compositions that specifically elicit sBnAbs and immunogens or vaccine compositions that do not elicit sBnAbs. As discussed further herein, immunogens and vaccines designed specifically to elicit sBnAbs may be useful to those individuals that are identified to possess the 51p1-like allele (i.e. at least one copy), while immunogens and/or vaccine compositions that do not elicit sBnAbs may be useful for individuals that do not possess the 51p1-like allele (i.e., possess the hv1263-like allele). In one embodiment, the B cells are in culture and antibody production is induced in culture. Methods for eliciting antibody production from a population of B cells in culture are well known. In some aspects, methods for eliciting antibody production may involve using antigen-presenting cells (i.e., dendritic cells) that present the immunogen or vaccine composition to be tested.

B cells at various stages of their ontogeny, for example: Pro-B, Pre-B, immature-B, transitional B, naïve B cells, memory B cells, B-1B cells, and plasma cells can be isolated from biological samples such as blood or a fraction OF the blood, according to methods known in the art. B cells can be isolated from whole blood, serum, or PBMCs (peripheral blood mononuclear cells) by various cell separation methods known in the art, such as differential centrifugation, filtration, flow cytometry sorting, immuno-affinity techniques; or magnetic sorting. Specific populations of B cell subsets may be isolated using cell surface markers by using positive or negative selection procedures. The following is a non-inclusive list of B-cell subset of interest and their associated CD markers (See, http://www.bdbiosciences.com/documents/Bcell_Brochure.pdf):

Pre-Pro-B; IgM−; positive CD markers: CD34, CD10, CD38; negative CD markers: ckitlow Pro-B; IgM−; positive CD markers: CD10, CD19, CD34, CD38, CD24, IL7/3R; negative CD markers: ckitlow.

Pre-B; IgM−; positive CD markers: CD10, CD19, CD20, CD24, CD38, IL7/4/3R; negative CD markers: CD34, ckit.

Immature B; IgM+, IgD−; positive CD markers: CD10, CD19, CD20, CD21, CD40, CD24high,CD38high, IL4R; negative CD markers: ckit, CD27, IL7R.

Transitional B; IgMhigh, IgDlow; positive CD markers: CD19, CD20, CDS, CD21, CD24high, CD38high; negative CD markers: CD27, CD10low.

Marginal Zone B; IgM+, IgDlow; positive CD markers: CD1c, CD19, CD20, CD2lhigh, CD27var.

Regulatory B; IgMhigh, IgDvar; positive CD markers: CDldhigh, CDS, CD19, CD21, CD24high; negative CD markers CD27var.

Follicular B; IgMlow, IgD+; positive CD markers: CD19, CD20, CD21, CD22, CD23, CD24; negative CD markers: CD10, CD27, CD38low, CD24low.

Activated B; IgM+, IgD+; positive CD markers: CD27, CD19, CD20, CD25, CD30, CD69,CD80, CD86, CD135.

Germinal center B; IgM/G/A/E+, IgDvar; positive CD markers: CD10, CD19, CD20, CD23, CD27, CD38high, CD269, BCMA; negative CD markers: CD24low.

Plasmablast IgM/G/A/E+; positive CD markers: CD19, CD38high, CD27 CD269, MHCII; negative CD markers: CD20, CD138.

Plasma cell long lived; Ig−; positive CD markers: CXCR4, CD27, CD38 CD138, CD269; negative CD markers: CD19low, CD20, MHCII.

Plasma cell short lived; Ig−; positive CD markers: CXCR4, CD27, CD38, CD138, CD269; negative CD markers: CD19low, CD20, MHCIIlow.

Memory B; IgM/G/A/E+, IgD−; positive CD markers: CD19, CD20, CD40, CD27var, CXCR4,5,7; negative CD markers: CD23low, CD38.

Of this list, in some embodiments, it is useful to separate or isolate cells that express CD19 (i.e., CD19+) for further analysis. In other embodiments, it is useful to separate or isolate cells that express CD27 (i.e., CD27+) or do not express CD27 (CD27−). For example, of the CD19-expressing (CD19+) population of B cells, the population can further be separate to CD27+ or CD27− for further analysis.

The immunogenetic composition of the antibody repertoire secreted by the mature B cells can be determined, for example, by isolating the nucleic acids from the B cells. For example, genomic DNA is isolated from the sample and the genomic sequences which encode the antibodies are analyzed or sequenced by various DNA sequencing methods known in the art (i.e., next generation sequencing platforms). Alternatively, RNA is isolated. Specific sequences of interest can be identified, for example, the presence or absence of the 51p1-like allele, the sequences in the IGHV1-69 germline gene comprising somatic mutations or sequences that encode any of the structural determinants described herein by use of techniques utilizing hybridizing primers and/or reporter probes. In another embodiment, RNA (i.e., mRNA) can be isolated from the B cells and reverse-transcribed using art-recognized methods into cDNA. The antibody molecular signature of the B cells or the sample can be determined by nucleic acid analysis techniques. Examples of suitable nucleic acid analysis techniques include RT-PCR, quantitative PCR analysis, and next generation sequencing technologies, including Illumina sequencing platforms, Solexa sequencing platforms, 454 pyrosequencing, SOLiD, Ion Torrent (proton), PacBio SMRT, or Nanopore.

The approach of personalized medicine is based on the understanding that genomic differences among individuals should be considered in therapy. This is also relevant to vaccines as it is known that immunological reaction to vaccines is highly variable among individuals. The Ig VH polymorphism can be the main cause of such variability, and therefore, assessment of the presence or absence of Ig VH polymorphisms (such as 51p1-like alleles and hv1263-like alleles) can indicate the efficacy of a vaccine in a subject, or the ability of the subject to elicit HV1-69-sBnAbs after vaccination. In addition, prediction of prior immunologic exposure or memory to an influenza virus and prediction of antigen responsiveness to vaccine or an influenza virus infection is useful information for a clinician for determining efficacy of a vaccine, selecting a type of vaccine for a subject, and predicting the response of the subject to subsequent influenza viral infection after vaccination. Such a personalized medicine approach allows for a method of identifying a subject that will be responsive to an influenza vaccine. This approach can incorporate determining the copy number of 51p1 and hv1263 genes in a subject. Furthermore, the identification of a subject that will be or has been responsive to an influenza vaccine can also be determined by the presence or absence of a broadly-neutralizing antibody molecular signature, by various assays, including, but not limited to, nucleic acid analysis. Following these determinations, the subjects that are determined to be responsive to the influenza vaccine can be administered said vaccine.

For example, individuals whom are 51p1-null (and express hv1263 alleles), are characterized by an anti-HA memory derived antibody repertoire that is significantly different than that of 51p1 allele-bearing individuals as 51p1-null individuals are not expected to produce HV1-69-sBnAbs. For robust elicitation of sBnAbs in 51p1-null individuals, a different vaccination approach than that used for the general population or for 51p1 allele bearing individuals may be needed. Once the antibody molecular signature is determined from an individual, a vaccine regimen can be tailored to result in the robust elicitation of sBnAbs. Likewise, differences in IGHV polymorphism might also prove to be important factor in responsiveness to new strains of influenza viruses. For example, 51p1 allele-bearing individuals would be better protected against new emerging/pandemic group 1 influenza subtypes since HV1-69-sBnAbs (elicited by the 51p1 allele) mainly neutralize group 1 influenza subtypes. Thus, 51p1 allele bearing individuals might be excluded from emergency vaccination procedures to the emerging pandemic strain while 51p1-null individuals would receive vaccinations.

The present invention also provides methods for predicting or evaluating the efficacy of a particular vaccine regimen based on the immunogenetic composition of the subject. For example, analysis and characterization of the subject's immunogenetic polymorphisms may indicate a favorable immunological reaction to a vaccine, i.e. increased elicitation of HV1-69-sBnAbs after vaccination. The immunogenetic composition of a subject comprises an antibody molecular signature. As used herein, the antibody molecular signature comprises the nucleic acid sequences encoding immunoglobulins.

In one embodiment, the genotypic (or immunogenetic) composition of a subject is used to predict the efficacy of a vaccine in a subject, or the ability of the subject to elicit HV1-69-sBnAbs after vaccination. A sample from the subject is obtained, for example, a serum sample. The genomic DNA can be isolated by methods known in the art. In this assay, the copy number of 51p1-like alleles or hv1263-like alleles is determined, for example using quantitative real-time PCR or TaqMan protocols known in the art. Exemplary Taqman primers and probes are described in Example 1.

As the expression of 51p1-like alleles is reported to be proportional to its germline gene copy number, those subjects that express one or more 51p1-like alleles will elicit more HV1-69-sBnAbs than those subjects that are null for the 51p1-like allele after vaccination. Accordingly, those subjects that express a high copy number, for example at least 2, at least 5, at least 10, at least 15, at least 20 copies of the 51p1 allele will elicit more Hv1-{69-sBnAbs after vaccination. Therefore, the efficacy of a vaccine can be determined by the copy number of the 51p1-like allele, wherein at least 1, at least 2, at least 3, at least 4, at least 5, at least 10, or at least 20 copies of the 51p1-like allele indicates that the vaccine will be effective in the subject. Preferably, the copy number is 1 copy, 2 copies, 3 copies, or 4 copies. Conversely, vaccines that are designed to elicit HV1-69-sBnAbs may not be effective in subjects that have one or more copies of hv1623 and do not have any copies of 51p1-like allele. Therefore, the methods described herein can be used to distinguish which subjects should receive a vaccine designed to elicit robust HV1-69-sBnAbs from those subjects that should not. The methods described herein can also be used to distinguish subjects with low or no copies of the 51p1-like allele, in which the vaccine would not elicit any or only a very low frequency of HV1-69-sBnAbs, and should not receive a vaccine designed specifically for HV1-69-sBnAbs elicitation.

In another embodiment, the phenotypic composition of a subject is used to predict the efficacy of a vaccine in a subject, or the ability of the subject to elicit HV1-69-sBnAbs after vaccination. Serum is obtained from the subject and the serum-derived immunoglobulins are isolated by any methods known in the art (i.e. immunoprecipitation, protein extraction). The reactivity of the serum-derived immunoglobulins can be tested with an anti-idiotype antibody, for example, an anti-51p1 antibody. Suitable examples of an anti-51p1 antibody includes the monoclonal anti-51p1 allele G6 antibody (as described in Mageed et al., Rheumatol. Int., 1986, 6:179-183; which is hereby incorporated by reference in its entirety), and any known or developed derivatives of the 51p1-recognizing antibodies, for example, the derivatives described in International Publication No. WO2011/153380 (the contents of which are hereby incorporated by reference in its entirety). The subjects that exhibit reactivity with the anti-51p1 antibody have the 51p1-like allele, and therefore can elicit HV1-69-sBnAbs after vaccination. Conversely, those subjects that do not exhibit reactivity with the anti-51p1 antibody do not have the 51p1-like allele, and therefore cannot elicit HV1-69-sBnAbs after vaccination. Thus, the method described herein can be used to predict the efficacy of a vaccine, or the ability of the vaccine to elicit HV1-69-sBnAbs after vaccination. The method can be used to distinguish those subjects that have the 51p1 allele, in which the vaccine will be effective from those subjects that do not have the 51p1 allele, in which the vaccine will be ineffective.

Furthermore, the methods provided herein can be used to determine the molecular signature of the antibodies produced by the B cells of a subject for predicting the efficacy of a vaccine in a subject, predicting prior immunologic exposure or memory to an influenza virus, or predicting antigen responsiveness to a vaccine or an influenza virus. For these methods, a sample is obtained from a subject, such as a blood or serum sample. In some embodiments, a population of B cells is isolated from the sample, for example, by magnetic beads. The B cells can be, for example, CD19+ cells. In some embodiments, naïve B cells and memory B cells are isolated, such as CD27+ and/or CD27− cells. Nucleic acids are then isolated from the B cell population(s), such as genomic DNA or RNA. The isolated RNA is reverse transcribed to complementary DNA (cDNA) using methods and kits known and commercially available in the art.

The molecular signature of the nucleic acids isolated from the sample (i.e., the B cells) is then detected or analyzed from the isolated nucleic acids. For example, the molecular signature is a broadly neutralizing antibody molecular signature, wherein the signature includes, at least one copy of the 51p1 allele, and optionally, does not contain any hv1263 alleles; a nucleic acid encoding an immunoglobulin variable heavy chain comprising any one of the following: a serine at position 24, a valine at position 27, an isoleucine or proline at position 28, a serine at position 29, an arginine at position 30, a valine at position 34, a serine at position 52, a glycine or an alanine at position 52a, a lysine at position 58, a glutamine at position 73, a phenylalanine at position 74, a methionine, isoleucine, valine or leucine at position 53, a phenylalanine at position 54, a tyrosine at position 97, a tyrosine at position 98, and a tyrosine at position 99, or any combination thereof; and a nucleic acid encoding an immunoglobulin variable heavy chain comprising a phenylalanine at position 54, a hydrophobic amino acid at position 53, and a tyrosine at amino acid positions 97, 98, and/or 99. Preferably, the molecule signature of the present invention comprises any combination of the above V-segment amino acids with CDR-H3 Tyrs at either positions 97, 98, 99 as well as these combinations: Gly52a with double or triple CDR-H3 Tyrs at positions 97-to-99; Gly52a with Met53 or with Val52;Val27 with Ser52 and with Gln73; Ser52 and with Gln73; Pro28 with Arg30; Pro28 with Arg30 with Ala52a; Arg30 and Ala52a; Ile28 with Ala52a; Ile28 with Arg30 and with Ala52a; Ile28 with Arg30. Detection of the nucleic acid sequences described herein that contribute to the molecular signature can be performed by using primers that recognize and amplify immunoglobulin transcripts, such as IgG, IgM, IgA, IgD, or IgE. Next generation sequencing can also be used to determine the presence, absence, or level of any of the nucleic acid sequences described herein that contribute to the molecular signature. In some embodiments, it is useful to calculate a ratio or absolute frequency of immunoglobulins that have the broadly neutralizing antibody molecular signature for each population of B cells tested. The comparison of these ratios or absolute frequency, for example between naïve and memory B cell populations, indicates whether the subject has had prior immunologic exposure and memory to influenza virus. Alternatively, the ratio or absolute frequency indicates the antigen responsiveness of a subject to a vaccine or influenza virus vaccine. These ratios can be derived from analysis of antibody libraries generated by next generation sequencing. For example, the antibody library is generated from the naïve B cell pool of a certain individual. Upon analysis it is shown, for example, that in a library of 1e7 Ab members, 1e5 Ab members are 51p1 allele germline based and they bear CDR-H3 Tyrs at either positions 97, 98, 99. Therefore it can be stated that in this particular individual the absolute frequency of naïve B-cells that are potential precursor HV1-69 B-cells is 1% (1e5/1e7). Similarly, such analysis can be performed on Ab libraries derived from the memory B-cell pool whereby the frequency of HV1-69-sBnAb like Abs can be determined based on the occurrence of HV1-69-sBnAbs associated molecular signatures. Estimating if HV1-69-sBnAbs were elicitated in response to the influenza virus can be deduced by dividing the frequency of memory Ab members that are 51p1 germline based and bear CDR-H3-Tyr 97,98,99 with their respective frequency as analyzed in the naïve Ab pool. If the ratio is higher than 1 then it is likely that HV1-69-sBnAbs were elicitated. If the ratio is less than 1 then it unlikely that there was robust elicitation of HV1-69-sBnAbs.

For example, the circulating antibodyome of an individual is sampled by isolating all CD19+ B cells from a tube of blood, using magnetic beads (or other known techniques in the art) to separate naïve (CD27−) and memory (CD27+) B cells. RNA is isolated from each B cell population (CD27− and CD27+), and cDNA is prepared from the isolated RNA. IgM and IgG isotype specific primers are used to amplify the IgM and IgG transcripts for next generation sequencing (NGS) using Illumina or other NGS technologies. This would result in analysis of 4 populations of B cells IgM+CD27−, IgM+CD27+ (Marginal zone B cells), IgG+CD27−, and IgG+CD27+ (switch memory cells). The analysis of IgM+CD27− versus IgM+CD27+ and IgG+CD27 versus IgG+CD27+ would allow the determination of B cell receptor (BCR) precursor frequency in the naïve and memory compartments. The relative ratio of these precursors and absolute frequency are used to predict prior exposure, antigen readiness responsiveness to vaccine or infection. Similar approach could be also performed using B-cells that express the other immunoglobulin isotypes IgA,IgE, and IgD whereby antibodyome (or antibody molecular signature) analysis can be compared across isotypes and the various B-cell populations, or B-cell subsets.

Antibodies

The studies described herein included the identification and isolation of new anti-influenza antibodies. The antibodies isolated from panning against H5VN04 are 1C2, 2B8, 2C4, 2D3, 2D9, 2E1, 2H4, 2H5, 4C4, 4E5, 4F5, 4G3, 4G5, 5A6, 5A8, 5B9, 6A2, 6C2, 6F3, 8A1, 8C1, 8D6, 9A1, 9C1, 9D11, 9E4, 9E7, 9H3, 10D4, 11A11, 11A6, 11B5, 1106, 11E9, and 11F8. The antibodies isolated from panning against H1CA0409 are 1D9, 1E6, 1F1, 1F12, 1F3, 1F5, 1F6, 1H2, 1H4, 2A1, 2A11, 2A12, 2B11, 2B6, 2C1, 2E11, 2E12, 2F1, 2G3, 2H3, 2H4, 4C4, 4F5, 5A8, 5B9, 6F3, and 9H3. Six antibodies were commonly identified in both panning methods, specifically, antibodies 4C4, 4F5, 6F3, 5A8, 5B9, and 9H3. Antibodies 2B11 and 2A12 did not bind to the stem region of HA. The antibodies disclosed herein have heterosubtypic binding activity, as shown in FIGS. 16A and 16D. The nucleic acid sequences and amino acid sequences of each of these antibodies are disclosed herein.

The amino acid sequences for the CDR regions of the heavy and light chains of the anti-H5VN04 antibodies are shown in Tables 1 and 2. Definition of the CDR domains was based on the IMGT definitions and numbering is based on the Kabat numbering system.

TABLE 1

Amino acid sequences for heavy chain CDRs for anti-H5VN04 antibodies.

| H5VN04 Ab | VH-CDR1 | SEQ ID NO: | VH-CDR2 | SEQ ID NO: | VH-CDR3 | SEQ ID NO: |
|---|---|---|---|---|---|---|
| 1C2 | GGPFSSYA | 1 | ISPMFGTA | 37 | ARDDGYAPSGGLREFDV | 73 |
| 2B8 | GGIFSSYA | 2 | ISPIFGTA | 38 | ARGRGAYMGPSMDV | 74 |
| 2C4 | GGTFSSYA | 3 | ISPIFGTA | 39 | ARGARYYAGGYFDV | 75 |
| 2D3 | GVTFSSYA | 4 | ISPIFGTA | 40 | ARDSGNYDGYGPGSRFDV | 76 |
| 2D9 | GVTFSSYA | 5 | IMPMFGTA | 41 | ARERGSWSFGYFDV | 77 |
| 2E1 | GVTFSSYA | 6 | ISPLFGTA | 42 | ARSRTYADGRTFDV | 78 |
| 2H4 | GGTFSSYA | 7 | ISPIFGTA | 43 | ARELGYLAGSPSPGFDY | 79 |
| 2H5 | GGTFSSYA | 8 | ISPIFGTA | 44 | ARSRRYWADGGFDY | 80 |
| 4C4 | GGTFSSYA | 9 | ISPMFGTA | 45 | AREGGYSPGGVDFDY | 81 |
| 4E5 | GVTFSSYA | 10 | ISPIFGTA | 46 | ARGTTYSTARYFDV | 82 |
| 4F5 | GVTFRSYA | 11 | ISGIFGTA | 47 | ARSPAYYFGPNMDV | 83 |
| 4G3 | GGTFSSYA | 12 | ISPMFGTA | 48 | ARSSRYAPSDSTNFDQ | 84 |
| 4G5 | GGPFSSYA | 13 | ISGIFGTA | 49 | ARGDRFYVGERFDV | 85 |
| 5A6 | GGTFSSYA | 14 | ISPIFGTA | 50 | ARGGGVGRIWIAGYGFDQ | 86 |
| 5A8 | GGTFSSYA | 15 | ISPIFGTA | 51 | ARGPGYHPAGASGQFFDL | 87 |
| 5B9 | GVTFSSYA | 16 | ISPMFGTA | 52 | ARGRGYAPDALTNFDV | 88 |

TABLE 1-continued

Amino acid sequences for heavy chain CDRs for anti-H5VN04 antibodies.

| H5VN04 Ab | VH-CDR1 | SEQ ID NO: | VH-CDR2 | SEQ ID NO: | VH-CDR3 | SEQ ID NO: |
|---|---|---|---|---|---|---|
| 6A2 | GVTFSSYA | 17 | ITPMFGTA | 53 | ARGRGYIAVAGDMDV | 89 |
| 6C2 | GVTFSSYA | 18 | ISPLFGTA | 54 | ARGDAYYVGGGARPFDL | 90 |
| 6F3 | GGPFSSYA | 19 | ISPMFGTA | 55 | ARGYSYYPGGGGRNFDY | 91 |
| 8A1 | GGPFSSYA | 20 | ISPLFGTA | 56 | ARAPTYYASRDSYNFDY | 92 |
| 8C1 | GVTFSSYA | 21 | ISPMFGTA | 57 | ARDTTYIAGGHFDV | 93 |
| 8D6 | GGTFSSYA | 22 | ISPLFGTA | 58 | ARASGYFTGWGTFDY | 94 |
| 9A1 | GGTFSSYA | 23 | ISPIFGTA | 59 | ARGRYYYTVGVYDV | 95 |
| 9C1 | GVTFSSYA | 24 | ISPIFGTA | 60 | ARGGGYSADGGAGNNTIFDV | 96 |
| 9D11 | GVTFSSYA | 25 | ISPLFGTA | 61 | ARERGYTVGGGMDV | 97 |
| 9E4 | GVTFSSYA | 26 | ISPIFGTA | 62 | AREYLGDDYSSGSYFDV | 98 |
| 9E7 | GGTFSSYA | 27 | ISPMFGTA | 63 | ARESGYSGTGQFDV | 99 |
| 9H3 | GGIFSSYA | 28 | ISPIFGTA | 64 | ARSGGYYDYGVGYDQ | 100 |
| 9H4 | GGTFSSYA | 29 | ITPIFGTA | 65 | ARSGGYSPSIGGFDV | 101 |
| 10D4 | GGTFSSYA | 30 | ISPIFGTA | 66 | ARGPGYDPSSLRGFDV | 102 |
| 11A11 | GGTFSSYA | 31 | IIPIFGTA | 67 | ARGEEAYYDL | 103 |
| 11A6 | GGTFSSYA | 32 | ITPMFGTA | 68 | ARGTSYLPGRSGFDV | 104 |
| 11B5 | GVTFRSYA | 33 | ISAMFGTA | 69 | ARGRGYDPSVGGFDV | 105 |
| 11C6 | GGTFSSYA | 34 | IIPIFGTA | 70 | ARDSTPSVTSSLYRIPAFDV | 106 |
| 11E9 | GGTFSSYA | 35 | ITPMFGTA | 71 | ARGPGYYPDSNNYDL | 107 |
| 11F8 | GVTFSSYA | 36 | ISPMFGTA | 72 | ARGGTYSPGGTYFDV | 108 |

TABLE 2

Amino acid sequences for light chain CDRs for the anti-H5VN04 antibodies.

| H5VN04 Ab | VL-CDR1 | SEQ ID NO: | VL-CDR2 | SEQ ID NO: | VL-CDR3 | SEQ ID NO: |
|---|---|---|---|---|---|---|
| 1C2 | RSVLYSSNNKNY | 109 | WAS | 145 | QQYYSGSWT | 181 |
| 2B8 | NIGSKS | 110 | DDS | 146 | QVWDRSSDHVV | 182 |
| 2C4 | QTVSNY | 111 | AAS | 147 | QQYDNLPPVT | 183 |
| 2D3 | SSNIGSNT | 112 | SNN | 148 | SAWDDSLGGEV | 184 |
| 2D9 | HIGSKS | 113 | SDT | 149 | QVWDSSNDHPV | 185 |
| 2E1 | SSDVGGYNH | 114 | DVS | 150 | TSYAGSNSLV | 186 |
| 2H4 | SSDVGGYNY | 115 | EVT | 151 | SSYAGGKWV | 187 |
| 2H5 | SSNMGRNT | 116 | DND | 152 | AAWDDSLNGPV | 188 |
| 4C4 | SGSIASTY | 117 | EDH | 153 | QSFDASTLV | 189 |
| 4E5 | SGSIASNY | 118 | EDN | 154 | QSYDSDNHEVI | 190 |
| 4F5 | SSNIGAGYD | 119 | DNS | 155 | QSYDSSLSVVV | 191 |
| 4G3 | SGSIASNY | 120 | EDN | 156 | QSYDTSNRKV | 192 |
| 4G5 | DIGSKS | 121 | DDI | 157 | QVWDTNSDPVFV | 193 |
| 5A6 | SGSVSTSNY | 122 | STN | 158 | VLYMGSGISM | 194 |

TABLE 2-continued

Amino acid sequences for light chain CDRs for the anti-H5VN04 antibodies.

| H5VN04 Ab | VL-CDR1 | SEQ ID NO: | VL-CDR2 | SEQ ID NO: | VL-CDR3 | SEQ ID NO: |
|---|---|---|---|---|---|---|
| 5A8 | SNNVGNQG | 123 | RNN | 159 | SAWDSSLSAWV | 195 |
| 5B9 | RSLFDSSDNKNY | 124 | WAS | 160 | QQYFSSPPIFT | 196 |
| 6A2 | RSVLYSSNNKNY | 125 | WAS | 161 | QQYYSTPPT | 197 |
| 6C2 | SSNIGVNY | 126 | RNN | 162 | GVWDDSLNGHWV | 198 |
| 6F3 | SSNIGSNT | 127 | SNN | 163 | AAWDDSLKGRV | 199 |
| 8A1 | QSVDRGY | 128 | GAS | 164 | QQYGSSRLS | 200 |
| 8C1 | SSDIGAYNY | 129 | EVS | 165 | SSYAGSNNVV | 201 |
| 8D6 | ALPKQY | 130 | KDS | 166 | QAWDSSTAV | 202 |
| 9A1 | SDNVGNQG | 131 | RDN | 167 | SAWDSSLTAVV | 203 |
| 9C1 | NNNVGNQG | 132 | RNN | 168 | SAWDSSLSAWV | 204 |
| 9D11 | SSDVGAHNF | 133 | EVN | 169 | AAWDDSLDGPV | 205 |
| 9E4 | QSVDSH | 134 | GAS | 170 | QQRSMWPLT | 206 |
| 9E7 | TSNVGRNT | 135 | NDN | 171 | SSWDDDLNGPV | 207 |
| 9H3 | RSNIGSNT | 136 | SNN | 172 | QSYDSSV | 208 |
| 9H4 | RSNIGRNT | 137 | SNN | 173 | AAWDVSLNGQV | 209 |
| 10D4 | SNNVGNQG | 138 | KNN | 174 | SAWDSSLSDWV | 210 |
| 11A11 | QSVSSF | 139 | DAS | 175 | QQRFNWPPT | 211 |
| 11A6 | ALPKQY | 140 | KDT | 176 | QSADASENSV | 212 |
| 11B5 | SGSIASNY | 141 | EDN | 177 | QSYDTSNLV | 213 |
| 11C6 | NGPSNYI | 142 | LNSDGSH | 178 | ETWDSNTHVV | 214 |
| 11E9 | QSVSSSY | 143 | GAS | 179 | QQVNSFPRT | 215 |
| 11F8 | SSNIGVSF | 144 | RDD | 180 | SAWDESLSSVL | 216 |

The nucleic acid and amino acid sequences of the light and heavy chains for the anti-H5VN04 antibodies are shown in Tables 3 and 4.

TABLE 3

Nucleic acid sequences of the light and heavy chains for the anti-H5-VN04 antibodies.

| anti-H5VN04 Ab | VH or VL | Nucleic Acid Sequence | SEQ ID NO: |
|---|---|---|---|
| 1C2 | VH | caggttcaattagtgcagtctggtgctgaagtgaaaaagcccggctcaagtgttaaag taagctgtaaggcgagcggtggcccattcagctcatacgccattagctgggtgcgaca ggctcctggtcagggcctcgaatggatgggcggcattagcccaatgtttggcactgca aattatgcccagaaatttcagggtagagtcacaattaccgcagacaagagcacctcaa ccgcctacatggaactgagtagcctgcgttccgaagatacagctgtgtattactgtgc gcgcgacgacggttacgctcctagtggtggtctgcgtgagtttgactgttggggccag gggaccttagtcactgtgtctagc | 397 |
| 1C2 | VL | gacatccagatgacccagtctccagactccctggctgtgtctctgggcgagagggcca ccatcaactgcaagtccagccggagtgttttatacagtccaacaacaagaactactt agcttggtaccaacaaaaaccgggacagcctcctaagttgctcatttattgggcttct acccgggaatccggggtccctgaccgattcagtggcagcgggtctgggacagatttca ctctcaccatcagcagcctgcaggctgaagatgtggcggtttattactgtcagcaata ttatagtggttcctggacattcggccaagggaccaaggtggaaatcaaac | 398 |
| 2B8 | VH | caggttcaattagtgcagtctggtgctgaagtgaaaaagcccggctcaagtgttaaag taagctgtaaggcgagcggaggcatctttagctcatacgccattagctgggtgcgaca ggctcctggtcagggcctcgaatggatgggcggcattagcccctatctaggcactgcaa attatgcccagaaatttcagggtagagtcacaattaccgcagataaagcacgaatac cgcctacatggaactgagtagcctgcgttccgaagatacagctgtgtattactgtgcg cgcggtcgtggtgcttacatgggtcctagtatggatgtgtggggccaggggaccttag tcactgtgtctagc | 399 |
| 2B8 | VL | cagcctgtgctgactcagccaccctcggtgtcagtggcccaggacagacggccagga ttacctgtgggggaaacaacattggaagtaaaagtgtgcactggtaccagcagaagcc aggccaggcccctgtgctggtcgtctatgatgatagcgaccggccctcagggatccct | 400 |

TABLE 3-continued

Nucleic acid sequences of the light and heavy chains for the anti-H5-VN04 antibodies.

| anti-H5VN04

TABLE 3-continued

Nucleic acid sequences of the light and
heavy chains for the anti-H5-VN04 antibodies.

| anti-H5VN04

TABLE 3-continued

Nucleic acid sequences of the light and heavy chains for the anti-H5-VN04 antibodies.

| anti-H5VN04

TABLE 3-continued

Nucleic acid sequences of the light and heavy chains for the anti-H5-VN04 antibodies.

| anti-H5VN04 Ab | VH or VL | Nucleic Acid Sequence | SEQ ID NO: |
|---|---|---|---|
| | | ccgtctatatggaactgagtagcctgcgttccgaagatac TABLE 3-continued Nucleic acid sequences of the light and
heavy chains for the anti-H5-VN04 antibodies.

| anti-H5VN04 Ab | VH or

TABLE 3-continued

Nucleic acid sequences of the light and heavy chains for the anti-H5-VN04 antibodies.

| anti-H5VN04 Ab | VH or VL | Nucleic Acid Sequence | SEQ ID NO: |
|---|---|---|---|
| 9E7 | VH | caggttcaattagtgcagtctggtgctgaagtgaaaaagcccggctcaagtgttaaag taagctgtaaggcgagcggaggtactttcagttcatacgccattagctgggtgcgaca ggctcctggtcagggcctcgaatggatgggcggcattagccctatgtttggtactgca aattatgcccagaaatttcagggtagagtcacaattaccgcagacaaaagtacctcaa ctgcatatatggaactgagtagcctgcgttccgaagatacagctgtgtattactgtgc gcgcgagagtggttacagtggtacaggtcaatttgacgtgtggggccaggggacctta gtcactgtgtctagc | 449 |
| 9E7 | VL | cagtctgtgctgactcagccaccctcagcgtctgggaccgccgggcagagggtcacaa tctcctgttttgggagaacctccaacgtcggacgaaacactgttaactggtaccaaca attgcccggagcggcccccaagatcctcatttttaacgataatcaacggccctcgggg gtccctgaccgcttctctggctccaagtctggcaccgccgcctccctgaccataagta ggctccagtccgcggatgaggctgattactattgttcatcatgggatgacgacctgaa cggtccggtcttcggcggagggaccaagctgagcgtcgtag | 450 |
| 9H3 | VH | caggttcaattagtgcagtctggtgctgaagtgaaaaagcccggctcaagtgttaaag taagctgtaaggcgagcggaggtatctttagttcttacgccattagctgggtgcgaca ggctcctggtcagggcctcgaatggatgggcggcattagcccaatcttcggtactgca aattatgcccagaaatttcagggtagagtcacaattaccgcagatgagagcacgaaca ccgcctatatggaactgagtagcctgcgttccgaagatacagctgtgtattactgtgc gcgcagtggtggttactacgactacggtgttggttacgaccaatggggccaggggacc ttagtcactgtgtctagc | 451 |
| 9H3 | VL | cagcctgtgctgactcagccaccctcagcgtctgggacccccgggcagagggtcacca tctcttgttctggaggcaggtccaacatcggaagtaatactgttaactggtaccagca gctcccaggaacggcccccaaactcctcatctatagtaataatcaccggccctcaggg gtccctgatcgcttctctggctccaagtctggcaacacggcctccctgaccatctctg ggctccaggcggaggatgaggctgattattactgccagtcctatgacagcagcgttgt attcggcggagggaccaagctgaccgtcctag | 452 |
| 9H4 | VH | caggttcaattagtgcagtctggtgctgaagtgaaaaagcccggctcaagtgttaaag taagctgtaaggcgagcggtggtaccttcagctcttacgccattagctgggtgcgaca ggctcctggtcagggcctcgaatggatgggcggcattacccctatctttggcactgca aattatgcccagaaatttcagggtagagtcacaattaccgcagacgagagtaccagca ctgcctacatggaactgagtagcctgcgttccgaagatacagctgtgtattactgtgc gcgcagtggtggttacagtcctagtatcggtggtttcgacgtttggggccaggggacc ttagtcactgtgtctagc | 453 |
| 9H4 | VL | cagcctgggctgactcagccaccctcagcgtctgggacccccgggcagagggtcacca tctcttgttctggaagcaggtccaatatcggaagaaatactgtaaactggtaccagca actcccaggaacggcccccaaactcctcatctatagtaacaatcagcggccctcaggg gtccctgaccgagtctctggctccaagtctggcacctcagcctccctggccatcagtg ggctccagtctgaggatgaggctgattattactgtgcagcatgggatgtgagcctgaa tggtcaggtcttcggaactgggaccaaggtcaccgtcctag | 454 |
| 10D4 | VH | caggttcaattagtgcagtctggtgctgaagtgaaaaagcccggctcaagtgttaaag taagctgtaaggcgagcggaggtacctttagttcatacgccattagctgggtgcgaca ggctcctggtcagggcctcgaatggatgggcggcatcagcccaatctttggtactgca aattatgcccagaaatttcagggtagagtcacaattaccgcagatcgcagtacgagca ccgcctacatggaactgagtagcctgcgttccgaagatacagctgtgtattactgtgc gcgcggtcctggttacgaccctagtagtctgcgtggttttgacgtttggggccagggg accttagtcactgtgtctagc | 455 |
| 10D4 | VL | tcctatgagctgactcagccaccctcggtgtccaaggacttgagacagaccgccacac tcacctgcactgggaacagcaacaatgttggcaaccaaggagcagcttggctgcagca gcaccagggccaccctcccaaactcctattctacaagaataacaaccggccctcaggg atttcagagagattatctgcatccaggtcaggaaacacagcctccctgaccattactg gactccagcctgaggacgaggctgactattactgctcagcatgggacagcagcctcag tgattgggtgttcggcggagggaccaagctgaccgtccta | 456 |
| 11A11 | VH | caggttcaattagtgcagtctggtgctgaagtgaaaaagcccggctcaagtgttaaag taagctgtaaggcgagcggtggcacttttagctcttacgccattagctgggtgcgaca ggctcctggtcagggcctcgaatggatgggcggcatcattccaatctttggtactgca aattatgcccagaaatttcagggtagagtcacaattaccgcagatgagagcacgaata ctgcctacatggaactgagtagcctgcgttccgaagatacagctgtgtattactgtgc gcgcggtgaggaggcttactacgacctttggggccaggggaccttagtcactgtgtct agc | 457 |

TABLE 3-continued

Nucleic acid sequences of the light and heavy chains for the anti-H5-VN04 antibodies.

| anti-H5VN04 Ab | VH or VL | Nucleic Acid Sequence | SEQ ID NO: |
|---|---|---|---|
| 11A11 | VL | gaaattgtgttgacgcagtctccaggcaccctgtctttgtctccaggggaaagagcca<br>ccctctcctgctgggccagtcagagtgttagcagcttcttagcctggtaccaacacaa<br>acctggccaggttcccaggctcctcatctatgatgcatccaatagggccactggcatc<br>ccagccaggttctctggcagtgggtctgggacacacttcactctcactatcagcagcc<br>tagagcctgaagattttgcagtttattactgtcagcagcgtttcaattggcctccgac<br>gttcggccaagggaccaaggtggaaagcaaac | 458 |
| 11A6 | VH | caggttcaattagtgcagtctggtgctgaagtgaaaaagcccggctcaagtgttaaag<br>taagctgtaaggcgagcggaggtacttttagttcatacgccattagctgggtgcgaca<br>ggctcctggtcagggcctcgaatggatgggcggcatcacccctatgttcggcactgca<br>aattatgcccagaaatttcagggtagagtcacaattaccgcagacaaaagtacgagca<br>ccgcctatatggaactgagtagcctgcgttccgaagatacagctgtgtattactgtgc<br>gcgcggtacaagttacctgcctggtcgtagtggttttgatgtttggggccaggggacc<br>ttagtcactgtgtctagc | 459 |
| 11A6 | VL | cagcctgggctgactcagccaccctcggtgtcagtgtccccaggacagacggccagga<br>tcacctgctctgcagatgcattgccaaagcaatatgcttattggtaccagcagaggcc<br>aggccaggcccctgtgttgctgatatataaagacactgagaggcccccagggatccct<br>gagcgattctctggctccagctcagggacaacagtcacgttgaccatcagtggagtcc<br>aggcagaagacgaggctgactactattgtcaatcagcagacgctagtgaaaattctgt<br>cttcggaggtgggaccaaggtcaccgtcctag | 460 |
| 11B5 | VH | caggttcaattagtgcagtctggtgctgaagtgaaaaagcccggctcaagtgttaaag<br>taagctgtaaggcgagcggtgttacttttcgttcatacgccattagctgggtgcgaca<br>ggctcctggtcagggcctcgaatggatgggcggcatcagcgcaatgtttggtactgca<br>aattatgcccagaaatttcagggtagagtcacaattaccgcagacaagagtacgaaca<br>ccgcatatatggaactgagtagcctgcgttccgaagatacagctgtgtattactgtgc<br>gcgcggtcgtggttacgaccctagtgttggtggttttgatgtgtggggccaggggacc<br>ttagtcactgtgtctagc | 461 |
| 11B5 | VL | aattttatgctgactcagccccactctgtgtcggagtctccggggaagacggtcagca<br>tctcctgcaccggcagcagtggcagcattgccagcaactatgtgcagtggtaccagca<br>gcgcccgggcagtgcccccgccactgtgatctatgaggataaccaaagaccctctggg<br>gtccctgatcggttctctggctccatcgacagctcctccaactctgcctccctcacca<br>tctctggactgaagactgaggacgaggctgactactactgtcagtcttatgataccag<br>caatctggtattcggcgtagggaccaagctgaccgtcctag | 462 |
| 11C6 | VH | caggttcaattagtgcagtctggtgctgaagtgaaaaagcccggctcaagtgttaaag<br>taagctgtaaggcgagcggtggtacctttagttcatacgccattagctgggtgcgaca<br>ggctcctggtcagggcctcgaatggatgggcggcattattcctatcttcggtactgca<br>aattatgcccagaaatttcagggtagagtcacaattaccgcagacgatagcacgtcaa<br>ccgcatacatggaactgagtagcctgcgttccgaagatacagctgtgtattactgtgc<br>gcgcgacagtacacctagtgttacaagtagtctgtaccgtatccctgcttttgatgtg<br>tggggccaggggaccttagtcactgtgtctagc | 463 |
| 11C6 | VL | ctgcctgtgctgactcaatcatcctctgcctctgcttccctgggatcctcggtcaagc<br>tcacctgcagtctgaccaatgggcccagtaactacatcatcgcatggcatcagcagca<br>gccagagaagggccctcggtacttgatgaagcttaacagtgatggcagccacagcaag<br>ggggacgggatccctgatcgcttctcaggctccagctctggggctgagcgctacctca<br>ccatctccaaccttaagtctgaggatgaggctgattattactgtgagacctgggacag<br>taacactcatgtggtattcggcggagggaccaagctgaccgtcctag | 464 |
| 11E9 | VH | caggttcaattagtgcagtctggtgctgaagtgaaaaagcccggctcaagtgttaaag<br>taagctgtaaggcgagcggaggtacctttagttcatacgccattagctgggtgcgaca<br>ggctcctggtcagggcctcgaatggatgggcggcattaccccaatgtttggtactgca<br>aattatgcccagaaatttcagggtagagtcacaattaccgcagacaagagcacgtcaa<br>ctacatacatggaactgagtagcctgcgttccgaagatacagctgtgtattactgtgc<br>gcgcggtcctggttactaccctgacagtaataattatgatctctggggccaggggacc<br>ttagtcactgtgtctagc | 465 |
| 11E9 | VL | gaaacgacactcacgcagtctccaggcaccctgtctttgtctccaggggaaagagcca<br>ccctctcctgcagggccagtcagagtgttagtagcagctacttagcctggtaccagca<br>gaaacctggccaggctcccaggctcctcatctatggtgcatcaagtagggccactggc<br>atcccagacaggttcagtggcagtgggtctgggacagacttcactctcaccatcagca<br>gactggagcctgaagattttgcaacctactattgtcaacaggttaacagcttccctcg<br>aacttttggccaggggaccaagctggagatgaaac | 466 |

TABLE 3-continued

Nucleic acid sequences of the light and
heavy chains for the anti-H5-VN04 antibodies.

| anti-H5VN04 Ab | VH or VL | Nucleic Acid Sequence | SEQ ID NO: |
|---|---|---|---|
| 11F8 | VH | caggttcaattagtgcagtctggtgctgaagtgaaaaagcccggctcaagtgttaaag taagctgtaaggcgagcggtgtgacctttagctcatacgccattagctgggtgcgaca ggctcctggtcagggcctcgaatggatgggcggcattagcccaatgtttggcactgca aattatgcccagaaatttcagggtagagtcacaattaccgcagaccagagcacgaaca ccgcctatatggaactgagtagcctgcgttccgaagatacagctgtgtattactgtgc gcgcggtggtacatacagtcctggtggtacatactttgatgtttggggccaggggacc ttagtcactgtgtctagc | 467 |
| 11F8 | VL | cagcctgtgctgactcagccaccctcagcgtctgcgaccccggacagacggtgacca tctcttgttctggcagcagttccaacatcggcgtgagctttgtctactggtatcaaca atttccaggaacggccccaagctcctcatttacagggatgatatgaggcagtcaggg gtccctgaccgattttctggcttcaagtctggctcctcagcctcctgaccatctctg ggctccagtccgaagatgaggccacttattattgttccgcgtgggatgagagcctgag tagtgtgttgttcggcggagggaccaaggtcaccgtcctag | 468 |

TABLE 4

Amino acid sequences of the light and
heavy chains for the anti-H5VN04 antibodies.

| anti-H5VN04 Ab | VH or VL | Amino Acid Sequence | SEQ ID NO: |
|---|---|---|---|
| 1C2 | VH | QVQLVQSGAEVKKPGSSVKVSCKASGGPFSSYAISW VRQAPGQGLEWMGGISPMFGTANYAQKFQGRVTITA DKSTSTAYMELSSLRSEDTAVYYCARDDGYAPSGGL REFDVWGQGTLVTVSS | 469 |
| 1C2 | VL | DIQMTQSPDSLAVSLGERATINCKSSRSVLYSSNNK NYLAWYQQKPGQPPKLLIYWASTRESGVPDRFSGSG SGTDFTLTISSLQAEDVAVYYCQQYYSGSWTFGQGT KVEIK | 470 |
| 2B8 | VH | QVQLVQSGAEVKKPGSSVKVSCKASGGIFSSYAISW VRQAPGQGLEWMGGISPIFGTANYAQKFQGRVTITA DKSTNTAYMELSSLRSEDTAVYYCARGRGAYMGPSM DVWGQGTLVTVSS | 471 |
| 2B8 | VL | QPVLTQPPSVSVAPGQTARITCGGNNIGSKSVHWYQ QKPGQAPVLVVYDDSDRPSGIPERFSGSNSGNTATL TISRVEAGDEADYYCQVWDRSSDHVVFGGGTKLTVL | 472 |
| 2C4 | VH | QVQLVQSGAEVKKPGSSVKVSCKASGGTFSSYAISW VRQAPGQGLEWMGGISPIFGTANYAQKFQGRVTITA DKSTSTVYMELSSLRSEDTAVYYCARGARYYAGGYF DVWGQGTLVTVSS | 473 |
| 2C4 | VL | EIVLTQSPGTLSLSPGERATLSCRASQTVSNYLAWY QQRPGQAPRLLIYAASTRATGVPARFSGSGSGTEFT LTISSLQSEDFAIYYCQQYDNLPPVTFGPGTTVDIK | 474 |
| 2D3 | VH | QVQLVQSGAEVKKPGSSVKVSCKASGVTFSSYAISW VRQAPGQGLEWMGGISPIFGTANYAQKFQGRVTITA DQSTNTVYMELSSLRSEDTAVYYCARDSGNYDGYGP GSRFDVWGQGTLVTVSS | 475 |
| 2D3 | VL | QPGLTQPPSASGTPGQRVTISCSGSSSNIGSNTVNW YQQLPGTAPKLLIYSNNQRPSGVPDRFSGSKSGTSA SLAISGLQSEDEADYFCSAWDDSLGGEVFGTGTKVN VL | 476 |
| 2D9 | VH | QVQLVQSGAEVKKPGSSVKVSCKASGVTFSSYAISW VRQAPGQGLEWMGGIMPMFGTANYAQKFQGRVTITA DKSTSTAYMELSSLRSEDTAVYYCARERGSWSFGYF DVWGQGTLVTVSS | 477 |
| 2D9 | VL | LPVLTQPPSMSAAPGQTARITCGGDHIGSKSVHWYQ RKPGQAPVLVIYSDTDRPSGIPERFSGSNSGNTATL TISRVEAGDEADYFCQVWDSSNDHPVFGGGTKLTVL | 478 |

TABLE 4-continued

Amino acid sequences of the light and heavy chains for the anti-H5VN04 antibodies.

| anti-H5VN04 Ab | VH or VL | Amino Acid Sequence | SEQ ID NO: |
|---|---|---|---|
| 2E1 | VH | QVQLVQSGAEVKKPGSSVKVSCKASGVTFSSYAISW VRQAPGQGLEWMGGISPLFGTANYAQKFQGRVTITA DKSTSTVYMELSSLRSEDTAVYYCARSRTYADGRTF DVWGQGTLVTVSS | 479 |
| 2E1 | VL | QVQLVQSGAEVKKPGSSVKVSCKASGVTFSSYAISW VRQAPGQGLEWMGGISPLFGTANYAQKFQGRVTITA DKSTSTVYMELSSLRSEDTAVYYCARSRTYADGRTF DVWGQGTLVTVSS | 480 |
| 2H4 | VH | QVQLVQSGAEVKKPGSSVKVSCKASGGTFSSYAISW VRQAPGQGLEWMGGISPIFGTANYAQKFQGRVTITA DKSTSTAYMELSSLRSEDTAVYYCARELGYLAGSPS PGFDYWGQGTLVTVSS | 481 |
| 2H4 | VL | QSVLTQPPSASGSPGQSVTISCTGTSSDVGGYNYVS WYQQHPGKAPKLIIYEVTKRPSGVPDRFSGSKSGNT ASLTVAGLQAEDEADYYCSSYAGGKWVFGTGTKVTV L | 482 |
| 2H5 | VH | QVQLVQSGAEVKKPGSSVKVSCKASGGTFSSYAISW VRQAPGQGLEWMGGISPIFGTANYAQKFQGRVTITA DTSTSTAYMELSSLRSEDTAVYYCARSRRYWADGGF DYWGQGTLVTVSS | 483 |
| 2H5 | VL | LPVLTQPPSASGTPGQRVTISCSGSSSNMGRNTVNW YRHLPGTAPELLIYDNDERPSGVPDRFSGSKSGTSA SLAISGLQSEDEGHYYCAAWDDSLNGPVFGGGTKLT VL | 484 |
| 4C4 | VH | QVQLVQSGAEVKKPGSSVKVSCKASGGTFSSYAISW VRQAPGQGLEWMGGISPMFGTANYAQKFQGRVTITA DKSTSTAYMELSSLRSEDTAVYYCAREGGYSPGGVD FDYWGQGTLVTVSS | 485 |
| 4C4 | VL | NFMLTQPHSVSESPGKTVTISCTRSSGSIASTYVQW YRQRPGSAPTTVIYEDHQRPSGVPDRFSGSLDSSSN SASLTISGLRTEDAATYYCQSFDASTLVFGGGTKLT VL | 486 |
| 4E5 | VH | QVQLVQSGAEVKKPGSSVKVSCKASGVTFSSYAISW VRQAPGQGLEWMGGISPIFGTANYAQKFQGRVTITA DESTNTVYMELSSLRSEDTAVYYCARGTTYSTARYF DVWGQGTLVTVSS | 487 |
| 4E5 | VL | NFMLTQPHSVSESPGKTVTISCTRRSGSIASNYVQW YQQRPGSAPTTVIYEDNQRPSGVPDRFSGSIDRSSN SASLTISGLKTEDEADYYCQSYDSDNHEVIFGGGTK LTVL | 488 |
| 4F5 | VH | QVQLVQSGAEVKKPGSSVKVSCKASGVTFRSYAISW VRQAPGQGLEWMGGISGIFGTANYAQKFQGRVTITA DESTSTAYMELSSLRSEDTAVYYCARSPAYYFGPNM DVWGQGTLVTVSS | 489 |
| 4F5 | VL | QSVLTQPPSVSGAPGQRVTISCTGSSSNIGAGYDVH WYQQLPGTVPKLIIYDNSNRPSGVPARFSGSKSGTS ASLAISGLQSEDEAAYYCQSYDSSLSVVVFGGGTKL SVL | 490 |
| 4G3 | VH | QVQLVQSGAEVKKPGSSVKVSCKASGGTFSSYAISW VRQAPGQGLEWMGGISPMFGTANYAQKFQGRVTITA DKSTSTAYMELSSLRSEDTAVYYCARSSRYAPSDST NFDQWGQGTLVTVSS | 491 |
| 4G3 | VL | NFMLTQPHSVSESPGKTVTISCTGSSGSIASNYVQW YQQRPGSAPTTVIYEDNQRPSGVPDRFSGSIDSSSN SASLTISGLKTEDEADYYCQSYDTSNRKVFGGGTKL TVL | 492 |

TABLE 4-continued

Amino acid sequences of the light and heavy chains for the anti-H5VN04 antibodies.

| anti-H5VN04 Ab | VH or VL | Amino Acid Sequence | SEQ ID NO: |
|---|---|---|---|
| 4G5 | VH | QVQLVQSGAEVKKPGSSVKVSCKASGGPFSSYAISW VRQAPGQGLEWMGGISGIFGTANYAQKFQGRVTITA DESTSTAYMELSSLRSEDTAVYYCARGDRFYVGERF DVWGQGTLVTVSS | 493 |
| 4G5 | VL | QSVLTQPPSVSVAPGQTARITCGGNDIGSKSVHWYQ QKPGQAPVLVVYDDIDRPSGIPERFSGSNYGDTATL TISWVEAGDEADYYCQVWDTNSDPVFVFGSGTKVTV L | 494 |
| 5A6 | VH | QVQLVQSGAEVKKPGSSVKVSCKASGGTFSSYAISW VRQAPGQGLEWMGGISPIFGTANYAQKFQGRVTITA DQSTSTAYMELSSLRSEDTAVYYCARGGGVGRIWIA GYGFDQWGQGTLVTVSS | 495 |
| 5A6 | VL | QTVVTQEPSFSVSPGGTVTLTCGLSSGSVSTSNYPS WYQQTPGQPPRTLIYSTNTRSSGVPDRFSGSILGNK AALTITGAQADDESDYYCVLYMGSISMFGGGTKLT VL | 496 |
| 5A8 | VH | QVQLVQSGAEVKKPGSSVKVSCKASGGTFSSYAISW VRQAPGQGLEWMGGISPIFGTANYAQKFQGRVTITA DESTSTVYMELSSLRSEDTAVYYCARGPGYHPAGAS GQFFDLWGQGTLVTVSS | 497 |
| 5A8 | VL | SYELTQPPSVSKDLRQTATLTCTGNSNNVGNQGAAW LQQHQGHPPKLLSYRNNHRPSGISDRSSASRSGDTA SLTITGLQPEDEADYYCSAWDSSLSAWVFGGGTKLT VL | 498 |
| 5B9 | VH | QVQLVQSGAEVKKPGSSVKVSCKASGVTFSSYAISW VRQAPGQGLEWMGGISPMFGTANYAQKFQGRVTITA DESTNTAYMELSSLRSEDTAVYYCARGRGYAPDALT NFDVWGQGTLVTVSS | 499 |
| 5B9 | VL | EIVLTQSPDSLAMSLGERATVNCKSSRSLFDSSDNK NYLAWYQKKPGQPPQLLIYWASTRQSGVPDRFSGSG SGTDFTLTISSLQAEDVAVYYCQQYFSSPPIFTFGP GTKVEIK | 500 |
| 6A2 | VH | QVQLVQSGAEVKKPGSSVKVSCKASGVTFSSYAISW VRQAPGQGLEWMGGITPMFGTANYAQKFQGRVTITA DKSTSTVYMELSSLRSEDTAVYYCARGRGYIAVAGD MDVWGQGTLVTVSS | 501 |
| 6A2 | VL | DIQMTQSPDSLAVSLGERATINCKSSRSVLYSSNNK NYLAWYQQKAGQPPKLLIYWASTRESGVPDRFSGSG SGTDFTLTISSLQAEDVAVYYCQQYYSTPPTFGQGT KVEIK | 502 |
| 6C2 | VH | QVQLVQSGAEVKKPGSSVKVSCKASGVTFSSYAISW VRQAPGQGLEWMGGISPLFGTANYAQKFQGRVTITA DKSTSTAYMELSSLRSEDTAVYYCARGDAYYVGGGA RPFDLWGQGTLVTVSS | 503 |
| 6C2 | VL | SYELTQPPSVSETPGQNVIISCSGGSSNIGVNYVYW YQVVPGAAPKLLIYRNNQRPSGVPDRFSGSKSGTSA SLAISGLQSEDEADYYCGVWDDSLNGHWVFGGGTDL TVL | 504 |
| 6F3 | VH | QVQLVQSGAEVKKPGSSVKVSCKASGGPFSSYAISW VRQAPGQGLEWMGGISPMFGTANYAQKFQGRVTITA DESTSTVYMELSSLRSEDTAVYYCARGYSYYPGGGG GRNFDYWGQGTLVTVSS | 505 |
| 6F3 | VL | LPVLTQPPSASGTPGQRVTISCSGSSSNIGSNTVNW YQQLPGTAPKLLIYSNNQRPSGVPDRFSGSKSGTSA SLAISGLQSEGEADYYCAAWDDSLKGRVFGGGTKVT VL | 506 |

TABLE 4-continued

Amino acid sequences of the light and heavy chains for the anti-H5VN04 antibodies.

| anti-H5VN04 Ab | VH or VL | Amino Acid Sequence | SEQ ID NO: |
|---|---|---|---|
| 8A1 | VH | QVQLVQSGAEVKKPGSSVKVSCKASGGPFSSYAISW VRQAPGQGLEWMGGISPLFGTANYAQKFQGRVTITA DESTSTAYMELSSLRSEDTAVYYCARAPTYYASRDS YNFDYWGQGTLVTVSS | 507 |
| 8A1 | VL | ETTLTQSPATLSVSPGERATLSCRASQSVDRGYLAW YQQKPGQAPRLLIYGASHRAAGIPDRFSGSGSGTDF TLTISRLEPEDFAVYFCQQYGSSRLSFGGGTKVEIQ | 508 |
| 8C1 | VH | QVQLVQSGAEVKKPGSSVKVSCKASGVTFSSYAISW VRQAPGQGLEWMGGISPMFGTANYAQKFQGRVTITA DKSTNTAYMELSSLRSEDTAVYYCARDTTYIAGGHF DVWGQGTLVTVSS | 509 |
| 8C1 | VL | QSVLTQPPSASGSPGQSVTISCTGTSSDIGAYNYVS WYQQHPDKAPKLIIYEVSKRPSGVPDRFSGSKSGNT ASLTVSGLQAEDEADYYCSSYAGSNNVVFGGGTKLT VL | 510 |
| 8D6 | VH | QVQLVQSGAEVKKPGSSVKVSCKASGVTFSSYAISW VRQAPGQGLEWMGGISPLFGTANYAQKFQGRVTITA DESTNTAYMELSSLRSEDTAVYYCARASGYFTGWGT FDYWGQGTLVTVSS | 511 |
| 8D6 | VL | SYELTQPPSVSVSPGQTARITCSGDALPKQYAYWYQ QKPGQAPVLVIYKDSERPSGIPERFSGSNSGNTATL TISGTQALDEADYYCQAWDSSTAVFGTGTKVTVL | 512 |
| 9A1 | VH | QVQLVQSGAEVKKPGSSVKVSCKASGGTFSSYAISW VRQAPGQGLEWMGGISPIFGTANYAQKFQGRVTITA DKSTSTAYMELSSLRSEDTAVYYCARGRYYYTVGVY DVWGQGTLVTVSS | 513 |
| 9A1 | VL | SYELTQPPSVSKGLRQTATLTCIGDSDNVGNQGVGW LQQHQGHPPKLLSYRDNTRPSGISERFSASRSGNTA SLTITGLQPEDEADYYCSAWDSSLTAVVFGGGTKLA VL | 514 |
| 9C1 | VH | QVQLVQSGAEVKKPGSSVKVSCKASGVTFSSYAISW VRQAPGQGLEWMGGISPIFGTANYAQKFQGRVTITA DKSTSTVYMELSSLRSEDTAVYYCARGGGYSADGGA GNNTIFDVWGQGTLVTVSS | 515 |
| 9C1 | VL | QPVLTQPPSVSKGLRQTATLTCTGNNNNVGNQGAAW LQQHQGHPPKLLSDRNNNRPSGISERLSASRSGNTA SLTITGLQAEDEADYYCSAWDSSLSAWVFGGGTKLT VL | 516 |
| 9D11 | VH | QVQLVQSGAEVKKPGSSVKVSCKASGVTFSSYAISW VRQAPGQGLEWMGGISPLFGTANYAQKFQGRVTITA DESTSTAYMELSSLRSEDTAVYYCARERGYTVGGGG MDVWGQGTLVTVSS | 517 |
| 9D11 | VL | QSALTQPPSASGSPGQSVTISCTGTSSDVGAHNFVS WYQQHPDKAPKLIIYEVNRRPSGVPDRFSGSKSGTS ASLAISGLQSDDEADYYCAAWDDSLDGPVFGGGTKL TVL | 518 |
| 9E4 | VH | QVQLVQSGAEVKKPGSSVKVSCKASGVTFSSYAISW VRQAPGQGLEWMGGISPIFGTANYAQKFQGRVTITA DKSTNTVYMELSSLRSEDTAVYYCAREYLGDDYSSG SYFDVWGQGTLVTVSS | 519 |
| 9E4 | VL | ETTLTQSPGTLSLSPGETAILSCRASQSVDSHLAWY QQKGGQAPRLLIYGASTRATGIPARFSGSGSGTDFT LTINGLEPEDFAIYFCQQRSMWPLTFGGGTKVEIK | 520 |
| 9E7 | VH | QVQLVQSGAEVKKPGSSVKVSCKASGGTFSSYAISW VRQAPGQGLEWMGGISPMFGTANYAQKFQGRVTITA DKSTSTAYMELSSLRSEDTAVYYCARESGYSGTGQF DVWGQGTLVTVSS | 521 |

TABLE 4-continued

Amino acid sequences of the light and heavy chains for the anti-H5VN04 antibodies.

| anti-H5VN04 Ab | VH or VL | Amino Acid Sequence | SEQ ID NO: |
|---|---|---|---|
| 9E7 | VL | QSVLTQPPSASGTAGQRVTISCFGRTSNVGRNTVNW YQQLPGAAPKILIFNDNQRPSGVPDRFSGSKSGTAA SLTISRLQSADEADYYCSSWDDDLNGPVFGGGTKLS VV | 522 |
| 9H3 | VH | QVQLVQSGAEVKKPGSSVKVSCKASGGIFSSYAISW VRQAPGQGLEWMGGISPIFGTANYAQKFQGRVTITA DESTNTAYMELSSLRSEDTAVYYCARSGGYYDYGVG YDQWGQGTLVTVSS | 523 |
| 9H3 | VL | QPVLTQPPSASGTPGQRVTISCSGGRSNIGSNTVNW YQQLPGTAPKLLIYSNNHRPSGVPDRFSGSKSGNTA SLTISGLQAEDEADYYCQSYDSSVVFGGGTKLTVL | 524 |
| 9H4 | VH | QVQLVQSGAEVKKPGSSVKVSCKASGGTFSSYAISW VRQAPGQGLEWMGGITPIFGTANYAQKFQGRVTITA DESTSTAYMELSSLRSEDTAVYYCARSGGYSPSIGG FDVWGQGTLVTVSS | 525 |
| 9H4 | VL | QPGLTQPPSASGTPGQRVTISCSGSRSNIGRNTVNW YQQLPGTAPKLLIYSNNQRPSGVPDRVSGSKSGTSA SLAISGLQSEDEADYYCAAWDVSLNGQVFGTGTKVT VL | 526 |
| 10D4 | VH | QVQLVQSGAEVKKPGSSVKVSCKASGGTFSSYAISW VRQAPGQGLEWMGGISPIFGTANYAQKFQGRVTITA DRSTSTAYMELSSLRSEDTAVYYCARGPGYDPSSLR GFDVWGQGTLVTVSS | 527 |
| 10D4 | VL | SYELTQPPSVSKDLRQTATLTCTGNSNNVGNQGAAW LQQHQGHPPKLLFYKNNNRPSGISERLSASRSGNTA SLTITGLQPEDEADYYCSAWDSSLSDWVFGGGTKLT VL | 528 |
| 11A11 | VH | QVQLVQSGAEVKKPGSSVKVSCKASGGTFSSYAISW VRQAPGQGLEWMGGIIPIFGTANYAQKFQGRVTITA DESTNTAYMELSSLRSEDTAVYYCARGEEAYYDLWG QGTLVTVSS | 529 |
| 11A11 | VL | EIVLTQSPGTLSLSPGERATLSCWASQSVSSFLAWY QHKPGQVPRLLIYDASNRATGIPARFSGSGSGTHFT LTISSLEPEDFAVYYCQQRFNWPPTFGQGTKVESK | 530 |
| 11A6 | VH | QVQLVQSGAEVKKPGSSVKVSCKASGGTFSSYAISW VRQAPGQGLEWMGGITPMFGTANYAQKFQGRVTITA DKSTSTAYMELSSLRSEDTAVYYCARGTSYLPGRSG FDVWGQGTLVTVSS | 531 |
| 11A6 | VL | QPGLTQPPSVSVSPGQTARITCSADALPKQYAYWYQ QRPGQAPVLLIYKDTERPPGIPERFSGSSSGTTVTL TISGVQAEDEADYYCQSADASENSVFGGGTKVTVL | 532 |
| 11B5 | VH | QVQLVQSGAEVKKPGSSVKVSCKASGVTFRSYAISW VRQAPGQGLEWMGGISAMFGTANYAQKFQGRVTITA DKSTNTAYMELSSLRSEDTAVYYCARGRGYDPSVGG FDVWGQGTLVTVSS | 533 |
| 11B5 | VL | NFMLTQPHSVSESPGKTVSISCTGSSGSIASNYVQW YQQRPGSAPATVIYEDNQRPSGVPDRFSGSIDSSSN SASLTISGLKTEDEADYYCQSYDTSNLVFGVGTKLT VL | 534 |
| 11C6 | VH | QVQLVQSGAEVKKPGSSVKVSCKASGGTFSSYAISW VRQAPGQGLEWMGGIIPIFGTANYAQKFQGRVTITA DDSTSTAYMELSSLRSEDTAVYYCARDSTPSVTSSL YRIPAFDVWGQGTLVTVSS | 535 |
| 11C6 | VL | LPVLTQSSSASASLGSSVKLTCSLTNGPSNYIIAWH QQQPEKGPRYLMKLNSDGSHSKGDGIPDRFSGSSSG AERYLTISNLKSEDEADYYCETWDSNTHVVFGGGTK LTVL | 536 |

TABLE 4-continued

Amino acid sequences of the light and heavy chains for the anti-H5VN04 antibodies.

| anti-H5VN04 Ab | VH or VL | Amino Acid Sequence | SEQ ID NO: |
|---|---|---|---|
| 11E9 | VH | QVQLVQSGAEVKKPGSSVKVSCKASGGTFSSYAISW VRQAPGQGLEWMGGITPMFGTANYAQKFQGRVTITA DKSTSTTYMELSSLRSEDTAVYYCARGPGYYPDSNN YDLWGQGTLVTVSS | 537 |
| 11E9 | VL | ETTLTQSPGTLSLSPGERATLSCRASQSVSSSYLAW YQQKPGQAPRLLIYGASSRATGIPDRFSGSGSGTDF TLTISRLEPEDFATYYCQQVNSFPRTFGQGTKLEMK | 538 |
| 11F8 | VH | QVQLVQSGAEVKKPGSSVKVSCKASGVTFSSYAISW VRQAPGQGLEWMGGISPMFGTANYAQKFQGRVTITA DQSTNTAYMELSSLRSEDTAVYYCARGGTYSPGGTY FDVWGQGTLVTVSS | 539 |
| 11F8 | VL | QPVLTQPPSASATPGQTVTISCSGSSSNIGVSFVYW YQQFPGTAPKLLIYRDDMRQSGVPDRFSGFKSGSSA SLTISGLQSEDEATYYCSAWDESLSSVLFGGGTKVT VL | 540 |

The amino acid sequences for the CDR regions of the heavy and light chains of the anti-H1CA0409 antibodies are shown in Tables 5 and 6.

TABLE 5

Amino acid sequences for the heavy chain CDRs for anti-H1CA0409 antibodies.

| anti-H1CA0409 Ab | VH-CDR1 | SEQ ID NO: | VH-CDR2 | SEQ ID NO: | VH-CDR3 | SEQ ID NO: |
|---|---|---|---|---|---|---|
| 1D9 | GGTFSSYA | 217 | IITIFGTA | 247 | ARGATGFYDV | 277 |
| 1E6 | GVTFSSYA | 218 | ISPIFGTA | 248 | ARGREYYASNGDSFDV | 278 |
| 1F1 | GGTFSSYA | 219 | ISAIFGTA | 249 | ARGSGYYVAASGAFDV | 279 |
| 1F12 | GGIFSSYA | 220 | ITPIFGTA | 250 | ARDLSRDSLNLPGSSPGYDL | 280 |
| 1F3 | GVIFSSYA | 221 | ISPIFGTA | 251 | ARSRGYAPGTSFHYDV | 281 |
| 1F5 | GGTFSSYA | 222 | ISPIFGTA | 252 | ARDQGGTRGNYFDV | 282 |
| 1F6 | GGTFSSYA | 223 | IITIFGTA | 253 | ARGGGGRFDV | 283 |
| 1H2 | GGPFRSYA | 224 | IIPIFGTA | 254 | ARGGVYSFDV | 284 |
| 1H4 | GVPFSSYA | 225 | ISPLFGTA | 255 | ARGLGTYSPSLYPRGMDV | 285 |
| 1H8 | GVTFSSYA | 226 | ISPMFGTA | 256 | ARGRAYLSVRGSFDV | 286 |
| 2A1 | GVIFSSYA | 227 | IIPIFGTA | 257 | ARGGSGSFDV | 287 |
| 2A11 | GVTFSSYA | 228 | ISPVFGTA | 258 | ARSRGYTVSSLAGRYFDQ | 288 |
| 2A12 | GGTFSSYA | 229 | IVPLFGTA | 259 | ARGLGLYFDV | 289 |
| 2B11 | GGTFSSYA | 230 | IIPIFGTA | 260 | ARVRGGYGPYGDFDV | 290 |
| 2B6 | GGPFSSYA | 231 | ISPIFGTA | 261 | ARGRSYIVSVSPGFDV | 291 |
| 2C1 | GGIFSSYA | 232 | ISAIFGTA | 262 | ARDSGIASGYTAYMDY | 292 |
| 2E1 | GGIFRSYA | 233 | IIPMFGTA | 263 | ARGAGSTFDV | 293 |
| 2E11 | GGTFSSYA | 234 | INPIFGTA | 264 | ARGESAYYSRNYDV | 294 |
| 2E12 | GVTFSSYA | 235 | ISPMFGTA | 265 | ARGGGYYPAGVGRYDV | 295 |

TABLE 5-continued

Amino acid sequences for the heavy chain CDRs for anti-H1CA0409 antibodies.

| anti-H1CA0409 Ab | VH-CDR1 | SEQ ID NO: | VH-CDR2 | SEQ ID NO: | VH-CDR3 | SEQ ID NO: |
|---|---|---|---|---|---|---|
| 2F1 | GGTFSSYA | 236 | ITPLFGTA | 266 | ARGPTLYSPPVFDV | 296 |
| 2G3 | GGTFRSYA | 237 | IMPIFGTA | 267 | ARGAGVSAGPSWPFDV | 297 |
| 2G4 | GGTFSSYA | 238 | ISPMFGTA | 268 | ARSRGYNVAASFGFDV | 298 |
| 2H3 | GGPFSSYA | 239 | IIPIFGTA | 269 | ARGTDYSGYRGFDV | 299 |
| 2H4 | GVTFSSYA | 240 | ITPIFGTA | 270 | ARGGGVFDV | 300 |
| 4C4 | GGTFSSYA | 241 | ISPMFGTA | 271 | AREGGYSPGGVDFDY | 301 |
| 4F5 | GVTFRSYA | 242 | ISGIFGTA | 272 | ARSPAYYFGPNMDV | 302 |
| 5A8 | GGTFSSYA | 243 | ISPIFGTA | 273 | ARGPGYHPAGASGQFFDL | 303 |
| 5B9 | GVTFSSYA | 244 | ISPMFGTA | 274 | ARGRGYAPDALTNFDV | 304 |
| 6F3 | GGPFSSYA | 245 | ISPMFGTA | 275 | ARGYSYYPGGGGRNFDY | 305 |
| 9H3 | GGIFSSYA | 246 | ISPIFGTA | 276 | ARSGGYYDYGVGYDQ | 306 |

TABLE 6

Amino acid sequences for the light chain CDRs for anti-H1CA0409 antibodies.

| anti-H1CA0409 Ab | VL-CDR1 | SEQ ID NO: | VL-CDR2 | SEQ ID NO: | VL-CDR3 | SEQ ID NO: |
|---|---|---|---|---|---|---|
| 1D9 | SSNIGSNT | 307 | SNN | 337 | AAWDDSLNGPV | 367 |
| 1E6 | NIATKS | 308 | HDS | 338 | AAWDDSLSGPWV | 368 |
| 1F1 | INNVGDQG | 309 | RNS | 339 | SAWDSSLSDWV | 369 |
| 1F12 | QSVSSN | 310 | GAS | 340 | QQYSSSPYT | 370 |
| 1F3 | NIGSKS | 311 | YDS | 341 | QLWDHTNSHVV | 371 |
| 1F5 | SNNVGNQG | 312 | RNN | 342 | SAWDNTVSGWV | 372 |
| 1F6 | TSNIGNNA | 313 | SLN | 343 | EAWDDSLSGPV | 373 |
| 1H2 | GSNVGSNV | 314 | RNN | 344 | AAWDDRLNGFV | 374 |
| 1H4 | SSNIGRND | 315 | GRD | 345 | AAWDASLMIYV | 375 |
| 1H8 | SSNIGSNT | 316 | SNN | 346 | AAWDDSLNGYV | 376 |
| 2A1 | SSNLGSNY | 317 | RNS | 347 | AAWDDSLNGVV | 377 |
| 2A11 | ESLCSTC | 318 | GAT | 348 | QQYGSSPQT | 378 |
| 2A12 | TGAVTSGYY | 319 | STS | 349 | LLYYGGPWV | 379 |
| 2B11 | SSNIGSHS | 320 | GNS | 350 | AAWDDGLSGWV | 380 |
| 2B6 | SSDVGGYNY | 321 | EVS | 351 | ASWDDSLNAYV | 381 |
| 2C1 | SLRTSY | 322 | QST | 352 | NSRGSGGNPYV | 382 |
| 2E1 | SSNIGSNT | 323 | SNN | 353 | AAWDDSLNGRV | 383 |
| 2E11 | SSNVGNQG | 324 | RND | 354 | SAWDNSLSAWV | 384 |
| 2E12 | QNVLYSSNNKNN | 325 | WAS | 355 | QQYYGKPFT | 385 |
| 2F1 | SGSVSTTNY | 326 | NTN | 356 | VLYMGRGIYV | 386 |
| 2G3 | SNNVGKQG | 327 | RNN | 357 | SAWDSSLSVWV | 387 |
| 2G4 | QYIDRS | 328 | YAS | 358 | HQTSSLPWT | 388 |
| 2H3 | SGSVSSFNY | 329 | NTN | 359 | ALYVGGGISV | 389 |
| 2H4 | SSNIGNNA | 330 | YDD | 360 | AAWDDSLSGPV | 390 |
| 4C4 | SGSIASTY | 331 | EDH | 361 | QSFDASTLV | 391 |
| 4F5 | SSNIGAGYD | 332 | DNS | 362 | QSYDSSLSVVV | 392 |
| 5A8 | SNNVGNQG | 333 | RNN | 363 | SAWDSSLSAWV | 393 |
| 5B9 | RSLFDSSDNKNY | 334 | WAS | 364 | QQYFSSPPIFT | 394 |
| 6F3 | SSNIGSNT | 335 | SNN | 365 | AAWDDSLKGRV | 395 |
| 9H3 | RSNIGSNT | 336 | SNN | 366 | QSYDSSVV | 396 |

The nucleic acid and amino acid sequences of the light and heavy chains for the anti-H1-CA0409 antibodies are shown in Tables 7 and 8.

TABLE 7

Nucleic acid sequences of the light and heavy chains for the anti-H1CA0409 antibodies.

| anti-H1CA0409 Ab | VH or VL | Nucleic Acid Sequence | SEQ ID NO: |
|---|---|---|---|
| 1D9 | VH | caggttcaattagtgcagtctggtgctgaagtgaaaaagcccggctcaagtgttaaagtaagctgt aaggcgagcggaggtacttttagctcatacgccattagctgggtgcgacaggctcctggtcaggg cctcgaatggatgggcggcattatcacaatctttggtactgcaaattatgcccagaaatttcaggt agagtcacaattaccgcagacaaaagtacctcaaccgcatacatggaactgagtagcctgcgttc cgaagatacagctgtgtattactgtgcgcgcggtgctacaggtttctacgacgtttggggccaggg gaccttagtcactgtgtctagc | 541 |
| 1D9 | VL | ctgcctgtgctgactcagccacccctcagcgtctgggaccccgggcagagggtcaccatctcttg ttctggaagcagctccaacatcggaagtaatactgtaaactggtaccagcagctcccaggaacgg cccccaaactcctcatctatagtaataatcagcggccctcaggggtccctgaccgattctctggctc caagtctggcacctcagcctccctggccatcagtgggctccagtctgaggatgaggctgattatta ctgtgcagcatgggatgacagcctgaatggtccggtattcggcggagggaccaagctgaccgtc ctag | 542 |
| 1E6 | VH | caggttcaattagtgcagtctggtgctgaagtgaaaaagcccggctcaagtgttaaagtaagctgt aaggcgagcggagttactttcagctcatacgccattagctgggtgcgacaggctcctggtcaggg cctcgaatggatgggcggcattagccctatcttcggcactgcaaattatgcccagaaatttcaggt agagtcacaattaccgcagatgaaagcacgtcaactgcatacatggaactgagtagcctgcgttc cgaagatacagctgtgtattactgtgcgcgcggtcgtgagtactacgctagtaatggtgacagtttc gatgtttggggccaggggaccttagtcactgtgtctagc | 543 |
| 1E6 | VL | cagcctgtgctgactcagccacccctcggtgtcagtggccccaggaaagacggccagcatttcctg tgagggaaacaacattgcgactaaaagtgtgcactggtaccagcagaagtcaggccacgcccct gtggtggtcgtctatcatgatagcgaccggccctcaggggtccctgaccgattctctggctccaag tctggcacctcagcctccctggccatcagtgggctccggtccgaggatgaggctgattattactgt gcagcatgggatgacagcctgagtggtcctgggtgttcggcggagggaccaagctgaccgtccc tag | 544 |
| 1F1 | VH | caggttcaattagtgcagtctggtgctgaagtgaaaaagcccggctcaagtgttaaagtaagctgt aaggcgagcggaggtacattagttcatacgccattagctgggtgcgacaggctcctggtcaggg cctcgaatggatgggcggcattagcgcaatcttcggcactgcaaattatgcccagaaatttcaggg tagagtcacaattaccgcagatgagagcacgcgcaccgcatacatggaactgagtagcctgcgtt ccgaagatacagctgtgtattactgtgcgcgcggtagtggttactacgttgctgctagtggtgctttc gacgtgtggggccaggggaccttagtcactgtgtctagc | 545 |
| 1F1 | VL | cagcctgggctgactcagccacccctcggtgtcaaagggcttgagacagaccgccacactcacct gcactgggaacatcaacaatgttggcgaccaaggagcaggttggctgcagcagcaccagggcc gccctcccaaactcctgtcgtacaggaatagcaaccggccctcaggtgtctcagagagattctctg catccaggtcaggaaatacagcctcccctgaccattactggactccagcctgaggacgaggctga ctattactgctcagcatgggacagcagcctcagtgattgggtgttcggcggagggaccaagctga ccgtcctag | 546 |
| 1F12 | VH | caggttcaattagtgcagtctggtgctgaagtgaaaaagcccggctcaagtgttaaagtaagctgt aaggcgagcggtggcatcttcagctcatacgccattagctgggtgcgacaggctcctggtcagg gcctcgaatggatgggcggcatcaccccaatcttcggcactgcaaattatgcccagaaatttcagg gtagagtcacaattaccgcagacgaaagcacgcgtaccgcatatatggaactgagtagcctgcgt tccgaagatacagctgtgtattactgtgcgcgcgaccgagtcgtgacagtctgaatctgcctggta gtagtcctggttacgatctctggggccaggggaccttagtcactgtgtctagc | 547 |
| 1F12 | VL | gaaacgacactcacgcagtctccaggcaccctgtctttgtctccaggagaaagagccaccctctc ctgcagggccagtcagagtgttagcagcaacttagcctggtaccagcagaaacctggccaggct cccaggctcctcatctatggtgcatccaccagggccactggtatcccagccaggttcagtggcag tgggtctgggacagagttcactctcaccatcagcagcctgcagtctgaagattttgcagtgtattact gtcagcagtatagtagttctccctacacttttggccaggggaccaaactggagatcaaac | 548 |
| 1F3 | VH | caggttcaattagtgcagtctggtgctgaagtgaaaaagcccggctcaagtgttaaagtaagctgt aaggcgagcggagtgattttcagctcatacgccattagctgggtgcgacaggctcctggtcaggg cctcgaatggatgggcggcattagccctatcttcggcactgcaaattatgcccagaaatttcaggt agagtcacaattaccgcagatgagagcacgtcaaccgcatatatggaactgagtagcctgcgttc cgaagatacagctgtgtattactgtgcgcgcagtcgtggtacgctcctggtacaagtttccactac gatgtgtggggccaggggaccttagtcactgtgtctagc | 549 |
| 1F3 | VL | ctgcctgtgctgactcaggcacccctcaatgtcagtggccccaggaaagacggccagtattacctg tggggagacaacattggaagtaaaagtgtgcactggtaccagcagaagccaggccaggcccc tgtgctggtcatgtattatgatagcgaccggccctcagggatccctgagcgattctctggctccaac tctgggaacacgccaccctgaccatcagcagggtcgaggccggggatgaggccgactatact gccagctgtgggatcatactaattctcatgtggtcttcggcggaaggaccaaactgaccgtcctag | 550 |

TABLE 7-continued

Nucleic acid sequences of the light and
heavy chains for the anti-H1CA0409 antibodies.

| anti-H1CA0409 Ab | VH or VL | Nucleic Acid Sequence | SEQ ID NO: |
|---|---|---|---|
| 1F5 | VH | caggttcaattagtgcagtctggtgctgaagtgaaaaagcccggctcaagtgttaaagtaagctgt aaggcgagcggtggcacctttagttcttacgccattagctgggtgcgacaggtcctggtcaggg cctcgaatggatgggcggcattagcccaatctttggcactgcaaattatgcccagaaatttcagggt agagtcacaattacctcagatgagagtaccagcactgcatacatggaactgagtagcctgcgttcc gaagatacagctgtgtattactgtgcgcgcgaccaaggtggtacacgtggtaattacttcgacgta gggggccaggggaccttagtcactgtgtctagc | 551 |
| 1F5 | VL | cagcctgtgctgactcagccacccctcggtgtccaagggcttgagacagaccgccacagtcacct gcactgggaacagcaacaatgttggcaaccaaggagcagcttggctgcagcagcaccagggc caccctcccaaactcctatcctacaggaataacaaccggcctcagggatttcagagagttatctct gcatccaggtcaggaaacacagcctccctgaccattgctggactccagcctgaggacgaggctg actattactgctcagcatgggacaacaccgtcagtggttgggtgttcggcggagggaccagggtg accgtcctag | 552 |
| 1F6 | VH | caggttcaattagtgcagtctggtgctgaagtgaaaaagcccggctcaagtgttaaagtaagctgt aaggcgagcggtggtactttcagttcatacgccattagctgggtgcgacaggtcctggtcaggg cctcgaatggatgggcggcattatcacaatcttcggtactgcaaattatgcccagaaatttcagggt agagtcacaattaccgcagatgagagcacgaacaccgcctacatggaactgagtagcctgcgtt ccgaagatacagctgtgtattactgtgcgcgcggtggtggtggtcgttttgacgtttggggccagg ggaccttagtcactgtgtctagc | 553 |
| 1F6 | VL | tcctatgagctgactcagccacccctcagtgtctgggaccccgggcagagggtcaccatctcttgt tctggaagcacctccaacatcggaaataatgctctaaactggtaccagaaactcccagggacggc cccaaactcctcatctatagtcttaatcagcgtccctcaggggtccctgaccgattctctggctcca gtctggcacctcagcctccctggccatcagtgggctccagtctgaggatgaggctgattattact gtgaagcatgggatgacagcctgagtggtccggtgttcggcggagggaccaaggtgaccgtcct ag | 554 |
| 1H2 | VH | caggttcaattagtgcagtctggtgctgaagtgaaaaagcccggctcaagtgttaaagtaagctgt aaggcgagcggaggtccatttcgctcatacgccattagctgggtgcgacaggtcctggtcagg gcctcgaatggatgggcggcattatcccaatcttcggcactgcaaattatgcccagaaatttcagg gtagagtcacaattaccgcagatgaaagtacgtcaactgcatacatggaactgagtagcctgcgtt ccgaagatacagctgtgtattactgtgcgcgcggtggtggtttacagttttgatgtgtggggccaggg gaccttagtcactgtgtctagc | 555 |
| 1H2 | VL | cagtctgggctgactcagccacccctcagcgtctgggaccccgggcagagggtcaccatttcttg ttctggaagcggctccaacgtcggaagtaatgttgtaaattggtaccagcatctcccaggaacggc cccaaactcctcatctatcgtaataatcagcggccctcagggtccctgaccgattctctggctcc aagtctggcacctcagcctccctggccatcagtgggctccagtctgaggatgaggctgattatatt gtgcagcatgggatgacagactgaatggctttgtctttggtactgggacgaaggtcaccgtcctga | 556 |
| 1H4 | VH | caggttcaattagtgcagtctggtgctgaagtgaaaaagcccggctcaagtgttaaagtaagctgt aaggcgagcggtgttcctttcagttcttacgccattagctgggtgcgacaggtcctggtcagggc ctcgaatggatgggcggcatcagcccactgtttggtactgcaaattatgcccagaaatttcagggt agagtcacaattaccgcagaccagagcacgtcaaccgtctacatggaactgagtagcctgcgttc cgaagatacagctgtgtattactgtgcgcgcggtctgggtacatacagtcctagtctgtaccctcgt ggtatggacgtttggggccaggggaccttagtcactgtgtctagc | 557 |
| 1H4 | VL | ctgcctgtgctgactcagccacccctcagcgtctgggaccccggacgagtgtcaccatctcttgt tctggaagcagctccaacatcggcagaaatgatgttaactggtaccagcaattcccgggaagggc cccaaactcctcatctatggtcgtgatgagcggccctcggggtccctgcccgattctctggctcc aagtctggcacctcagcctccctggccatcagtgggctccagtctgaggatgaggctgattattac tgtgctgcatgggatgccagtctgatgatctatgtcttcggaactgggaccacggtcaccgtcctg g | 558 |
| 1H8 | VH | caggttcaattagtgcagtctggtgctgaagtgaaaaagcccggctcaagtgttaaagtaagctgt aaggcgagcggagtgacctttagttcatacgccattagctgggtgcgacaggtcctggtcaggg cctcgaatggatgggcggcatcagcccatgttcggcactgcaaattatgcccagaaatttcaggg tagagtcacaattaccgcagacgaaagtacgaatactgtctatatggaactgagtagcctgcgttc cgaagatacagctgtgtattactgtgcgcgcggtcgtgcttacctgagtgttcgtggtagtttcgac gtgtggggccaggggaccttagtcactgtgtctagc | 559 |
| 1H8 | VL | tcctatgagctgactcagccacccctcagtgtctgggaccccgggcagagggtcaccatctcttgt tctggaagcagctccaacatcggaagtaacactgtaaactggtaccagcagctcccaggaacggc cccaaactcctcatctatagtaataatcagcggccctcaggggtccctgaccgattctctggctc caagtctggcacctcagcctccctggccatcagtgggctccagtctgaggatgaggctgattatta ctgtgcagcatgggatgacagcctgaatggttatgtcttcggaactgggaccaaggtcaccgtcct ag | 560 |
| 2A1 | VH | caggttcaattagtgcagtctggtgctgaagtgaaaaagcccggctcaagtgttaaagtaagctgt aaggcgagcggtgtgattttcagttcttacgccattagctgggtgcgacaggtcctggtcagggc ctcgaatggatgggcggcatcatcccaatctttggcactgcaaattatgcccagaaatttcaggta gagtcacaattaccgcagataaaagtacgtcaactgcctatatggaactgagtagcctgcgttccg | 561 |

TABLE 7-continued

Nucleic acid sequences of the light and
heavy chains for the anti-H1CA0409 antibodies.

| anti-H1CA0409 Ab | VH or VL | Nucleic Acid Sequence | SEQ ID NO: |
|---|---|---|---|
| | | aagatacagctgtgtattactgtgcgcgcggtggtagtggtagtttcgacgtttggggccaggggaccttagtcactgtgtctagc | |
| 2A1 | VL | cagcctgggctgactcagccaccctcagcgtctgggaccccgggcagagggtcaccatctcttgttctggaagcagttccaacctcggaagtaattatgtcttctggtaccagcacctcccaggagcggccccccaaactcctcatctatagaaatagtcagcggccctctgggattccctgaccgattctctggctccaagtctggcacctcagcctccctggccatcagtgggctccagtctgaggatgaggctgattattactgtgcagcatgggatgacagcctgaatggtgtggtattcggcggagggaccaagctgaccgtcctag | 562 |
| 2A11 | VH | caggttcaattagtgcagtctggtgctgaagtgaaaaagcccggctcaagtgttaaagtaagctgtaaggcgagcggagtgactttcagctcttacgccattagctgggtgcgacaggctcctggtcagggcctcgaatggatgggcggcatcagccctgtgtttggtactgcaaattatgcccagaaatttcaggtagagtcacaattaccgcagatgatagtacgaataccgcctacatggaactgagtagcctgcgttccgaagatacagctgtgtattactgtgcgcgcagtcgtggttacacagttagtagtctggctggtcgttacttcgaccagtggggccaggggaccttagtcactgtgtctagc | 563 |
| 2A11 | VL | gaaacgacactcacgcagtctccaggcaccctgtccttgtctccaggggaaagagcctccctctcctgcaaggccagtgagagtctttgcagcacttgcttggcctggtaccagcagaaacctggccaggctcccaggctcatcgtctatggtgcaaccagcagggccactggcatcccagacaggttcagtggcagtgggtctgggacagacttcactctcaccatcagcagactggagcctgaagattttgcagtgtattactgtcagcagtatggtagctcacctcagacgttcggccaagggaccaaggtggaaatcaaac | 564 |
| 2A12 | VH | caggttcaattagtgcagtctggtgctgaagtgaaaaagcccggctcaagtgttaaagtaagctgtaaggcgagcggaggcacttttagctcatacgccattagctgggtgcgacaggctcctggtcagggcctcgaatggatgggcggcatcgtgccactgtaggcactgcaaattatgcccagaaatttcagggtagagtcacaattaccgcagacgaaagtaccagcactgcatatatggaactgagtagcctgcgttccgaagatacagctgtgtattactgtgcgcgcggtctgggtctgtactttgacgtgtggggccaggggaccttagtcactgtgtctagc | 565 |
| 2A12 | VL | cagactgtggtgactcaggagccctcactgactgtgtccccaggagagacagtcactctcacctgtgcttccagcactggagcagtcaccagtggttactatccaaactggttccagcagaaacctggacaagcacccagggcactgatttatagtacaagcaacaaacactcctggaccctgcccggttctcaggctcccctcctggggcaaagctgccctgacactgtcaggtgtgcagcctgaggacgaggctgagtattattgtctgctctactatggtggtccttgggtgttcggcggagggaccaagttgaccgtcctgg | 566 |
| 2B11 | VH | caggttcaattagtgcagtctggtgctgaagtgaaaaagcccggctcaagtgttaaagtaagctgtaaggcgagcggtggtactttcagctcatacgccattagctgggtgcgacaggctcctggtcagggcctcgaatggatgggcggcattatcccaatcttcggtactgcaaattatgcccagaaatttcagggtagagtcacaattaccgcagacgaaagcacgaacaccgcctacatggaactgagtagcctgcgttccgaagatacagctgtgtattactgtgcgcgcgttcgtggtggttacggtccttacggtgactttgacgtttggggccaggggaccttagtcactgtgtctagc | 567 |
| 2B11 | VL | cagcctgggctgactcagccaccctcagcgtctgggaccccgggcagagggtcaccatctcttgttctggaagcagctccaacatcggaagtcattctgtgaactggtaccggcagctcccaggaacggccccccaactcctcatctatggtaacagcaatcggccctcaggggtccctgaccgattctctggctccaagtctggcacctcagcgtccctggccatcagtgggctccagtctgaggatgaggctgattattttctgtgcggcatgggatgacggcctgagtggtgggtgttcggcggagggaccaaattgaccgtcctag | 568 |
| 2B6 | VH | caggttcaattagtgcagtctggtgctgaagtgaaaaagcccggctcaagtgttaaagtaagctgtaaggcgagcggtggcccttttagctcatacgccattagctgggtgcgacaggctcctggtcagggcctcgaatggatgggcggcattagccccaatcttcggcactgcaaattatgcccagaaatttcagggtagagtcacaattaccgcagataagagtacgaacaccgcatacatggaactgagtagcctgcgttccgaagatacagctgtgtattactgtgcgcgcggtcgtagttacatcgttagtgttagtcctggttttgacgtgtggggccaggggaccttagtcactgtgtctagc | 569 |
| 2B6 | VL | cagtctgtgctgactcagccaccctccgcgtccgggtctcctggacagtcagtcaccatctcctgcactggaaccagcagtgacgttggtggttataactatgtctcctggtaccaacagtacccaggcaaagcccccaaactcatgatttatgaggtcagtaagcggccctcaggggtccctgatcgtttctctggctccaagtctggcacctcagcctccctggccatcagtgagctccaatctgaggatgaggctgattattactgtgcatcatgggatgacagcctgaatgcttatgtcttcggaagtgggaccaaggtcaccgtcctgg | 570 |
| 2C1 | VH | caggttcaattagtgcagtctggtgctgaagtgaaaaagcccggctcaagtgttaaagtaagctgtaaggcgagcggaggcattttcagttcatacgccattagctgggtgcgacaggctcctggtcagggcctcgaatggatgggcggcatcagcgcaatctttggtactgcaaattatgcccagaaatttcagggtagagtcacaattaccgcagatgagagtaccagccgcatatatggaactggagtagcctgcgttccgaagatacagctgtgtattactgtgcgcgcgcagtcgtggtatcgctagtggttacacagcttacatggattattggggccaggggaccttagtcactgtgtctagc | 571 |
| 2C1 | VL | tcttctgagctgactcaggaccctgctgtgtctgtggccttgggacagacagtcaggatcacatgccaaggagacagcctcagaaacctcttacgcaagctggtaccagcagaagccaggccagtcccct | 572 |

TABLE 7-continued

Nucleic acid sequences of the light and
heavy chains for the anti-H1CA0409 antibodies.

| anti-H1CA0409 Ab | VH or VL | Nucleic Acid Sequence | SEQ ID NO: |
|---|---|---|---|
| | | gtactggtcatctatcaaagtactaagcggccctcagggatccctgagcgattctctgcctccagct caggaaacacagcttccctgaccatcactggggctcaggcggaagatgaggctgactattactgt aactcccggggcagcgggggtaaccccctatgtcttcggaactgggaccaaggtcaccgtcctg | |
| 2E1 | VH | caggttcaattagtgcagtctggtgctgaagtgaaaaagcccggctcaagtgttaaagtaagctgt aaggcgagcggtggcatttttccgttcatacgccattagctgggtgcgacaggctcctggtcaggg cctcgaatggatgggcggcattatcccaatgttcggtactgcaaattatgcccagaaatttcaggg tagagtcacaattaccgcagatgagagtacgactactgtctatatggaactgagtagcctgcgttcc gaagatacagctgtgtattactgtgcgcgcggtgctggtagtacatttgatgtgtggggccagggg accttagtcactgtgtctagc | 573 |
| 2E1 | VL | cagtctgtgctgactcagccacccctcagcgtctgggaccccgggcagagggtcaccatctcttg ttctggaagcagctccaacatcggaagtaatactgtaaactggtaccagcagctcccaggaacgg ccccagactcctcatctatagtaataatcagcggccctcagggtccctgaccgattctctggctc caagtctggcacctcagcctccctggccatcagtgggctccagtctgaggatgaggctgattatta ctgtgcagcatgggatgacagcctgaatggtcgggtgttcggcggagggaccaagctgaccgtc ctag | 574 |
| 2E11 | VH | caggttcaattagtgcagtctggtgctgaagtgaaaaagcccggctcaagtgttaaagtaagctgt aaggcgagcggtggtaccttcagctcatacgccattagctgggtgcgacaggctcctggtcagg gcctcgaatggatgggcggcattaaccctatattggtactgcaaattatgcccagaaatttcaggg tagagtcacaattaccgcagatgagagcacgaatactgcctacatggaactgagtagcctgcgttc cgaagatacagctgtgtattactgtgcgcgcggtgagagtgcttactacagtcgtaattacgatgtg tggggccaggggaccttagtcactgtgtctagc | 575 |
| 2E11 | VL | tcctatgagctgactcagccacccctcggtgtccaagggcttgagacagaccgccacactcacctg cactgggaacagcagcaatgttggcaaccaaggagcatcttggctgcagcagcaccagggcca cccctcccaaactcctatcctacaggaatgacaaccggccctcagggatctcagagagattctctgc atccaggtcaggaaatacagcctccctgaccattactggactccagcctgaggacgaggctgact attactgctcagcatgggacaacagcctcagtgcttgggtgttcggtggagggaccaagctgacc gtcctag | 576 |
| 2E12 | VH | caggttcaattagtgcagtctggtgctgaagtgaaaaagcccggctcaagtgttaaagtaagctgt aaggcgagcggtgtgactttagctcatacgccattagctgggtgcgacaggctcctggtcaggg cctcgaatggatgggcggcatcagcccaatgttcggcactgcaaattatgcccagaaatttcagg gtagagtcacaattaccgcagatgagagcacgaataccgcatatatggaactgagtagcctgcgt tccgaagatacagctgtgtattactgtgcgcgcggtggtggttactaccctgctggtgttggtcgtta tgatgtagggggccaggggaccttagtcactgtgtctagc | 577 |
| 2E12 | VL | gacatcgtgatgacccagtctccagactccctggctgtgtctctgggcgagagggccaccatcaa ctgcaagtccagccagaatgttttatacagctccaacaataagaataacttagcttggtaccaacaa agaccaggacagcctcctaaagtgctcctttattgggcatctacccgggcatccggggtccctga ccgattcagtggcagcgggtctgggacagatttcactctcaccatcaacagccttcaggctgaag atgtggcactttattactgtcaacaatattatggtaaacccttcactttcggccctgggaccaaagtg gagatcaaac | 578 |
| 2F1 | VH | caggttcaattagtgcagtctggtgctgaagtgaaaaagcccggctcaagtgttaaagtaagctgt aaggcgagcggaggtaccttttagctcatacgccattagctgggtgcgacaggctcctggtcagg gcctcgaatggatgggcggcattaccctctgttcggcactgcaaattatgcccagaaatttcagg gtagagtcacaattaccgcagacgatagtacgtcaactgcatatatggaactgagtagcctgcgtt ccgaagatacagctgtgtattactgtgcgcgcggtcctacactgtacagtcctcctgttttttgatgtgt ggggccaggggaccttagtcactgtgtctagc | 579 |
| 2F1 | VL | cagactgtggtgactcaggagccatcgttctcagtgtccctggagggacaatcaccctcacttgt ggcttgagttctggctcagtctctactactaattatcccagctggtaccagcagaccccaggccga actccacgcacgctcatctacaacacaaacactcgctcttcgtggccctgatcgtctctggct ccatccttgggaacaaagctgccctcaccatcacgggggcccaggcaggtgatgaatctgattat tactgtgttttatatatgggtcgtggcatttatgtcttcggaagtgggaccaaggtctccgtcctgg | 580 |
| 2G3 | VH | caggttcaattagtgcagtctggtgctgaagtgaaaaagcccggctcaagtgttaaagtaagctgt aaggcgagcggaggcacttttcgctcttacgccattagctgggtgcgacaggctcctggtcaggg cctcgaatggatgggcggcatcatgccaatcttggtactgcaaattatgcccagaaatttcaggt agagtcacaattaccgcagacgagagtacgacaaccgtgtacatggaactgagtagcctgcgttc cgaagatacagctgtgtattactgtgcgcgcggtgctggtgttagtgctggtcctagttggcctttttg acgtttggggccaggggaccttagtcactgtgtctagc | 581 |
| 2G3 | VL | cagcctgggctgactcagccacccctcggtgtccaaggacttgaggcagaccgccacactcacct gcactgggaacagcaacaatgttggcaaacaaggagctacttggctgcagcagcaccagggcc acccctcccaaactcctatcctacaggaataacaaccggccctcagggatctcagagagattctctg catccaggtcaggagacacagcctccctgaccattactggcctccagcctgaggacgaggctga ctattactgctcagcatgggacagcagcctcagtgtatgggtgttcggcggagggaccaagctga ccgtcctag | 582 |

TABLE 7-continued

Nucleic acid sequences of the light and
heavy chains for the anti-H1CA0409 antibodies.

| anti-H1CA0409 Ab | VH or VL | Nucleic Acid Sequence | SEQ ID NO: |
|---|---|---|---|
| 2G4 | VH | caggttcaattagtgcagtctggtgctgaagtgaaaaagcccggctcaagtgttaaagtaagctgt aaggcgagcggtggtaccttcagctcatacgccattagctgggtgcgacaggctcctggtcagg gcctcgaatggatgggcggcattagccctatgtttggtactgcaaattatgcccagaaatttcaggg tagagtcacaattaccgcagatgagagcacgtcaaccgtgtacatggaactgagtagcctgcgtt ccgaagatacagctgtgtattactgtgcgcgcagtcgtggttacaatgttgctgctagtttcggtttc gatgtgtggggccaggggaccttagtcactgtgtctagc | 583 |
| 2G4 | VL | gaaattgtgttgacgcagtctccatccttcctgtctgcatctgtaggagacagagtcaccatcacttg ccgggccagtcagtacattgatcgtagcttacactggtaccagcagaaaccagatcagtctccaa agctcctcatcaagtatgcttctcagtccatctcaggggtcccctcgaggttcagtggcagtggatc tgggacagatttcagcctcaccatcaatagcctggaaactgaagatgctgcaacctattactgccat cagaccagtagttttgccgtggacattcggccaagggaccacggtgaaatcaaac | 584 |
| 2H3 | VH | caggttcaattagtgcagtctggtgctgaagtgaaaaagcccggctcaagtgttaaagtaagctgt aaggcgagcggtggcccatttagctcatacgccattagctgggtgcgacaggctcctggtcagg gcctcgaatggatgggcggcatcatccctatcttcggcactgcaaattatgcccagaaatttcagg gtagagtcacaattaccgcagatgaaagtacgtcaaccgcctatatggaactgagtagcctgcgtt ccgaagatacagctgtgtattactgtgcgcgcggtacagactacagtggttaccgtggttttgacgt ttggggccaggggaccttagtcactgtgtctagc | 585 |
| 2H3 | VL | cagactgtggtgactcaggagccatcgttctcagtgtccctggagggacagtcacactcacctgt gctttgagttctggctcagtctccagttttaactacgccagctggtaccagcagaccccaggccag gcgccacgcacactcatctccaacacaaacactcgctcttctggggtccctgatcgcttctctggct ccatccttgggaacaaagctaccctcaccatcacggggcccaggcagatgatgaatctcattatt actgtgcactgtatgtgggtggtggcatttccgtgttcggcggagggaccaagttgaccgtcctag | 586 |
| 2H4 | VH | caggttcaattagtgcagtctggtgctgaagtgaaaaagcccggctcaagtgttaaagtaagctgt aaggcgagcggtgttactttagctcatacgccattagctgggtgcgacaggctcctggtcagggc ctcgaatggatgggcggcatcacccccaatctaggcactgcaaattatgcccagaaatttcagggt agagtcacaattaccgcagatcagagtacgagcactgcatacatggaactgagtagcctgcgttc cgaagatacagctgtgtattactgtgcgcgcggtggtggtgttttcgacgtttggggccaggggac cttagtcactgtgtctagc | 587 |
| 2H4 | VL | tcctatgagctgactcagccaccctcggtgtctggagcccccgacagagggtcaccatctcctgt tctggaagcagctccaacatcggaaataatgctgtaaactgttaccagcagctcccaggaaagg ctcccaaactcctcatctattatgatgatatgctgccctcagggtctctgaccgattctctggctcca agtctggctcctcagcctccctggccatcagtgggctccagtctgaggatgaggctgactattattg tgcagcatgggatgacagcctgagcggtccggttttcggcggagggaccaacctgaccgtcctag | 588 |
| 4C4 | VH | caggttcaattagtgcagtctggtgctgaagtgaaaaagcccggctcaagtgttaaagtaagctgt aaggcgagcggaggtactttttagttcttacgccattagctgggtgcgacaggctcctggtcagggc cctcgaatggatgggcggcattagccctatgttcggtactgcaaattatgcccagaaatttcagggt agagtcacaattaccgcagacaaaagtaccagcactgcctacatggaactgagtagcctgcgttc cgaagatacagctgtgtattactgtgcgcgcgagggtggtacagtcctggtggtgttgacttcgac tactggggccaggggaccttagtcactgtgtctagc | 589 |
| 4C4 | VL | aattttatgctgactcagcccccactctgtgtcggagtctccggggaagacggtaaccatctcctgca cccgcagcagtggcagcattgccagcacctatgtgcagtggtaccggcagcgcccgggcagtg ccccaccactgtgatctatgaggatcatcagagaccctctggggtccctgatcggttctccggct ccctcgacagctcctccaactctgcctccctcaccatctctggactgaggactgaggacgcggca acctactactgtcagtcttttgatgccagcactctggtgttcggcggcgggaccaagctgaccgtc ctcg | 590 |
| 4F5 | VH | caggttcaattagtgcagtctggtgctgaagtgaaaaagcccggctcaagtgttaaagtaagctgt aaggcgagcggagtgacttttcgttcatacgccattagctgggtgcgacaggctcctggtcaggg cctcgaatggatgggcggcatcagcggtatctttggtactgcaaattatgcccagaaatttcagggt agagtcacaattaccgcagatgagagcacgtcaaccgcatatatggaactgagtagcctgcgttc cgaagatacagctgtgtattactgtgcgcgcagtcctgcttactacttcggtcctaatatggacgtgt ggggccaggggaccttagtcactgtgtctagc | 591 |
| 4F5 | VL | cagtctgtgctgactcagccaccctcagtgtctggggcccagggcagagggtcaccatctcctg cactgggagcagctccaacatcggggcaggttatgatgtacactggtaccagcaacttccaggaa cagtcccaaaactcatcatctatgataatagcaatcggccctcaggggtccctgcccgattctctgg ctccaagtctggcacctcagcctccctggccatcagtgggctccagtctgaggatgaggccgcat attattgccagtcgtatgacagcagcctgagtgttgtggtattcggcggtgggaccaagctgtccgt cctag | 592 |

TABLE 7-continued

Nucleic acid sequences of the light and heavy chains for the anti-H1CA0409 antibodies.

| anti-H1CA0409 Ab | VH or VL | Nucleic Acid Sequence | SEQ ID NO: |
|---|---|---|---|
| 5A8 | VH | caggttcaattagtgcagtctggtgctgaagtgaaaaagcccggctcaagtgttaaagtaagctgt aaggcgagcggtggtacttttagttcatacgccattagctgggtgcgacaggctcctggtcaggg cctcgaatggatgggcggcattagcccaatctttggtactgcaaattatgcccagaaatttcaggg agagtcacaattaccgcagacgaaagcaccagcactgtgtacatggaactgagtagcctgcgttc cgaagatacagctgtgtattactgtgcgcgcggtcctggttaccaccctgctggtgctagtggtcaa ttctttgatctttggggccaggggaccttagtcactgtgtctagc | 593 |
| 5A8 | VL | tcctatgagctgactcagccaccctcggtgtccaaggacttgagacagaccgccacactcacctg cactgggaacagcaacaatgttggcaaccaaggagcagcttggctgcagcagcaccagggcca ccctcccaaactcctatcctacaggaataaccaccggccctcaggatctcagacagatcatctgc atccaggtcaggagacacagcctcctgaccattactggactccagcctgaggacgaggctgac tattactgctcagcatgggacagcagcctcagtgcttgggtgttcggcggagggaccaagctgac cgtcctag | 594 |
| 5B9 | VH | caggttcaattagtgcagtctggtgctgaagtgaaaaagcccggctcaagtgttaaagtaagctgt aaggcgagcggtgtgaccttcagctcatacgccattagctgggtgcgacaggctcctggtcagg gcctcgaatggatgggcggcattagccctatgtttggtactgcaaattatgcccagaaatttcaggg tagagtcacaattaccgcagatgaaagcaccaacaccgcctatatggaactgagtagcctgcgtt ccgaagatacagctgtgtattactgtgcgcgcggtcgtggttacgctcctgacgctctgacaaatttt gacgtttggggccaggggaccttagtcactgtgtctagc | 595 |
| 5B9 | VL | gaaattgtgctgactcagtctccagactccctggctatgtctctgggcgagagggccaccgtcaac tgcaagtccagccggagtctttcgacagctccgacaataagaactacttagcttggtaccagaag aaaccaggacagcctcctcaattgctcatttactgggcatctacccgacaatccggggtccctgac cgattcagtggcagcgggtctgggacagatttcactctcaccatcagcagcctgcaggctgaaga tgtggcagtttattactgtcagcaatattttagtagtcctcccatattccttcggccctgggaccaa agtggagatcaaac | 596 |
| 6F3 | VH | caggttcaattagtgcagtctggtgctgaagtgaaaaagcccggctcaagtgttaaagtaagctgt aaggcgagcggtggtccatttagctcatacgccattagctgggtgcgacaggctcctggtcaggg cctcgaatggatgggcggcattagccctatgtttggtactgcaaattatgcccagaaatttcaggg agagtcacaattaccgcagatgaaagcacgtcaaccgtgtacatggaactgagtagcctgcgttc cgaagatacagctgtgtattactgtgcgcgcggttacagttactaccctggtggtggtggtggtcgt aatttcgactactggggccaggggaccttagtcactgtgtctagc | 597 |
| 6F3 | VL | ctgcctgtgctgactcagccaccctcagcgtctgggaccccgggcagagggtcaccatctcttg ttctggaagcagctccaacatcggaagtaatactgtaaactggtaccagcagctcccaggaacgg ccccccaaactcctcatctatagtaataatcagcggccctcagggtccctgaccgattctctggctc caagtctggcacctcagcctccctggccatcagtgggctccagtctgagggtgaggctgattatta ctgtgcagcatgggatgacagcctgaaggtcgggtgttcggcggagggaccaaggtgaccgt cctag | 598 |
| 9H3 | VH | caggttcaattagtgcagtctggtgctgaagtgaaaaagcccggctcaagtgttaaagtaagctgt aaggcgagcggaggtatctttagttcttacgccattagctgggtgcgacaggctcctggtcagggg cctcgaatggatgggcggcattagcccaatcttcggtactgcaaattatgcccagaaatttcaggg agagtcacaattaccgcagatgagagcacgaacaccgcctatatggaactgagtagcctgcgttc cgaagatacagctgtgtattactgtgcgcgcagtggtggttactacgactacggtgttggttacgac caatggggccaggggaccttagtcactgtgtctagc | 599 |
| 9H3 | VL | cagcctgtgctgactcagccaccctcagcgtctgggaccccgggcagagggtcaccatctcttg ttctggaggcaggtccaacatcggaagtaatactgttaactggtaccagcagctcccaggaacgg ccccccaaactcctcatctatagtaataatcaccggccctcaggggtccctgatcgcttctctggctc caagtctggcaacacggcctccctgaccatctctgggctccaggcggaggatgaggctgattatt actgccagtcctatgacagcagcgttgtattcggcggagggaccaagctgaccgtcctag | 600 |

TABLE 8

Nucleic acid sequences of the light and heavy chains for the anti-H1CA0409 antibodies.

| anti-H1CA0409 Ab | VH or VL | Amino Acid Sequence | SEQ ID NO: |
|---|---|---|---|
| 1D9 | VH | QVQLVQSGAEVKKPGSSVKVSCKASGGTFSSYAISWVRQAPG QGLEWMGGIITIFGTANYAQKFQGRVTITADKSTSTAYMELS SLRSEDTAVYYCARGATGFYDVWGQGTLVTVSS | 601 |

TABLE 8-continued

Nucleic acid sequences of the
light and heavy chains for the anti-
H1CA0409 antibodies.

| anti-H1CA0409 Ab | VH or VL | Amino Acid Sequence | SEQ ID NO: |
|---|---|---|---|
| 1D9 | VL | LPVLTQPPSASGTPGQRVTISCSGSSSNIGSNTVNWYQQLPG TAPKLLIYSNNQRPSGVPDRFSGSKSGTSASLAISGLQSEDE ADYYCAAWDDSLNGPVFGGGTKLTVL | 602 |
| 1E6 | VH | QVQLVQSGAEVKKPGSSVKVSCKASGVTFSSYAISWVRQAPG QGLEWMGGISPIFGTANYAQKFQGRVTITADESTSTAYMELS SLRSEDTAVYYCARGREYYASNGDSFDVWGQGTLVTVSS | 603 |
| 1E6 | VL | QPVLTQPPSVSVAPGKTASISCEGNNIATKSVHWYQQKSGHA PVVVVYHDSDRPSGVPDRFSGSKSGTSASLAISGLRSEDEAD YYCAAWDDSLSGPWVFGGGTKLTVL | 604 |
| 1F1 | VH | QVQLVQSGAEVKKPGSSVKVSCKASGGTFSSYAISWVRQAPG QGLEWMGGISAIFGTANYAQKFQGRVTITADESTRTAYMELS SLRSEDTAVYYCARGSGYYVAASGAFDVWGQGTLVTVSS | 605 |
| 1F1 | VL | QPGLTQPPSVSKGLRQTATLTCTGNINNVGDQGAGWLQQHQG RPPKLLSYRNSNRPSGVSERFSASRSGNTASLTITGLQPEDE ADYYCSAWDSSLSDWVFGGGTKLTVL | 606 |
| 1F12 | VH | QVQLVQSGAEVKKPGSSVKVSCKASGGIFSSYAISWVRQAPG QGLEWMGGITPIFGTANYAQKFQGRVTITADESTRTAYMELS SLRSEDTAVYYCARDLSRDSLNLPGSSPGYDLWGQGTLVTVS S | 607 |
| 1F12 | VL | ETTLTQSPGTLSLSPGERATLSCRASQSVSSNLAWYQQKPGQ APRLLIYGASTRATGIPARFSGSGSGTEFTLTISSLQSEDFA VYYCQQYSSSPYTFGQGTKLEIK | 608 |
| 1F3 | VH | QVQLVQSGAEVKKPGSSVKVSCKASGVIFSSYAISWVRQAPG QGLEWMGGISPIFGTANYAQKFQGRVTITADESTSTAYMELS SLRSEDTAVYYCARSRGYAPGTSFHYDVWGQGTLVTVSS | 609 |
| 1F3 | VL | LPVLTQAPSMSVAPGKTASITCGGDNIGSKSVHWYQQKPGQA PVLVMYYDSDRPSGIPERFSGSNSGNTATLTISRVEAGDEAD YFCQLWDHTNSHVVFGGRTKLTVL | 610 |
| 1F5 | VH | QVQLVQSGAEVKKPGSSVKVSCKASGGTFSSYAISWVRQAPG QGLEWMGGISPIFGTANYAQKFQGRVTITSDESTSTAYMELS SLRSEDTAVYYCARDQGGTRGNYFDVWGQGTLVTVSS | 611 |
| 1F5 | VL | QPVLTQPPSVSKGLRQTATVTCTGNSNNVGNQGAAWLQQHQG HPPKLLSYRNNNRPSGISERLSASRSGNTASLTIAGLQPEDE ADYYCSAWDNTVSGWVFGGGTRVTVL | 612 |
| 1F6 | VH | QVQLVQSGAEVKKPGSSVKVSCKASGGTFSSYAISWVRQAPG QGLEWMGGIITIFGTANYAQKFQGRVTITADESTNTAYMELS SLRSEDTAVYYCARGGGGRFDVWGQGTLVTVSS | 613 |
| 1F6 | VL | SYELTQPPSVSGTPGQRVTISCSGSTSNIGNNALNWYQKLPG TAPKLLIYSLNQRPSGVPDRFSGSKSGTSASLAISGLQSEDE ADYYCEAWDDSLSGPVFGGGTKVTVL | 614 |
| 1H2 | VH | QVQLVQSGAEVKKPGSSVKVSCKASGGPFRSYAISWVRQAPG QGLEWMGGIIPIFGTANYAQKFQGRVTITADESTSTAYMELS SLRSEDTAVYYCARGGVYSFDVWGQGTLVTVSS | 615 |
| 1H2 | VL | QSGLTQPPSASGTPGQRVTISCSGSGSNVGSNVVNWYQHLPG TAPKLLIYRNNQRPSGVPDRFSGSKSGTSASLAISGLQSEDE ADYYCAAWDDRLNGFVFGTGTKVTVL | 616 |
| 1H4 | VH | QVQLVQSGAEVKKPGSSVKVSCKASGVPFSSYAISWVRQAPG QGLEWMGGISPLFGTANYAQKFQGRVTITADQSTSTVYMELS SLRSEDTAVYYCARGLGTYSPSLYPRGMDVWGQGTLVTVSS | 617 |
| 1H4 | VL | LPVLTQPPSASGTPGQSVTISCSGSSSNIGRNDVNVVYQQFP GRAPKLLIYGRDERPFGVPARFSGSKSGTSASLAISGLQSED EADYYCAAWDASLMIYVFGTGTTVTVL | 618 |
| 1H8 | VH | QVQLVQSGAEVKKPGSSVKVSCKASGVTFSSYAISWVRQAPG QGLEWMGGISPMFGTANYAQKFQGRVTITADESTNTVYMELS SLRSEDTAVYYCARGRAYLSVRGSFDVWGQGTLVTVSS | 619 |

TABLE 8-continued

Nucleic acid sequences of the light and heavy chains for the anti-H1CA0409 antibodies.

| anti-H1CA0409 Ab | VH or VL | Amino Acid Sequence | SEQ ID NO: |
|---|---|---|---|
| 1H8 | VL | SYELTQPPSVSGTPGQRVTISCSGSSSNIGSNTVNWYQQLPG TAPKLLIYSNNQRPSGVPDRFSGSKSGTSASLAISGLQSEDE ADYYCAAWDDSLNGYVFGTGTKVTVL | 620 |
| 2A1 | VH | QVQLVQSGAEVKKPGSSVKVSCKASGVIFSSYAISWVRQAPG QGLEWMGGIIPIFGTANYAQKFQGRVTITADKSTSTAYMELS SLRSEDTAVYYCARGGSGSFDVWGQGTLVTVSS | 621 |
| 2A1 | VL | QPGLTQPPSASGTPGQRVTISCSGSSSNLGSNYVFWYQHLPG AAPKLLIYRNSQRPSGVPDRFSGSKSGTSASLAISGLQSEDE ADYYCAAWDDSLNGVVFGGGTKLTVL | 622 |
| 2A11 | VH | QVQLVQSGAEVKKPGSSVKVSCKASGVTFSSYAISWVRQAPG QGLEWMGGISPVFGTANYAQKFQGRVTITADDSTNTAYMELS SLRSEDTAVYYCARSRGYTVSSLAGRYFDQWGQGTLVTVSS | 623 |
| 2A11 | VL | ETTLTQSPGTLSLSPGERASLSCKASESLCSTCLAWYQQKPG QAPRLIVYGATSRATGIPDRFSGSGSGTDFTLTISRLEPEDF AVYYCQQYGSSPQTFGQGTKVEIK | 624 |
| 2A12 | VH | QVQLVQSGAEVKKPGSSVKVSCKASGGTFSSYAISWVRQAPG QGLEWMGGIVPLFGTANYAQKFQGRVTITADESTSTAYMELS SLRSEDTAVYYCARGLGLYFDVWGQGTLVTVSS | 625 |
| 2A12 | VL | QTVVTQEPSLTVSPGETVTLTCASSTGAVTSGYYPNWFQQKP GQAPRALIYSTSNKHSWTPARFSGSLLGGKAALTLSGVQPED EAEYYCLLYYGGPWVFGGGTKLTVL | 626 |
| 2B11 | VH | QVQLVQSGAEVKKPGSSVKVSCKASGGTFSSYAISWVRQAPG QGLEWMGGIIPIFGTANYAQKFQGRVTITADESTNTAYMELS SLRSEDTAVYYCARVRGGYGPYGDFDVWGQGTLVTVSS | 627 |
| 2B11 | VL | QPGLTQPPSASGTPGQRVTISCSGSSSNIGSHSVNVVYRQLP GTAPQLLIYGNSNRPSGVPDRFSGSKSGTSASLAISGLQSED EADYFCAAWDDGLSGWVFGGGTKLTVL | 628 |
| 2B6 | VH | QVQLVQSGAEVKKPGSSVKVSCKASGGPFSSYAISWVRQAPG QGLEWMGGISPIFGTANYAQKFQGRVTITADKSTNTAYMELS SLRSEDTAVYYCARGRSYIVSVSPGFDVWGQGTLVTVSS | 629 |
| 2B6 | VL | QSVLTQPPSASGSPGQSVTISCTGTSSDVGGYNYVSWYQQYP GKAPKLMIYEVSKRPSGVPDRFSGSKSGTSASLAISELQSED EADYYCASWDDSLNAYVFGSGTKVTVL | 630 |
| 2C1 | VH | QVQLVQSGAEVKKPGSSVKVSCKASGGIFSSYAISWVRQAPG QGLEWMGGISAIFGTANYAQKFQGRVTITADESTSTAYMELS SLRSEDTAVYYCARDSGIASGYTAYMDYWGQGTLVTVSS | 631 |
| 2C1 | VL | SSELTQDPAVSVALGQTVRITCQGDSLRTSYASWYQQKPGQS PVLVIYQSTKRPSGIPERFSASSSGNTASLTITGAQAEDEAD YYCNSRGGGNPYVFGTGTKVTVL | 632 |
| 2E1 | VH | QVQLVQSGAEVKKPGSSVKVSCKASGGIFRSYAISWVRQAPG QGLEWMGGIIPMFGTANYAQKFQGRVTITADESTTTVYMELS SLRSEDTAVYYCARGAGSTFDVWGQGTLVTVSS | 633 |
| 2E1 | VL | QSVLTQPPSASGTPGQRVTISCSGSSSNIGSNTVNWYQQLPG TAPRLLIYSNNQRPSGVPDRFSGSKSGTSASLAISGLQSEDE ADYYCAAWDDSLNGRVFGGGTKLTVL | 634 |
| 2E11 | VH | QVQLVQSGAEVKKPGSSVKVSCKASGGTFSSYAISWVRQAPG QGLEWMGGINPIFGTANYAQKFQGRVTITADESTNTAYMELS SLRSEDTAVYYCARGESAYYSRNYDVWGQGTLVTVSS | 635 |
| 2E11 | VL | SYELTQPPSVSKGLRQTATLTCTGNSSNVGNQGASWLQQHQG HPPKLLSYRNDNRPSGISERFSASRSGNTASLTITGLQPEDE ADYYCSAWDNSLSAWVFGGGTKLTVL | 636 |
| 2E12 | VH | QVQLVQSGAEVKKPGSSVKVSCKASGVTFSSYAISWVRQAPG QGLEWMGGISPMFGTANYAQKFQGRVTITADESTNTAYMELS SLRSEDTAVYYCARGGGYYPAGVGRYDVWGQGTLVTVSS | 637 |

TABLE 8-continued

Nucleic acid sequences of the light and heavy chains for the anti-H1CA0409 antibodies.

| anti-H1CA0409 Ab | VH or VL | Amino Acid Sequence | SEQ ID NO: |
|---|---|---|---|
| 2E12 | VL | DIVMTQSPDSLAVSLGERATINCKSSQNVLYSSNNKNNLAWY QQRPGQPPKVLLYWASTRASGVPDRFSGSGSGTDFTLTINSL QAEDVALYYCQQYYGKPFTFGPGTKVEIK | 638 |
| 2F1 | VH | QVQLVQSGAEVKKPGSSVKVSCKASGGTFSSYAISWVRQAPG QGLEWMGGITPLFGTANYAQKFQGRVTITADDSTSTAYMELS SLRSEDTAVYYCARGPTLYSPPVFDVWGQGTLVTVSS | 639 |
| 2F1 | VL | QTVVTQEPSFSVSPGGTITLTCGLSSGSVSTTNYPSWYQQTP GRTPRTLIYNTNTRSSGVPDRFSGSILGNKAALTITGAQAGD ESDYYCVLYMGRGIYVFGSGTKVSVL | 640 |
| 2G3 | VH | QVQLVQSGAEVKKPGSSVKVSCKASGGTFRSYAISWVRQAPG QGLEWMGGIMPIFGTANYAQKFQGRVTITADESTTTVYMELS SLRSEDTAVYYCARGAGVSAGPSWPFDVWGQGTLVTVSS | 641 |
| 2G3 | VL | QPGLTQPPSVSKDLRQTATLTCTGNSNNVGKQGATWLQQHQG HPPKLLSYRNNNRPSGISERFSASRSGDTASLTITGLQPEDE ADYYCSAWDSSLSVWVFGGGTKLTVL | 642 |
| 2G4 | VH | QVQLVQSGAEVKKPGSSVKVSCKASGGTFSSYAISWVRQAPG QGLEWMGGISPMFGTANYAQKFQGRVTITADESTSTVYMELS SLRSEDTAVYYCARSRGYNVAASFGFDVWGQGTLVTVSS | 643 |
| 2G4 | VL | EIVLTQSPSFLSASVGDRVTITCRASQYIDRSLHWYQQKPDQ SPKLLIKYASQSISGVPSRFSGSGSGTDFSLTINSLETEDAA TYYCHQTSSLPWTFGQGTTVEIK | 644 |
| 2H3 | VH | QVQLVQSGAEVKKPGSSVKVSCKASGGPFSSYAISWVRQAPG QGLEWMGGIIPIFGTANYAQKFQGRVTITADESTSTAYMELS SLRSEDTAVYYCARGTDYSGYRGFDVWGQGTLVTVSS | 645 |
| 2H3 | VL | QTVVTQEPSFSVSPGGTVTLTCALSSGSVSSFNYASWYQQTP GQAPRTLISNTNTRSSGVPDRFSGSILGNKATLTITGAQADD ESHYYCALYVGGGISVFGGGTKLTVL | 646 |
| 2H4 | VH | QVQLVQSGAEVKKPGSSVKVSCKASGVTFSSYAISWVRQAPG QGLEWMGGITPIFGTANYAQKFQGRVTITADQSTSTAYMELS SLRSEDTAVYYCARGGGVFDVWGQGTLVTVSS | 647 |
| 2H4 | VL | SYELTQPPSVSGAPRQRVTISCSGSSSNIGNNAVNWYQQLPG KAPKLLIYYDDMLPSGVSDRFSGSKSGSSASLAISGLQSEDE ADYYCAAWDDSLSGPVFGGGTNLTVL | 648 |
| 4C4 | VH | QVQLVQSGAEVKKPGSSVKVSCKASGGTFSSYAISWVRQAPG QGLEWMGGISPMFGTANYAQKFQGRVTITADKSTSTAYMELS SLRSEDTAVYYCAREGGYSPGGVDFDYWGQGTLVTVSS | 649 |
| 4C4 | VL | NFMLTQPHSVSESPGKTVTISCTRSSGSIASTYVQWYRQRPG SAPTTVIYEDHQRPSGVPDRFSGSLDSSSNSASLTISGLRTE DAATYYCQSFDASTLVFGGGTKLTVL | 650 |
| 4F5 | VH | QVQLVQSGAEVKKPGSSVKVSCKASGVTFRSYAISWVRQAPG QGLEWMGGISGIFGTANYAQKFQGRVTITADESTSTAYMELS SLRSEDTAVYYCARSPAYYFGPNMDVWGQGTLVTVSS | 651 |
| 4F5 | VL | QSVLTQPPSVSGAPGQRVTISCTGSSSNIGAGYDVHWYQQLP GTVPKLIIYDNSNRPSGVPARFSGSKSGTSASLAISGLQSED EAAYYCQSYDSSLSVVVFGGGTKLSVL | 652 |
| 5A8 | VH | QVQLVQSGAEVKKPGSSVKVSCKASGGTFSSYAISWVRQAPG QGLEWMGGISPIFGTANYAQKFQGRVTITADESTSTVYMELS SLRSEDTAVYYCARGPGYHPAGASGQFFDLWGQGTLVTVSS | 653 |
| 5A8 | VL | SYELTQPPSVSKDLRQTATLTCTGNSNNVGNQGAAWLQQHQG HPPKLLSYRNNHRPSGISDRSSASRSGDTASLTITGLQPEDE ADYYCSAWDSSLSAWVFGGGTKLTVL | 654 |
| 5B9 | VH | QVQLVQSGAEVKKPGSSVKVSCKASGVTFSSYAISWVRQAPG QGLEWMGGISPMFGTANYAQKFQGRVTITADESTNTAYMELS SLRSEDTAVYYCARGRGYAPDALTNFDVWGQGTLVTVSS | 655 |

TABLE 8-continued

Nucleic acid sequences of the
light and heavy chains for the anti-
H1CA0409 antibodies.

| anti-H1CA0409 Ab | VH or VL | Amino Acid Sequence | SEQ ID NO: |
|---|---|---|---|
| 5B9 | VL | EIVLTQSPDSLAMSLGERATVNCKSSRSLFDSSDNKNYLAWY QKKPGQPPQLLIYWASTRQSGVPDRFSGSGSGTDFTLTISSL QAEDVAVYYCQQYFSSPPIFTFGPGTKVEIK | 656 |
| 6F3 | VH | QVQLVQSGAEVKKPGSSVKVSCKASGGPFSSYAISWVRQAPG QGLEWMGGISPMFGTANYAQKFQGRVTITADESTSTVYMELS SLRSEDTAVYYCARGYSYYPGGGGGRNFDYWGQGTLVTVSS | 657 |
| 6F3 | VL | LPVLTQPPSASGTPGQRVTISCSGSSSNIGSNTVNWYQQLPG TAPKLLIYSNNQRPSGVPDRFSGSKSGTSASLAISGLQSEGE ADYYCAAWDDSLKGRVFGGGTKVTVL | 658 |
| 9H3 | VH | QVQLVQSGAEVKKPGSSVKVSCKASGGIFSSYAISWVRQAPG QGLEWMGGISPIFGTANYAQKFQGRVTITADESTNTAYMELS SLRSEDTAVYYCARSGGYYDYGVGYDQWGQGTLVTVSS | 659 |
| 9H3 | VL | QPVLTQPPSASGTPGQRVTISCSGGRSNIGSNTVNWYQQLPG TAPKLLIYSNNHRPSGVPDRFSGSKSGNTASLTISGLQAEDE ADYYCQSYDSSVVFGGGTKLTVL | 660 |

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, chimeric, dAb (domain antibody), single chain, $F_{ab}$, $F_{ab'}$ and $F_{(ab')2}$ fragments, scFvs, and $F_{ab}$ expression libraries.

A single chain Fv ("scFv") polypeptide molecule is a covalently linked $V_H$:$V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the term "epitope" includes any protein determinant capable of specific binding to an immunoglobulin, an scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a influenza epitope when the equilibrium binding constant ($K_d$) is ☐1 ☐M, preferably ☐ 100 nM, more preferably ☐ 10 nM, and most preferably ☐ 100 pM to about 1 pM, as measured by assays such as radioligand binding assays or similar assays known to those skilled in the art.

An influenza protein (e.g., HA or neuramindase) of the invention, or a derivative, fragment, analog, homolog or ortholog thereof, may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to the HA protein of the influenza virus. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the influenza HA protein, with which it is normally reactive, and then add the human monoclonal antibody being tested to determine if the human monoclonal antibody being tested is inhibited in its ability to bind the HA protein. If the human monoclonal antibody being tested is inhibited then, in all likelihood, it has the same, or functionally equivalent, epitopic specificity as the monoclonal antibody of the invention. Screening of human monoclonal antibodies of the invention, can be also carried out by utilizing the influenza virus and determining whether the test monoclonal antibody is able to neutralize the influenza virus.

Various procedures known within the art may be used for the production of polyclonal or monoclonal antibodies directed against a protein of the invention, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of an influenza virus in a sample. The antibody can also be used to try to bind to and disrupt influenza virus cell membrane fusion.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating influenza. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), Momordica Charantia inhibitor, curcin, crotin, Sapaonaria Officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14- labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS(N-hydroxysulfosuccinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab fragments of the antibody of the present invention can be conjugated to the liposomes as described in Martin et al., J. Biol. Chem., 257: 286-288 (1982) via a disulfide-interchange reaction.

Use of Antibodies Against Influenza Virus

Methods for the screening of antibodies that possess the desired specificity include, but are not limited to, enzyme linked immunosorbent assay (ELISA) and other immunologically mediated techniques known within the art.

Antibodies directed against a influenza virus protein such as HA (or a fragment thereof) may be used in methods known within the art relating to the localization and/or quantitation of a influenza virus protein (e.g., for use in measuring levels of the influenza virus protein within appropriate physiological samples, for use in diagnostic methods, for use in imaging the protein, and the like). In a given embodiment, antibodies specific to an influenza virus protein, or derivative, fragment, analog or homolog thereof, that contain the antibody derived antigen binding domain, are utilized as pharmacologically active compounds (referred to hereinafter as "Therapeutics").

An antibody specific for an influenza virus protein of the invention can be used to isolate an influenza virus polypeptide by standard techniques, such as immunoaffinity, chromatography or immunoprecipitation. Antibodies directed against an influenza virus protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, □-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies of the invention, including polyclonal, monoclonal, humanized and fully human antibodies, may used as therapeutic agents. Such agents will generally be employed to treat or prevent an influenza virus-related disease or pathology (e.g., bird flu) in a subject. An antibody preparation, preferably one having high specificity and high affinity for its target antigen, is administered to the subject and will generally have an effect due to its binding with the target. Administration of the antibody may abrogate or inhibit or interfere with the internalization of the virus into a cell. In this case, the antibody binds to the target and masks a binding site of the naturally occurring ligand, thereby blocking fusion the virus to the cell membrane inhibiting internalization of the virus.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding an influenza virus protein or a fragment thereof of the invention, as well as other molecules identified by the screening assays disclosed herein, can be administered for the treatment of an influenza virus-related disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of an influenza virus (or a protein or a protein fragment thereof) in a sample. Preferably, the antibody contains a detectable label. Antibodies can be polyclonal, or more preferably, monoclonal. An intact antibody, or a fragment thereof (e.g., $F_{ab}$, scFv, or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL☐ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with the fusion of an influenza virus to the cell membrane. Also provided are methods of indentifying compounds useful to treat influenza infection. The invention also encompasses compounds identified using the screening assays described herein.

For example, the invention provides assays for screening candidate or test compounds which modulate the interaction between the influenza virus and the cell membrane. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233,409.).

In one embodiment, a candidate compound is introduced to an antibody-antigen complex and determining whether the candidate compound disrupts the antibody-antigen complex, wherein a disruption of this complex indicates that the candidate compound modulates the interaction between an influenza virus and the cell membrane. For example, the antibody may be monoclonal antibody D7, D8, F10, G17, H40, A66, D80, E88, E90, and H98 and the antigen may be located on the HA protein of an influenza virus.

In another embodiment, at least one HA protein is provided, which is exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat a an influenza virus-related disease or disorder, e.g. bird flu. For example, the at least one influenza virus protein may be provided as an influenza virus molecule.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a an influenza virus neutralizing antibody, such as monoclonal antibody D7, D8, F10, G17, H40, A66, D80, E88, E90, and H98. Additionally, the antigen may be a HA protein, or a portion thereof. In any of the assays described herein, the ability of a candidate compound to interfere with the binding between the D7, D8, F10, G17, H40, A66, D80, E88, E90, and H98 monoclonal antibody and the HA protein indicates that the candidate compound will be able to interfere with or modulate the fusion of the influenza virus and the cell membrane Moreover, because the binding of the HA protein to cell is responsible for influenza virus entry into cells such candidate compounds will also be useful in the treatment of a influenza virus related disease or disorder, e.g. bird flu.

The screening methods disclosed herein may be performed as a cell-based assay or as a cell-free assay. The cell-free assays of the invention are amenable to use of both the soluble form or the membrane-bound form of the HA proteins and fragments thereof. In the case of cell-free assays comprising the membrane-bound forms of the HA proteins, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-{2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody or the antigen (e.g. the can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention can be detected by appropriate assays, e.g., conventional types of immunoassays. For example, a an assay can be performed in which a influenza protein (e.g., HA1, HA 2 or neurominidase) or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide is subsequently incubated with a second, labeled antibody or antibody bound to a coupling agent such as biotin or avidin. This second antibody may be another anti-influenza antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

An exemplary method for detecting the presence or absence of a influenza virus (in a biological sample involves obtaining a biological sample from a test subject and contacting the biological sample with a labeled monoclonal or scFv antibody according to the invention such that the presence of the influenza virus is detected in the biological sample.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect an influenza virus in a biological sample in vitro as well as in vivo. For example, in vitro techniques for detection of an influenza virus include enzyme linked immunosorbent assays (ELISAs), Western blots, immunoprecipitations, and immunofluorescence. Furthermore, in vivo techniques for detection of an influenza virus include introducing into a subject a labeled anti-influenza virus antibody. For example, the antibody can be labeled with a radioactive marker whose presence and location in a subject can be detected by standard imaging techniques.

In one embodiment, the biological sample contains protein molecules from the test subject. One preferred biological sample is a peripheral blood leukocyte sample isolated by conventional means from a subject.

The invention also encompasses kits for detecting the presence of an influenza virus in a biological sample. For example, the kit can comprise: a labeled compound or agent capable of detecting an influenza virus (e.g., an anti-influenza scFv or monoclonal antibody) in a biological sample; means for determining the amount of an influenza virus in the sample; and means for comparing the amount of an influenza virus in the sample with a standard. The compound or agent can be packaged in a suitable container. The kit can further comprise instructions for using the kit to detect an influenza virus in a sample.

Passive Immunization

Passive immunization has proven to be an effective and safe strategy for the prevention and treatment of viral diseases. (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference)). Passive immunization using neutralizing human monoclonal antibodies could provide an immediate treatment strategy for emergency prophylaxis and treatment of influenza such as bird flu while the alternative and more time-consuming development of vaccines and new drugs in underway.

Subunit vaccines potentially offer significant advantages over conventional immunogens. They avoid the safety hazards inherent in production, distribution, and delivery of conventional killed or attenuated whole-pathogen vaccines. Furthermore, they can be rationally designed to include only confirmed protective epitopes, thereby avoiding suppressive T epitopes (see Steward et al., J. Virol. 69:7668 (1995)) or immunodominant B epitopes that subvert the immune system by inducing futile, non-protective responses (e.g. "decoy" epitopes). (See Garrity et al., J. Immunol. 159:279 (1997)).

Moreover, those skilled in the art will recognize that good correlation exists between the antibody neutralizing activity in vitro and the protection in vivo for many different viruses, challenge routes, and animal models. (See Burton, Natl. Rev. Immunol. 2:706-13 (2002); Parren et al., Adv. Immunol. 77:195-262 (2001)). The data presented herein demonstrate that the D7, D8, F10, G17, H40, A66, D80, E88, E90, and H98 human monoclonal antibodies can be further developed and tested in in vivo animal studies to determine its clinical utility as a potent viral entry inhibitor for emergency prophylaxis and treatment of influenza.

Antigen-Ig Chimeras in Vaccination

It has been over a decade since the first antibodies were used as scaffolds for the efficient presentation of antigenic determinants to the immune systems. (See Zanetti, Nature 355:476-77 (1992); Zaghouani et al., Proc. Natl. Acad. Sci. USA 92:631-35 (1995)). When a peptide is included as an integral part of an IgG molecule (e.g., the 11A or 256 IgG1 monoclonal antibody described herein), the antigenicity and immunogenicity of the peptide epitopes are greatly enhanced as compared to the free peptide. Such enhancement is possibly due to the antigen-IgG chimeras longer half-life, better presentation and constrained conformation, which mimic their native structures.

Moreover, an added advantage of using an antigen-Ig chimera is that either the variable or the Fc region of the antigen-Ig chimera can be used for targeting professional antigen-presenting cells (APCs). To date, recombinant Igs have been generated in which the complementarity-determining regions (CDRs) of the heavy chain variable gene ($V_H$) are replaced with various antigenic peptides recognized by B or T cells. Such antigen-Ig chimeras have been used to induce both humoral and cellular immune responses. (See Bona et al., Immunol. Today 19:126-33 (1998)).

Chimeras with specific epitopes engrafted into the CDR3 loop have been used to induce humoral responses to either HIV-1 gp120 V3-loop or the first extracellular domain (D1) of human CD4 receptor. (See Lanza et al., Proc. Natl. Acad. Sci. USA 90:11683-87 (1993); Zaghouani et al., Proc. Natl. Acad. Sci. USA 92:631-35 (1995)). The immune sera were able to prevent infection of CD4 SupT1 cells by HIV-1MN (anti-gp120 V3C) or inhibit syncytia formation (anti-CD4-D1). The CDR2 and CDR3 can be replaced with peptide epitopes simultaneously, and the length of peptide inserted can be up to 19 amino acids long.

Alternatively, one group has developed a "troybody" strategy in which peptide antigens are presented in the loops of the Ig constant (C) region and the variable region of the chimera can be used to target IgD on the surface of B-cells or MHC class II molecules on professional APCs including B-cells, dendritic cells (DC) and macrophages. (See Lunde et al., Biochem. Soc. Trans. 30:500-6 (2002)).

An antigen-Ig chimera can also be made by directly fusing the antigen with the Fc portion of an IgG molecule. You et al., Cancer Res. 61:3704-11 (2001) were able to obtain all arms of specific immune response, including very high levels of antibodies to hepatitis B virus core antigen using this method.

DNA Vaccination

DNA vaccines are stable, can provide the antigen an opportunity to be naturally processed, and can induce a longer-lasting response. Although a very attractive immunization strategy, DNA vaccines often have very limited potency to induce immune responses. Poor uptake of injected DNA by professional APCs, such as dendritic cells (DCs), may be the main cause of such limitation. Combined with the antigen-Ig chimera vaccines, a promising new DNA vaccine strategy based on the enhancement of APC antigen presentation has been reported (see Casares, et al., Viral Immunol. 10:129-36 (1997); Gerloni et al., Nat. Biotech. 15:876-81 (1997); Gerloni et al., DNA Cell Biol. 16:611-25 (1997); You et al., Cancer Res. 61:3704-11 (2001)), which takes advantage of the presence of Fc receptors (Fc□Rs) on the surface of DCs.

It is possible to generate a DNA vaccine encoding an antigen (Ag)—Ig chimera. Upon immunization, Ag-Ig fusion proteins will be expressed and secreted by the cells taking up the DNA molecules. The secreted Ag-Ig fusion proteins, while inducing B-cell responses, can be captured and internalized by interaction of the Fc fragment with Fc□Rs on DC surface, which will promote efficient antigen presentation and greatly enhance antigen-specific immune responses. Applying the same principle, DNA encoding antigen-Ig chimeras carrying a functional anti-MHC II specific scFv region gene can also target the immunogens to all three types of APCs. The immune responses could be further boosted with use of the same protein antigens generated in vitro (i.e.,"prime and boost"), if necessary. Using this strategy, specific cellular and humoral immune responses against infection of influenza virus were accomplished through intramuscular (i.m.) injection of a DNA vaccine. (See Casares et al., Viral. Immunol. 10:129-36 (1997)).

Vaccine Compositions

Therapeutic or prophylactic compositions are provided herein, which generally comprise mixtures of one or more monoclonal antibodies or ScFvs and combinations thereof. The prophylactic vaccines can be used to prevent an influenza virus infection and the therapeutic vaccines can be used to treat individuals following an influenza virus infection. Prophylactic uses include the provision of increased antibody titer to an influenza virus in a vaccination subject. In this manner, subjects at high risk of contracting influenza can be provided with passive immunity to an influenza virus These vaccine compositions can be administered in conjunction with ancillary immunoregulatory agents. For example, cytokines, lymphokines, and chemokines, including, but not limited to, IL-2, modified IL-2 (Cys125→Ser125), GM-CSF, IL-12, □-interferon, IP-10, MIP1β, and RANTES.

Methods of Immunization

The vaccines of the present invention have superior immunoprotective and immunotherapeutic properties over other anti-viral vaccines The invention provides a method of immunization, e.g., inducing an immune response, of a subject. A subject is immunized by administration to the subject a composition containing a membrane fusion protein of a pathogenic enveloped virus. The fusion protein is coated or embedded in a biologically compatible matrix.

The fusion protein is glycosylated, e.g. contains acarbohydrate moiety. The carbohydrate moiety may be in the form of a monosaccharide, disaccharide(s). oligosaccharide(s), polysaccharide(s), or their derivatives (e.g. sulfo- or phospho-substituted). The carbohydrate is linear or branched. The carbohydrate moiety is N-linked or O-linked to a polypeptide. N-linked glycosylation is to the amide nitrogen of asparagine side chains and O-linked glycosylation is to the hydroxy oxygen of serine and threonine side chains.

The carbohydrate moiety is endogenous to the subject being vaccinated. Alternatively, the carbohydrate moiety is exogenous to the subject being vaccinated. The carbohydrate moiety are carbohydrate moieties that are not typically expressed on polypeptides of the subject being vaccinated. For example, the carbohydrate moieties are plant-specific carbohydrates. Plant specific carbohydrate moieties include for example N-linked glycan having a core bound □ 1,3 fucose or a core bound □□ 1,2 xylose. Alternatively, the carbohydrate moiety are carbohydrate moieties that are expressed on polypeptides or lipids of the subject being vaccinate. For example many host cells have been genetically engineered to produce human proteins with human-like sugar attachments.

For example, the fusion protein is a trimeric hemagglutinin protein. Optionally, the hemagglutinin protein is produced in a non-mammalian cell such as a plant cell.

The subject is at risk of developing or suffering from a viral infection. Enveloped viruses include for example, epstein-barr virus, herpes simplex virus, type 1 and 2, human cytomegalovirus, human herpesvirus, type 8, varicella zoster virus, hepatitis B virus, hepatitis C virus, human immunodeficiency virus, influenza virus, measles virus, mumps virus, parainfluenza virus, respiratory syncytial virus, rabies virus, and rubella virus.

The methods described herein lead to a reduction in the severity or the alleviation of one or more symptoms of a viral infection. Infections are diagnosed and or monitored, typically by a physician using standard methodologies A subject requiring immunization is identified by methods know in the art. For example subjects are immunized as outlined in the CDC's General Recommendation on Immunization (51(RR02) pp1-36) Cancer is diagnosed for example by physical exam, biopsy, blood test, or x-ray.

The subject is e.g., any mammal, e.g., a human, a primate, mouse, rat, dog, cat, cow, horse, pig, a fish or a bird. The treatment is administered prior to diagnosis of the infection. Alternatively, treatment is administered after diagnosis.

Efficaciousness of treatment is determined in association with any known method for diagnosing or treating the particular disorder or infection. Alleviation of one or more symptoms of the disorder indicates that the compound confers a clinical benefit.

Evaluation of Antigenic Protein Fragments (APFs) for Vaccine Potential

A vaccine candidate targeting humoral immunity must fulfill at least three criteria to be successful: it must provoke a strong antibody response ("immunogenicity"); a significant fraction of the antibodies it provokes must cross-react with the pathogen ("immunogenic fitness"); and the antibodies it provokes must be protective. While immunogenicity can often be enhanced using adjuvants or carriers, immunogenic fitness and the ability to induce protection (as evidenced by neutralization) are intrinsic properties of an antigen which will ultimately determine the success of that antigen as a vaccine component.

Evaluation of Immunogenic Fitness

"Immunogenic fitness" is defined as the fraction of antibodies induced by an antigen that cross-react with the pathogen. (See Matthews et al., J. Immunol. 169:837 (2002)). It is distinct from immunogenicity, which is gauged by the titer of all of the antibodies induced by an antigen, including those antibodies that do not cross-react with the pathogen. Inadequate immunogenic fitness has probably contributed to the disappointing track record of peptide vaccines to date. Peptides that bind with high affinity to antibodies and provoke high antibody titers frequently lack adequate immunogenic fitness, and, therefore, they fail as potential vaccine components. Therefore, it is important to include immunogenic fitness as one of the criteria for selecting influenza vaccine candidates.

A common explanation for poor immunogenic fitness is the conformational flexibility of most short peptides. Specifically, a flexible peptide may bind well to antibodies from patients, and elicit substantial antibody titers in naïve subjects. However, if the peptide has a large repertoire of conformations, a preponderance of the antibodies it induces in naïve subjects may fail to cross-react with the corresponding native epitope on intact pathogen.

Like short peptides, some APFs may be highly flexible and, therefore may fail as vaccine components. The most immunogenically fit APFs are likely to consist of self-folding protein subdomains that are intrinsically constrained outside the context of the whole protein.

Because immunogenic fitness is primarily a property of the APF itself, and not of the responding immune system, immunogenic fitness can be evaluated in an animal model (e.g. in mice) even though ultimately the APF will have to perform in humans.

The immunogenic fitness achieved by APFs is evaluated by immunosorption of anti-APF sera with purified spike or membrane protein, in a procedure analogous to that described in Matthews et al., J. Immunol. 169:837 (2002). IgG is purified from sera collected from mice that have been immunized. Purified, biotinylated proteins (as appropriate, depending on the particular APF with which the mice were immunized) are mixed with the mouse IgG and incubated. Streptavidin-coated sepharose beads are then added in sufficient quantity to capture all of the biotinylated protein, along with any bound IgG. The streptavidin-coated beads are removed by centrifugation at 13,000 rpm in a microcentrifuge, leaving IgG that has been depleted of antibodies directed against the protein, respectively. Mock immunoabsorptions are performed in parallel in the same way, except that biotinylated BSA will be substituted for influenza protein as a mock absorbent.

To measure the immunogenic fitness of APFs, the absorbed antibodies and the mock-absorbed antibodies are titered side-by-side in ELISA against the immunizing APF. For APFs affinity selected from a phage display NPL, the antigen for these ELISAs will be purified APF-GST fusion proteins. For the potentially glycosylated APFs from the mammalian cell display NPL, the antigen for these ELISAs will be APF-Fc fusion proteins secreted by mammalian cells and purified with protein A. The percentage decrease in the anti-APF titer of absorbed antibodies compared with the mock-absorbed antibodies will provide a measure of the immunogenic fitness of the APF.

Methods of Treatment

The invention provides for both prophylactic and therapeutic methods of treating a subject at risk of (or susceptible to) an influenza virus-related disease or disorder. Such diseases or disorders include but are not limited to, e.g., bird flu.

Prophylactic Methods

In one aspect, the invention provides methods for preventing an influenza virus-related disease or disorder in a subject by administering to the subject a monoclonal antibody or scFv antibody of the invention or an agent identified according to the methods of the invention. For example, scFv and/or monoclonal antibody 8-A1, 1-C2, 4-G3, 4-C4, 4-F5, 9-C1, 2-D3, 11-F8, 5-B9, and 6-A2 may be administered in therapeutically effective amounts. Optionally, two or more anti-influenza antibodies are co-administered.

Subjects at risk for an influenza virus-related diseases or disorders include patients who have come into contact with an infected person or who have been exposed to the influenza virus in some other way. Administration of a prophylactic agent can occur prior to the manifestation of symptoms characteristic of the influenza virus-related disease or disorder, such that a disease or disorder is prevented or, alternatively, delayed in its progression.

The appropriate agent can be determined based on screening assays described herein. Alternatively, or in addition, the agent to be administered is a scFv or monoclonal antibody that neutralizes an influenza virus that has been identified according to the methods of the invention.

Therapeutic Methods

Another aspect of the invention pertains to methods of treating an influenza virus-related disease or disorder in a patient. In one embodiment, the method involves administering an agent (e.g., an agent identified by a screening assay described herein and/or an scFv antibody or monoclonal antibody identified according to the methods of the invention), or combination of agents that neutralize the influenza to a patient suffering from the disease or disorder.

The invention will be further described in the following examples, which do not limit the scope of the invention described in the claims.

EXAMPLES

Example 1: General Methods

Described herein are the general methods and assays used in the working examples.

Materials

The anti-HA antibodies F10, A66, G17, and D8 were previously described in the study of Sui et al (1) and International Application No. WO 2009/079259, herein incorporated by reference in their entireties. The mAbs CR6261 and CR6331 were synthesized by Genewiz, North Brunswick, N.J. Recombinant HA of H5VN04 was produced as described (1). A/California/04/2009 (H1CA0409) and A/Singapore/1/57 (H2 SIN 57) recombinant HAs were supplied by Biodefense and Emerging Infections Research Resources Repository (BEI Resources)

Cloning of Antibody Variants

IGHV1-69*01 germline V-segment was synthesized by Geneart (Regensburg, Germany). The germline variant of IGHVI-69/F 10 was constructed by ligating the IGHV1-69*01 gene (NcoI 5', BssHII 3') with F10 gene segment that included the CDR-H3+light chain (BssHII 5' NotI 3') into the pET22b vector, which was digested with NcoI-NotI. The various HV1-69-sBnAbs derivatives of F10, A66, G17, D8, CR6261, and CR6331, as well as the F10 and A66 CDR-H2 variants were constructed using QuikChange® Lightning Site-Directed Mutagenesis kit.

Expression and Purification of scFv

The scFv antibody sequences were cloned into the bacterial expression vector pET22b with an in-frame fusion of streptactin tag at the carboxy-terminus end. Plasmids were transformed into the expression BL21 (DE3) strain and the scFvs were produced by using the overnight express™ medium (29) according to the manufacturer protocol (Novagen). The scFvs were purified from clear bacterial cell lysates using the high-bind sepharose streptactin beads.

Kinetic Studies

Surface plasmon resonance (SPR) analysis was utilized for all kinetic measurements with a Biacore T100. For H5 binding kinetic studies, carboxyl terminus histidine tagged-H5 (1) was captured on a NTA-Ni+activated chip. After stabilization period of 300 sec, the scFv in question was injected by using the single cycle kinetics function. Mobile phase contained HBS-P supplemented with 50□M EDTA. Chip regeneration was carried out with two pulses of 0.3 MEDTA followed by injection of Nickel 50□M of Ni+ solution.

Binding of scFvs to H5VN04 as Determined by Standard ELISA Assay

Standard ELISA assay was used to detect binding of the scFvs to H5VN04. Briefly, 2 µg/ml of H5VN04 was coated onto 384-well plates. Upon blocking with 2% BSA, purified strep-tagged scFvs were added onto the H5-coated plates and the binding was detected with Strep-Tactin®-HRP mAb conjugate (IBA, GMBH) using PolarStar at 450 nm.

Binding of Antibodies to HA Antigens as Determined by MSD-Based ELISA Assays

The Sector⊐ Imager 2400 from Meso Scale Discovery (MSD, Rockville, Md.) is utilized for interrogating the binding activities between antibody and their respective antigens based on the manufacturer's instructions. For testing of F10 germline phage-Ab variants, 6.25 ng of purified H5VN04 HA antigens were spot-coated onto 384-well high-bind MSD plates followed by incubation with serially diluted phage-Ab prep in triplicates. For F10-epitope competition assay with anti-H5VN04/H1CA0409 phage-Abs, the phage-Abs were added in duplicates to a plate precoated with purified HA from H5VN04 or H1CA0409, and blocked with F10-scFv or an irrelevant control scFv. Phage-Ab binding was detected with Sulfo-tagged anti-M13 mAb and assayed with a MSD Sector Imager 2400.

To study the human serum samples, binding reactivity of pre-vaccination sera to the 51p1 allele-specific mouse anti-idiotypic mAb G6 coated MSD plates were detected with goat anti-human sulfo-tagged mAb in trplicates. Serum competition assay with biotiniylated-F10 for H1CA0409 binding was performed by addition of the serial dilution of serum samples in triplicates to the MSD plate that were precoated with H1CA0409. Upon incubation at 37° C. for 45 minutes, biotiniylated-F10 was added for additional 45 min at a concentration corresponding to ~50% of the maximal signal (320 ng/ml), followed by washing and addition of streptavidin-sulfo-tagged mAb for detection in Sector Imager 2400.

B-Cell Activation Induced by BCR Cross-Linking

B-cell activation induced by BCR cross-linking was performed according to the study of Hoot et al (30).

Panning of the Phage Display Libraries

Panning of the phage display libraries was performed by standard immunotube approach (1).

Phage-Ab Mediated Neutralization Assay

Phage-Ab mediated neutralization assay with H5V04 or H1PR8 pseudotyped luciferase-reporter lentiviral particles was performed according to previous published protocol (1) using purified phage-Abs at the concentration of 1.07e13 phage particles per ml.

qPCR Assay for Determining the Presence of 51p1 and hv1263 Allele Related Genes.

Two allelic-group-specific TaqMan (Applied Biosystems) probes were designed to overlapping the codon of IGHV1-69 encoding CDR-H2 Leu54/Phe54, allowing for individual copy number estimation of 51p1 and hv1263 alleles. Taqman probes were custom synthesized 51p1 Primers

```
hv1263 Forward:
                         (SEQ ID NO: 663)
TGGACAAGGGCTTGAGTGGAT hv1263 Reverse:
                         (SEQ ID NO: 664)
CCCTGGAACTTCTGTGCGTAGT hv1263 Reporter Sequence:
                         (SEQ ID NO: 665)
CCTATCCTTGGTATAGCA
``` hv1263 Primers

```
VH1-69 51p1 Forward:
                         (SEQ ID NO: 666)
TGGACAAGGGCTTGAGTGGAT VH1-69 51p1 Reverse:
                         (SEQ ID NO: 667)
CCCTGGAACTTCTGTGCGTAGT 51p1 Reporter Sequence:
                         (SEQ ID NO: 668)
CCCTATCTTTGGTACAGC
```

Data Assembly and Statistical Analysis

HV1-69-sBnAb sequences were obtained through the NCBI website or published patents. The reference dataset of functional IGHV1-69 51p1-allele germline based Abs was constructed using the Ig Blast website. Default parameters were kept for the categories of length and identity, synthetic Ab sequences were excluded, and in the germline gene name category the IGHV1-69 51p1 allele group gene were entered as IGHV1-69*01, 03, 05, 06, 07, 12 and 13.

The retrieved 7 datasets were compiled into one 51p1 allele based Ab dataset and duplicated sequences were removed. In order to obtain a dataset characterized by Abs that start with first V-segment codon of Q1 (C.A.G) and do not surpass S113 (the last amino acid of the J-segment), the dataset was first mapped to the reference IGHV1-69*01 gene to crop Ab sequences that start with Q1. The cropped dataset was then mapped against a consensus J-segment (WGQGTLVTVSS; SEQ ID NO: 669) allowing the deletion of nucleotide sequences that go beyond S113 from the dataset. To facilitate the removal of clonally related Abs from the dataset, a CDR-H3 sub-alignment (C92-to-W103) was extracted and a sequence similarity matrix was organized by the name of the study. Studies found to be composed of identical CDR-H3 sequences (100% sequence identity) were taken out of the dataset. The resultant dataset was further cleaned by removal of sequence characterized by ambiguous nucleotide notations and of the studies detailed in Table 9. The entire dataset was translated, and was deleted of duplicated V-segments.

Identification of Unique Amino Acid Substitutions in the HV1-69-sBnAb Dataset.

Using the UGENE software a matrix of amino acid substitutions was generated for the HV1-69-sBnAb and for the reference IGHV1-69-Ab datasets. A two-step method was used to identify distinctive amino acid substitutions associated with the HV1-69-sBnAb dataset. First, a Fisher's exact test was used to compare the distribution of amino acid substitutions at each position within the V-segment in the HV1-69-Abs dataset with that in the IGHV1-69-Ab reference dataset. Next, for germline positions where a significant statistical difference was found (P<0.05), another set of Fisher's exact tests were performed to compared the frequency of single amino acid substitutions. For the comparisons of individual substitution pattern at a given position, Bonferroni adjusted P-values were used to determine statistical significance in order to maintain an overall Type I error rate of 0.05 or less at each V-segment position.

Statistical Analysis of the Nucleotide Substitution Profiles.

To investigate whether the unique amino acid substitutions identified in FIG. 2B occur in conserved CDR germline positions, logistic regressions were employed to compare the odds of codon nucleotides substitution frequency associated with the HV1-69-sBnAbs versus the codon nucleotides substitution frequency that are not associated with HV1-69-sBnAbs. An odds ratio<1 indicates that the odd of codon nucleotide substitution is less than that for the codons of the non-distinctive HV1-69-sBnAb germline positions. Accordingly the lower the odds ratio the more conserved is the codon position. P-values were obtained by using the Wald tests.

Structural Analysis and Modeling

Molecular graphics and analyses were performed with the UCSF Chimera package (31). Chimera is developed by the Resource for Biocomputing, Visualization, and Informatics at the University of California, San Francisco (supported by NIGMS P41-GM103311). The in-silico mutagenesis modeling was preformed according to the study of Fahmy et al (32).

The Design Principles of the Semi-Synthetic VH1-69 Ab Library.

The main goal of the semi-synthetic IGHV1-69 Ab library diversification scheme was to obtain an Ab library characterized by the V-segment molecular determinants associated with HV1-69-sBnAbs, while maintaining overall low V-segment amino acid substitution frequency. At the time the library was designed our knowledge of V-segment molecular determinants of IGHV1-69-sBnAbs was based on the structural analysis of F10 and CR6261 solved structures, and from an alignment made of HV1-69-sBnAbs reported by Thorsby et al., (2008)(2) Sui et al., (2009)(1) and Corti et al (2010)(6). This analysis has suggested that the amino acid substitutions of CDR-H1: Val27, Ile28, Pro29, Arg30; CDR-H2: Ser52, Gly52a, Ala52a; and CDR-H4 Glu73 and Phe74 were uniquely associated with HV1-69-sBnAbs and consequently are important for conveying strong binding kinetics to HA. Accordingly it was decided that these amino acid substitutions should be included in the library diversification scheme at the relatively elevated frequencies of 5-to-10% (FIG. 14A).

In order to explore if generation of HV1-69-sBnAbs based on amino acid substitutions occurring in positions CDR-H2 52 and 52a is restricted to SER52, GLY52a and PRO52a, these positions were also diversified with naturally occurring amino acid substitutions at a frequencies observed in a CDR-H2 alignment composed of IGHV1-69 51p1 allele based Abs that were devoid of germline CDR-H2 sequences (n=800). In addition, CDR-H2 position 53 was also diversified according to this alignment for the reason that HV1-69-sBnAbs characterized by I52aG were always found to be accompanied by mutated positions 53 (either I53V or I53M) suggesting the existence of structural dependency. Likewise, since it was noticed that several HV1-69-sBnAbs are highly diversified in the surrounding CDR-H4 domain area (FIG. 7), we decided that positions of 73, 74, 76 and 78 will be diversified with naturally occurring amino acid substitutions at a frequencies that were observed in a 73-to-78 alignment made from IGHV1-69 51p1 allele based Abs (n=1477). To insure that the library would maintain "germline" characteristics, the frequency of the respective germline amino acids in each of the diversified positions was maintained at high frequencies of 72%-to-95%.

For the CDR-H3/J domain, the strategy was to have an equal presentation of CDR-H3 lengths of 5, 7, 9, 10, 11, 12, 13, and 15, whereby diversification scheme (FIG. 14B) was based on the natural diversity observed in alignment composed of 1217 non-duplicated IGHV1-69 51p1 allele based Abs. In order to avoid skewing of the observed CDR-H3 frequencies due to residues associated with J-segments, the CDR-H3 sequences were aligned and deleted of amino acids post position 100 (which is Phe in IGHJ1-5). Additionally, the CDR-H3 sequences were also omitted of IGHJ6'-s quintuple tyrosine residues (YYYYYGMDVWGQGTTVTVSS; SEQ ID NO: 670) as these were found to distort the amino acid frequency and diversity in the alignment. The design of the J-segment was based on a consensus sequence of: F̲D̲V̲WGQGTLVTVSS (SEQ ID NO: 671), in which F̲ and V̲ were diversified according to the frequency scheme presented in FIG. 14A.

The library light chains were obtained from the previously constructed Mehta I/II naïve human light chain Ab libraries and were linked to the VH synthetic library via a $(GLY_3SER)_4$ linker (GGGSGGGSGGGSGGGS; SEQ ID NO: 672). Synthesis of the IGHV1-69 library was performed by MorphosysGmBH based on the technology developed by Sloning GmBH. Construction of scFv phage display libraries was performed as described previously (33). Phage library size consisted of $7.7 \times 10^8$ members. Randomly sequencing of 164 Ab library members validated the diversification scheme (data not shown) and confirmed low V-segment amino acid diversity with a mean of 1.9-☐1.1 amino acid substitutions per V-segment.

Example 2: Identification of Anchor Residues in the Heavy Chains of HVI-69-sBNABs The co-crystal structures of the HV1-69-sBnAbs, F10 (1), CR6261 (3), and CR9114 (5) with H5VN04 established that binding is mediated exclusively by the IGHV1-69 heavy chains. Estimates of the binding free energy contributions for heavy chain CDR residues using ANCHOR server (17) (FIG. 1A) have identified three common anchor points: a hydrophobic residue at CDR-H2 position 53 (generally Ile/Met), a Phe at CDR-H2 position 54, and a Tyr residue at CDR-H3 position 98. Structural analysis shows (FIGS. 1B and 6) that the common aromatic pair of CDR-H2 Phe54 and CDR-H3 Tyr98 pack closely together (~4 Å) in order to bind to adjacent pockets formed by elements of the fusion peptide. Tyr98 makes both hydrophobic interactions as well as a strong H-bond with the fusion peptide (the main chain carbonyl of $Asp19_2$), and adopts a single conformation in the 3 known structures. The side-chains of Phe54 converge in one location, packing on top of a prominent loop in the fusion peptide (residues $18_2$-$21_2$), and orthogonally against the $Trp21_2$ side-chain of H5VN04 (FIGS. 1B and 6). In contrast to their side-chains the Cα positions of Phe54 diverge, so that the upstream residues at position 53 adopt distinct locations along a groove formed at the interface between HA1 and HA2 elements of the same H5 subunit. Although, the 3 sBnAbs do not align identically with the respective binding epitope, variable residues in CDR-H1 (FIG. 1A) and CDR-H4 (defined in FIG. 7) are estimated to form high energy contacts within the grove that continues upwards from $Trp21_2$ (FIG. 1A-B). The importance of the two main common anchor residues, CDR-H2 Phe54 and CDR-H3-Tyr, was confirmed by mutagenesis (FIG. 1C). The F54A mutation completely ablated binding of F10 and reduced the CR6261 binding by 800-fold, which is consistent with previous studies (2, 18). The Y98A reduced binding by >3000-fold and >4,000-fold for F10 and CR6261, respectively, indicating Tyr98 contributes significantly in HA stem recognition.

The conserved triad of residues at position 53, Phe54, and Tyr98, led us to explore the commonality of these residues in the reported studies (Table 9). FIG. 2A shows that hydrophobic residues are always found at CDR-H2 position 53; Phe54 is nearly invariant, and tyrosines are highly frequent in the CDR-H3 domain, clustering around positions 97-99 in 27 out of the 38 HV1-69-sBnAbs (FIG. 8B). Further immunogenetic analysis demonstrated that 37 of these encode the critical Phe54 (FIG. 9A), which belong to the IGHV1-69 51p1 allele group (FIG. 9B); whereas the D-segments or J-segments are highly diverse (FIG. 9C-D). Taking into account that tyrosines are one of the most highly utilized amino acids in CDR-H3 domains (19, 20), our results suggest that HV1-69-sBnAbs binding to the stem epitope can be achieved by use of multiple IGHV1-69 51p1 alleles and various VDJ recombination events.

TABLE 9

Summary of various studies that have analyzed antibody responses towards hemagglutinin of group 1 influenza subtypes.

| Study† | Panning method | Panning target | # of Positive clones[a] | Frequency of IGHV1-69 Abs | # of anti-stem binding clones | Frequency of IGHV1-69 based anti-stem Abs |
|---|---|---|---|---|---|---|
| Kashyap et al. | Phage display library generated | H5N1 | The study reports 61 clonally related IGHV1-69 based sequences. However, the full extent of | | | |

TABLE 9-continued Summary of various studies that have analyzed antibody responses towards hemagglutinin of group 1 influenza subtypes.

| Study[†] | Panning method | Panning target | # of Positive clones[a] | Frequency of IGHV1-69 Abs | # of anti-stem binding clones | Frequency of IGHV1-69 based anti-stem Abs |
|---|---|---|---|---|---|---|
| (2008) | from bone marrow B cells of H5N1 Turkish survivors. | | | isolated Abs was not reported. | | |
| Throsby et al. (2008) | Phage display library generated from IgM+ memory B cells of H5N1 vaccinated donors. | H5N1 | 43 | 15/43 | 13 | 12/13 (92%) |
| Sui et al. (2009) | Naïve human antibody phage display library. | H5N1 | 6 | 5/6 | 6 | 5/6 (83%) |
| Corti et al. (2010) | Panning B-cells from donors vaccinated with the seasonal influenza vaccine. | H5N1/H1N1 | 20 | 14/20 | 19 | 14/19 (74%) |
| Wrammert et al. (2011) | Panning plasmablasts from 2009 pandemic H1N1 infected donors. | H1N1 | 15 | 4/15 | 5 | 4/5 (80%) |
| Thomson et al. (2012) | Panning B-cells and plasmablasts from 2009 pandemic H1N1 infected and vaccinated donors. | H1N1 | 48 | 25/48 | 7* | 7/7 (100%) |
| Li et al. (2012) | Panning plasmablasts from 2009 pandemic H1N1 vaccinated donors. | H1N1 | 28 | 1 | 3 | 1/3 (33%) |

[a]number represents distinctive VH sequence.
*Not all positive clones were epitope mapped.
[†]Dreyfus et al. (2012) has reported the isolation of one IGHV1-69 germline based anti-stem Ab.

Example 3: Genetic Analysis of Somatic Mutations in Rearranged IGHV1-69 Genes of the SBNABS A mean of 12.6 ☐4.2 V-segment substitutions are found among the published HV1-69-sBnAbs, ranging from 5 in CR6331/CR6432 to 22 in FE43/CR6334 (FIG. 2B), which is similar to the average range for rearranged IGHV genes (21). This distribution indicates the pathways for potent HV1-69-sBnAbs formation do not necessarily require multiple maturation events, but rather the incorporation of key residues. Further examination of the V-segments of HV1-69-sBnAbs revealed common substitutions such as the hydrophobic residue at position 74 (in CDR-H4) and changes in CDR-H1 and CDR-H2 (FIG. 2A). To investigate which of these substitutions are unique for HV1-69-sBnAbs, we compared the frequency of specific somatic mutations in the HV1-69-sBnAbs V-segments with the identical mutations in a control set of unique Ab sequences derived from the IGHV1-69-51p1 germline group (IgBlast, n=287). Thirteen HV1-69-sBnAb distinctive V-segment substitutions were identified using Fisher's exact test with Bonferroni adjustment (highlighted in FIG. 2A and respective frequencies shown in FIG. 2C). Ranking showed that the CDR-H1 and CDR-H2 substitutions are highly enriched in the HV1-69-sBnAbs dataset (f1) (FIG. 10A-C), but are scarce in the IGHV1-69-Ab reference dataset (f0).

The scarcity of the highest ranking CDR-H1/H2 residue substitutions in the IGHV1-69-Ab dataset (FIG. 2C) prompted further analysis of the nucleotide substitutions and predicted location of AID and pol η "hotspot" somatic hypermutation (SHM) motifs (22, 23) (FIG. 2D). Logistic regressions were used to compare the odds of the substitution frequency of codon nucleotides associated with the HV1-69-sBnAbs (residues colored in red) versus the frequency of those substitutions not related with HV1-69-sBnAbs (residues colored in black). The data shows that HV1-69-sBnAbs associated substitutions such as CDR-H2 I52S and P52aG/A (FIG. 2D) and CDR-H1 G27V, T28P/I and F29S (FIG. 11) occur in positions that are otherwise relatively conserved in the IGHV1-69-Ab reference dataset. In addition, these rare HV1-69-sBnAbs residue substitutions occur towards the 5' end while the AID/pol η hotspots are clustered towards the 3' end of both CDR-H1/H2 domains. Hence, it appears that in response to influenza infection or vaccination critical amino acid substitutions are frequently required at positions that are sparse or devoid of AID/Pol η hotspots which may limit the generation of HV1-69-sB-nAbs.

Figure 3:
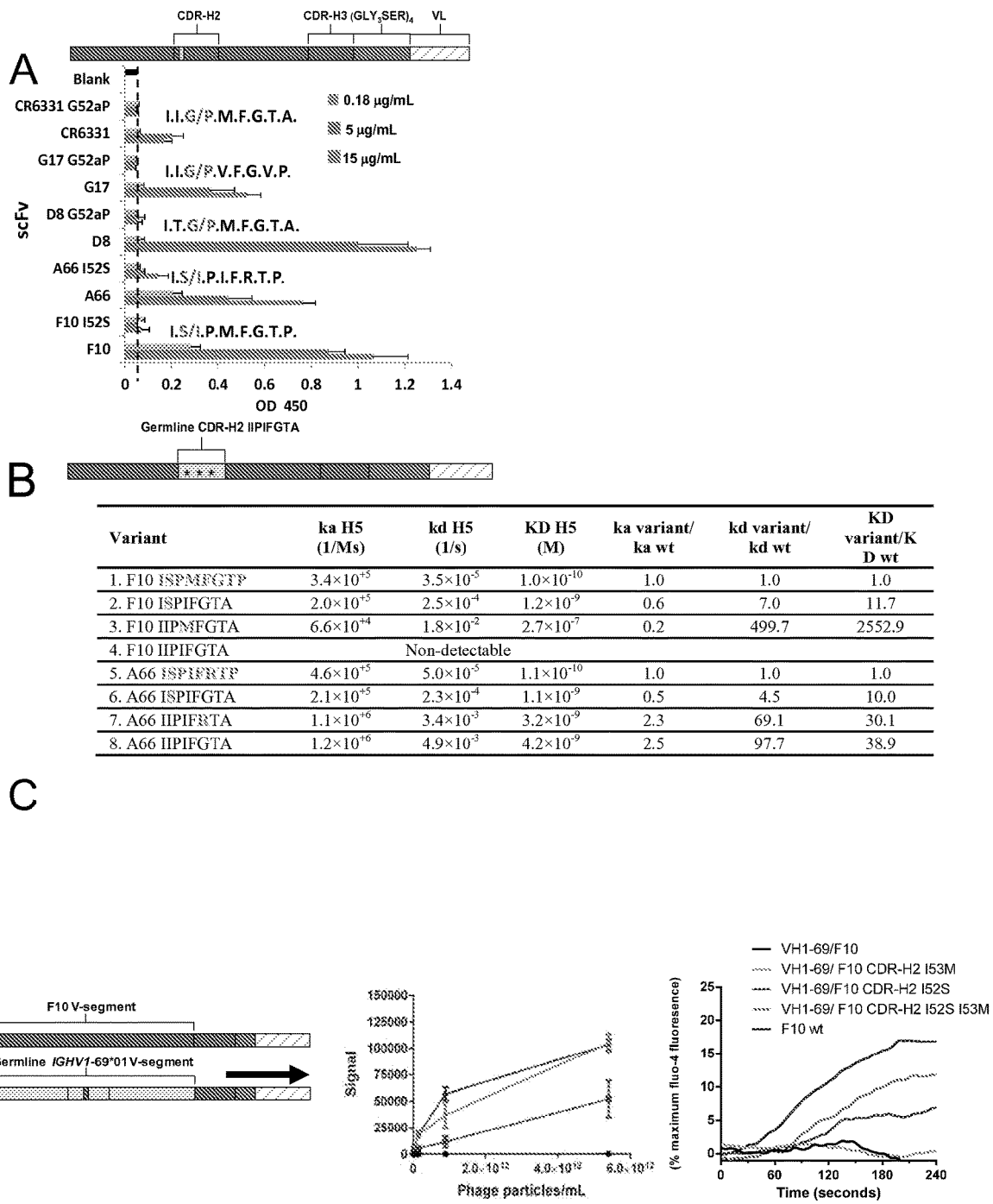
FIG. 3. Understanding the structural role of the HV1-69-sBnAbs distinctive CDR-H2 amino acid substitutions.
A) HV1-69-sBnAb variants of 152S in F10 and A66, G52aP in CR6331, G17 and D8 were analyzed for H5VN04 reactivity by ELISA.

Example 4: Confirming the Importance of the CDR-H2 Substitutions in HVI-69-SBNABS Since the substitutions in CDR-H1 and CDR-H4 are believed to form direct contact with HA stem (FIG. 1B) (1, 3, 18) ENREF 18, we focused our efforts on examining if the high frequency CDR-H2 substitutions occurring at positions I52S, P52aG and P52aA (FIG. 10) play an important role in HV1-69-sBnAb antigen recognition. To test this hypothesis, we mutated five representative HV1-69-sBnAbs carrying either I52S or P52aG mutation back to the germline gene residue. All five variants had drastically reduced or abolished binding reactivity to H5VN04 (FIG. 3A). In comparison, a revertant proline substitution at CDR-H2 position 57 in F10 and A66 resulted in enhanced or no change in H5 binding, respectively (data not shown).

To further interrogate the structural effect of the mutated residues in the CDR-H2 loop of F10 and A66, we constructed CDR-H2 germline variants then back introduced the substitutions of Ser52 (F10/A66), Met53 in F10, and Arg55 in A66. The kinetic data presented in FIG. 3B shows only small differences in association rate (ka) constants among the wild-type and variants, whereas much greater effects were observed with the dissociation rate ($k_d$) constants. Replacing wild-type CDR-H2 with the germline sequence (I.I.P.I.F.G.T.A (SEQ ID NO: 673)) led to a 98-fold higher dissociation rate in A66 (construct #5 vs. #8) and no detectable binding activity in F10 (construct #1 vs. #4). Circular dichroism (CD) analysis indicated that protein misfolding is not responsible for loss of binding as a similar profile was observed for the F10 germline CDR-H2 variant and F10 wt (FIG. 12). Restoring the single amino acid of Ser52 (I.S.P.I.F.G.T.A.; SEQ ID NO: 674) (mutants #2 & 6) resulted in recovery of binding kinetics for both sBnAbs, as seen by the dramatic improvement in $k_d$ values. Other single amino acid CDR-H2 reversions (F10 I.I.P.M.F.G.T.A (SEQ ID NO: 675), A66 I.I.P.I.F.R.T.A (SEQ ID NO: 676)) (mutants #3 and 7) did not restore binding to the same extent and showed extremely fast $k_d$ rates (FIG. 3B).

We next tested the effect of back introducing Ser52 and Met53 into a F10 variant containing an IGHV1-69*01 germline V-segment in the context of CDR-H3-Tyr98. In order to utilize avidity to increase detection of weak interactions, the F10 variants were either expressed on the surface of phage particles and binding tested with an MSD ELISA assay (FIG. 3C, left); or expressed as B-cell receptors and analyzed for their ability to activate B-cells through cross-linking with purified H5VN04 trimeric HA (FIG. 3C, right). In both cases, we detected no binding of H5VN04 with either the germline or the I53M variant. However, the I52S variant was active, and the I52S/I53M variant had even higher activity. These data demonstrated that Ser52 plays an important role for binding of HV1-69-sBnAbs to HA.

Example 5: Understanding the Structural Role of the Unique CDR-H2 Amino Acid Substitutions of Ser52, Gly52a and Ala52A Ser52 of F10 and CR9114 do not form high energy contacts with the respective H5VN04 HAs as indicated by Van der Waals (VDW) contact analysis (FIG. 8A), thus direct HA contacts are not responsible for the dramatic effect of Ser52. Examination of the distances between Phe54 and Tyr98 in F10, CR9114 and CR6261 suggests that I52S substitution in F10 and CR9114 allows Phe54 to make a close, orthogonal, contact with TYR98 without steric interference while presence of germline Ile52 will cause steric clashes (FIG. 3D, right panel). By contrast, in CR6261, the 2 rings are further apart and nearly coplanar thus Ile52 can be accommodated. The close distance between Phe54 and CDR-H3-Tyr is also expected to be a structural feature in HV1-69-sBnAbs characterized by the P52aG/A substitutions. This claim is supported by the observation that HV1-69-sBnAbs characterized by I52S/P52aG/P52aA substitutions are also characterized by a narrow distribution of CDR-H3 Tyr residues clustered around positions 97-to-99 (FIG. 8B). In addition, the well-known flexible nature of Ser/Gly/Ala is predicted to reduce inter-chain VDW contacts (modeled for F10 in FIG. 13A-B), consequently a flexible CDR-H2 loop might provide Phe54 with a better access to the buried Trp21$_2$ of the fusion peptide. In addition, structural alignment between unbound CR9114 and the H5-bound structure (FIG. 8C) shows that only CDR-H2 residues, Ile53 and Phe54, adopt markedly different positions (>1.7 Å shifts) following HA binding. Distance analysis suggests an induced-fit process, in which the Cα-Cβ atoms of Phe54 are shifted closer to the CDR-H3 Tyr98 domains in the bound state. We propose that this induced fit process could not occur if the large germline Ile52 is maintained in that position.

Example 6: Validating the Structural Roles of the SER52 and Tyr98 in HV1-69-SBNABS Using Semi-Synthetic IGHV1-69 Libraries The genetic analysis suggests that the SHM machinery is constrained in introducing the key CDR-H1/H2 substitutions in the affinity maturation process. Therefore to bypass AID/Pol ☐ restrictions in the generation of HV1-69-sBnAbs a semi-synthetic library was designed with a low V-segment amino acid substitution frequency (1.9±1.1) that incorporated 9 of the 13 distinctive HV1-69 sBnAb amino acid substitutions at a frequency no higher than 10% and with a completely randomized CDR-H3 of varying length (see Example 1). The library is strongly skewed towards selection of Ab-members that display germline residues. For example, the combination of the V-segment germline residues of CDR-H1 Gly27 (90%) and CDR-H2 Ile52 (71%) with CDR-H3 Tyr98 (11%) is expected to occur in 7% of the phage members whereas the combination of the distinctive HV1-69-sBnAb substitutions of Val27 (10%), Ser52 (10%) with CDR-H3 Tyr98 is expected to occur in 0.1% of the phage members (FIG. 16).

Figure 4:
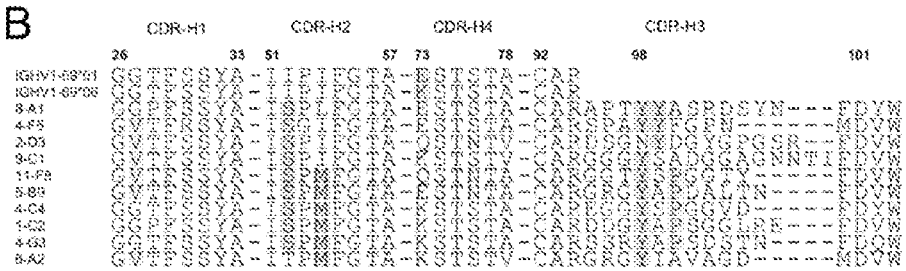
FIG. 4. Semi-synthetic HV1-69 phage-Ab library yields potent anti-H5VN04/H1CA0409 Abs characterized by minimal V-segment amino acid substitutions.
A) Characterization of binding activities of anti-H5VN04 and anti-H1CA0409 phage-Abs isolated from the semi-synthetic HV1-69 phage-display library. Sequences are detailed in FIGS. 16A and 16D. B) Heavy chain CDR sequences (SEQ ID NOS 877-922, respectively, in order of appearance) of anti-H5VN04 phage Abs characterized by >95% neutralization activity against both H5VN04 and H1PR8 pseudotyped viruses. The highlighted residues in the CDRs refer to panel C) which describes the result of a Chi$^2$ statistical analysis approach used to identify residues that were significantly enriched as compared to their frequency in the library (p<0.05).

Panning the library against the H5-VN04 or H1CA0409 trimeric HA proteins resulted in the isolation of 36/36 and 28/30 stem targeted unique phage-Ab clones, characterized by low V-segment amino acid substitution frequency of 2.89-☐1.24 and 2.93-☐1.31, respectively (FIG. 4A). The data further indicate that of all 36 anti-H5VN04 phage Ab, 10 cross-reacted with H1CA0409; 2 cross-reacted with H2 A/Singapore/1/1957 (H2 SIN 57); and 9 cross-reacted with both H1CA0409 and H2 SIN 57(FIG. 16A). Likewise, of all 30 anti-H1CA0409 phage Abs, 11 cross-reacted only with H5VN04; cross-reacted only with H2 SIN 57; and 9 cross-reacted against both H1CA0409 and H2 SIN 57(FIG. 16D).

Heterosubtypic neutralization activity was tested for thirty-one anti-H5VN04-stem phage-Abs by using H5VN04 and H1PR8 pseudotyped viruses. In FIG. 4B heavy chain CDR sequences are shown for the 10 phage-Ab characterized by >95% neutralization activity against both strains.

Chi² based statistical analysis of these 10 neutralizing Abs that compares the frequency of substituted amino acids before and after selection (FIG. 4C) reveals a sequence solution conveyed by the two distinctive HV1-69-sBnAb substitutions of CDR-H1 Val27 (6/10), CDR-H2 Ser52 (9/10) and CDR-H3 CDR-H3-Tyr 98 (9/10). The non-HV1-69-sBnAb distinctive substitution Met53 (6/10) and CDR-H3 Pro100 (5/10) were found in this pool. In the remaining pool of anti-H5VN04 phage-Abs (FIG. 16B), the substitutions of CDR-H4 Asn76 and CDR-H3 Gly97, Tyr99, and Gly100B were also significantly enriched.

Sequence analysis of the stem-directed heterosubtypic phage-Abs from both anti-H5VN04 and anti-H1CA0409 Ab pools showed the dominance of CDR-H2 Ser52 and CDR-H3 Tyr in position 98 as exemplified by FIG. 16. The Ser52 and Tyr 98-99 combination were also observed in 6 common phage-Abs isolated from both H5VN04 and H1CA0409 panning campaigns (FIG. 15A). The sequence alignment of the CDR-H3 domains of these common clones reveals they recapitulate similar naturally-occurring CDR-H3s (FIG. 15B).

FIG. 16A also shows that the dominant sequence motif of Ser52/Tyr98 occurs in both the heterosubtypic (16/21) and the non-heterosubtypic anti-H5VN04 phage-Ab subsets (8/15). In order to understand if heterosubtypic activity of phage-Abs characterized by the Ser52/Tyr98 sequence motif is associated with other amino acids, the composition of the CDR-H3 domain of the two subsets was analyzed separately for the occurrence of enriched residues. The statistical analysis in FIG. 16C shows that in the heterosubtypic Ser52/Tyr98 subset Tyr99, Pro100, and Gly100B were significantly enriched whereas no significant enrichment of these same residues were found to occur in the CDR-H3 of the non-heterosubtypic subset. Furthermore, although not statistically significant, the high frequency of glycines in the heterosubtypic subset is also shown to occur 5' to CDR-H3-Tyr98 where 46% of the amino acids at positions 95-to-97 are glycines as opposed to the non-heterosubtypic subset where 21% are glycines at these positions. This analysis suggests that a flexible CDR-H3 loop is beneficial in mediating heterosubtypic activity for anti-H5VN04 stem binders characterized by CDR-H2 Ser52 and CDR-H3-Tyr98.

A similar amino acid enrichment profile was also observed in the H1CA0490 phage-Ab pool (FIG. 16D-E) that are characterized by the dominant pair of Ser52/Tyr98 as well as by CDR-H1 Val27, CDR-H4 Asn76 and CDR-H3 Gly97. These substitutions are also shown to dominate the heterosubtypic phage-Ab subset whereas in the non-heterosubtypic subset CDR-H1 Val27 and CDR-H2 Ser52 appear only once (1/9) and Tyr residues in positions 98 or 99 appear only in three phage-Abs (3/9).

The unexpected predominant recovery of Ser52 over Gly52a and Ala52a encoding phage-Abs from the pannings despite similar coding frequency in the library (FIG. 14) was examined. FIG. 2A shows that the frequency of Gly52a or Ala52a substitutions is even higher than Ser52 for the naturally occurring HV1-69-sBnAbs. However, the Gly52a subset is restricted to double or triple tyrosines in the CDR-H3 domain, whereas the Ala52a subset is shown to be strongly associated with CDR-H1 Arg30 (6/8). In contrast, the Ser52 does not appear to be as strongly associated with other V-segment substitutions. Thus, the incorporation of Ser52 likely provides a higher diversity of structural solutions than that of Gly52a and Ala52a, which may be more restricted.

Example 7: Exploring the Effect of IGVH1-69 Genomic Makeup on the Ability to Generate Stem-Directed ABS The biased use of 51p1 alleles of IGHVI-69 germline genes of sBnAbs prompted us to assess the frequency of sBnAb elicitation in individuals who lack the 5 1p1 alleles. We genotyped a cohort of 20 individuals enrolled in a 2007 HS-vaccination study [(rgA/Vietnam/1203/04 X A/PR/8/34) manufactured by Sanofi Pasteur Inc, Swiftwater, Pa.](10) using a qPCR assay that identifies 51p 1 and hv1263 allele composition from genomic-derived DNA. The genotyping identified five hv1263 homozygous, four 51p 1 homozygous and 11 heterozygous subjects. A sensitive MSD ELISA assay that utilized pre-vaccination, 1-month post vaccination, and 4-years post vaccination sera against the 51p1 allele-specific mouse anti-idiotypic mAb G6 (15) confirmed the qPCR results and also demonstrated that frequency of total 51p1-alleles based IgGs did not rise post H5 vaccination (FIG. 5a). To further investigate if IGHV1-69 allele family usage had an effect on hemagglutinin binding activities, the individual sera that were available from one-month post last vaccination were tested by ELISA at several dilutions for h5VN04 binding. Grouping the obtained EC50 values according to IGHV1-69 allele composition showed an apparent higher H5VN04 binding activity for the 51p1 homozygous group compared to the 51p1/hv263 heterozygous and hv1263 homozygous groups (FIG. 5b). When tested by ELISA assay for binding to the H5VN04 HAI_protein, which is devoid of the stem region, similar binding activities in the 3 groups (FIG. 5c), suggesting that the higher binding activity of the 51p1 homozygous group to the full length H5VN04 may be attributed to larger proportion of stem reactive Abs. This was confirmed in an assay that examines serum competition for biotinylated F10 mAb stem antibody binding to full-length hemagglutinin. Indeed, these results showed that the 51p1 homozygous had higher heterosubtypic stem antibody titers against pdmH1N1 CA04/09 HA that was not circulated at that time as compared to the and 51p1/hv1263 heterozygous and hv1263 homozygous group (FIG. 5d). These observations demonstrate that IGHV1-69 germline gene allele composition is correlated with the frequency of circulating sBnAbs against the F10, CR6261 and CR9114 epitope.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. J. Sui et al., Structural and functional bases for broad-spectrum neutralization of avian and human influenza A viruses. *Nat Struct Mol Biol* 16, 265 (March 2009).
2. M. Throsby et al., Heterosubtypic neutralizing monoclonal antibodies cross-protective against H5N1 and H1N1 recovered from human IgM+ memory B cells. *PLoS One* 3, e3942 (2008).
3. D. C. Ekiert et al., Antibody recognition of a highly conserved influenza virus epitope. *Science* 324, 246 (Apr. 10, 2009).

4. A. K. Kashyap et al., Combinatorial antibody libraries from survivors of the Turkish H5N1 avian influenza outbreak reveal virus neutralization strategies. *Proc Natl Acad Sci USA* 105, 5986 (Apr. 22, 2008).

5. C. Dreyfus et al., Highly conserved protective epitopes on influenza B viruses. *Science* 337, 1343 (Sep. 14, 2012).

6. D. Corti et al., Heterosubtypic neutralizing antibodies are produced by individuals immunized with a seasonal influenza vaccine. *J Clin Invest* 120, 1663 (May 3, 2010).

7. J. Wrammert et al., Broadly cross-reactive antibodies dominate the human B cell response against 2009 pandemic H1N1 influenza virus infection. *The Journal of experimental medicine* 208, 181 (Jan. 17, 2011).

8. C. A. Thomson et al., Pandemic H1N1 Influenza Infection and Vaccination in Humans Induces Cross-Protective Antibodies that Target the Hemagglutinin Stem. *Frontiers in immunology* 3, 87 (2012).

9. G. M. Li et al., Pandemic H1N1 influenza vaccine induces a recall response in humans that favors broadly cross-reactive memory B cells. *Proc Natl Acad Sci USA* 109, 9047 (Jun. 5, 2012).

10. J. Sui et al., Wide prevalence of heterosubtypic broadly neutralizing human anti-influenza A antibodies. *Clinical infectious diseases: an official publication of the Infectious Diseases Society of America* 52, 1003 (Apr. 15, 2011).

11. N. Pica et al., Hemagglutinin stalk antibodies elicited by the 2009 pandemic influenza virus as a mechanism for the extinction of seasonal H1N1 viruses. *Proc Natl Acad Sci USA* 109, 2573 (Feb. 14, 2012).

12. M. S. Miller et al., 1976 and 2009 H1N1 influenza virus vaccines boost anti-hemagglutinin stalk antibodies in humans. *The Journal of infectious diseases* 207, 98 (Jan. 1, 2013).

13. S. D. Boyd et al., Individual variation in the germline Ig gene repertoire inferred from variable region gene rearrangements. *J Immunol* 184, 6986 (Jun. 15, 2010).

14. P. D. Kwong, I. A. Wilson, HIV-1 and influenza antibodies: seeing antigens in new ways. *Nature immunology* 10, 573 (June 2009).

15. K. N. Potter, Y. Li, R. A. Mageed, R. Jefferis, J. D. Capra, Molecular characterization of the VH1-specific variable region determinants recognized by anti-idiotypic monoclonal antibodies G6 and G8. *Scandinavian journal of immunology* 50, 14 (July 1999).

16. E. H. Sasso, T. Johnson, T. J. Kipps, Expression of the immunoglobulin VH gene 51p1 is proportional to its germline gene copy number. *J Clin Invest* 97, 2074 (May 1, 1996).

17. L. M. Meireles, A. S. Domling, C. J. Camacho, ANCHOR: a web server and database for analysis of protein-protein interaction binding pockets for drug discovery. *Nucleic acids research* 38, W407 (July 2010).

18. D. Lingwood et al., Structural and genetic basis for development of broadly neutralizing influenza antibodies. *Nature* 489, 566 (Sep. 27, 2012).

19. G. C. Ippolito et al., Antibody repertoires in humanized NOD-scid-IL2Rgamma(null) mice and human B cells reveals human-like diversification and tolerance checkpoints in the mouse. *PLoS One* 7, e35497 (2012).

20. Ivanov, II et al., Development of the expressed Ig CDR-H3 repertoire is marked by focusing of constraints in length, amino acid use, and charge that are first established in early B cell progenitors. *J Immunol* 174, 7773 (Jun. 15, 2005).

21. T. R. Poulsen, A. Jensen, J. S. Haurum, P. S. Andersen, Limits for antibody affinity maturation and repertoire diversification in hypervaccinated humans. *J Immunol* 187, 4229 (Oct. 15, 2011).

22. J. U. Peled et al., The biochemistry of somatic hypermutation. *Annual review of immunology* 26, 481 (2008).

23. I. B. Rogozin, Y. I. Pavlov, K. Bebenek, T. Matsuda, T. A. Kunkel, Somatic mutation hotspots correlate with DNA polymerase eta error spectrum. *Nature immunology* 2, 530 (June 2001).

24. C. T. Watson et al., Complete Haplotype Sequence of the Human Immunoglobulin Heavy-Chain Variable, Diversity, and Joining Genes and Characterization of Allelic and Copy-Number Variation. *American journal of human genetics*, (Mar. 26, 2013).

25. T. Han, W. A. Marasco, Structural basis of influenza virus neutralization. Annals of the New York Academy of Sciences 1217, 178 (January 2011).

26. S. Kuchen et al., Essential role of IL-21 in B cell activation, expansion, and plasma cell generation during CD4+ T cell-B cell collaboration. *J Immunol* 179, 5886 (Nov. 1, 2007).

27. C. G. Vinuesa, M. A. Linterman, C. C. Goodnow, K. L. Randall, T cells and follicular dendritic cells in germinal center B-cell formation and selection. i Immunological reviews 237, 72 (September 2010).

28. T. A. Schwickert et al., A dynamic T cell-limited checkpoint regulates affinity-dependent B cell entry into the germinal center. *The Journal of experimental medicine* 208, 1243 (Jun. 6, 2011).

29. F. W. Studier, Protein production by auto-induction in high density shaking cultures. *Protein expression and purification* 41, 207 (May 2005).

30. S. Hoot et al., Recombinant HIV Envelope Proteins Fail to Engage Germline Versions of Anti-CD4bs bNAbs. *PLoS pathogens* 9, e1003106 (January 2013).

31. E. F. Pettersen et al., UCSF Chimera—a visualization system for exploratory research and analysis. *Journal of computational chemistry* 25, 1605 (October 2004).

32. A. Fahmy, G. Wagner, Optimization of van der Waals energy for protein side-chain placement and design. *Biophysical journal* 101, 1690 (Oct. 5, 2011).

33. O'Connell D, Becerril B, Roy-Burman A, Daws M, Marks J D (2002) Phage versus phagemid libraries for generation of human monoclonal antibodies. J Mol Biol 321: 49-56.

34. S. W. Fanning, J. R. Horn, An anti-hapten camelid antibody reveals a cryptic binding site with significant energetic contributions from a nonhypervariable loop. *Protein science: a publication of the Protein Society* 20, 1196 (July 2011).

35. B. S. Briney, J. R. Willis, J. E. Crowe, Jr., Location and length distribution of somatic hypermutation-associated DNA insertions and deletions reveals regions of antibody structural plasticity. *Genes and immunity* 13, 523 (October 2012).

36. L. Ohm-Laursen, T. Barington, Analysis of 6912 unselected somatic hypermutations in human VDJ rearrangements reveals lack of strand specificity and correlation between phase II substitution rates and distance to the nearest 3' activation-induced cytidine deaminase target. *J Immunol* 178, 4322 (Apr. 1, 2007).

What is claimed is:

1. A method of improving the neutralization capacity or affinity of antibodies that bind to the HA protein of an influenza virus, wherein the antibody comprises in the VH domain a methionine, isoleucine, valine, or leucine at position 53, a phenylalanine at position 54, and a tyrosine at position 97, 98 or 99, wherein the method comprises mutating at least one amino acid in the VH domain, wherein the at least one mutation is selected from the following:

a serine from alanine at position 24, a valine from glycine at position 27, an isoleucine or proline from threonine at position 28, a serine from phenylalanine at position 29, an arginine from serine at position 30, a valine from isoleucine at position 34, a serine from isoleucine at position 52, glycine or alanine from proline at position 52a, a lysine from asparagine at position 58, a glutamine from glutamate at position 73, a phenylalanine from serine at position 74, or any combination thereof; wherein the positions of the amino acids are numbered based on the Kabat numbering system; and wherein the VH domain is encoded by the immunoglobulin VH1-69 germline gene.

* * * * *